(12) United States Patent
Sykes et al.

(10) Patent No.: US 10,023,840 B2
(45) Date of Patent: Jul. 17, 2018

(54) GENERATION OF AUTOLOGOUS T-CELLS IN MICE

(71) Applicants: THE TRUSTEES OF COLUMBIA UNIVERSITY IN THE CITY OF NEW YORK, New York, NY (US); The General Hospital Corporation, Boston, MA (US)

(72) Inventors: Megan Sykes, Bronx, NY (US); Hannes Kalscheuer, Heidelberg (DE)

(73) Assignees: The Trustees of Columbia University in the City of New York, New York, NY (US); The General Hospital Corporation, Boston, MA (US)

(*) Notice: Subject to any disclaimer, the term of this patent is extended or adjusted under 35 U.S.C. 154(b) by 518 days.

(21) Appl. No.: 13/931,659

(22) Filed: Jun. 28, 2013

(65) Prior Publication Data

US 2014/0101786 A1 Apr. 10, 2014

Related U.S. Application Data

(63) Continuation-in-part of application No. PCT/US2011/068155, filed on Dec. 30, 2011.

(60) Provisional application No. 61/428,949, filed on Dec. 31, 2010, provisional application No. 61/454,266, filed on Mar. 18, 2011, provisional application No. 61/532,950, filed on Sep. 9, 2011.

(51) Int. Cl.
| | |
|---|---|
| *A01K 67/027* | (2006.01) |
| *C12N 5/073* | (2010.01) |
| *C12N 5/0789* | (2010.01) |
| *C12N 5/0783* | (2010.01) |
| *A61K 49/00* | (2006.01) |

(52) U.S. Cl.
CPC ........ *C12N 5/0636* (2013.01); *A01K 67/0271* (2013.01); *A61K 49/0008* (2013.01); *A01K 2227/105* (2013.01); *A01K 2267/025* (2013.01); *A01K 2267/03* (2013.01); *A01K 2267/0387* (2013.01)

(58) Field of Classification Search
CPC .. C12N 5/065; C12N 5/0647; A61K 49/0008; A01K 2227/105; A01K 2267/025; A01K 2267/0387; A01K 67/0271
USPC .......................... 424/93.1, 577, 580; 800/8, 9
See application file for complete search history.

(56) References Cited

U.S. PATENT DOCUMENTS

| | | | |
|---|---|---|---|
| 6,808,710 B1 | 10/2004 | Wood et al. | |
| 2007/0237763 A1* | 10/2007 | Banchereau | ....... A01K 67/0271 424/133.1 |
| 2008/0199495 A1 | 8/2008 | Boyd | |
| 2010/0255009 A1 | 10/2010 | Siemionow | |

FOREIGN PATENT DOCUMENTS

| | | | |
|---|---|---|---|
| WO | WO 2010/051634 | * | 5/2010 |
| WO | WO-2010/051634 A1 | | 5/2010 |
| WO | WO 2010/065546 | * | 6/2010 |
| WO | WO-2010/065546 A2 | | 6/2010 |
| WO | WO 2010/126278 | * | 11/2010 |
| WO | WO-2010/126278 A2 | | 11/2010 |

OTHER PUBLICATIONS

Onoe et al. (2010) J. Immunol., vol. 184(12), 6756-6765.*
Lan et al. (2006) Blood, vol. 108, 487-492.*
Galy et al. (1995) Human Hematopoiesis in SCID Mice, Chapter 2, edited by Maria-Grazia Roncarolo.*
Georgiou et al. (1995) Diabetes, vol. 44(1), 49-59.*
Akkina, Ramesh, "New generation humanized mice for virus research: Comparative aspects and future prospects," Virology, vol. 435, No. 1, pp. 14-28, 32 pages (Jan. 5, 2013).
European Search Report issued by the European Patent Office for Application No. 11852397.6 dated Oct. 29, 2014 (12 pages).
Hu, Z. et al., "Human lymphohematopoietic reconstitution and immune function in immunodeficient mice receiving cotransplantation of human thymic tissue and CD34+ cells," Cellular & Molecular Immunology, vol. 9, pp. 232-236 (2012).
International Search Report and Written Opinion issued by the International Searching Authority for International Application No. PCT/US11/68155 dated May 4, 2012 (10 pages).
Joo S.-Y. et al., "Development of Functional Human Immune System With the Transplantations of Human Fetal Liver/Thymus Tissues and Expanded Hematopoietic Stem Cells in RAG2-/-γc-/- MICE," Transplantation Proceedings, vol. 41, pp. 1885-1890 (2009).
Kalscheuer, H. et al., "A model for personalized in vivo analysis of human immune responsiveness," Sci. Transl. Med., vol. 4, No. 125, 22 page (Mar. 14, 2012).
Kalscheuer, H. et al., "Xenograft Tolerance and Immune Function of Human T Cells Developing in Pig Thymus Xenografts," The Journal of Immunology, vol. 192, pp. 3442-3450, 12 pages (Mar. 3, 2014).
Lan, P. et al., "Induction of human T-cell tolerance to porcine xenoantigens through mixed hematopoietic chimerism," Blood, vol. 103, No. 10, pp. 3964-3969 (May 15, 2004).
Lan, P. et al., "Reconstitution of a functional human immune system in immunodeficient mice through combined human fetal thymus/liver and CD34+ cell transplantation," Blood, vol. 108, No. 2, pp. 487-492 (Jul. 15, 2006).
Lepus, C. M. et al., "Comparison of human fetal liver, umbilical cord blood, and adult blood hematopoietic stem cell engraftment in NOD-scid/γc-/-, Balb/c-Rag1-/-γc-/-, and C.B-17-scid/bg immunodeficient mice," Human Immunology, vol. 70, pp. 790-802 (2009).
Onoe, T. et al., "Homeostatic Expansion and Phenotypic Conversion of Human T Cells Depend on Peripheral Interactions with APCs," The Journal of Immunology, vol. 184, pp. 6756-6765, 11 pages (May 10, 2010).

(Continued)

*Primary Examiner* — Anne Marie S Wehbe
(74) *Attorney, Agent, or Firm* — Leason Ellis LLP

(57) ABSTRACT

The invention provides an animal model and methods of generating large numbers of diverse, functional, naïve T cells in mice using bone marrow cells from adult donors.

30 Claims, 80 Drawing Sheets
(33 of 80 Drawing Sheet(s) Filed in Color)

(56) References Cited

OTHER PUBLICATIONS

Onoe, T. et al., "Human Natural Regulatory T Cell Development, Suppressive Function, and Postthymic Maturation in a Humanized Mouse Model," The Journal of Immunology, vol. 187, pp. 3895-3903, 10 pages (Aug. 29, 2011).

* cited by examiner

Cryopreserved THY grafts      7 GY irradiated THY grafts

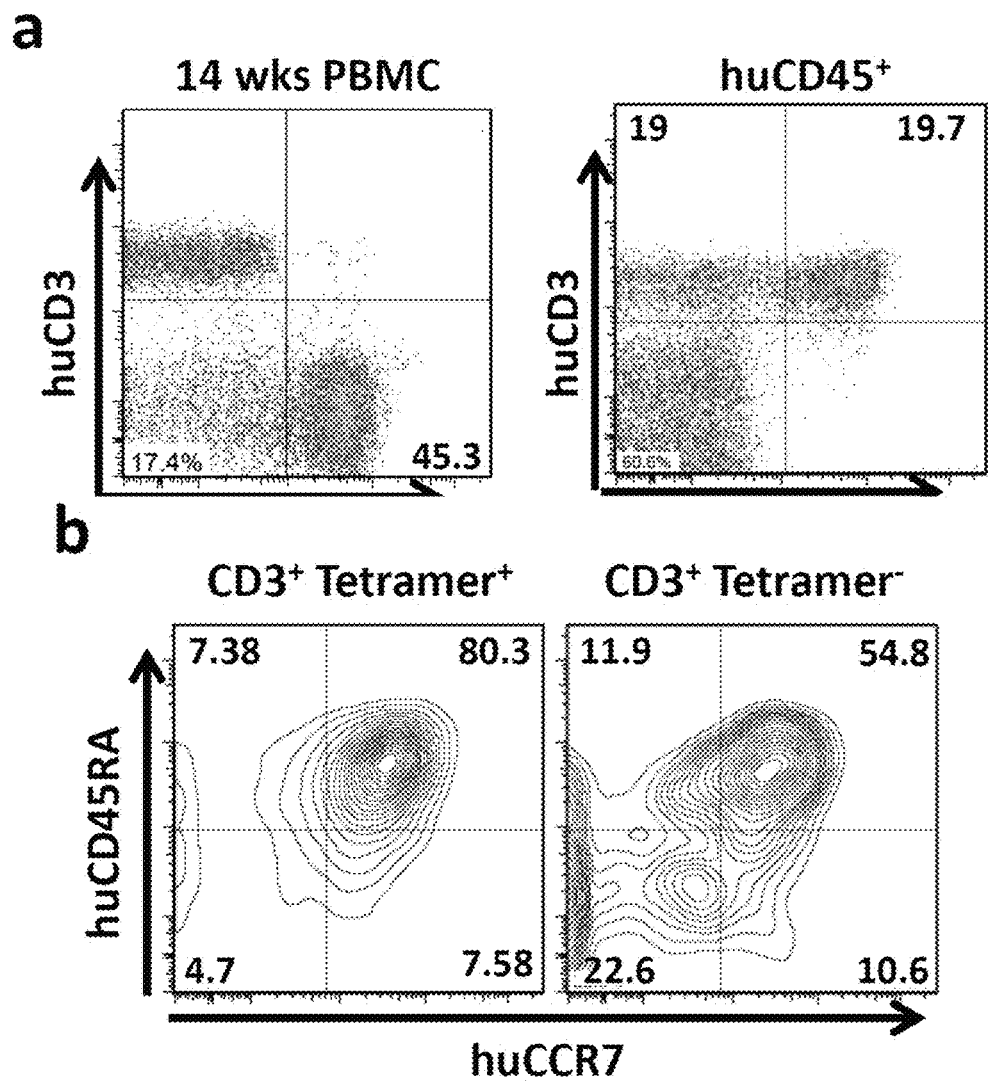
FIGS. 66A-B

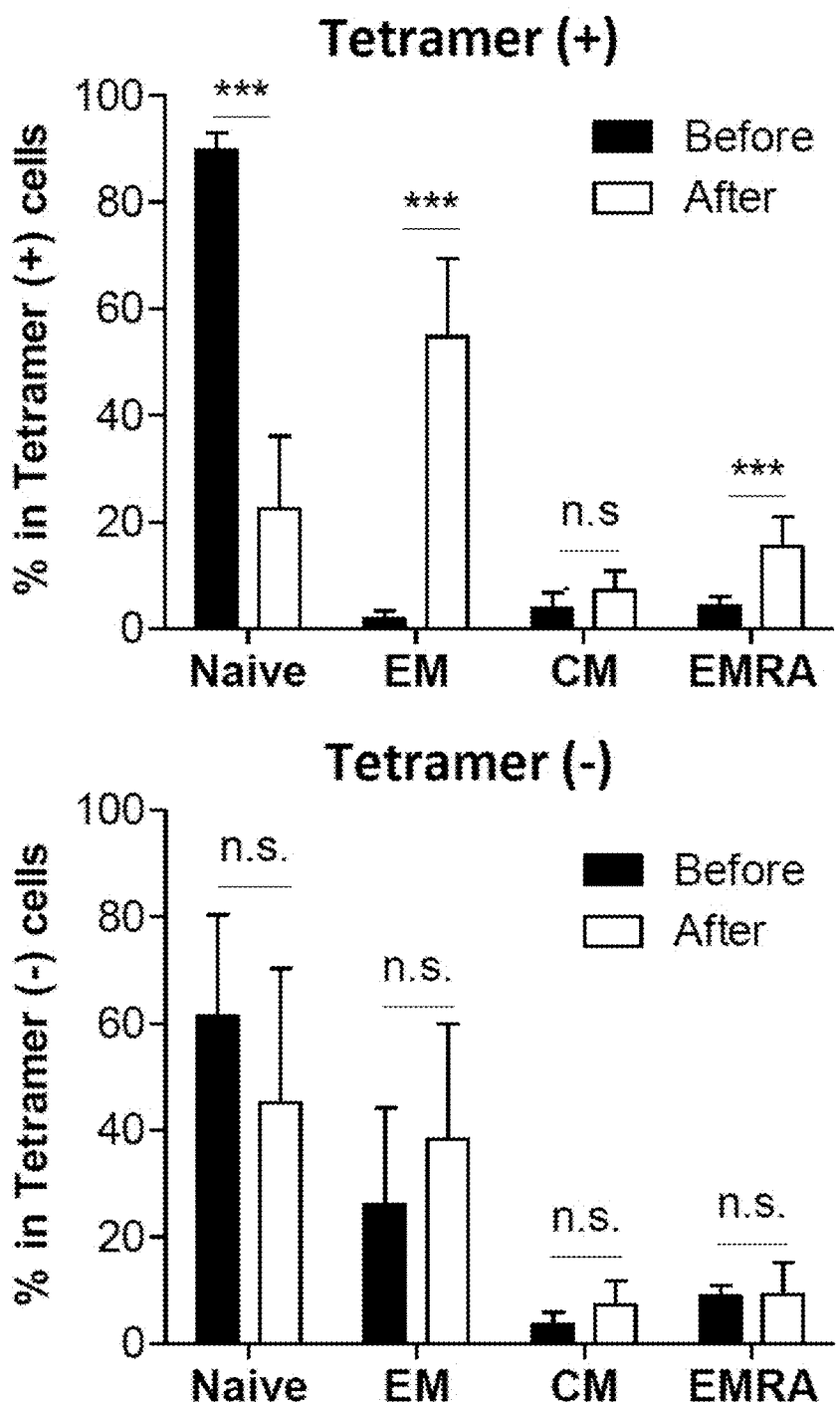
FIG. 67B – Cont.

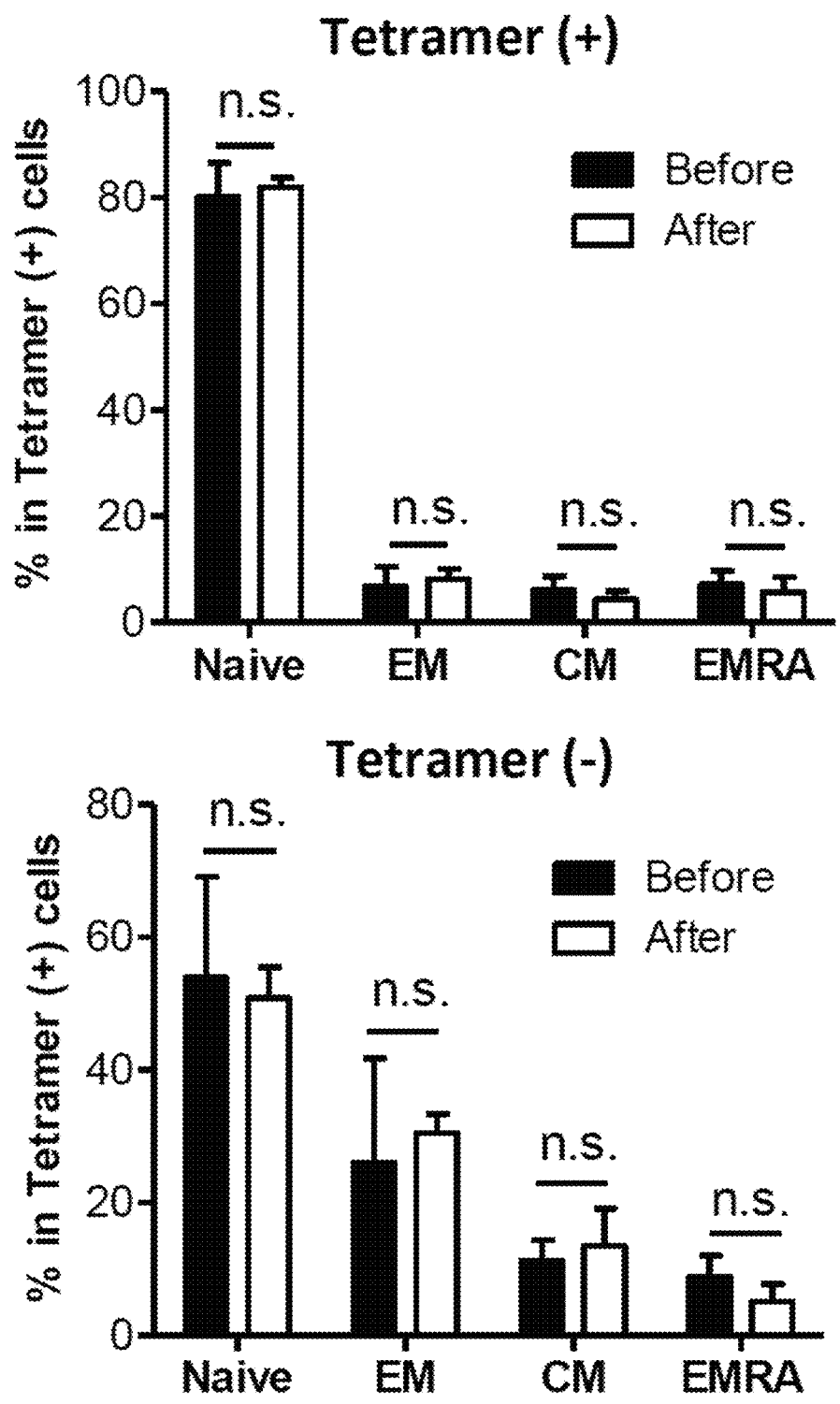
FIG. 67E – cont.

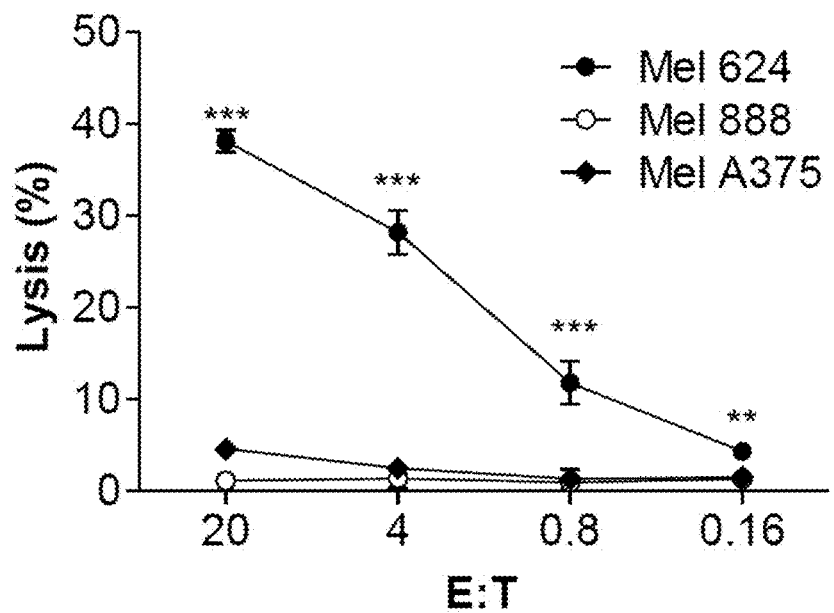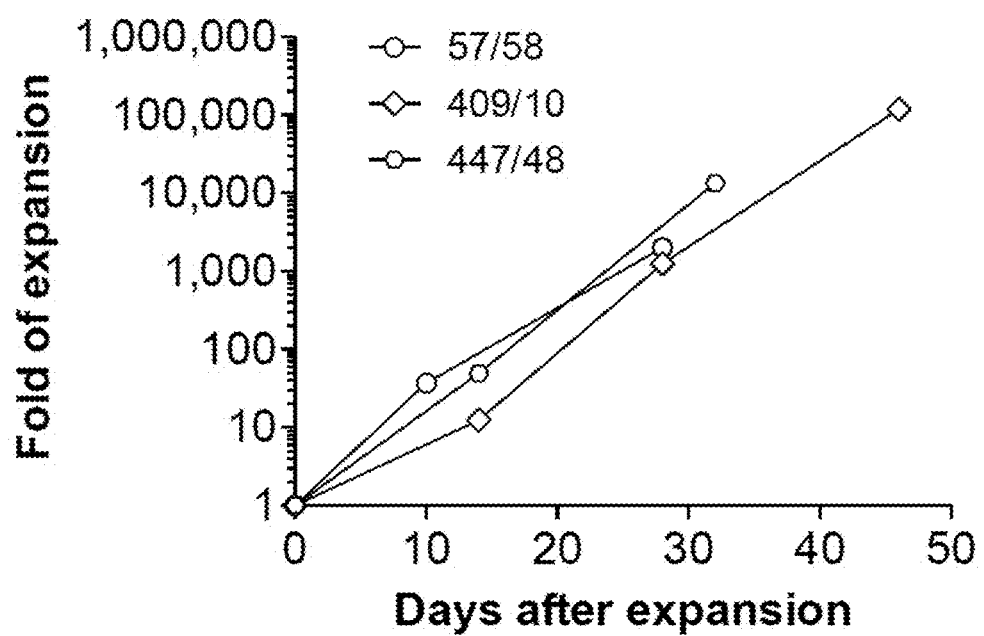
FIGS. 68A-B

GENERATION OF AUTOLOGOUS T-CELLS IN MICE

This application is a continuation-in-part of International Application No. PCT/US2011/068155, filed on Dec. 30, 2011, which claims priority to U.S. Application Ser. No. 61/428,949, filed on Dec. 31, 2010, U.S. Application Ser. No. 61/454,266, filed on Mar. 18, 2011, and U.S. Application Ser. No. 61/532,950, filed on Sep. 9, 2011, the contents of each of which are hereby incorporated by reference in their entireties.

All patents, patent applications and publications, and other literature references cited herein are hereby incorporated by reference in their entirety. The disclosures of these references in their entireties are hereby incorporated by reference into this application in order to more fully describe the state of the art as known to those skilled therein as of the date of the invention described herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND

The human immune system is still not fully understood and there are a great many diseases that involve defects in the immune system, such as autoimmune diseases. Many autoimmune diseases are mediated by autoreactive T cells. There is a need for methods to provide a diverse pool of naïve T cells which could be useful in the therapeutic treatment of such diseases and disorders.

SUMMARY OF THE INVENTION

In certain aspects, the invention provides an animal model that supports immune system reconstitution, including but not limited to thymopoiesis, the non-human animal model comprising: (a) a recipient immunodeficient non-human animal, which animal is optionally conditioned prior to transplantation, for example, but not limited, by treatment with low dose or sublethal dose of radiation, for example, but not limited to, a range of 1-1.5 Gy, a range of 1.5-4 Gy, a range of 1-4 Gy, 2.5 Gy, or by using busulfan, for example, on the same day of transplantation, one day, 1.5 days, 2 days prior to transplantation; (b) fetal thymus tissue transplanted under a kidney capsule of the recipient mouse, wherein the fetal thymus tissue has been depleted of viable T-cells; and (c) adult-bone-marrow-donor CD34+ cells, wherein the fetal thymus tissue and the CD34+ cells share HLA alleles.

In certain aspects, the invention provides a non-human animal that carries out human thymopoiesis comprising: (a) a recipient immunodeficient animal, which animal is optionally conditioned prior to transplantation, for example, but not limited to, by treatment with low dose or sublethal dose of radiation, for example, but not limited to, a range of 1-1.5 Gy, a range of 1.5-4 Gy, a range of 1-4 Gy, 2.5 Gy, or by using busulfan, for example, on the same day of transplantation, one day, 1.5 days, 2 days prior to transplantation; (b) human fetal thymus tissue transplanted under a kidney capsule of the recipient animal, wherein the human fetal thymus tissue is depleted of T-cells, and (c) human adult-bone-marrow-donor CD34+ cells, wherein the human fetal thymus tissue and the human CD34+ cells share HLA alleles.

In other aspects, the invention provides an animal model made by a method comprising: (a) gamma irradiating with sublethal total body irradiation a recipient immunodeficient animal, prior to or concomitantly with step (b) or (c); (b) transplanting into the recipient animal a fetal thymus tissue, wherein the fetal thymus tissue is depleted from T cells, and (c) administering for example but not limited to 1-5×10^5 adult-bone-marrow-donor CD34+ cells, wherein the fetal thymus tissue and the CD34+ cells share HLA alleles.

In certain embodiments, the animal model further comprises an antigen, whereby T cells with desired specificity are expanded.

In certain embodiments, the animal is conditioned by treatment with low dose or sublethal dose of radiation, for example but not limited to, a range of 1-1.5 Gy, a range of 1.5-4 Gy, a range of 1-4 Gy, 2.5 Gy, or by using busulfan, for example, on the same day of transplantation, one day, 1.5 days, 2 days prior to transplantation. In certain embodiments, recipient animal is any suitable animal, for example but not limited to a mouse, a rat, or a pig.

In certain embodiments, the fetal thymus tissue is human fetal thymus tissue and the adult-bone-marrow-donor CD34+ cells are human. In certain embodiments, the fetal thymus tissue is from any suitable animal for example but not limited to canine, equine, feline, swine fetal thymus tissue. In other embodiments, the adult-bone-marrow-donor CD34+ cells are from any suitable animal for example but not limited to canine, equine, feline, swine fetal thymus tissue. In certain embodiments, the recipient animal is NOD/SCID, NOG or NSG mouse.

In certain embodiments, the mouse model supports human thymopoiesis, exhibits rejuvenated T-cell phenotype, which is characterized by the presence of predominantly naïve CD45RA+CD45RO−CD62L+ CCR7+ cells, exhibits peripheral multilineage cell reconstitution, or any combination thereof, wherein the characteristics of the mouse model are described herein, inter alia in Example 2.

In certain embodiments, the adult-bone-marrow-donor CD34+ cells are from a donor suffering from Type I Diabetes. In certain embodiments, administering is by i.v. injection.

In certain embodiments, the animal model, further comprises 1-5×10^5 allograft-donor CD34+ cells, or 1-5×10^5 hematopoetic cell transplant (HCT) recipient CD34+ cells, wherein the allograft-donor CD34+ cells and HCT recipient CD34+ cells share HLA alleles with the fetal thymus tissue and the adult-bone-marrow-donor CD34+ cells, so as to reconstitute T-cells which are mutually tolerant of one another so as to generate T-cells in the recipient animal, which T-cells are tolerant of both the adult-bone-marrow-donor as well as the allograft-donor or HCT recipient.

In certain aspects, the invention provides a method to make an animal model of thymopoiesis comprising: (a) gamma irradiating with sublethal total body irradiation a recipient immunodeficient animal, prior to or concomitantly with step (b) or (c); (b) transplanting into the recipient animal a fetal thymus tissue, wherein the fetal human thymus tissue is depleted from T cells, and (c) administering, for example but not limited to 1-5×10^5, adult-bone-marrow-donor CD34+ cells, wherein the fetal thymus tissue and the CD34+ cells share HLA alleles.

In certain embodiments, the CD34+ cells, including but not limited to the adult-bone-marrow-donor CD34+ cells, have a genetic modification. In certain embodiments, the genetic modification is such that the T-cells derived the adult-bone-marrow-donor CD34+ cells are resistant to viruses that persist in the adult donor.

In certain aspects, the invention provides a method to expand T-cells with desired specificity, comprising (a) gamma irradiating with sublethal total body irradiation a recipient immunodeficient animal, prior to or concomitantly with step (b) or (c); (b) transplanting into the recipient animal a fetal thymus tissue, wherein the fetal human thymus tissue is depleted from T cells, and (c) administering, for example but not limited to 1-5×10^5, adult-bone-marrow-donor CD34+ cells, wherein the fetal thymus tissue and the CD34+ cells share HLA alleles, and further comprising (d) administering to the animal model an antigen whereby the T-cells recognize the antigen, wherein step (d) is carried out prior to step (a), (b), or (c), concomitantly with step (a), (b), or (c), or after step (a), (b), and (c).

In certain aspects, the invention provides a method to differentiate T-cells, comprising (a) gamma irradiating with sublethal total body irradiation a recipient immunodeficient animal, prior to or concomitantly with step (b) or (c); (b) transplanting into the recipient animal a fetal thymus tissue, wherein the fetal human thymus tissue is depleted from T cells, and (c) administering, for example but not limited to 1-5×10^5, adult-bone-marrow-donor CD34+ cells, wherein the fetal thymus tissue and the CD34+ cells share HLA alleles, and further comprising (d) exposing the animal model to an antigen in a manner conductive to differentiation of regulatory T-cell, wherein step (d) is carried out prior to step (a), (b), or (c), concomitantly with step (a), (b), or (c), or after step (a), (b), and (c). In certain embodiments, exposing is conducted via APCs, or cytokines, or combination thereof.

In other aspects, the invention provides a method to treat or prevent thymic insufficiency, graft rejection, GVHD, autoimmune disease, or a combination thereof comprising administering to a subject in need thereof human T-cells generated in the animal model described herein.

Isolated CD4, CD8 T cells, B cells, monocytes, or dendritic cells, or a combination thereof generated in the animal model are described herein. The invention provides for the generation of subsets of CD4 or CD8 T cells (selected by phenotype, e.g. naïve or memory or by specificity using tetramers identifying T cells with particular specificities).

The invention provides a humanized mouse model of human thymopoiesis from adult bone marrow donor CD34+ cells in allogenic human fetal thymus graft, the mouse model comprising, consisting essentially of, or consisting of: a recipient NOD/SCID, NOG, or NSG mouse, or RAG KO common gamma chain KO, which mouse is irradiated with low dose or sublethal dose of radiation, for example but not limited to, a range of 1-1.5 Gy, a range of 1.5-4 Gy, a range of 1-4 Gy, 2.5 Gy, or treated with busulfan, for example, on the same day of transplantation, one day, 1.5 days, 2 days prior to transplantation, HLA-typed fetal human thymus tissue transplanted under a kidney capsule of the recipient mouse, wherein the HLA-typed fetal human thymus tissue is depleted of fetal mature T-cells, wherein in a non-limiting embodiment the transplanted thymus is cryopreserved and thawed prior to transplantation, and i.v. administered HLA-typed CD34+ cells derived from adult bone marrow donor, wherein in non-limiting embodiments, the mouse model supports human thymopoiesis, exhibits rejuvenated T-cell phenotype, which is characterized with predominantly naïve CD45RA+CD45RO− CD62L+ cells, exhibits peripheral multilineage cell reconstitution, the thymic development is phenotypically normal, and the peripheral T cells are functional, the T cells undergo normal homeostatic changes when transferred to T cell deficient mice, the mouse model generates normal, functional regulatory T cells, the T cell repertoire is polyclonal, or any combination thereof. The characteristics of the animal model are described herein, inter alia, in Example 2.

In another aspect, the invention provides a humanized mouse model to generate diverse, for example as evidenced by VB usage and CDR3 length distributions of individual VB families, functional, naïve T-cells which are CD45RA+ RO− CD62L+ CCR7+ from adult bone marrow donor CD34+cells in allogenic human fetal thymus graft, the mouse model made by a method comprising, consisting essentially of, or consisting of: (a) gamma irradiating a recipient NOD/SCID, NOG, or NSG mouse, or RAG KO common gamma chain KO prior or concomitantly with step (b); (b) transplanting into the NOD/SCID, NOG, or NSG, or RAG KO common gamma chain KO mouse an HLA-typed human thymus tissue, wherein in certain embodiments fetal thymic tissue is transplanted, wherein the HLA-typed fetal human thymus tissue is depleted from mature T-cells, in certain embodiments by treatment with dGuo, or cryopreserved and thawed, (c) administering by i.v. 1-5×10^5, 1-4×10^5, 1-3×10^5, 1-2×10^5, 1.5-2×10^5 HLA-typed CD34+ cells derived from an adult bone marrow donor, wherein in certain embodiments reconstitution is achieved by administering 1.8×10^5 cells. A skilled artisan knows that these numbers can vary, for example within the limits of error of the method which is used to determine the cell number. HLA typing is carried out so as to determine shared HLA alleles.

In one aspect of the invention, dependent upon the disease being treated, various numbers of HLA alleles are to be shared. For example, in a situation where global T cell reconstitution is desired, sharing of at least one class I (A or B) and one class II (DQ or DR) allele would be needed, and sharing of more (at least one A, B, DQ and DR allele) would be desirable. In another example, for certain tumor or viral antigen-specific responses, sharing for particular class I alleles known to present to CTLs to a specific peptide would be desired. In another example, for studies of T1DM pathogenesis, sharing of specific disease associated class II (HLA DR3/4,DQ8 for T1DM) alleles is desired.

In certain embodiments, the humanized mouse model generates a large number of maximum 2.5×10^7 per mouse, wherein up to 15 mice per 15 ml aspirate, and a total 3.75×10^8 T cells from simple bedside bone marrow aspirate are generated. More bone marrow could be aspirated with patient sedation, thereby providing bone marrow for the generation of additional mice from the same subject.

In certain embodiments, the animal recipient of the HLA-typed fetal human thymus tissue is optionally treated with anti-CD2 mAb.

In certain embodiments, the non-human animal recipient of the invention that carries out human thymopoiesis does not comprise liver tissue from the adult bone marrow donor. In certain embodiments, the non-human animal recipient of the invention that carries out human thymopoiesis does not comprise liver tissue from the fetal tissue donor.

In another aspect, the invention provides a humanized mouse model of human thymopoiesis made by a method comprising, consisting essentially of, consisting of:
  (a) gamma irradiating a recipient NOD/SCID, NOG, or NSG mouse, or RAG KO common gamma chain KO prior or concomitantly with step (b);
  (b) transplanting into the NOD/SCID, NOG, or NSG, or RAG KO common gamma chain KO mouse an HLA-typed human thymus tissue, wherein in certain embodiments 1 mm³ fetal thymic tissue is transplanted, and fewer than 20, or 20, 21, 22, 23, 24, 25, or 20-25, 21-26, 22-27 mice may be transplanted with a tissue from the same thymus, wherein the HLA-typed fetal human thymus tissue is depleted from mature T-cells, in certain embodiments by treatment with dGuo, or cryopreserved and thawed as described, (c) administering by i.v. 1-5×10^5, 1-4×10^5, 1-3×10^5, 1-2×10^5, 1.5-2×10^5 HLA-typed CD34+ cells derived from an adult bone marrow donor, wherein in certain embodiments reconstitution is achieved by administering 1.8×10^5 cells. A skilled artisan knows that these numbers can vary, for example within the limits of error of the method which is used to determine the cell number.

In certain aspects, the invention provides a method to make a humanized mouse model of human thymopoiesis whereby a subject's immune system is reconstituted, or a method to make naïve T-cells in a humanized mouse model, or a method to induce and recapitulate human thymopoiesis in a humanized mouse model, the method comprising, consisting essentially of, or consisting of: (a) gamma irradiating a recipient NOD/SCID, NOG, or NSG mouse, or RAG KO common gamma chain KO prior or concomitantly with step (b); (b) transplanting into the NOD/SCID, NOG, or NSG, or RAG KO common gamma chain KO mouse an HLA-typed human thymus tissue, wherein in certain embodiments 1 mm³ fetal thymic tissue is transplanted, wherein the HLA-typed fetal human thymus tissue is depleted from mature T-cells, in certain embodiments by treatment with dGuo, or cryopreserved and thawed as described, (c) administering by i.v. 1-5×10^5, 1-4×10^5, 1-3×10^5, 1-2×10^5, 1.5-2×10^5 HLA-typed CD34+ cells derived from an adult bone marrow donor, wherein in certain embodiments reconstitution is achieved by administering 1.8×10^5 cells. A skilled artisan knows that these numbers can vary, for example within the limits of error of the method which is used to determine the cell number.

In certain aspects of the claimed methods, the recipient of HLA-typed fetal human thymus tissue is optionally treated with anti-CD2 mAb.

In certain aspects, the invention provides a method to make a humanized mouse model as described herein, wherein the method further comprises administering by i.v. 1-5×10^5, 1-4×10^5, 1-3×10^5, 1-2×10^5, 1.5-2×10^5 HLA-typed CD34+ cells derived from an allograft donor, or an HCT recipient, in addition to similar numbers from the patient, wherein in certain embodiments reconstitution is achieved by administering 1.8×10^5 cells, so as to reconstitute T-cells which are mutually tolerant of one another, thereby providing a reconstituted immune system which is characterized by mixed chimerism. In other aspects, the invention provides a humanized mouse model as described, wherein the mouse shows mixed chimerism. Cells isolated from mouse models showing mixed chimerism may be used for therapeutic methods in bone marrow transplantation and organ transplantation.

In certain embodiments, the CD34+ cells from the adult bone marrow donor, or from the allograft donor, or the HCT recipient have a genetic modification, which imparts a desired characteristic of the cells generated from the CD34+ cells. In certain embodiments, the genetic modifications of the CD34+ cells used in the methods of the invention, are such that the T-cells derived from the these CD34+ cells are resistant to viruses that persist in the adult donor. In non-limiting examples, the genetic modification comprises a knockdown or a mutation of CCR5, or CXCR4, or a combination thereof, whereby the T-cells derived from the donor CD34+ cells are less susceptible or resistant to viruses, for example HIV.

In certain aspects, the invention provides a method to expand in vivo human T-cells with desired specificity, which T cells recognize a specific antigen(s), the method comprising, consisting essentially of, consisting of steps which make a humanized mouse model as described herein, and further comprising a step of immunizing the humanized mouse with an antigen(s) whereby the T-cells recognize the antigen(s). In certain embodiments, the antigen is a tumor specific antigen, or an antigen derived from a tumor, or a viral antigen. Such antigens may be known in the art, or may be identified by methods known in the art. Non-limiting examples of such antigens include, MART1, NY-ESO, BCR-ABL, MAGE, MUC-1, etc), or a viral antigen (e.g. cytomegalovirus [CMV] or Epstein Barr virus [EBV] peptides.

In certain aspects, the invention provides a method to differentiate human T-cells, comprising, consisting essentially of, consisting of steps which make a humanized mouse model as described herein and further comprising administering or exposing the humanized mouse to an antigen or autoantigen in a manner conductive to differentiation of regulatory T-cell. In certain embodiments, exposing is conducted via adjuvant, APCs, or cytokines, or combination thereof.

In certain aspects, the invention provides a method to treat or prevent graft rejection, GVHD, an autoimmune disease, or a combination thereof comprising administering human T-cells differentiated by the claimed methods. In certain embodiments, the T cells are Tregs. In certain embodiments, the T-cells are isolated from the humanized mouse.

In certain aspects, the invention provides human reconstituted cells comprising CD4 and CD8 T cells, B cells, monocytes, dendritic cells, wherein the cells are generated in the instant humanized model. In certain embodiments, the T cells are tolerant to the donor because of exposure during development to cells which are derived from the i.v. administered CD34+ cells. In certain embodiments, the cells are naïve T-cells which are CD45RA+RO− CD62L+ CCR7+. In certain embodiments, the human reconstituted cells are isolated from the mouse. In certain embodiments, specific cell populations, for example but not limited to CD4 or CD8 T cells, B cells, monocytes, dendritic cells, or any combination, or any other subpopulation are purified from the total population of reconstituted cells. Methods to isolate and purify T cells, or specific cell populations are known in the art. In certain embodiments, these cells generated by the instant humanized model and are used in therapeutic methods of the invention. In certain embodiments, the human reconstituted cells of the invention are comprised in a pharmaceutical formulation suitable for use in adoptive transfer methods.

In certain aspects, the invention provides therapeutic methods wherein the immune cells generated by the instant mouse model are used in adoptive transfer methods to treat a disease or disorder in a subject in need thereof. In certain embodiments, the adult bone marrow donor is the recipient of the cells generated in the non-human animal. In certain embodiments, the disease or disorder is caused by T-cell abnormalities. In certain embodiments, the disease or disorder is cancer. In certain embodiments, the therapeutic methods are used to treat subjects who are recipients of organ, tissue or cell transplants.

The therapeutic methods comprise, consist essentially of, consist of administering to a subject T-cells which are isolated from the humanized mouse with reconstituted immune system from the subject's CD34+ cells. In certain embodiments of the therapeutic methods, the reconstituted immune system is characterized by mixed chimerism. In certain embodiments, the T cells are isolated from a humanized mouse model which has been exposed to an antigen or autoantigen in a manner conductive to differentiation of subpopulations, for example but not limited to regulatory T-cell. In certain embodiments, exposing is conducted via APCs, or cytokines, or combination thereof.

In certain embodiments, the therapeutic methods improve the immune response of cancer patients towards an autologous tumor, which evades the subject's immune system. Non-limiting examples include malignant melanoma, renal cell carcinoma, Hodgkin and non-Hodgkin lymphomas, multiple myeloma, chronic myelogenous leukemia, prostate cancer.

In certain embodiments, the therapeutic methods treat immunosuppressed individuals who have developed lymphoproliferative diseases caused by for example but not limited to EBV, or who have an opportunistic infection. In these methods, immunosuppressed individuals are treated with autologous T-cells isolated from the instant humanized mouse model. In certain embodiments, the mouse has been i.v. injected with CD34+ cells from the immunosuppressed individual. In certain embodiments, the mouse model exhibits mixed chimerism because it has been i.v. injected with CD34+ cells from the immunosuppressed individual and with CD34+cells from an organ or tissue donor. In other embodiments, the mouse has been immunized with an antigen so as to expand in vivo T-cells which recognize the specific antigen.

In certain embodiments, the individual is immunosuppressed due to an HIV infection, or due to immunosuppressive treatment, for example but not limited after organ, tissue or cell transplantation. In certain embodiments, the lymphoproliferative diseases caused by EBV is post-transplant lymphoproliferative disease. In certain embodiments, the opportunistic infection is CMV disease, aspergillosis, other viral, bacterial and fungal infections, or a combination thereof.

In certain aspects, the invention provides methods of using the humanized mouse model or reconstituted cells thereof, as tools to screen and determine an effect of a drug or treatment on a subject, the method comprising, consisting essentially of, or consisting of: (a) optionally, providing a humanized mouse model as described herein, having a reconstituted subject's immune system, (b) administering a drug or treatment to the mouse model of step (a) and (c) determining the effect of the drug or treatment on the reconstituted immune system, whereby the effect of the drug or treatment on the reconstituted immune system is indicative of the effect of the drug or treatment on the immune system of the subject. In certain embodiments, the screening methods can be used to evaluate candidate immunosuppressive drugs for their ability to suppress skin allograft rejection in the humanized mice.

In certain aspects, the invention provides that immunodeficient mice receiving human fetal thymus grafts and fetal CD34+ cells i.v. generate robust human immune systems. The human thymus efficiently supports human thymopoiesis and peripheral human antigen-presenting cells promote optimal function of exported T cells. To study human immune-mediated disorders, adult hematopoietic cells must populate allogeneic fetal thymus grafts with shared HLA alleles while avoiding rejection by mature graft thymocytes. The invention provides reconstituted mice with hematopoietic stem cells aspirated from bone marrow of adult Type 1 diabetic and control volunteers. Fetal thymic cryopreservation permits HLA typing while preventing adult allogenic CD34+ cell rejection. Newly generated T cells are functional and self-tolerant, have a diverse repertoire and include regulatory T cells (Tregs). The immune phenotype of the adult CD34+ cell donor is rejuvenated. In certain embodiments, this "Mini Me" mouse allows prospective analysis of immune pathogenesis and responsiveness to immunotherapeutic agents and suggests an approach to immune reconstitution in adults with thymic insufficiency.

In certain embodiments of the invention, treatment is with low dose or sublethal dose of radiation, for example, but not limited to, 100 cGy, a range of 1-1.5 Gy, a range of 1.5-4 Gy, a range of 1-4 Gy, 2.5 Gy, or any other suitable radiation dose, or agent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Gross appearance. The originally small (1 mm3) fetal thymic fragment has grown to cover the entire exposed surface of the kidney. (FIG. 1B) Histologic appearance, showing normal cortical and medullary structure. (FIG. 1C) Staining profile with anti-CD4 and anti-CD8, showing normal thymocyte staining pattern. (FIG. 1D) HLA class I staining, showing normal profile, with the majority of immature thymocytes expressing only low levels of class I. The class I high population represents mainly mature thymocytes.

FIG. 4C. Survival of pig skin grafts in NOD/SCID-Tg mice that received no human tissues (●; n=5), THY/LIV alone (○; n=5) or THY/LIV/CD34+FLC (■; n=6). FIG. 4D. Macroscopic (left panel) and microscopic (H&E, Middle panel; human CD3 staining, right panel) appearances of a surviving graft from the THY/LIV alone group (top) and a rejected graft from the group receiving Thy/Liv/CD34+FLC (bottom). FIGS. 4E-F. Rejection of adult pig islet xenografts in human Thy/Liv/CD34+

FLC-transplanted NOD/SCID mice. Porcine islet xenografts from control NOD/SCID mice (FIG. 4E) and human Thy/Liv/CD34+FLC-transplanted NOD/SCID mice (FIG. 4F) were sectioned and stained with antibodies specific for porcine insulin, human CD3, human CD20, and human CD68, respectively. Grafts from the control NOD/SCID mice remained intact and stained positive for pig insulin. In contrast, grafts from the humanized NOD/SCID mice had no detectable pig insulin-producing cells, but showed intense infiltration of human T cells, B cell and macrophages. Porcine islets were implanted under the mouse kidney capsule, grafts were removed 4-10 weeks after transplantation. Representative results from 5-week grafts are shown.

Figure 5:
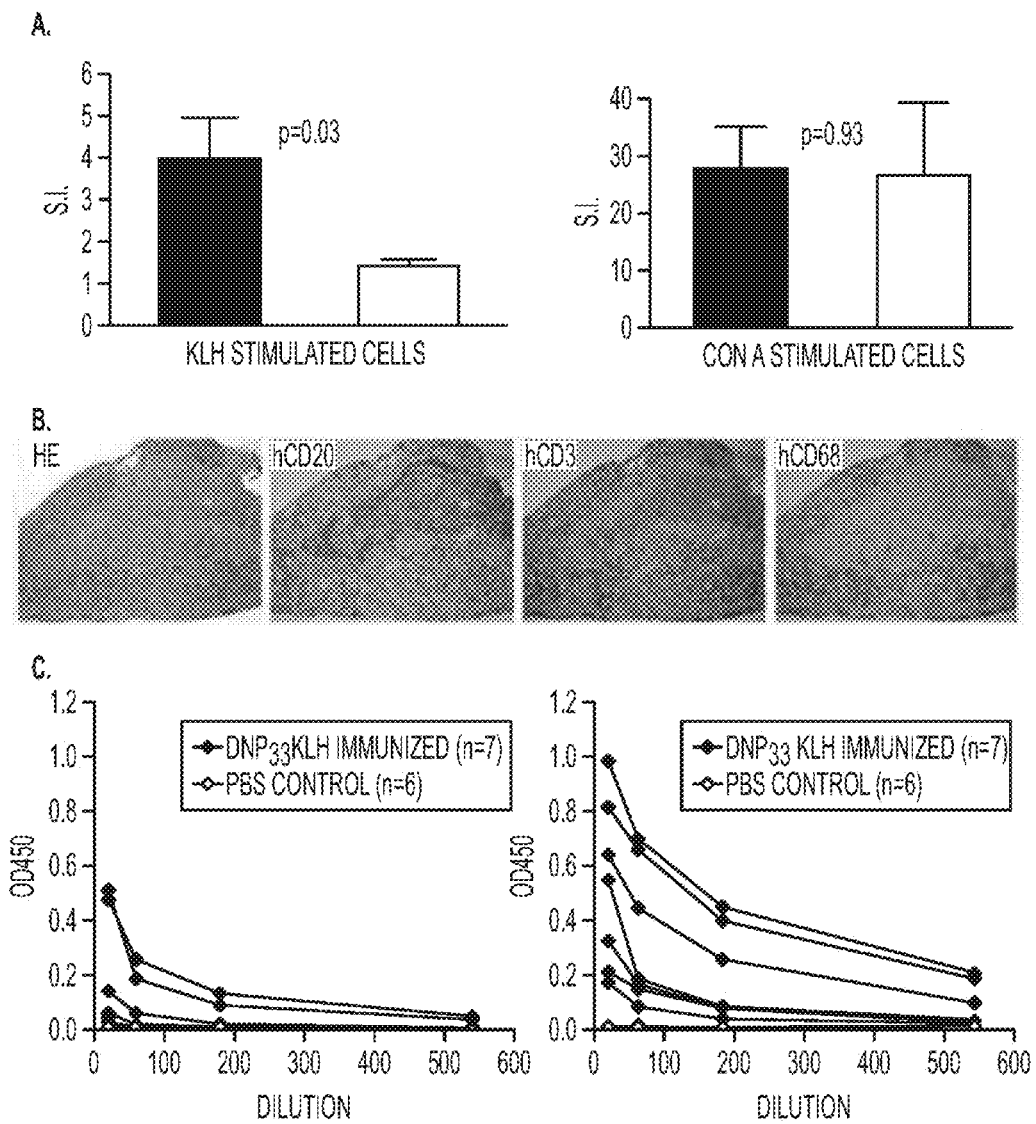

FIGS. 5A-C. FIG. 5A Simulation indices (SI) of human T cells from DNP-KLH-immunized (●) and PBS control (□) hu-NOD/SCID mice (n=3 per group). Left and right figures show the DNP-KLH- and Con A-stimulated cells, respectively. FIG. 5B Germinal center formation in the secondary lymphoid organs from immunized hu-mice. FIG. 5C Serum levels of anti-DNP human IgG in sera collected from DNP-KLH-immunized (●) and PBS control (○) Hu-mice at weeks 1 (left) and 4 (right) following booster immunization.

Figure 6:
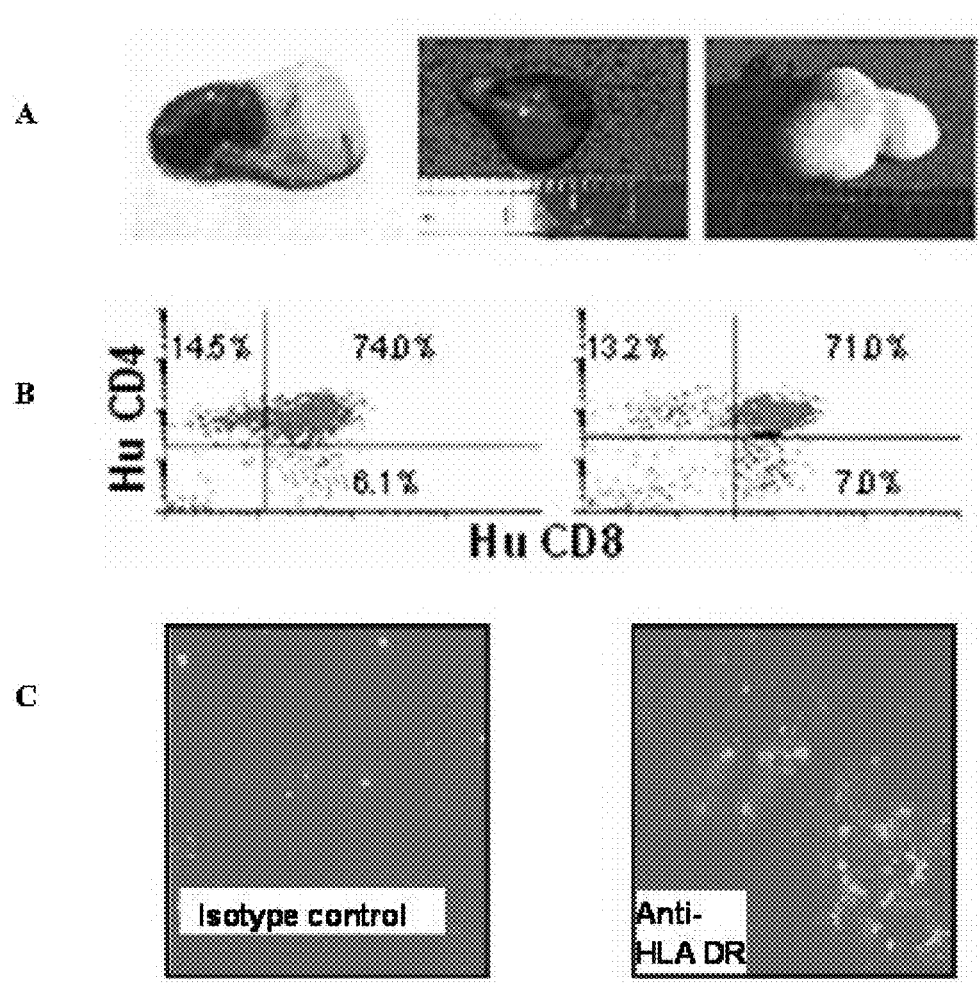

FIGS. 6A-C. FIG. 6A, Macroscopie appearance of human thymus/human liver (HU/HU) (left), swine thymus/swine liver (SW/SW) (middle), and SW/HU (right) fetal thymus/liver implants. HU/HU SCID, SW/SW SCID, and SW/HU SCID mouse recipients were sacrificed 13 wk after graft implantation. FIG. 6B Phenotype of human thymocytes in human (left) and porcine (right) thymus grafts implanted with human fetal liver SCID mice. FIG. 6C. Immunofluorescent staining of a representative SW/HU graft showing the presence of Human (HLA/DR+) APC in the graft.

Figure 7:
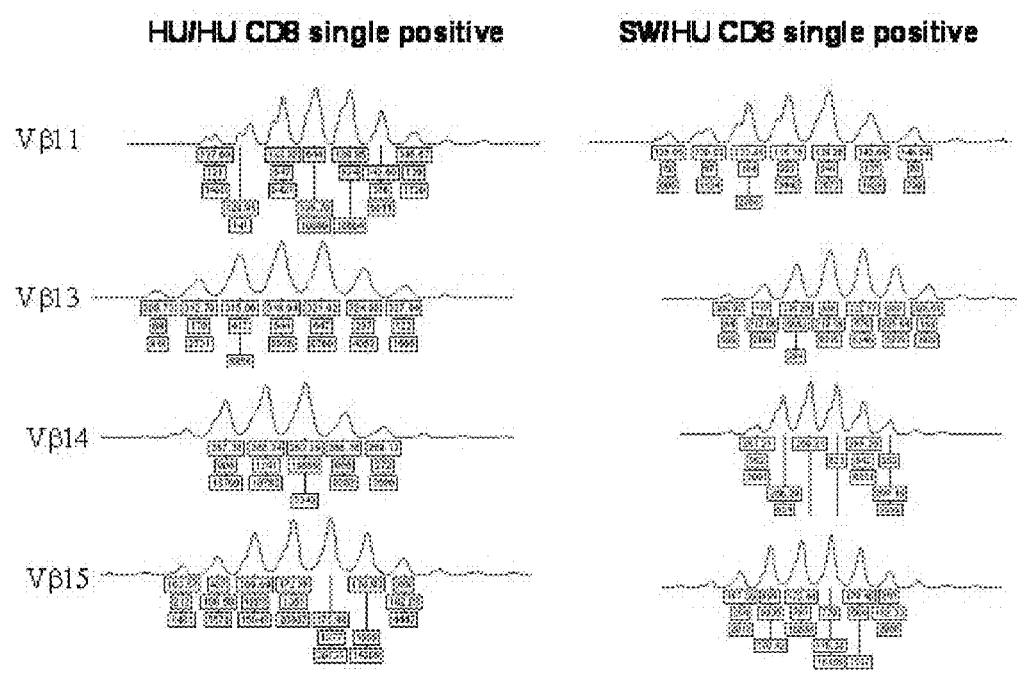

FIG. 7. Human single positive (SP) thymocytes developing in porcine thymic (SWI/HU) graft are polyclonal, showing normal CDR3 length distributions for each Vβ, similar to those developing in human (HU/HU) thymus grafts. Shown are representative CDR3 spectratying profiles of human CD8+ SP thymocytes developing in HU/HU (left) and SW/HU (right) THY/LIV grafts in NOD/SCID mice/ Analyses were performed at week 21 after THY/LIV implantation.

Figure 8:
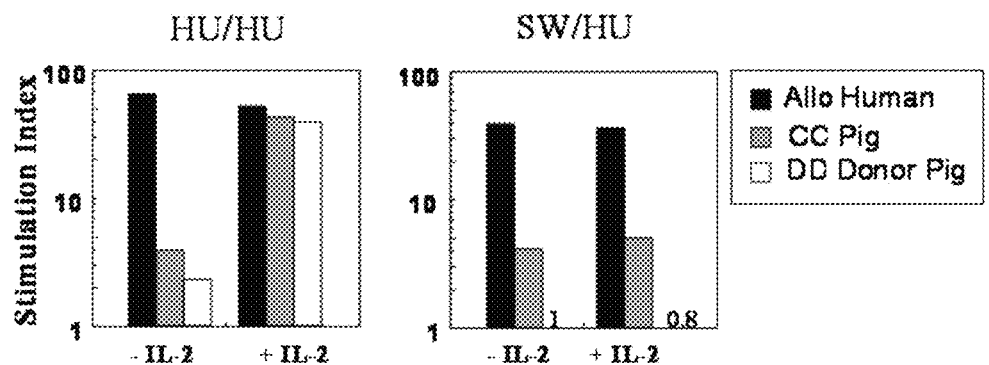

FIG. 8. MLR of HU/HU (left) and SW/HU (right) thymocytes stimulated with allogeneic human, xenogeneic porcine thymus donor MHC-matched (SLAdd) or donor MHC-mismatched (SLAcc) PBMC. The data shown are representative of responses obtained in 3 independent experiments (4 SW/HU and 3 HU/HU). SD values for triplicates are <20%.

Figure 9:
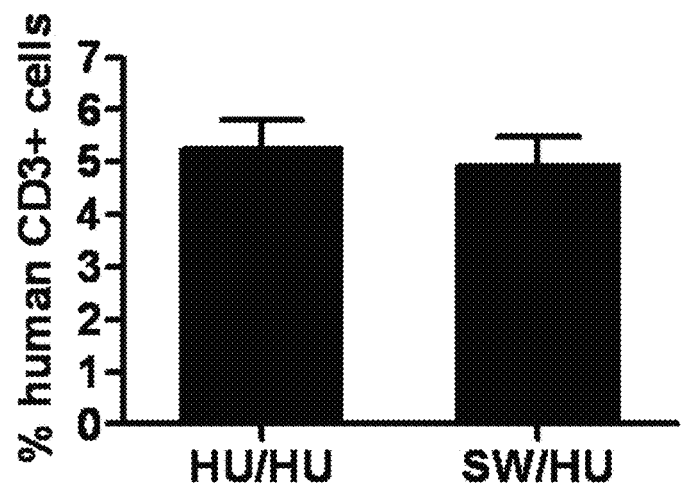

FIG. 9. Similar human T cell reconstitution in PBMC of NOD-SCID mice receiving SW/HU vs HU/HU THY/LIV grafts plus i.v. CD34 cells. NOD-SCID mice received 1.5 Gy WBI, followed by transplantation of HU/HU THY/LIV plus human CD34+ cells, or SW/HU THY/LIV plus human CD34+ cells. Blood was collected 8 week after transplantation and levels of human CD3+ T cells were determined by FACS.

FIGS. 10A-C. Comparison of thymocyte subsets of SW/HU and HU/HU grafts. Similar cellularity (FIG. 10A) and normal subset distribution (FIG. 10B) as well as Treg percentages of CD4 cells (FIG. 10C) were detected in porcine versus human fetal thymus grafts implanted with HU FL 18 weeks earlier in NOD-SCID mice that also received HU FL CD24 cells i.v.

Figure 11:
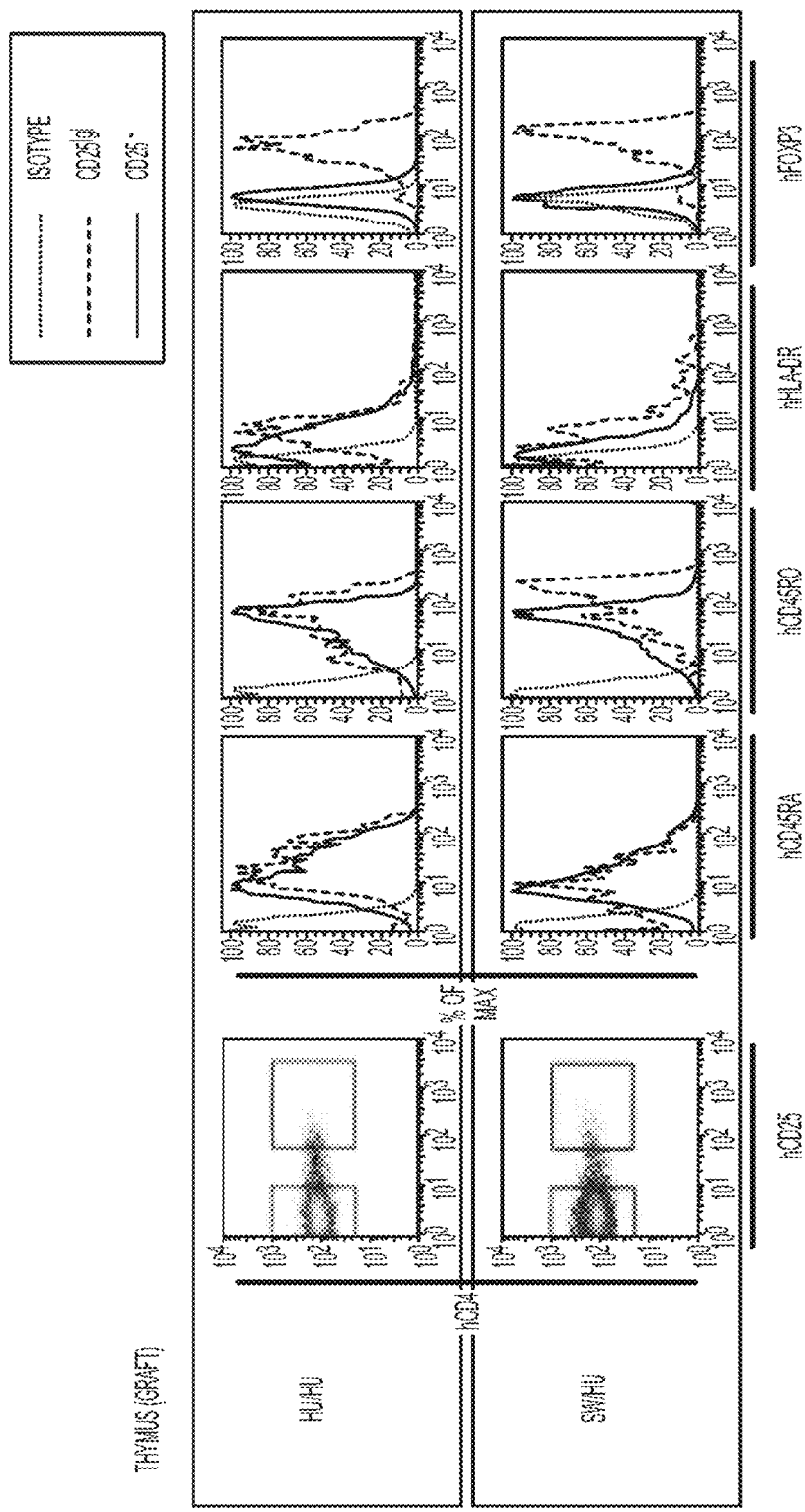

FIG. 11. Similar phenotype of human CD4 SP CD45$^{hi}$ thymocytes in the grafts of HU/HU & SW/HU mice. Gated CD4+CD8-thymocytes were analyzed from HU/HU and SW/HU grafts 18 weeks post-implantation.

Figure 12:
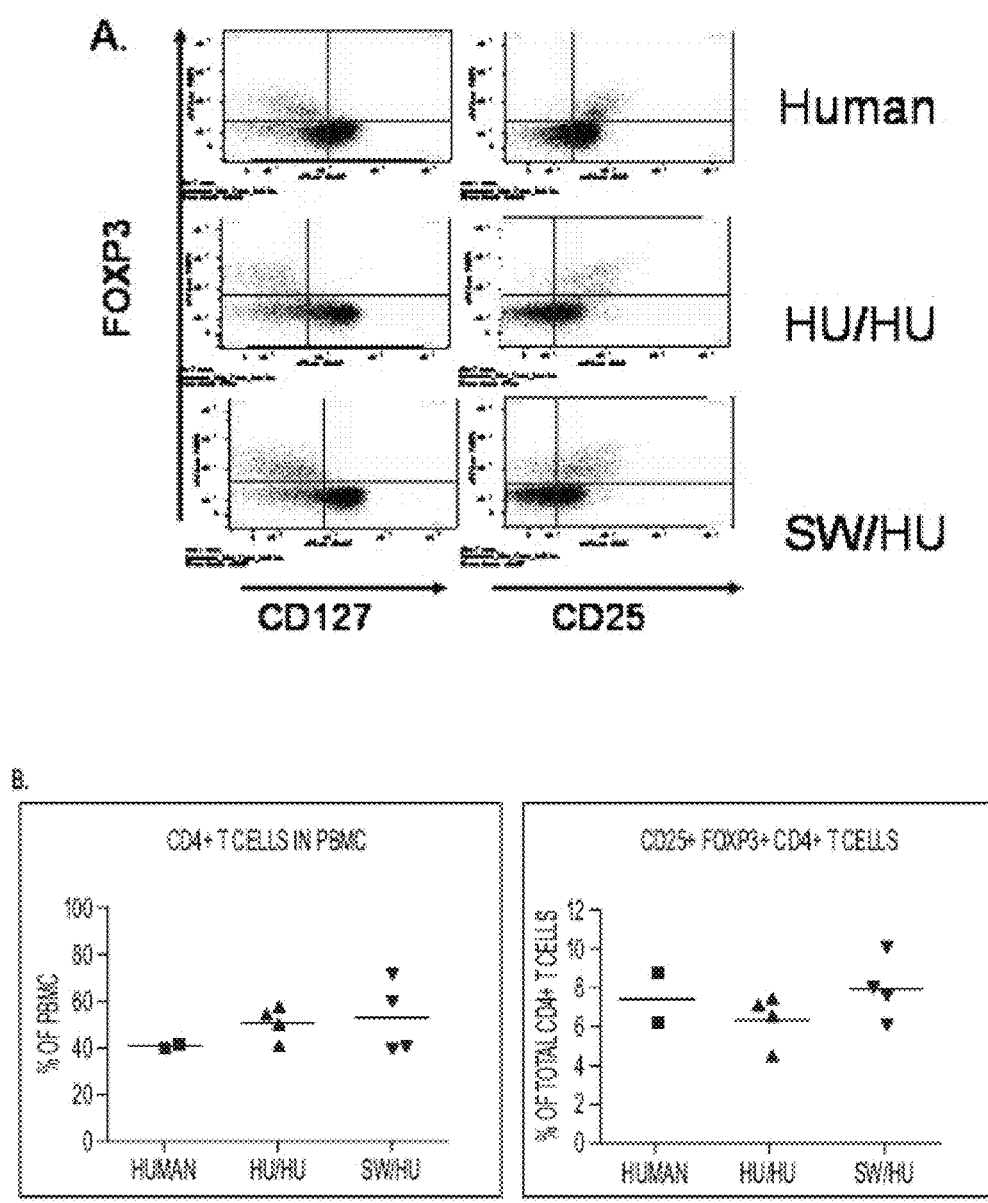

FIGS. 12A-B. Normal percentages of FoxP3+CD127–CD25+ Treg among CD4+PBMC of SW/HU and HU/HU mice. (FIG. 12A) Typical phenotypic appearance of gated CD4+ PBMC; (FIG. 12B) Summary of data obtained from gated CD4+ cells from normal human PBMC and from PBMC and from PBMC of SW/HU and HU/HU mice at 18 weeks post-implantation of THY/LIV grafts and CD24 cells i.v.

Figure 13:
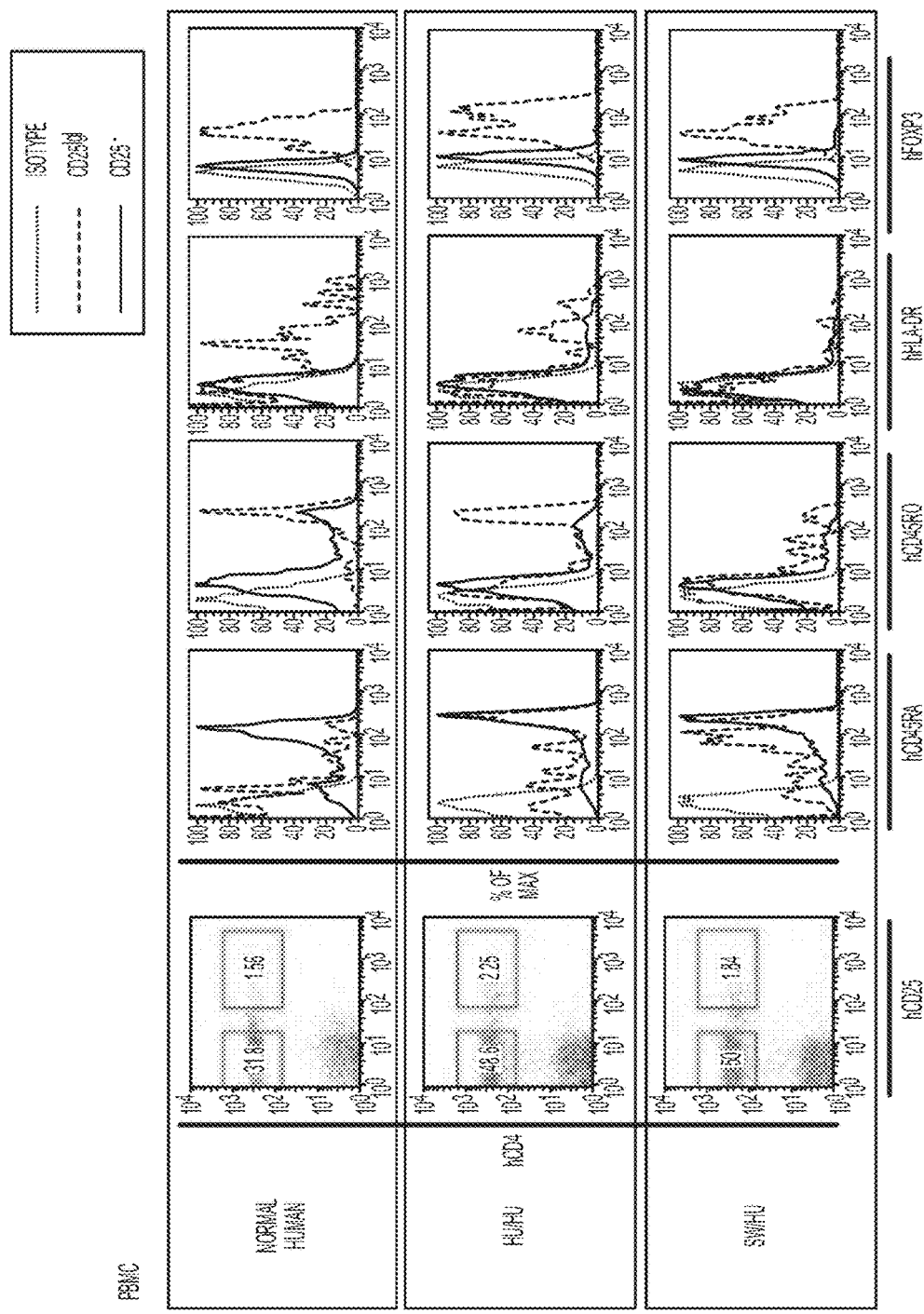

FIG. 13. Human CD4+ CD25$^{hi}$ T cells acquire the "memory" phenotype and express HLA-DR in the periphery of HU/HU mice to a greater extent than in SW/HU mice. Gated peripheral blood CD4+CD25+ cells were analyzed 18 weeks post-graft implantation.

Figure 14:
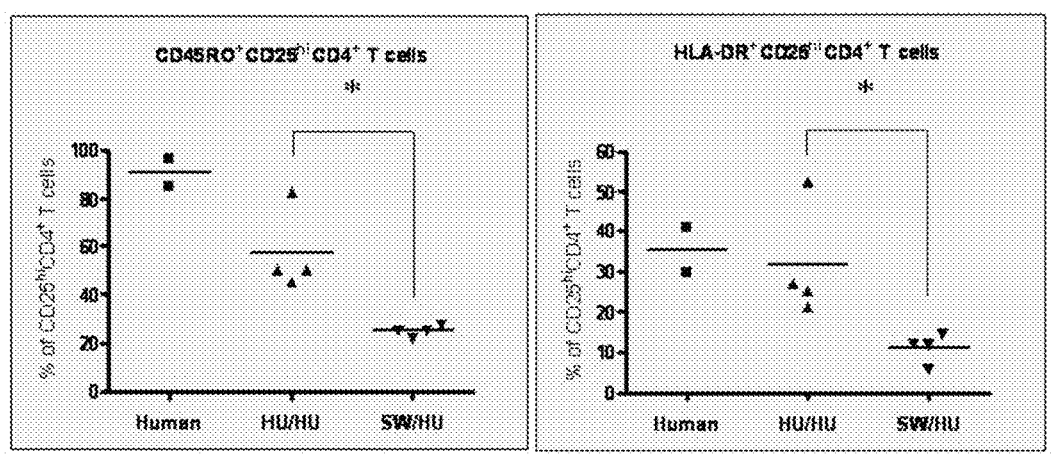

FIG. 14. Reduced conversion to the CD45RO+ HLA-DR+ phenotype among human CD4+CD25hi T cells in the periphery of SW/HU compared to HU/HU mice. Each symbol represents an individual human or grated NOD-SCID mouse analyzed 18 weeks post-implantation.

Figure 15:
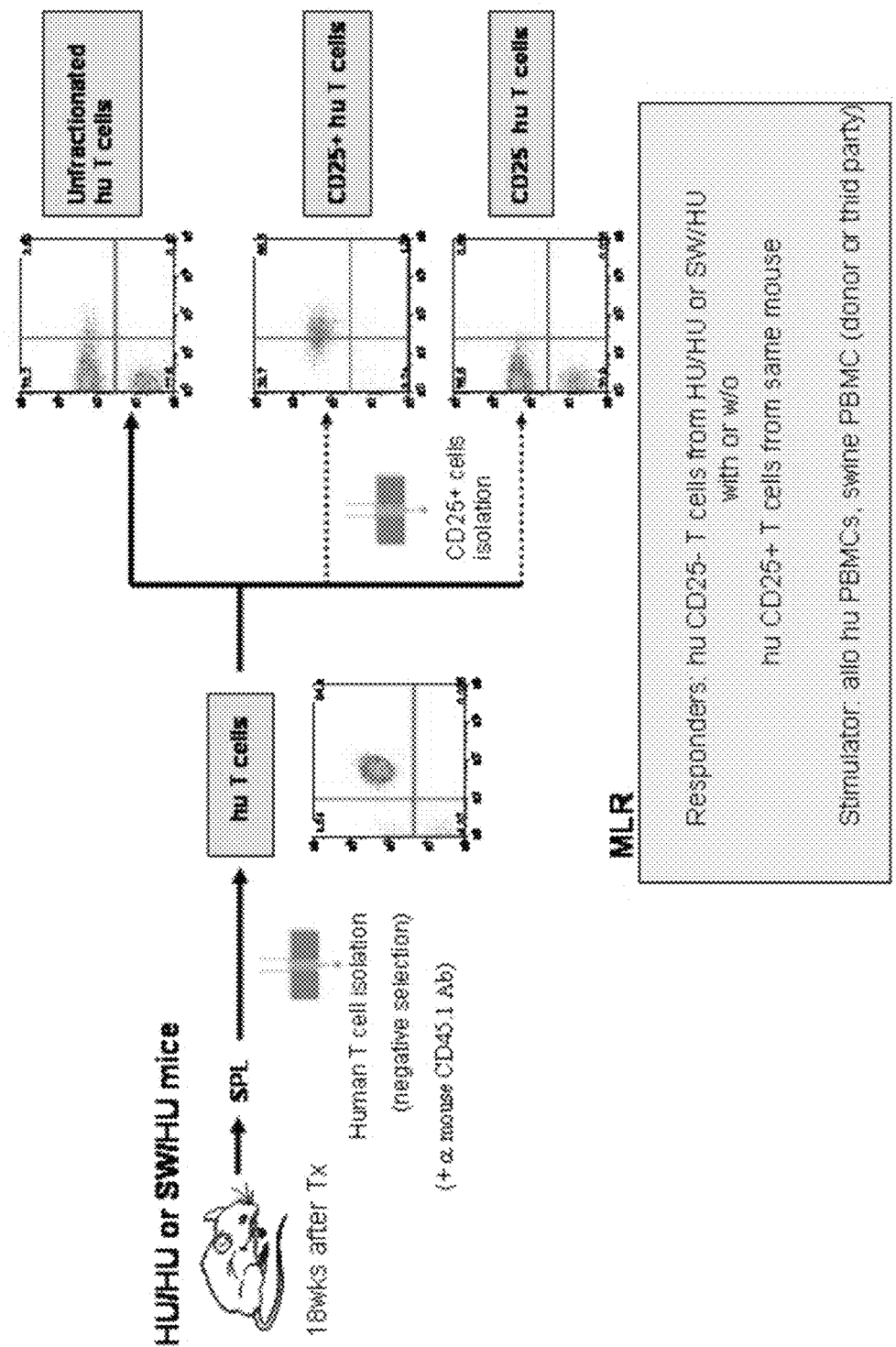

FIG. 15. Separation of human CD4+CD25+ T cells from splenocytes of HU/HU and SW/HU mice and design of MLR assay for suppression.

FIGS. 16A-B. Human CD4+CD25+ T cells in the periphery of HU/HU mice have greater suppressive function than Treg in SW/HU mice. (FIG. 16A) Titrate suppression of alloresponse by CD25+CD4 cells from spleen of a typical HU/HU mouse. (FIG. 16B) Each symbol represents suppressive activity of CD25+CD$ cells from PBMC of a normal human, or from spleen of a HU/HU or a SW/HU recipient. The percent proliferation of CD25–cells (compared to CD25–cells alone) in the presence of CD25+ cells from the indicated source is shown with 3 different stimulators.

Figure 16:
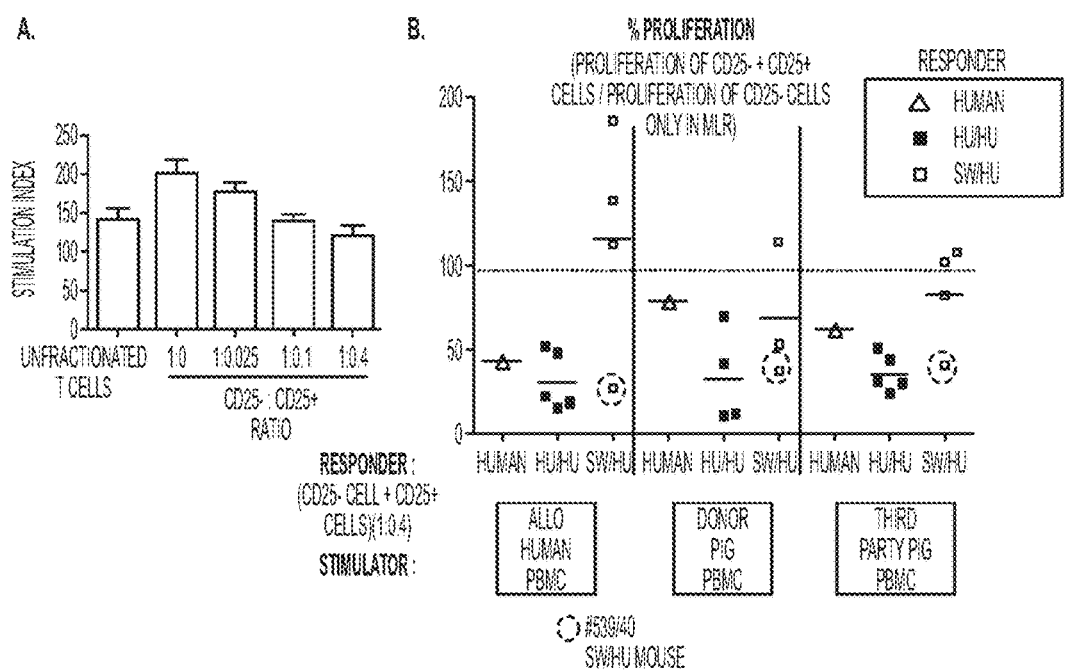
Figure 17:
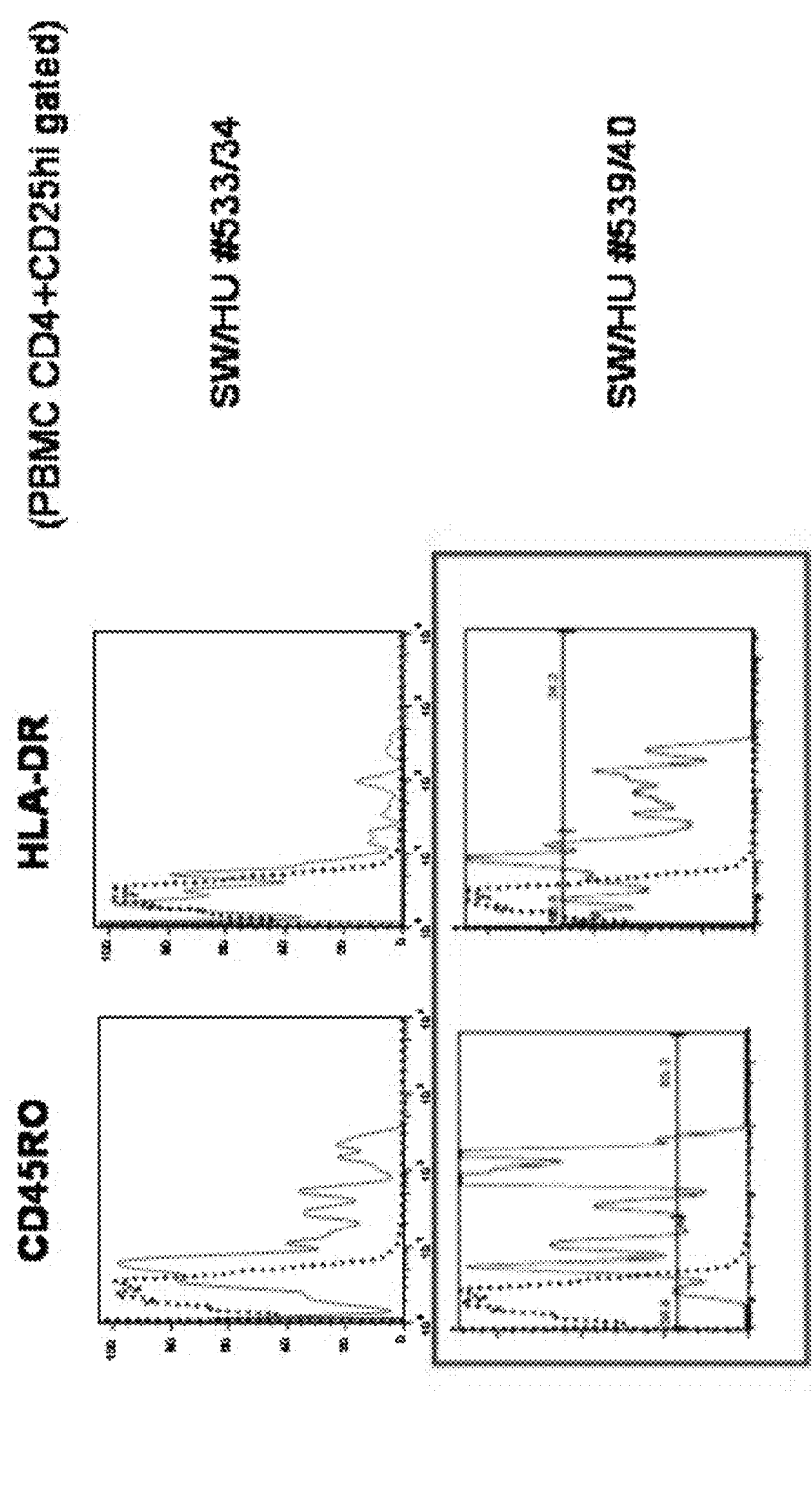

FIG. 17. Impaired suppressive function of Tregs in SW/HU mice is associated with retained naïve phenotype. Expression of CD45RO and HLA-DR for PBMC CD4+ CD25high cells of two individual SW/HU mice tested in FIGS. 16A-B in shown. The cells from the animal with the higher level of CD45RO and HLA-DR expression showed markedly greated suppressive activity (#539/40) circled in red in FIGS. 16A-B) than animals whose Treg retained the naïve phenotype, such ad #533/34 shown here.

Figure 18:
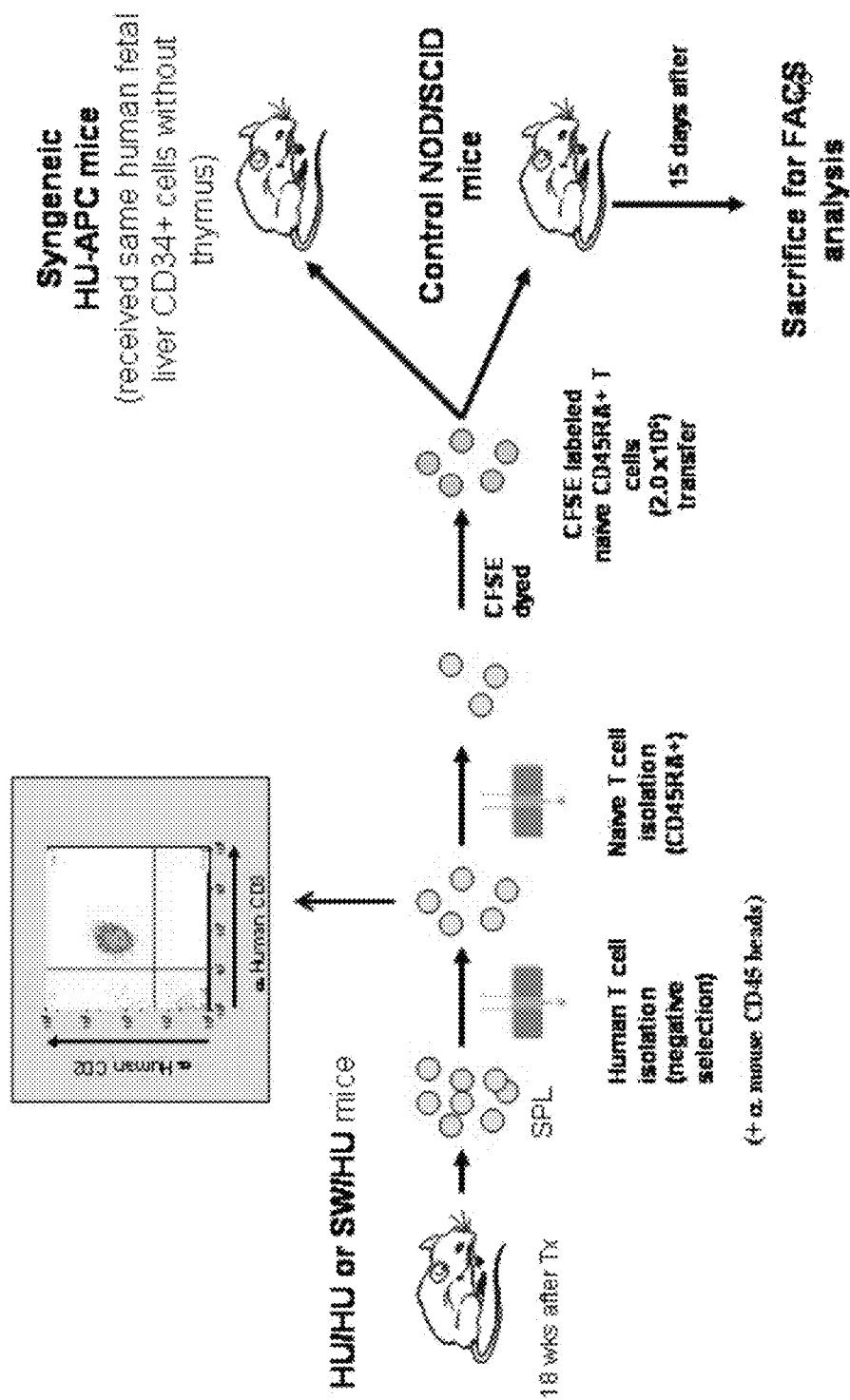

FIG. 18. Method for transfer of CFSE-labeled human T cells from HU/HU or SW/HU mice to HU-APC mice.

FIGS. 19A-B. FIG. 19A. Creation of "HU-APC" mice for adoptive transfer experiments. FIG. 19B. Human APC mice (without Thy) do not have any human T cells but have human B cells and other human bone marrow-derived cells.

Figure 20:
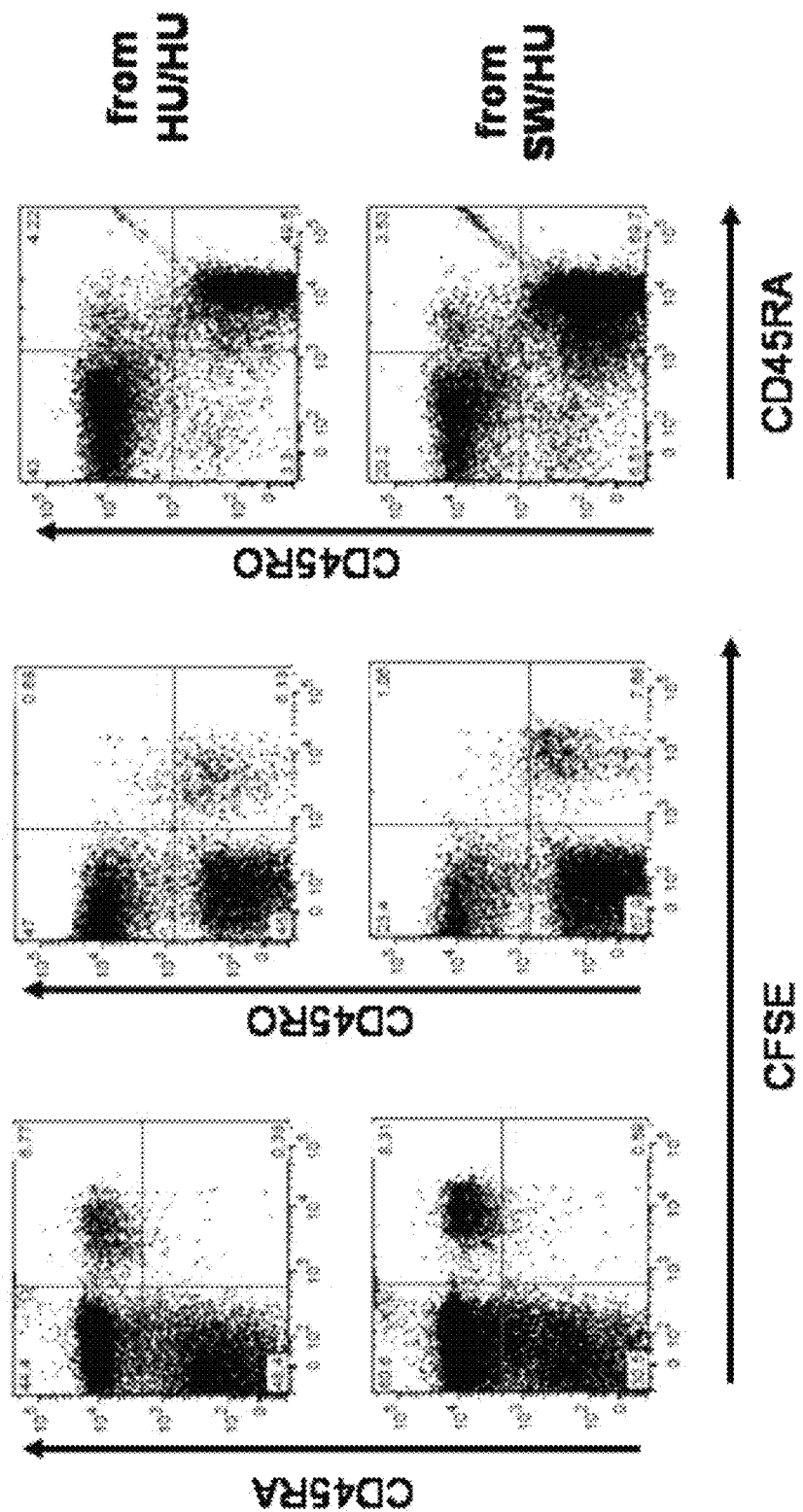

FIG. 20. Proliferation and phenotypic change of transferred naïve T cells. HU APC mice receiving CFSE-labeled CD45RA+ T cells from SW/HU or HU/HU mice were sacrificed 15 days later and the phenotype of their splenic T cells was analyzed. Extensive division of T cells from both SW/HU and HU/HU donors was observed, but the degree of conversion to the CD45RO+CD45RA– "memory" phenotype was greater for T cells that had had developed in an autologous thymus (cells from HU/HU mice).

Figure 21:
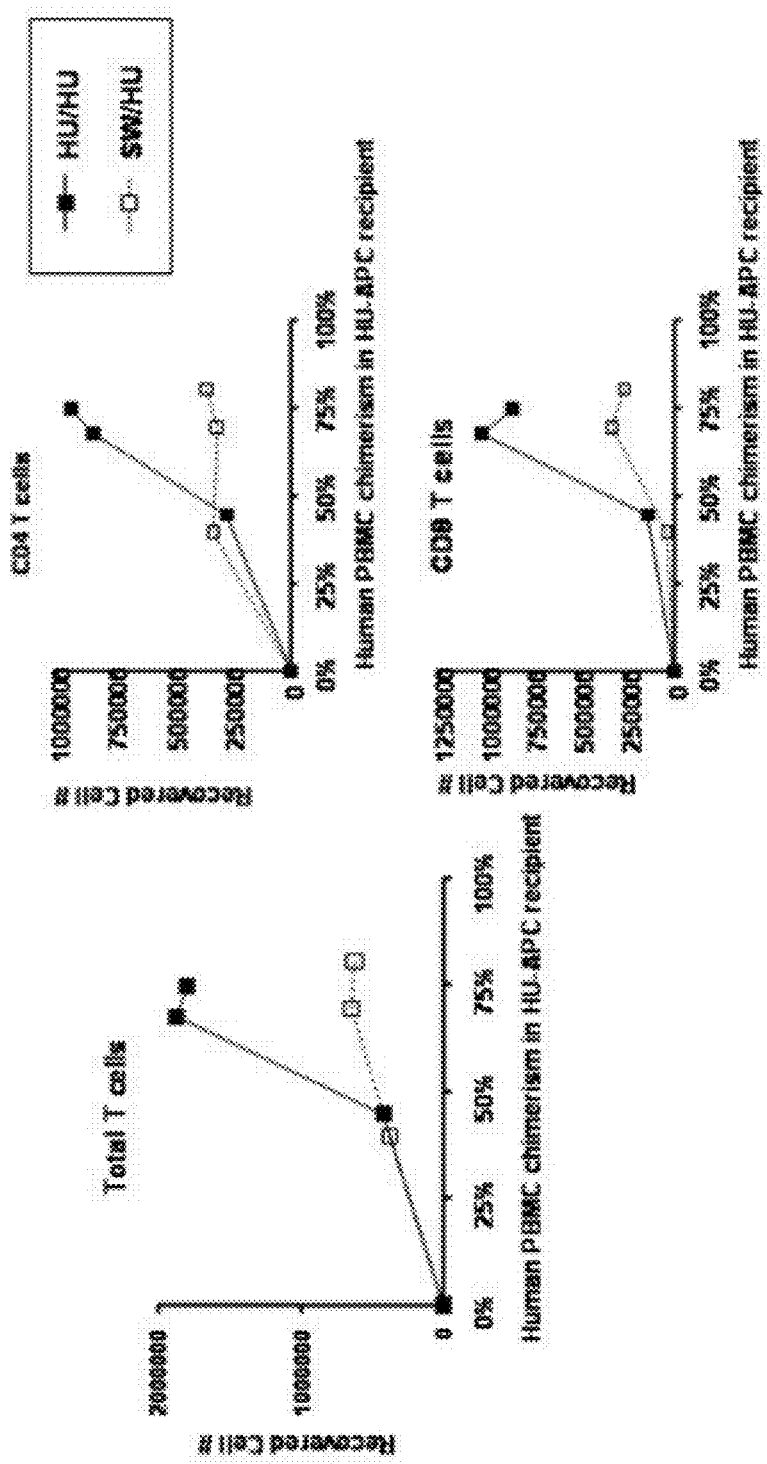

FIG. 21. Recovery of adoptively transferred T cells from SW/HU and HU/HU mice in HU-APC recipients correlates with the level of human APC reconstitution in the HU-APC recipients. No T cells could be recovered from the unreconstituted NOD-SCID mice that also received adoptively transferred naïve T cells (0% human chimerism point). The data indicate that self (human)APC are required to maintain human T cells developing in human or porcine thymus. However, maintenance of both CD4 and CD8 T cells from SW/HU mice by human APC is suboptimal.

Figure 22:
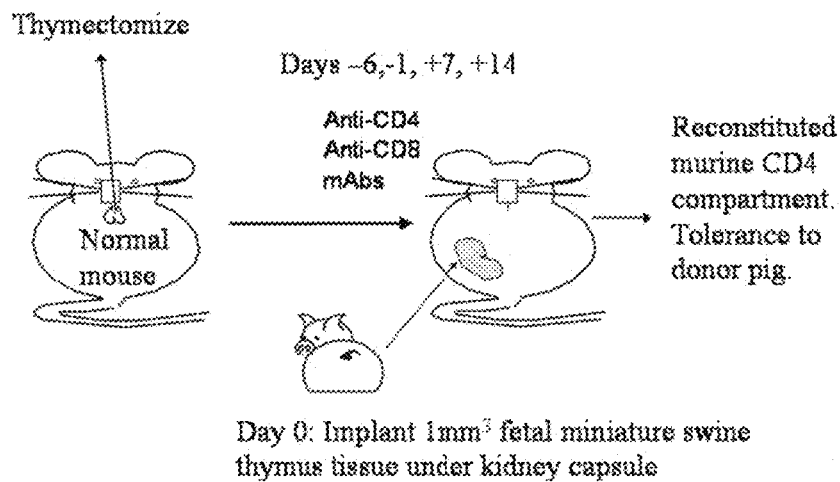

FIG. 22. Replacement of recipient thymus with a xenogeneic thymus in thymectomized, T cell-depleted mice.

Figure 23:
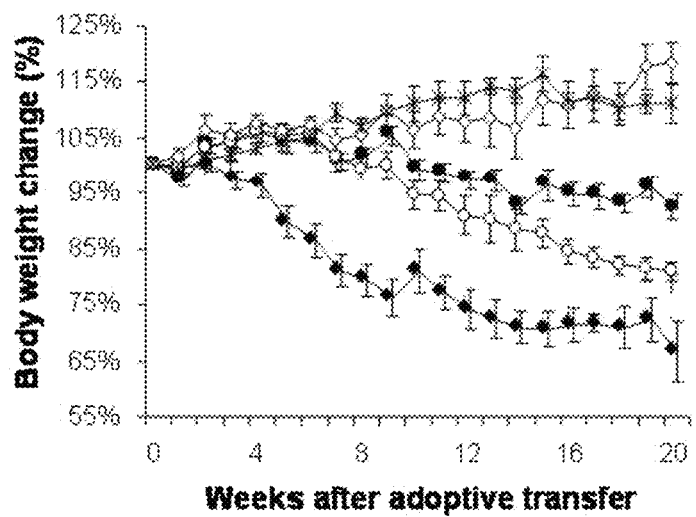

FIG. 23. Mouse thymic epithelial cells facilitate the generation of regulatory cells in porcine thymus grafts in BALB/c nude mice. BALB/c nude mice (no conditioning) were implanted with FP THY/LIV under the kidney capsule. Enriched mouse thymic epithelial cells (m TEC) were prepared from normal BALB/c mice are injected into the porcine thymic graft at day 0 and at week 5. At 13 weeks after porcine THY/LIV transplantation, splenocytes were prepared and adoptively transferred into 3 Gy-irradiated secondary BALB/c nude mice. Shown are percentages (mean±SEM) of body weight changes for the secondary recipient mice that received 2×107 splenocytes (SPL) from primary BALB/c nude mouse recipients of FP THY/LIV without mTEC (THY/LIV/no-mTEC) (◆; n=5), FP THY/LIV injected with mTEC at day 0 and week 5 (THY/LIV/d0+w5-mTEC) (●; n=5), or mixed splenocytes of THY/LIV/no-mTEC and THY/LIV/d0+w5-mTEC (○; n=5). BALB/c nude mice that received 2×107 splenocytes from normal BALB/c mice (◇; n=5) or no cell transfer (X; n=4) were used as controls.

Figure 24:
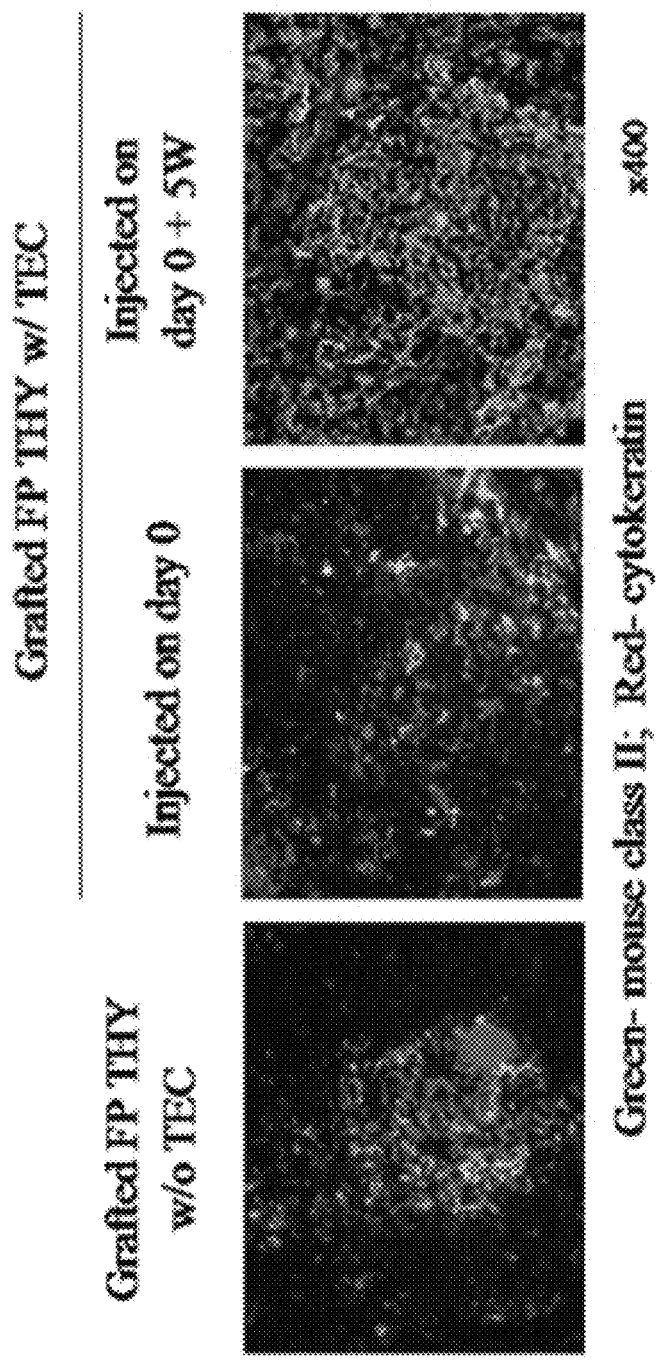

FIG. 24. Detection of injected mouse thymic epithelial cells in grafted FP THY harvested 12 weeks after grafting. Red strain: anti-cytokeratin mAb (recognizing mouse and pig cytokeratin); green stain: anti-mouse class II MHC mAb. Graft not injected with mouse TEC (left) shows only pig cytokeratin and mouse class II+ cells are presumably hematopoietic APC. In grafts injected with mouse TEC at the indicated times, yellow staining denotes co-staining of cytokeratin and mouse class II, indicating the presence of mouse TEC.

Figure 25:
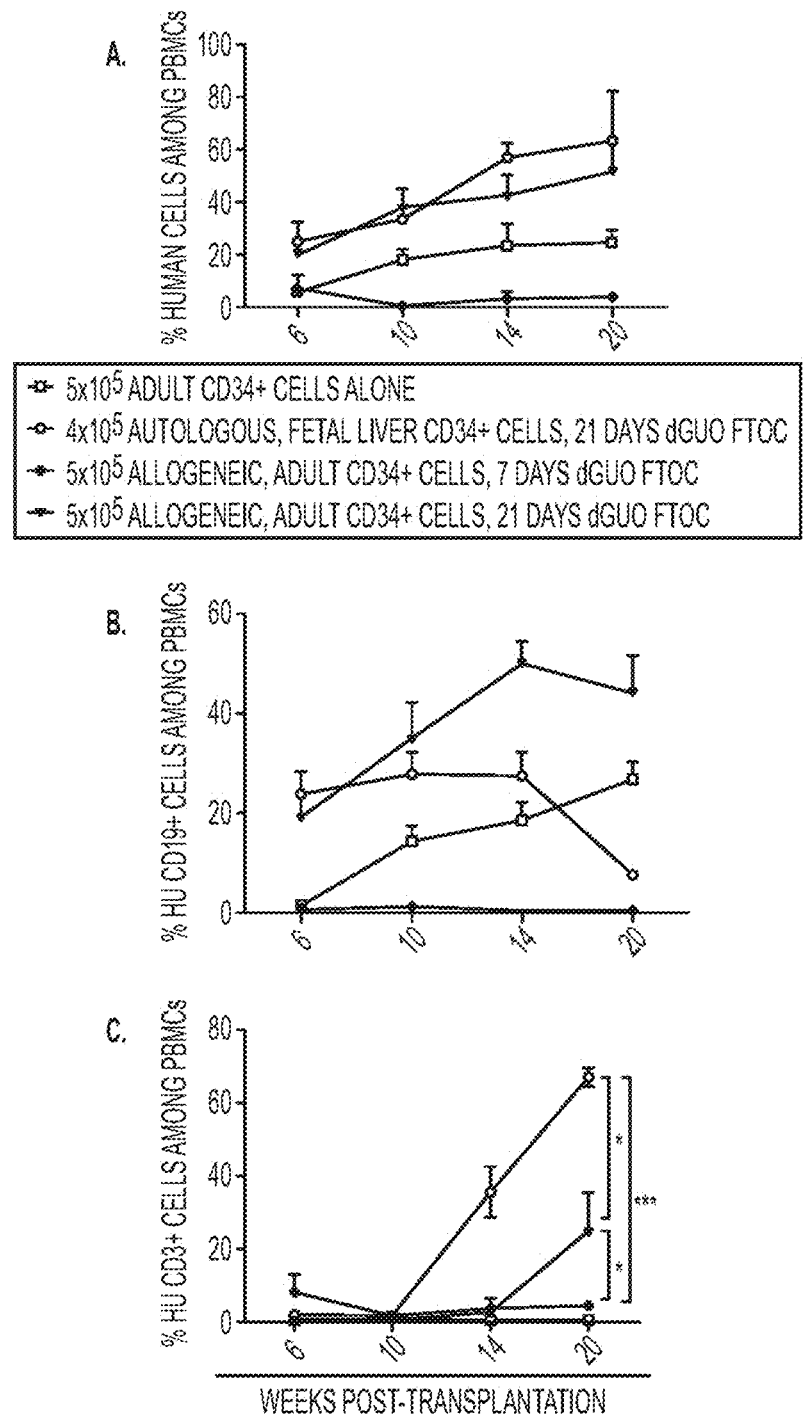

FIGS. 25A-C. Peripheral human cell reconstitution in NOD/SCID mice following transplantation of dGuo-treated thymic tissue. Fetal thymic tissue was treated with dGuo for 7 (black circles, n=4) or 21 days (black triangles, n=5) before transplantation into sublethally irradiated NOD/SCID that received $5\times10^5$ allogeneic, adult CD34+ or $4\times10^5$ autologous fetal liver CD34+ cells (open circles, n=5) intravenously. Age-matched control animals received $5\times10^5$ adult CD34+ cells alone (open squares, n=5). FIG. 25A. The mice were bled to measure human (hu) cell reconstitution in (total mouse plus human) peripheral blood mononuclear cells (PBMCs) at the indicated time points. FIG. 25B. Single cell suspensions of PBMCs were stained for the markers of human B cells (CD19). FIG. 25C. Single cell suspensions of PBMCs were stained for the markers of human T cells (CD3).

FIGS. 26A-C. Multilineage human cell reconstitution in NSG mice receiving cryopreserved/thawed thymic grafts and allogeneic, adult CD34+ cells. (FIG. 26A) Sublethally irradiated NSG mice that received a cryopreserved/thawed fetal thymus graft in combination with $3\times10^5$ (black squares, n=6) or $5\times10^5$ (black triangles, n=6) adult CD34+ cells and two doses of anti-CD2 mAb i.v. were bled to measure human cell reconstitution in (total mouse plus human) peripheral blood mononuclear cells (PBMCs) at the indicated time points. Age-matched control animals received $3\times10^5$ adult HSCs alone (white squares, n=6). Single cell suspensions of PBMCs were stained for the markers of human hematopoietic cells (CD45), T cells (CD3), B cells (CD19) and monocytes (CD14). Dead cells and mouse red blood cells were excluded from the analysis by gating out forward scatter and high propidium iodide (PI)-retaining and anti-mouse Ter119-positive cells. (FIG. 26B) Representative graft appearance 20 weeks post-transplantation. NSG mice that were transplanted with cryopreserved/thawed fetal thymus tissue had abundant, viable thymic tissue underneath the kidney capsule that was supporting thymopoiesis from allogeneic adult CD34+ cells demonstrated by high numbers of double positive human thymocytes (FIG. 26C). Photograph and FCM analysis is representative of 12 grafts.

Figure 27:
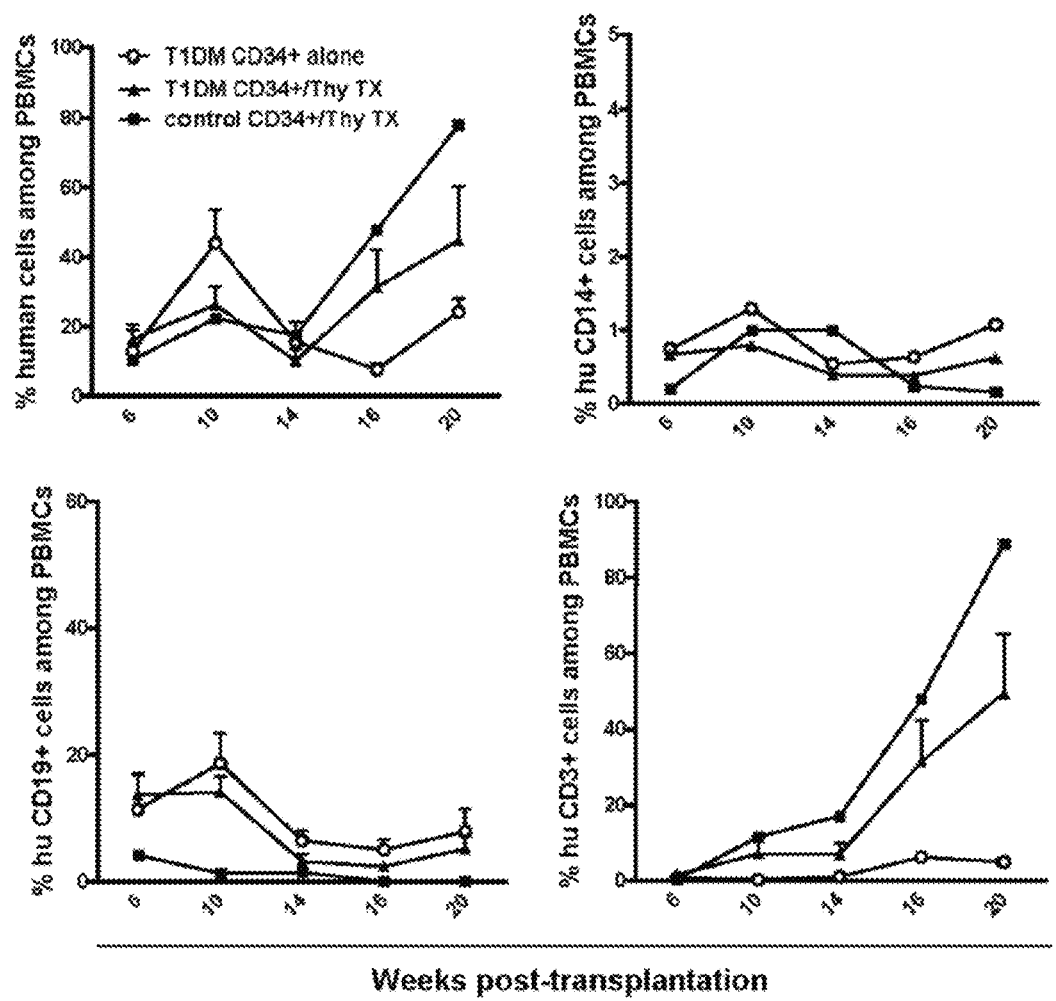

FIG. 27. Multilineage human cell reconstitution in NSG mice receiving cryopreserved/thawed thymic grafts and allogeneic, adult CD34+ cells isolated from a bedside bone marrow aspirate. Sublethally irradiated NSG mice that received a cryopreserved/thawed fetal thymus graft in combination with $1.8\times10^5$ adult CD34+ cells isolated from a bone marrow aspirate of a healthy volunteer (black squares, n=2) and a T1DM patient (black triangles, n=4) were bled to measure human cell reconstitution in peripheral blood mononuclear cells (PBMCs) at the indicated time points. Age-matched control animals received $1.8\times10^5$ adult HSCs alone, isolated from the bone marrow aspirate of the T1DM patient (open circles, n=5).

FIGS. 28A-D. FIG. 28A. Reconstitution of a functional immune system and normal Treg development in NSG mice after transplantation of a fetal thymus graft and allogeneic, adult CD34+ cells. NSG mice (n=3) that received a 7 Gy irradiated thymic graft in addition with $3\times10^5$ adult CD34+ cells reconstituted high T cell levels >30 weeks after transplantation, indicating that irradiation delays thymic growth and function. 39 weeks after transplantation, the humanized mice received an allogeneic human and xenogeneic pig skin graft. "Mini Me" mice reject allogeneic human and xenogeneic (porcine) skin grafts (n=3). FIG. 28B. T cells in reconstituted humanized mice demonstrate self-tolerance and functionality in a proliferation assay, data shows self-tolerant T cells in "Mini Me" mice and proliferation in response to stimulation with allogeneic PBMCs, but not self PBMCs. To analyze functionality 20 weeks after transplantation, human T cells (>90% pure) were enriched from the spleen and peripheral lymph nodes of NSG mice 20 weeks following transplantation of cryopreserved/thawed THY grafts and allogeneic bone marrow CD34+ cells from a healthy control (black bar) or T1D subject (dotted bars). Purity >90% was confirmed by FACS. T cells isolated from the PBL of the healthy bone marrow donor served as control (open bar). Allogeneic human PBMCs from a healthy volunteer served as stimulators. In self-stimulated control cultures, responder cells were incubated with autologous PBMCs, depleted of mouse CD45+ and Ter119 cells. Table 11 shows the naïve/memory cell distribution of CD4 cells in the 3 mice reconstituted from T1D CD34+ cells. FIG. 28C. 20 weeks after transplantation, single cells suspensions were prepared from half of the thymus graft of NSG mice that received a cryopreserved/thawed THY graft and allogeneic CD34+ cells isolated from a bone marrow aspirate of a healthy volunteer (circles) or T1DM patient (black squares). Cells were stained for human CD4, CD8, CD25 and FoxP3 and the number of natural Tregs calculated. FIG. 28D. Proportions of Tregs in PBL 20 weeks after transplantation of a cryopreserved/thawed fetal thymus graft in combination with adult CD34+ cells from healthy controls (black squares) or a T1DM patient (black triangles) in comparison to two healthy volunteers (black circles).

FIGS. 29A-C. Reconstitution of a diverse and rejuvenated immune system in NSG mice after transplantation of a cryopreserved/thawed thymic graft and allogeneic, adult CD34+ cells from a bedside bone marrow aspirate. FIG. 29A. Spectratyping of human CD4 and CD8 SP T cells developing in NSG mice grafted with fetal human thymus tissue and allogeneic, bone-marrow derived adult CD34+ cells. Human CD4 or CD8 SP thymocytes were collected from thymus grafts at 20 weeks after transplantation. RT-PCR was performed using human BV (Vβ) family-specific primers, and spectratyping was performed after run-off reaction with Cβ-specific FAM-labeled primer. Spectratypes from one representative animal of eight are shown. The vertical axis is relative fluorescence units (full scale=6,000 units). The horizontal axis is nucleotide size and shows the three nucleotide separation of the peaks. Reference size markers are seen as low fainter peaks. Representative BV are shown from a total of 11-12 analyzed per sample. A diverse TCR repertoire in reconstituted NSG mice is seen. The Hamming distances of all 6 samples, a measure of the relative distances of the observed TCR β-chain length distribution from a reference distribution of healthy adult CD4 T cells, are shown in Table 12, and each indicates the reconstitution of a polyclonal repertoire. Naive/memory markers for T cells (FIG. 29B) and Tregs (FIG. 29C) were stained in single cells suspensions of PBMCs of healthy volunteers as well as of NSG mice, 20 weeks after receiving a cryopreserved/thawed THY plus i.v. infusion of CD34+ cells from a T1DM patient (black squares) or a healthy controls (black triangles), including (open circle) the donor of CD34 cells for the control mouse indicated with an open triangle. The rejuvenated T cell phenotype in the "Mini Me" mouse is shown. Subgated regulatory T cells were further differentiated into naive and memory type cells based on expression of CD45RA and CD45RO.

Figure 30:
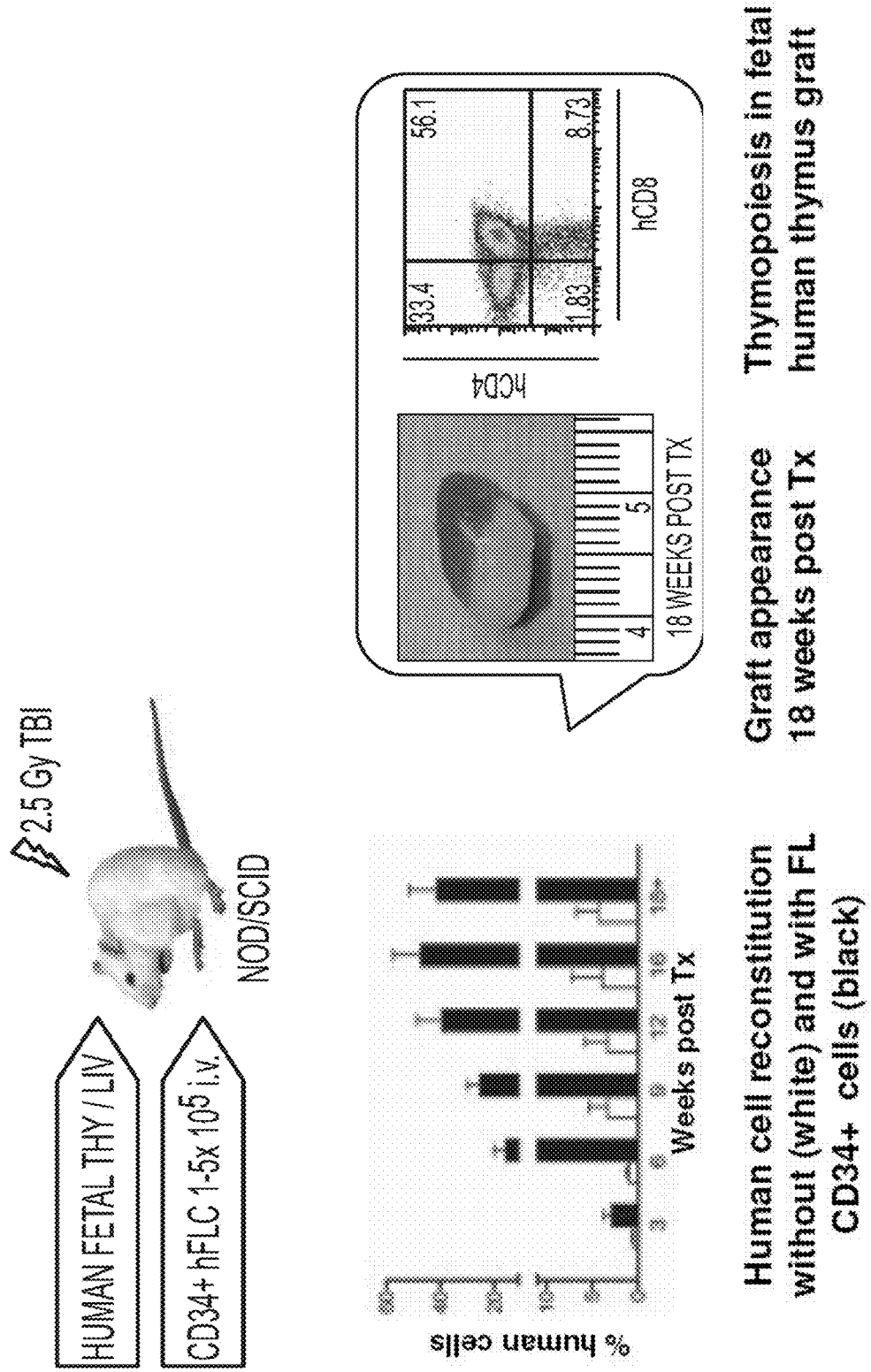

FIG. 30 shows an embodiment of the development of a humanized mouse model with multilineage human lympho-hematopoietic cells.

Figure 31:
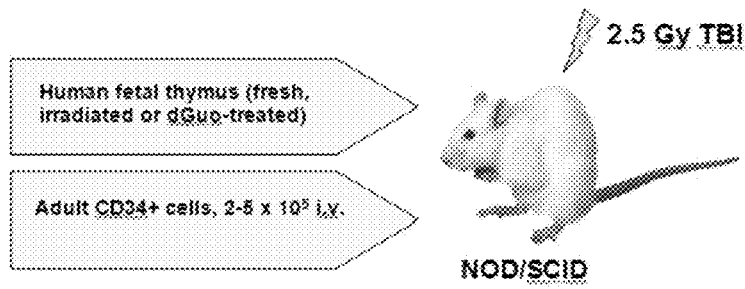

FIG. 31 shows attempts to achieve peripheral multilineage cell reconstitution from adult CD34+ cells.

Figure 32:
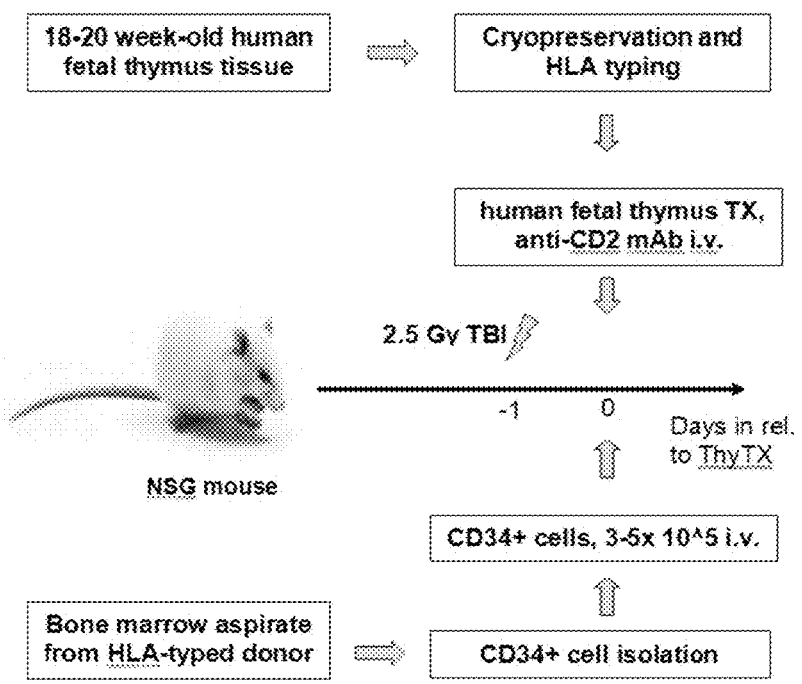

FIG. 32 shows a method to make a successful humanized mouse model to achieve peripheral multilineage cell reconstitution from adult, HLA-defined CD34+ cells in NSG mice.

Figure 33:
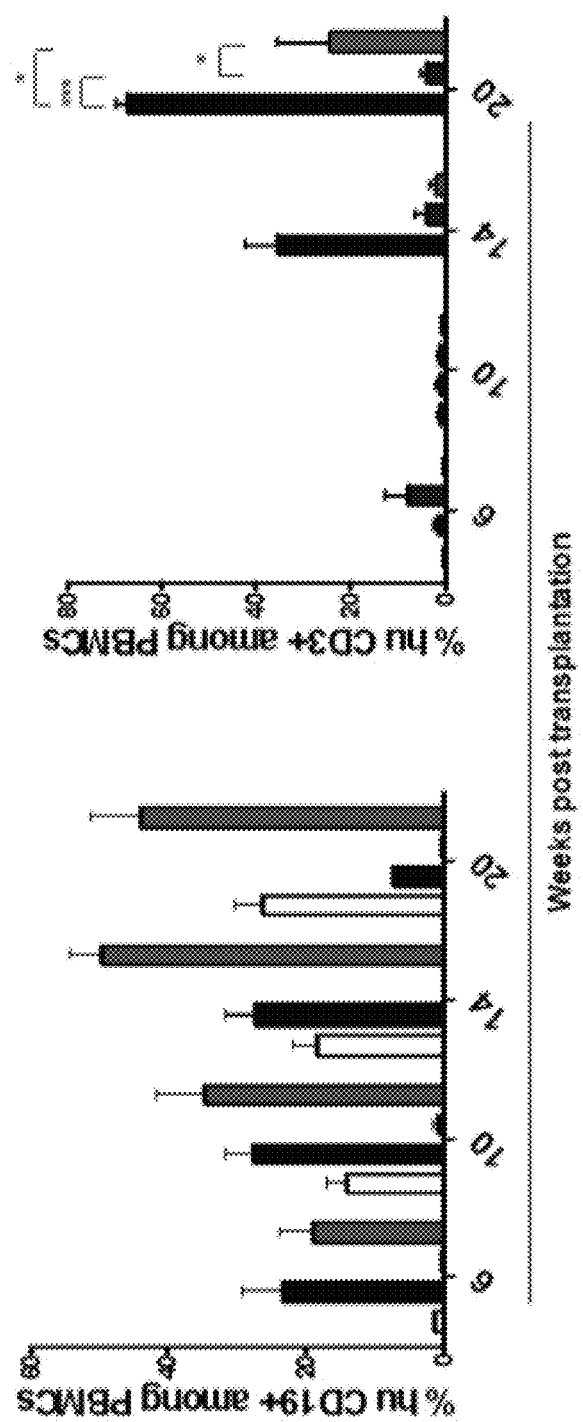

FIG. 33 shows rejection of CD34+ cells by allogeneic thymic T cells that escaped 7-day dGuo-depletion. Human peripheral leukocyte reconstitution in 2.5 Gy irradiated NOD/SCID mice following infusion of 5×10⁵ allogeneic, adult CD34+ cells. CD19+ cell but no T cell reconstitution was observed in mice that received adult CD34+ cells alone (white bars). Pre-transplant thymus tissue treatment with deoxyguanosine (dGuo) for 7 days (blue bars) resulted in early CD3+ cell detection by 6 weeks post TX. However, no CD19+ cells appeared at any time point, indicating that these T cells escaped depletion with dGuo and emigrated from the thymus graft into the periphery, where they rejected the infused allogeneic CD34+ cells. Successful human thymopoiesis and peripheral reconstitution with CD19+ cells occurred after dGuo treatment for 21 days (red bars). However, T cell reconstitution following adult, allogeneic CD34+ cell infusion was less efficient compared to mice receiving a 21 day dGuo-treated graft with 4×10⁵ autologous fetal HSCs (black bars).

Figure 34:
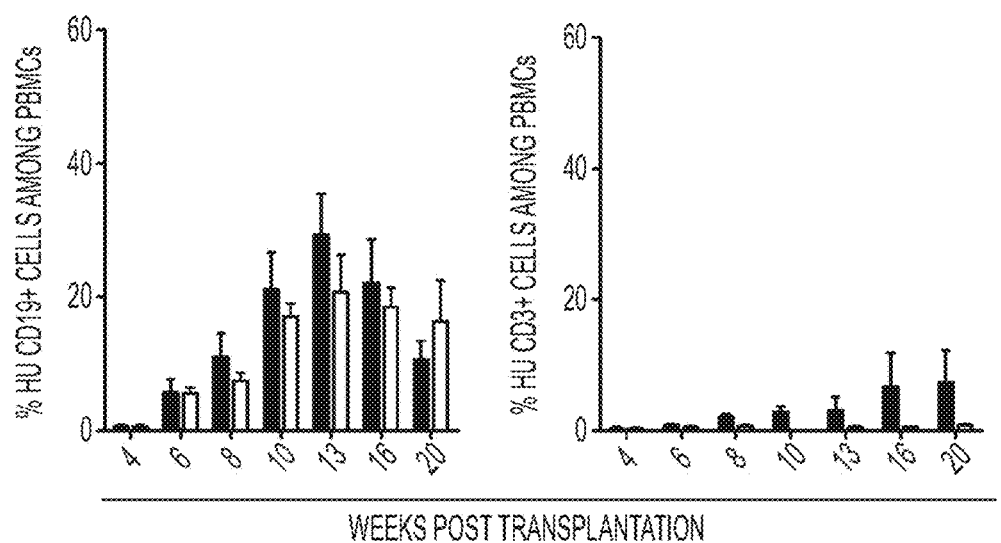
Figure 34:
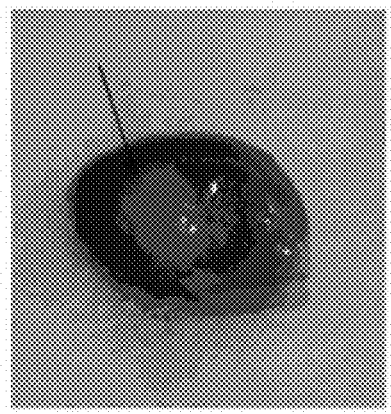

FIGS. 34A-B shows that 7 Gy irradiation impairs thymic growth and/or function. Sublethally irradiated NSG mice transplanted with a 7 Gy irradiated fetal thymus graft in combination with 3×10⁵ adult CD34+ cells with (white bar) or without (black bars) treatment with anti-CD2 mAb i.v. generated only very low numbers of T cells (FIG. 34A). Graft appearances at 20 weeks post-TX indicate that irradiated thymus grafts did not grow or function (FIG. 34B).

Figure 35:
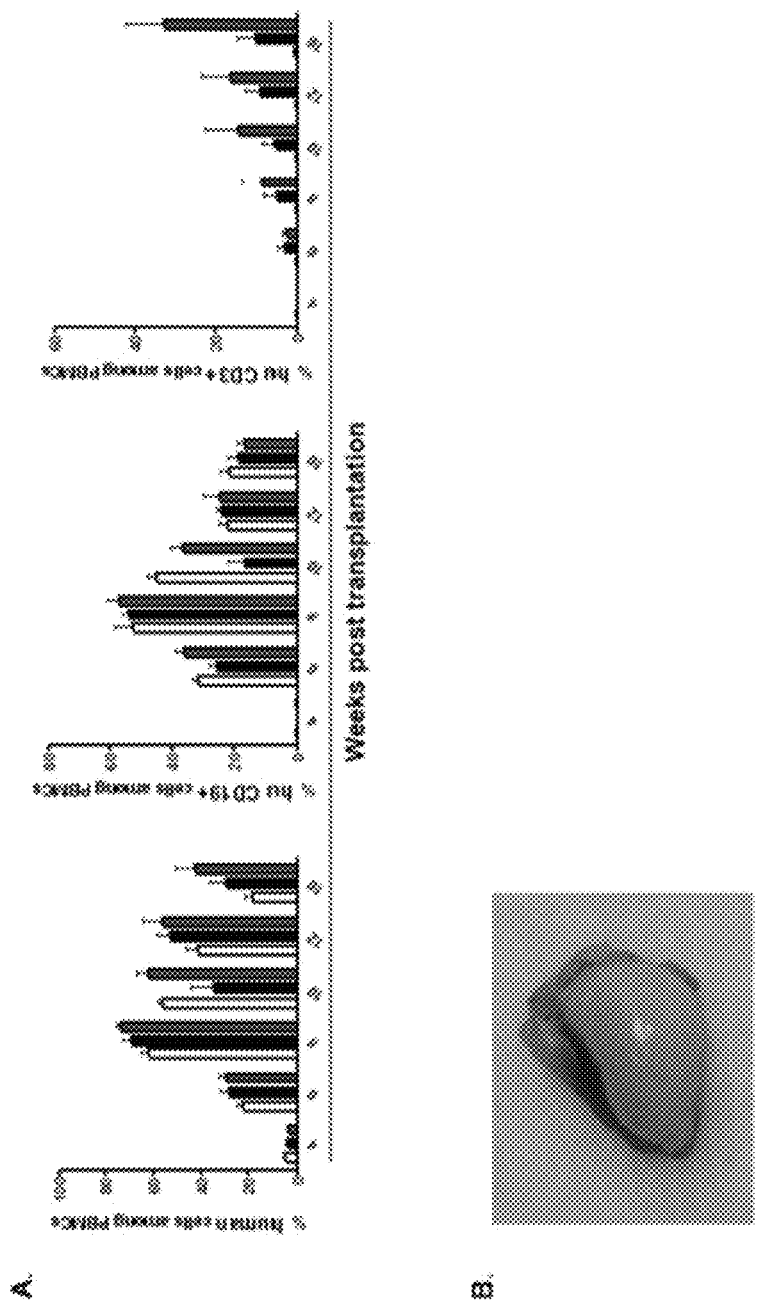

FIGS. 35A-B show that a cryopreserved/thawed fetal thymus graft in combination with allogeneic, adult CD34+ cells allows peripheral reconstitution of multilineage hematopoietic cells. Sublethally irradiated NSG mice, transplanted with cryopreserved/thawed human fetal thymus tissue in combination with anti-CD2 mAb and 3×10⁵ (black bars) or 5×10⁵ (red bars) adult, allogeneic CD34+ cells showed robust multilineage human leukocyte reconstitution (FIG. 35A). Recipients of HSCs alone (white bars) did not show peripheral CD3+ cells at any time point. 20 weeks post transplantation thymic tissue grafts were markedly enlarged (FIG. 35B). Control animals that received cryopreserved human fetal thymus tissue without i.v. CD34+ cells did not generate significant human cells in the periphery.

FIGS. 36A-B shows thymic graft appearance 20 weeks post-TX for cryopreserved THY grafts (FIG. 36A) and for 7 GY irradiated THY grafts (FIG. 36B).

Figure 37:
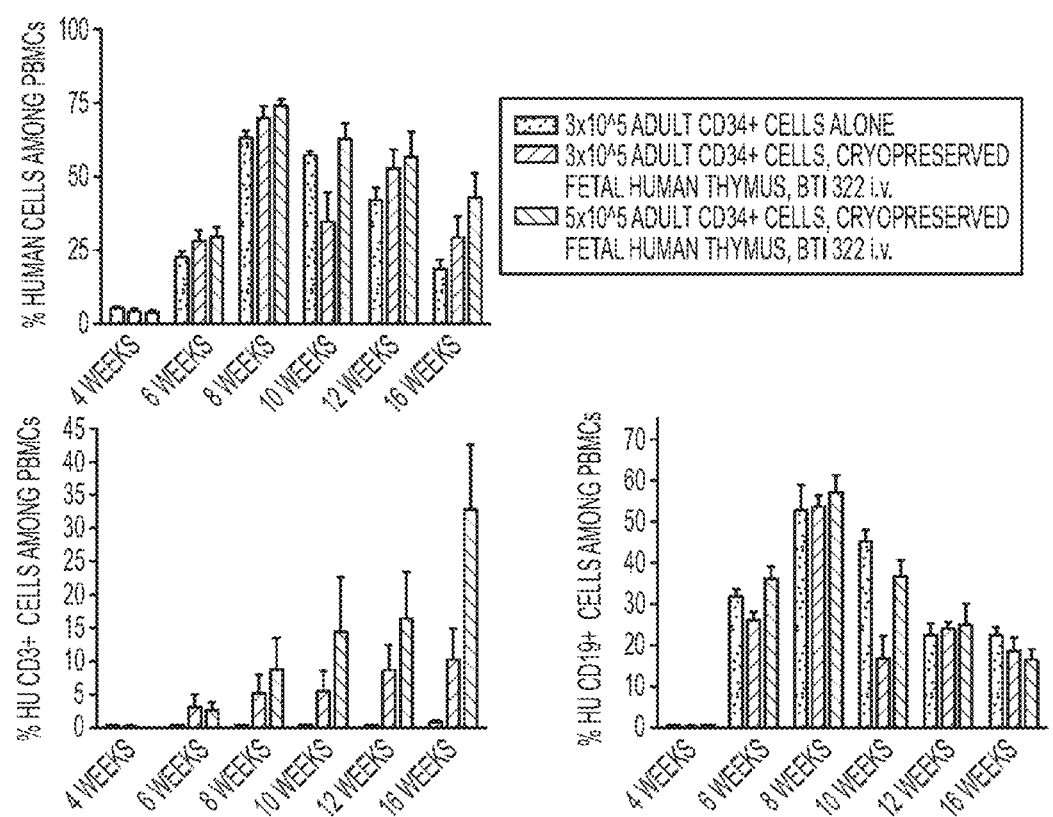
Figure 38:
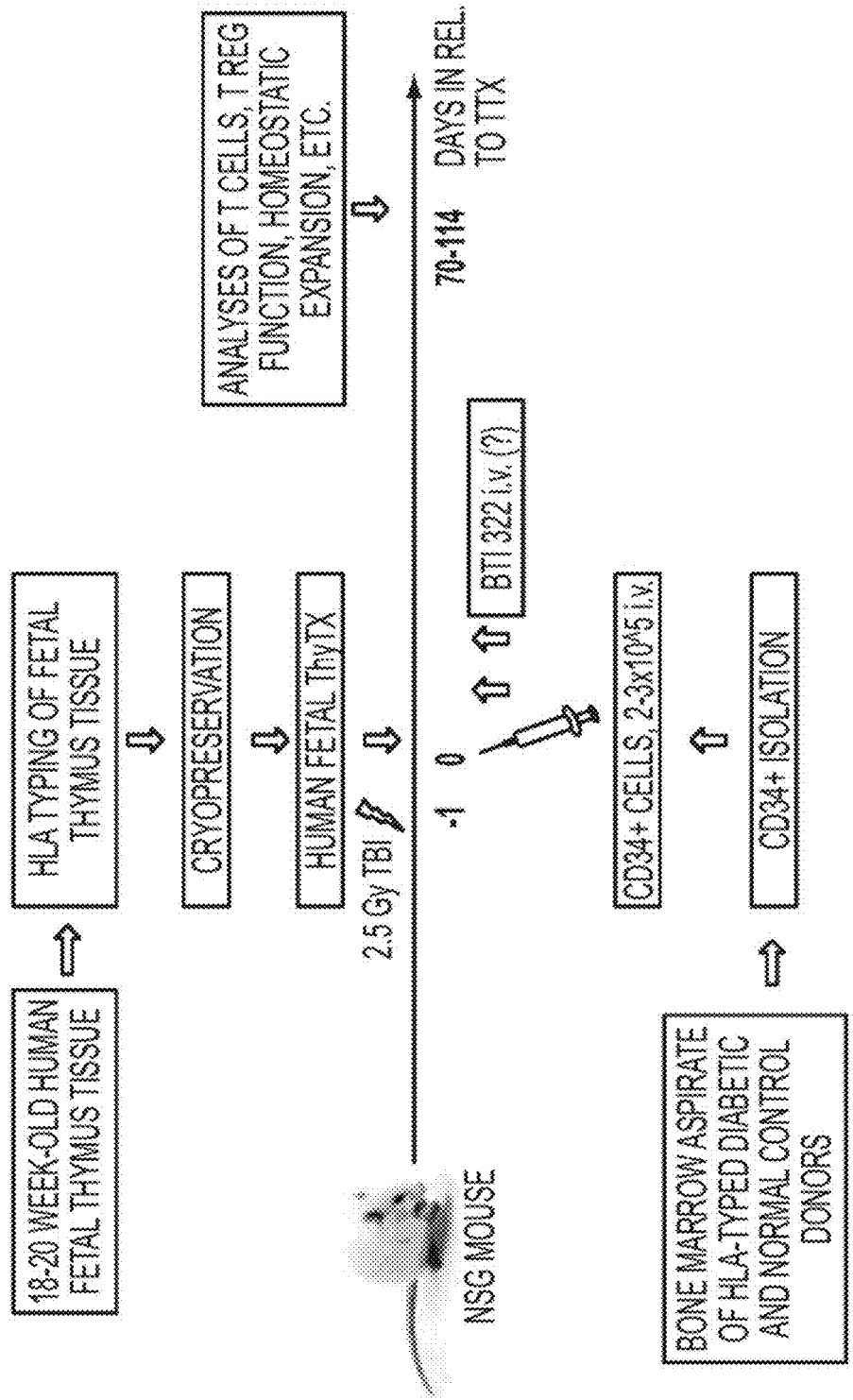

FIG. 37 shows human cell reconstitution in NSG mice following adult human CD34+ cell injection FIG. 38 shows an embodiment of an experimental design of a regimen that allows a reconstitution of human CD3+ cells.

FIGS. 39A-B. FIG. 39A. Staining of human IgM and IgG in the islet grafts from control NOD/SCID, human Thy/Liv/CD34+ cell-grafter NOD/SCID mice (Hu/Hu mice, 2$^{nd}$ and 3$^{rd}$ rows) and human Thy/Liv/CD34+ cell grafter NOD/SCID mice that were depleted of human T cells by BTI322 prior to islet transplant (bottom row). Porcine islets were implanted under the mouse kidney capsule; grafts were removed 4-10 weeks after transplantation. Shown are representative results from 5 weeks-grafts. FIG. 39B. Islet xenografts from control NOD/SCID (1$^{st}$ row), Hu/Hu mice (middle), and Hu/Hu mice that were depleted of human T cells by BTI322 prior to islet transplant (bottom) were stained for H&E, pig insulin, huCD3, huCD20, and huCD68.

Figure 40:
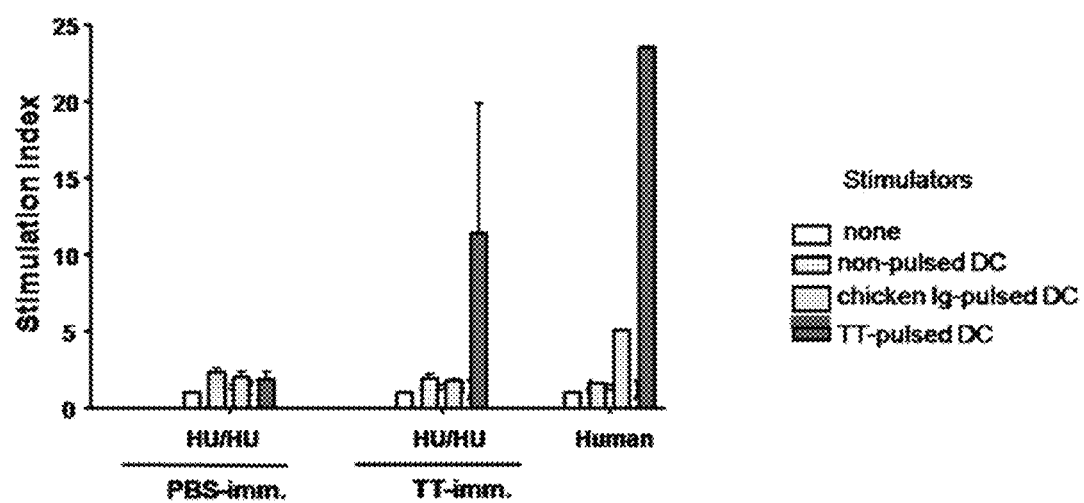

FIG. 40 shows a proliferation assay with Ag stimulation 1 week after boost with IFA+TT. HU/HU mice immunized with CFA+TT (130 µg/mouse) were boosted with IFA+TT (130 µg/mouse) 3 weeks after the first immunization and assessed for proliferative responses one week later following coculture with Ag-pulsed syngeneic DC derived from CD34+ FLCs or (for human PBMC) monocytes. Responders: mCD45&Ter119 depleted human T cells from spleen and LNs DCs for humanized mice and human were generated to human donor CD34+FLCs and PBMC monocytes, respectively.

Figure 41:
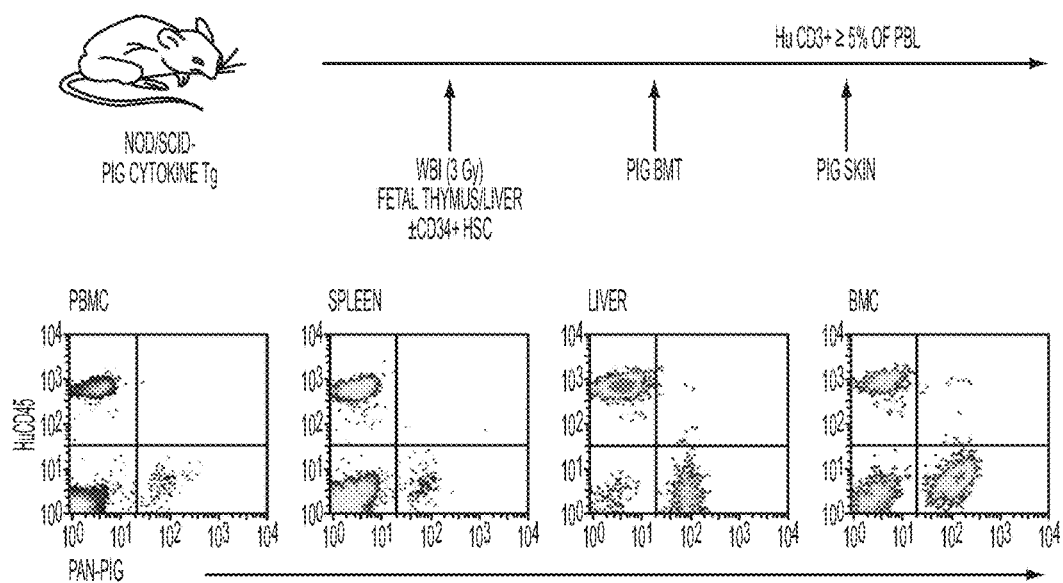

FIG. 41 shows the co-existence of porcine and human cells in humanized pig cytokine-transgenic mice receiving pig BMT. The protocol is shown above and the dot-plots show the presence of both human (y axis) and porcine (x axis) cells in the PBMC, spleen, liver and bone marrow at 25 weeks after pig BMT.

Figure 42:
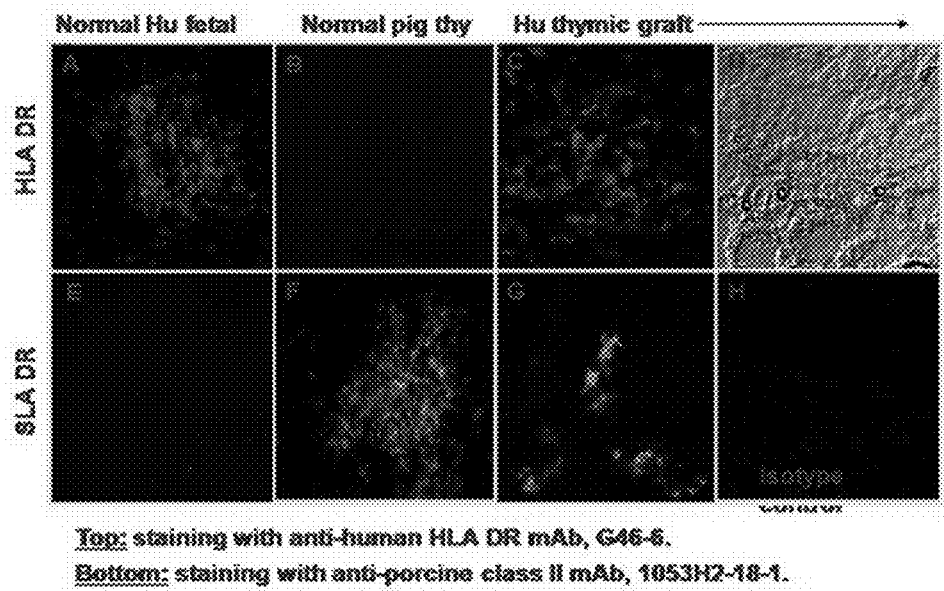

FIG. 42 shows the presence of pig class II$^{high}$ cells in medulla of long-term human thymus graft in pig cytokine transgenic NOD-scid mice that received human THY/LIV/CD34 cells plus porcine BMT ("Hu thymic graft", right panels). Controls include human fetal thymic tissue (left) and normal pig thymus (center).

Figure 43:
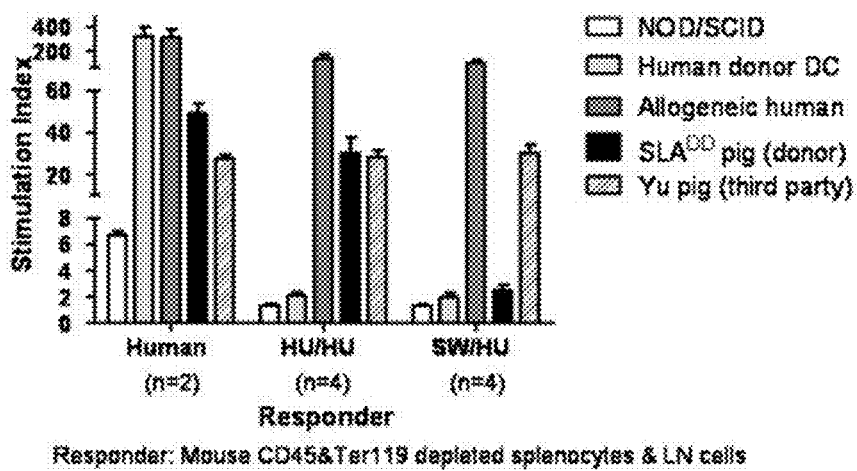

FIG. 43 shows the specific tolerance to human and porcine donors and mouse recipients among T cells generated in porcine thymus grafts. Human T cells generated in human thymus grafts do not show tolerance to pig. MLR assay is shown with responder cells (human, depleted of mouse CD45 and Ter119+ cells) from pooled SPL & LNs of SW/HU and HU/HU mice. "Human" denotes normal human donor from whom responders were purified T cells from PBMC. PBMC from another human were "allogeneic human" stimulators. Human donor-derived Dcs were generated from FLCs.

Figure 44:
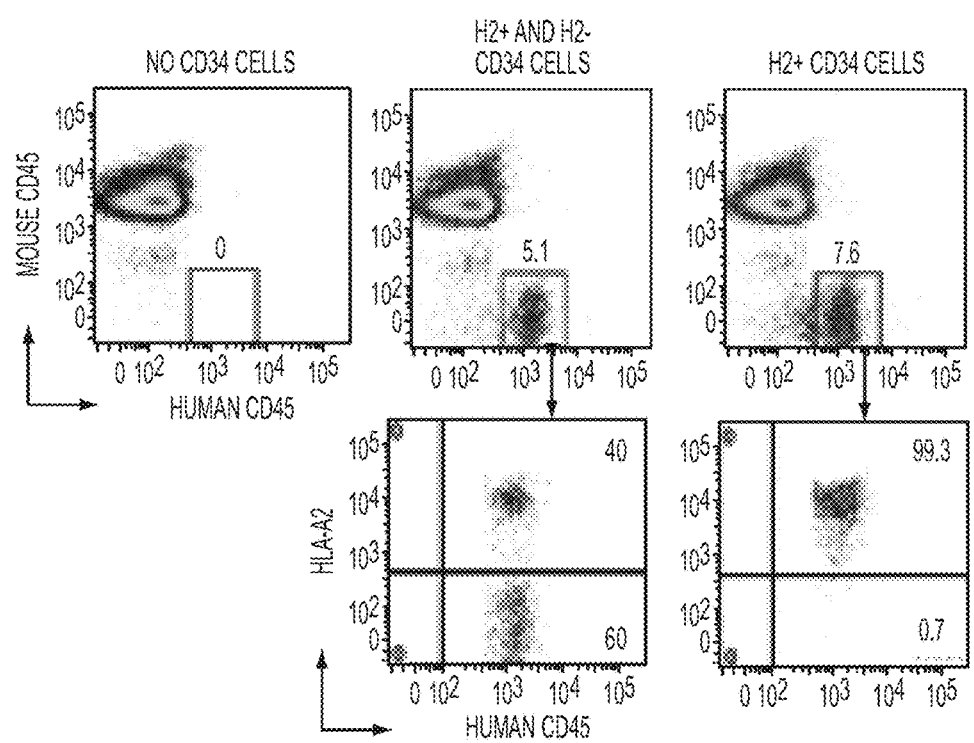

FIG. 44 shows the induction of mixed chimerism in humanized mice. Irradiated (2.5 Gy) NSG mice were transplanted with no CD34 cells, HLA-A2+ or HLA-A2+ and HLA-A2− CD34+ cells. Mixed chimerism was assayed at 6 weeks post-BMT. No human cells were found in mice not transplanted with CD34 cells. Mice receiving CD34 cells from HLA-A2+ and HLA-A2−CD34 cells developed mixed chimerism.

FIGS. 45A-B: FIG. 45A. Left: Hu-mouse spleen and liver cells stained with anti-huVα24Jα18(6B11) and anti-huCD3; Right, CD4 and CD8 expression on gated huCD3+ Vα24Jα18+ iNKT cells. FIG. 45B.: Human IL-4 intracellular staining of spleen cells from α-GalCer-immunized hu-mice. IL-4+ cells in gated huCD3+Vα24Jα18+ iNKT (left) and huCD3+Vα24Jα18− T cells (right) are shown.

FIGS. 46A-B is shows autologous human EBV-lymphoma in a humanized mouse. Blood cells were collected from humanized mice generated by cotransplantation of human THY/CD34+cells. Humanized mouse PBMC were cultured with EBV until >90% of the cell became huCD45+ CD19+CD23+B− lymphoma cells. Autologous EBV-transformed cells were injected into humanized mice, which were followed for tumor development. B-lymphoma (i.e., huCD45+CD19+CD23+) cells became detectable in blood approximately 10 days after injection and all mice became moribund by 2-4 weeks. Shown are flow cytometric analysis (FIG. 46A) and organs with tumors (FIG. 46B) from a representative humanized mouse 17 days after injection of autologous EBV-transformed human cells.

Figure 47:
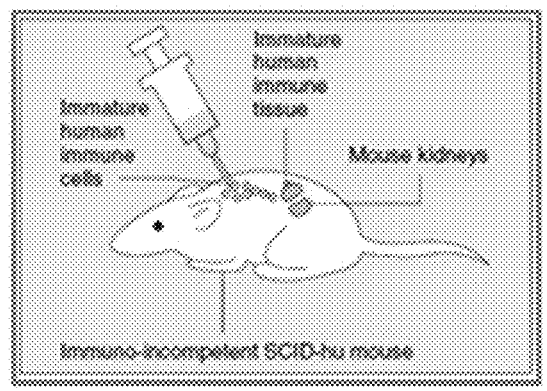

FIG. 47 shows the development of a humanized mouse model that achieves multilineage human immune cell reconstitution from adult CD34+ HSCs transplanted with allogeneic fetal thymus tissue into NOD/SCID/IL2Rgnull mice.

Figure 48:
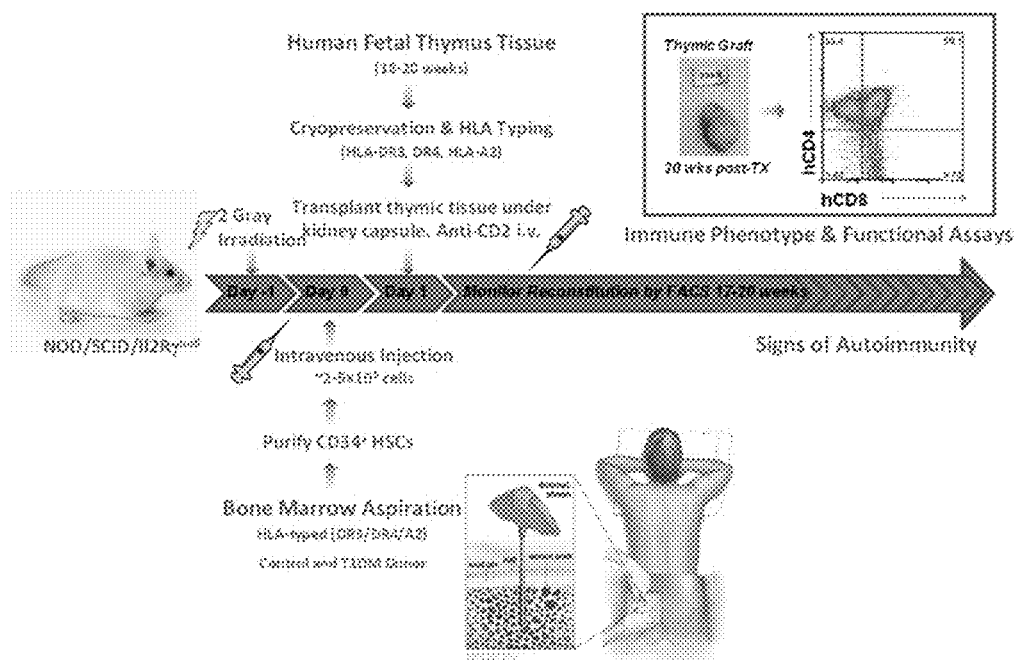

FIG. 48 shows the making of the "Mini Me" mouse by reconstitution with fetal thymus graft and adult HSCs.

Figure 49:
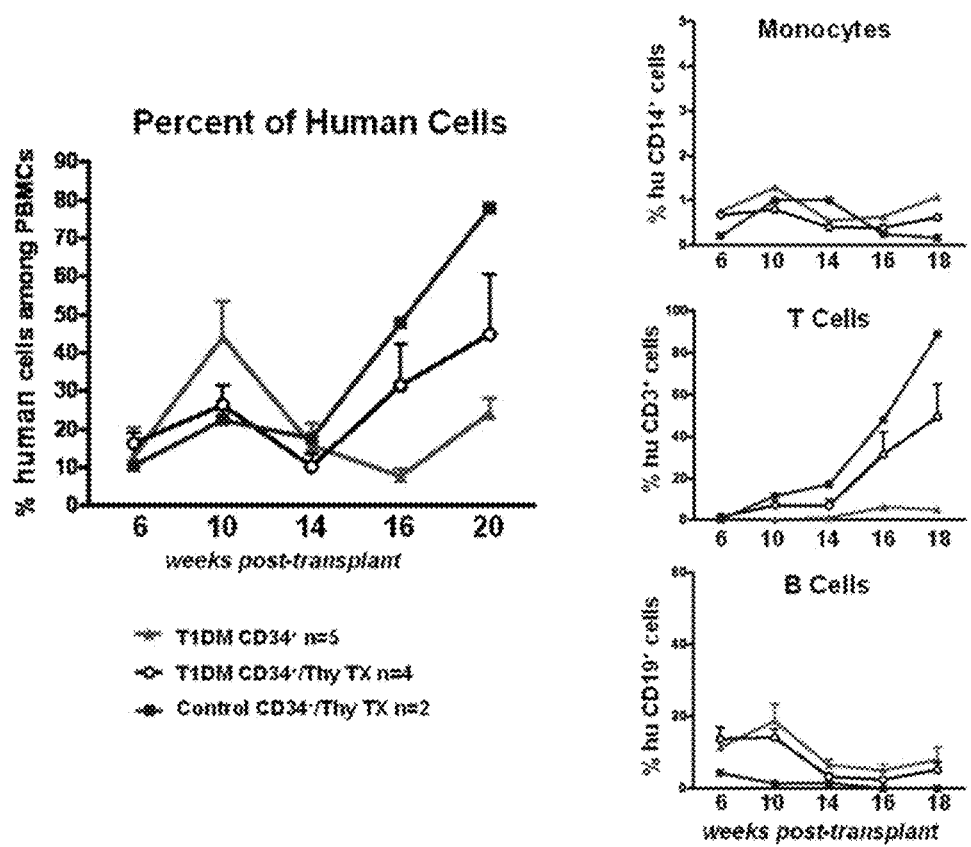

FIG. 49 shows multilineage human immune cell reconstitution from adult CD34+ HSCs. Sublethally irradiated NSG mice that received a cryopreserved/thawed fetal thymus graft in combination with $1.8 \times 10^5$ adult CD34+ cells isolated from a bone marrow aspirate of a healthy volunteer and a T1DM patient were bled to measure human cell reconstitution in peripheral blood mononuclear cells (PBMCs) at the indicated time points. Age-matched control animals received $1.8 \times 10^5$ adult HSCs alone, isolated from the bone marrow aspirate of the T1DM patient.

Figure 50:
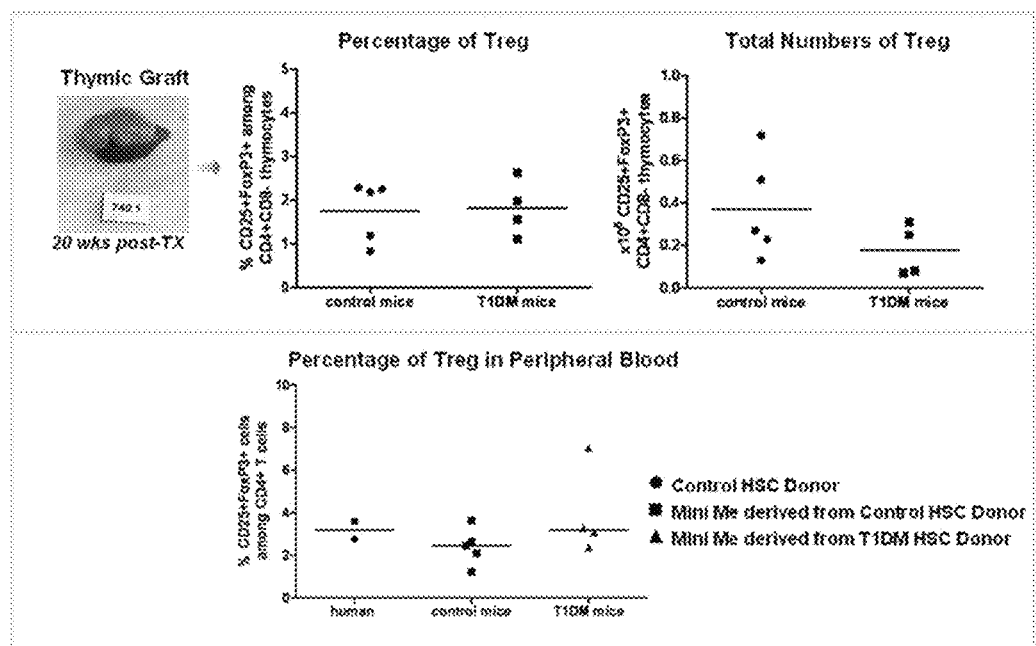

FIG. 50 shows regulatory T cell development in "Mini Me" mice and similar numbers of regulatory T Cells in thymic grafts and peripheral blood of "Mini Me" mice generated from control and T1DM HSCs. Top Graphs 20 weeks after transplantation, single cells suspensions were prepared from half of the thymus graft of NSG mice that received a cryopreserved/thawed THY graft and allogeneic CD34+ cells isolated from a bone marrow aspirate of a healthy volunteer (circles) or T1DM patient (black squares). Cells were stained for human CD4, CD8, CD25 and FoxP3 and the number of natural Tregs calculated. Bottom Graph Proportions of Tregs in PBL 20 weeks after transplantation of a cryopreserved/thawed fetal thymus graft in combination with adult CD34+ cells from healthy controls or a T1DM patient in comparison to two healthy volunteers.

Figure 51:
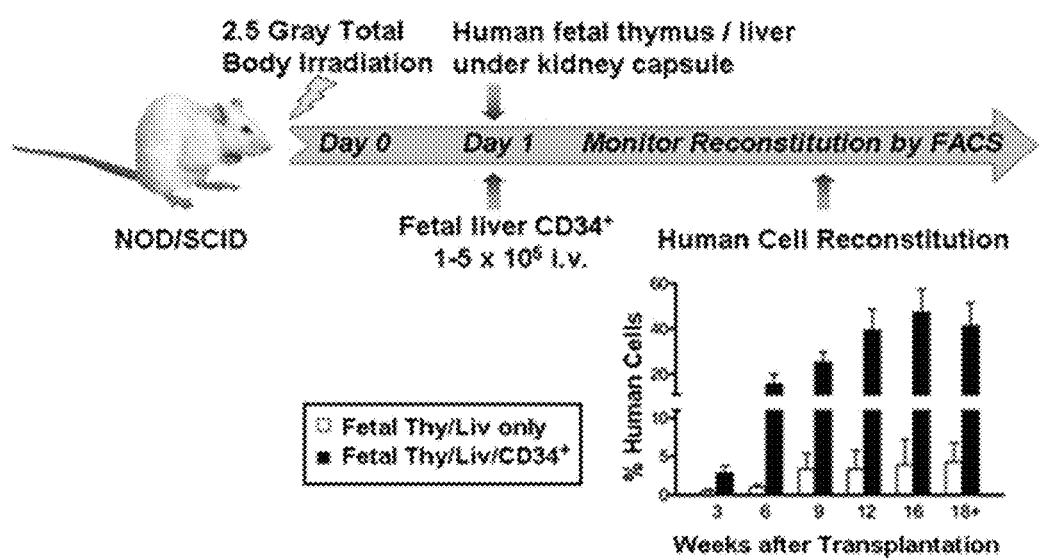

FIG. 51 shows a previous humanized mouse model.

Figure 52:
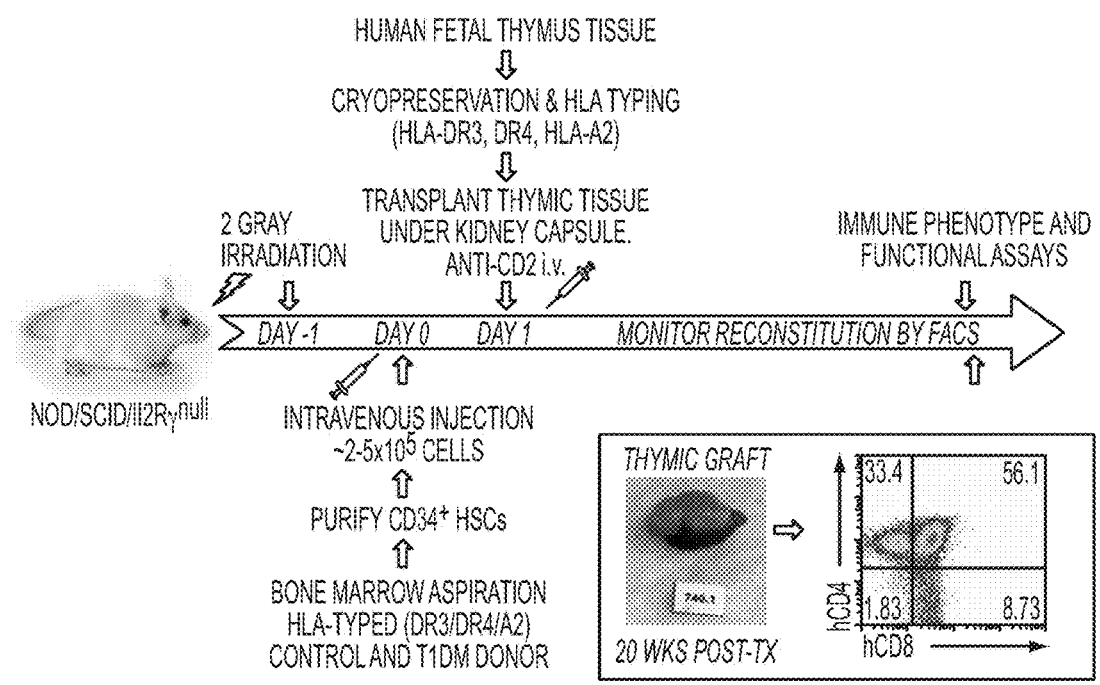

FIG. 52 shows the making of the Mini Me Mouse.

Figure 53:
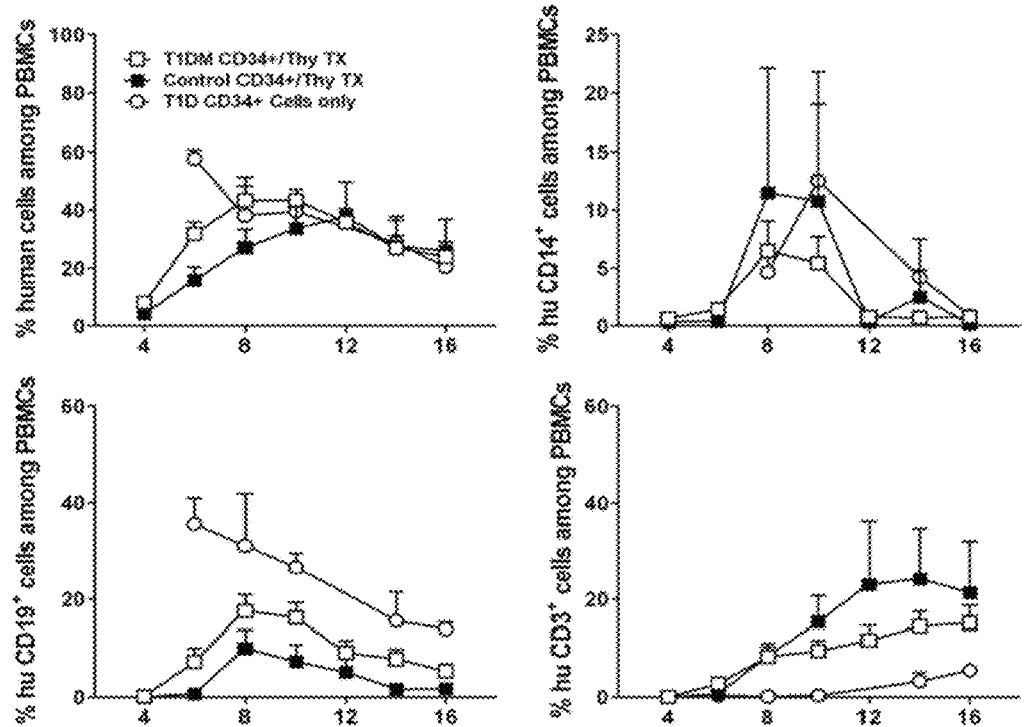

FIG. 53 Multilineage human cell reconstitution in NSG mice receiving cryopreserved/thawed thymic grafts and allogeneic, adult CD34+ cells isolated from bedside bone marrow aspirates. Sublethally irradiated NSG mice received cryopreserved/thawed fetal thymus tissue in combination with $1.8-3.0 \times 10^5$ adult CD34+ cells isolated from bone marrow aspirates from healthy volunteers (black squares, n=3 donors, 6 recipients) and T1D subjects (open squares, n=4 donors, 29 recipients). Mean levels of human cell reconstitution in (total mouse plus human) PBMCs are shown over time. Control animals received adult HSCs alone from the T1D subjects (open circles, n=2 donors, 7 recipients). Thymus grafts and bone marrow donors were HLA-typed for T1D-associated DRB and DQB alleles and HLA A*201 using SNP genotyping assays. The thymic tissue and bone marrow donors shared at least HLA*A201 and DRB*0302 and/or DQB*0301.

Figure 54:
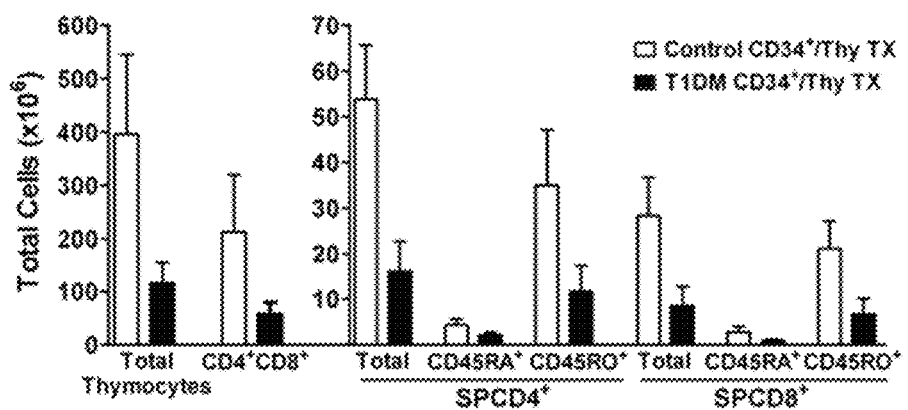

FIG. 54 Absolute numbers and surface phenotype of thymocytes developing in the human thymic graft. Sublethally irradiated NSG mice received cryopreserved/thawed fetal thymus tissue in combination with $2 \times 10^5$ adult CD34+ cells isolated from the bone marrow aspirate from a healthy volunteer (open bar, 3 recipients) and a T1D subject (filled bar, 5 recipients). Graft thymocytes were analyzed 22-25 weeks post-transplantation for CD4+CD8+, CD4+, CD8+, CD45RA and CD45RO by FCM. Mean+SEM are shown, No significant differences between T1D and control animals were noted.

Figure 55:
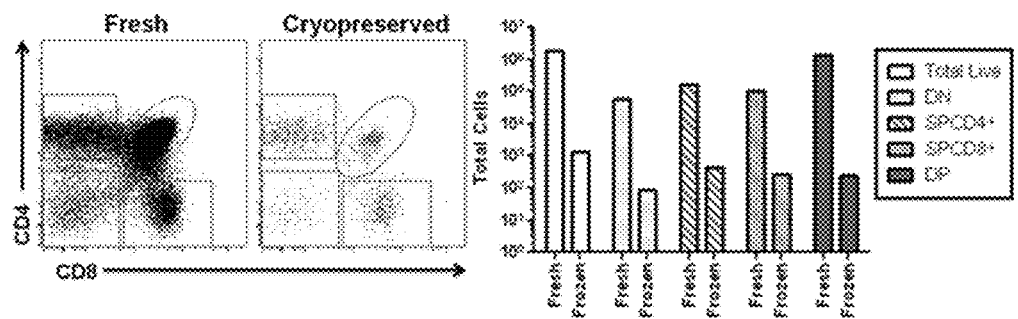

FIG. 55. Cryopreservation depletes thymocytes in human fetal graft. Fresh and cryopreserved thymus (~0.002 g of tissue) from the same donor were dissociated and stained for live cells and thymocyte markers CD4 and CD8. $1 \times 10^5$ total events were collected and subgated on live (DAPI-) thymocytes. FCM plots are shown on the left and total cell number for CD4CD8 double negative, single positive and double positive populations are shown in the graph on the right.

Figure 56:
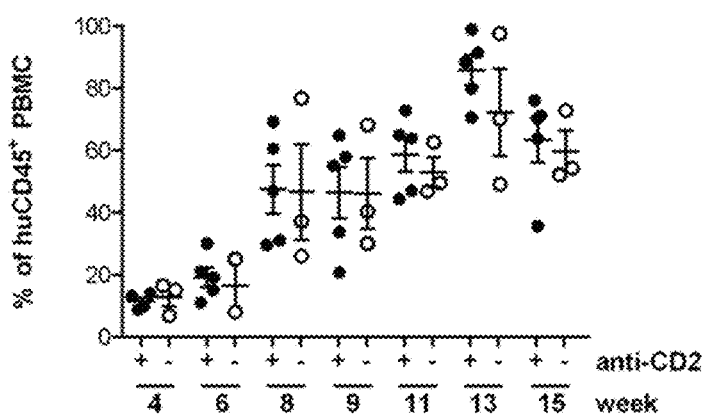

FIG. 56. Effect of anti-CD2 mAB BTI322 on chimerism in humanized mice. Comparison of human cell reconstitution in blood of NSG mice receiving cryopreserved fetal thymic tissue and allogeneic CD34+ cells with or without treatment with anti-CD2 mAb BTI322. Percentages of human CD45+ cells among peripheral blood mononuclear cells are shown at the indicated times. No differences in percentages of human T cells, B cells or monocytes were detected between the two groups.

Figure 57:
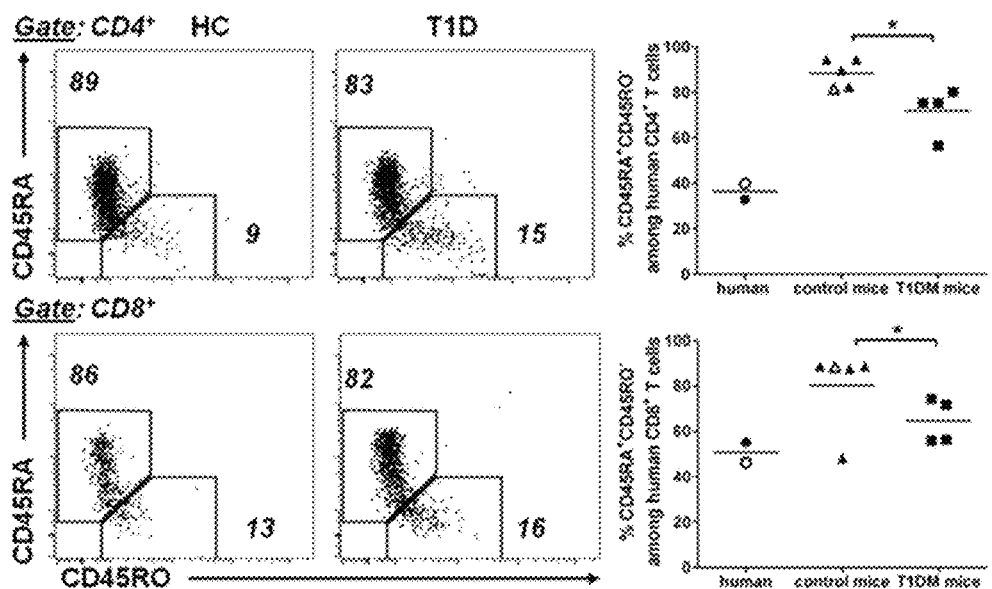

FIG. 57. Naive/Memory phenotype in NSG transplanted with adult CD34+ cells and allogeneic human fetal thymus. Proportions of CD45RA+ CD4 (top row) and CD8 (bottom row) T cells in PBMCs of healthy volunteers and of NSG mice 20 weeks after THY implantation plus i.v. infusion of CD34+ cells from one T1D subject (black squares) or one of two healthy controls (black triangles), including (open circle) the donor of CD34 cells for the control mouse indicated with an open triangle (*p<0.05, excluding the outlier in the CD8 population of controls from statistical analysis).

Figure 58:
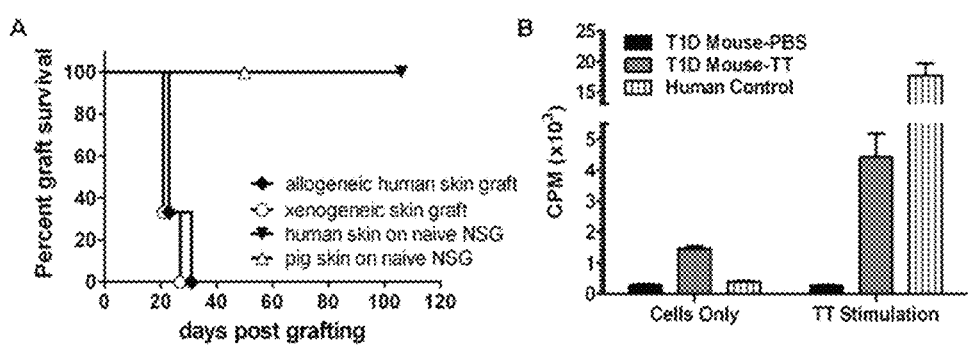

FIGS. 58A-B. Rejection of allogeneic human skin transplant and response to tetanus toxin immunization. Functional and self-tolerant immune systems in NSG mice receiving fetal thymus graft and adult CD34+ cells. FIG. 58A. NSG mice (n=3) that received a 7 Gy irradiated fetal thymic graft plus $3 \times 10^5$ adult CD34+ bone marrow cells reconstituted peripheral T cells >30 weeks post-transplantation. Thirty-nine weeks after transplantation, they were grafted with allogeneic human skin and xenogeneic pig skin. Survival of the human and pig skin grafts (n=3 and 4, respectively) on untreated control NSG mice denoted "naive NSG" is also shown. FIG. 58B. Responsiveness to tetanus toxoid of peripheral T cells from T1D HSC donor-derived NSG mouse following in vivo immunization compared to unimmunized mouse from the same donor and an immunized normal adult human donor.

Figure 59:
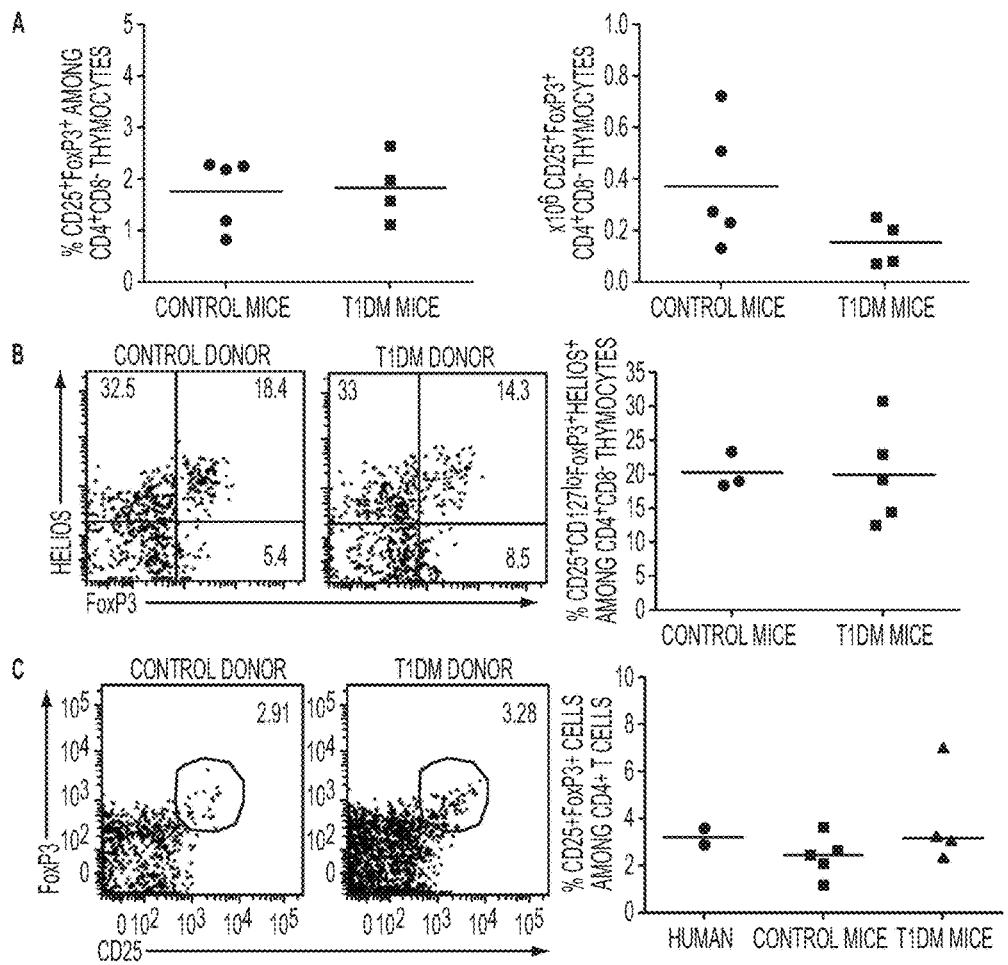

FIGS. 59A-C. Development of natural regulatory T cells in NSG mice transplanted with fetal thymus and adult CD34+ cells. FIG. 59A. 20-22 weeks after transplantation, single cell suspensions were prepared from thymus grafts of NSG mice that received a cryopreserved THY graft and allogeneic CD34+ cells from one of two healthy volunteers (circles) or one T1D subject (squares) and analysed by FCM. FIG. 59B. As a marker for natural Tregs, helios expression in CD4+CD8−CD25+CD127$^{lo}$FoxP3+ thymocytes is shown in NSG mice derived from a second human donor pair in the bottom row. FIG. 59C. Similar proportions of Tregs in PBMCs 20 weeks after transplantation of cryopreserved fetal thymus grafts with CD34+ cells from one of two healthy controls (squares) or one T1D subject (triangles) compared to two healthy humans (circles). Left plots show CD25 and FoxP3 staining on CD4+ T cells from NSG mice generated reconstituted from control and T1D donors.

FIGS. 60A-B. Activation of STAT5 in T cells from NSG mice reconstituted with T1D or healthy control-derived CD34+ cells. Human cells enriched by depletion mouse erythrocytes and leukocytes were isolated from PBMC and splenocytes from NSG mice reconstituted with either T1D or healthy control CD34+ cells. Human PBMCs isolated from a different healthy control are shown as a control. Human cells were stimulated with 1000 U/ml in PBS for the timepoints indicated. Cells were fixed and stained for human and mouse CD45, human CD4, CD8, CD25, FoxP3 and antiphosphroylated STAT5 with the BD Phosflow system. Data were analyzed using analysis programs at Cytobank.org. IL-2 stimulated activation are shown for CD4+ cells (FIG. 60A) and CD4+CD25+FoxP3+ cells (FIG. 60B). The fold median change in signal intensity over time for each sample is plotted on the right.

FIGS. 61A-B. Multilineage human cell reconstitution in NSG mice receiving cryopreserved/thawed thymic grafts and allogeneic, adult CD34+ cells isolated from bedside bone marrow aspirates. FIG. 61A. Sublethally irradiated NSG mice received cryopreserved/thawed fetal thymus tissue in combination with $1.8-3.0\times10^5$ adult CD34+ cells isolated from bone marrow aspirates from healthy volunteers (black squares, n=3 donors, 6 recipients) and T1D subjects (black triangles, n=4 donors, 29 recipients). Mean levels of human cell reconstitution in (total mouse plus human) PBMCs are shown over time. Control animals received adult HSCs alone from the T1D subjects (open circles, n=2 donors, 7 recipients). Thymus grafts and bone marrow donors were HLA-typed for T1D-associated DRB and DQB alleles and HLA A*201 using SNP genotyping assays. The thymic tissue and bone marrow donors shared at least HLA*A201 and DRB*0302 and/or DQB*0301. FIG. 61B. Graft thymocytes were analyzed 22-25 weeks post-transplantation in T1D (n=5) and control (n=3) HSC-reconstituted animals. Mean+SEM are shown. No significant differences between T1D and control animals were noted.

Figure 62:
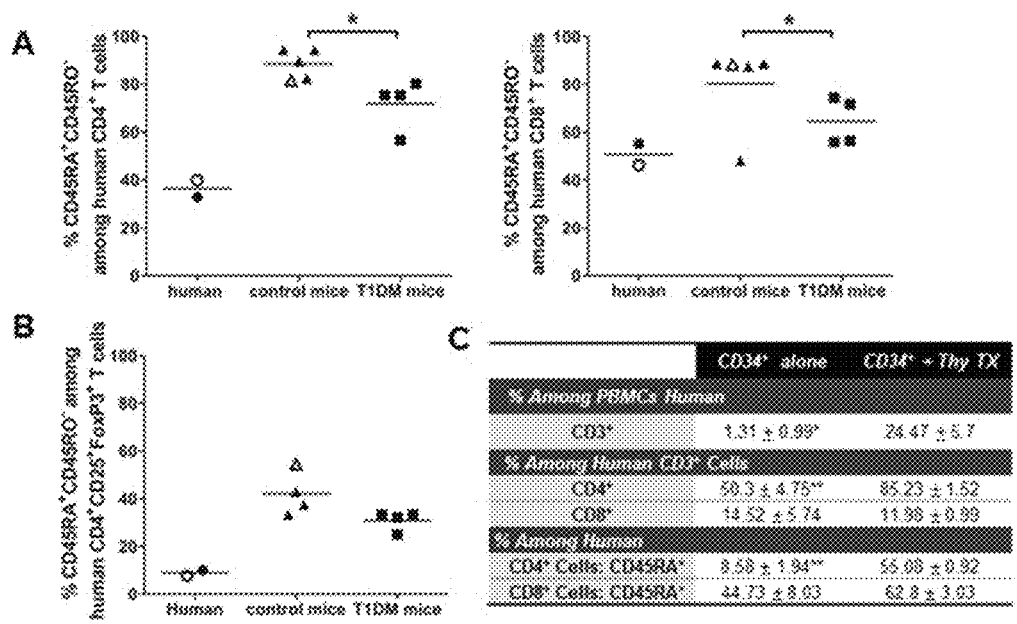

FIGS. 62A-C. Naive/memory phenotype of T cells in IIR mice. FIG. 62A. and FIG. 62B. Proportions of CD45RA+ CD4 and CD8 T cells (FIG. 62B) and Tregs (FIG. 62C) in PBMCs of healthy volunteers and of IIR mice 20 weeks after THY implantation plus i.v. infusion of CD34+ cells from one T1D subject (black squares) or one of two healthy controls (black triangles), including (open circle) the donor of CD34+ cells for the control mouse indicated with an open triangle (*p<0.05, excluding the outlier in the CD8 population of controls from statistical analysis). FIG. 62C. T cell populations were assayed by FCM in NSG mice injected with CD34+ fetal liver cells with or without allogeneic thymus at 7 weeks post-transplant. Mean±SEM are shown, n=4 for each group. *p<0.05, **p<0.005.

Figure 63:
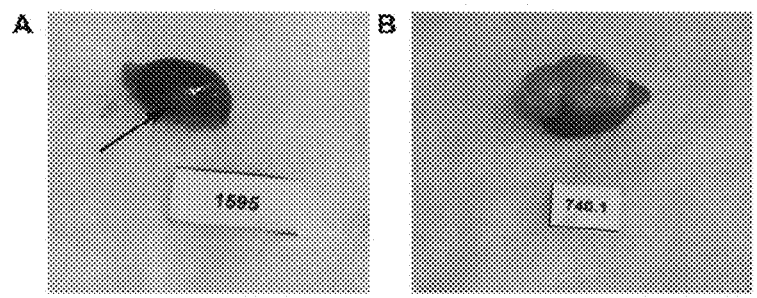

FIGS. 63A-B. Irradiation of THY graft inhibits growth. The appearance of the thymic graft 20 weeks post transplantation in mice that received adult CD34+ cells plus a thymic graft that was irradiated prior to transplantation (arrow in FIG. 63A) or cryopreserved prior to transplantation (FIG. 63B).

Figure 64:
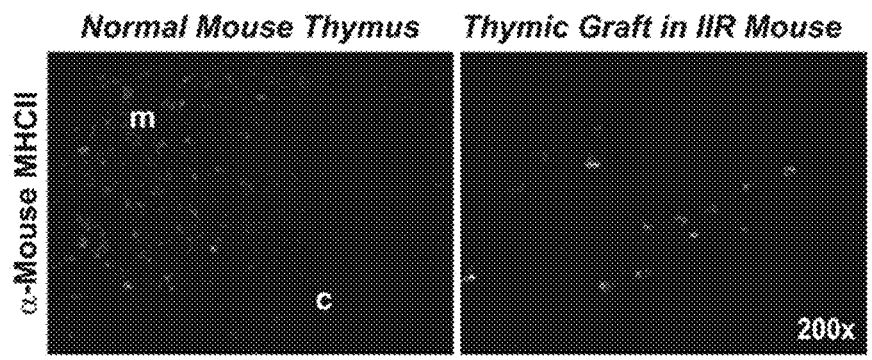

FIG. 64. Antigen-presenting cells from recipient mouse in human thymic graft of IIR mouse. The thymic graft from a IIR mouse reconstituted with adult CD34+ cells and a thymus from a normal C57BL/6 mouse were sectioned and stained with anti-mouse pan-MHC class II mAb to reveal the presence of mouse-derived MHC class II positive cells. In the normal mouse thymus, m denotes the medullary and c denotes the cortical region. When tested for cross-reactivity, the anti-mouse MHCII antibody did not bind to human thymus tissue.

Figure 65:
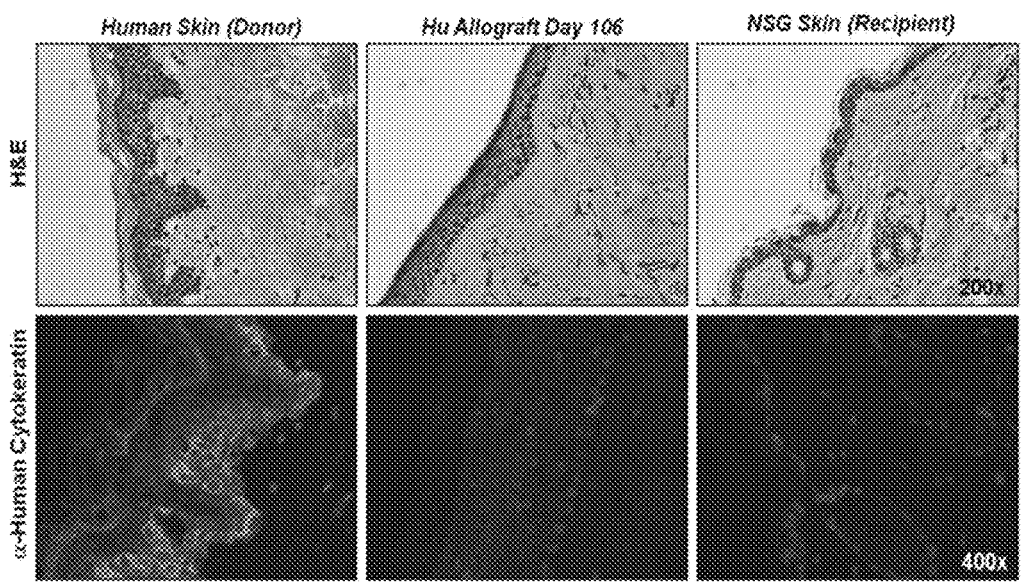

FIG. 65 Human allografts are accepted by unmanipulated NSG mice. NSG mice were transplanted with human skin (center panels) and monitored for rejection for 106 days. All NSG mice (n=3) accepted the human skin graft. Hematoxylin and eosin (top row) show general tissue morphology and anti-human cytokeratin stain (bottom row) shows specific stain in the human skin and human allograft on the NSG mouse. NSG skin alone does not stain with anti-human cytokeratin (bottom right). Human allograft is representative of n=3.

FIGS. 66A-B. Generation of MART-1-specific T cells in humanized mice made by transplantation of human FTHY and TCR-engineered CD34$^+$ FLCs. (FIG. 66A) Representative flow cytometric profiles showing reconstitution of human T and B cells (left) and MART-1 TCR$^+$ T cells (right) in PBMCs of humanized mice. (FIG. 66B) FACS analysis of MART-1 TCR$^+$ and MART-1 TCR$^-$ T cells for CD45RA and CCR7 expression.

Figure 66C:
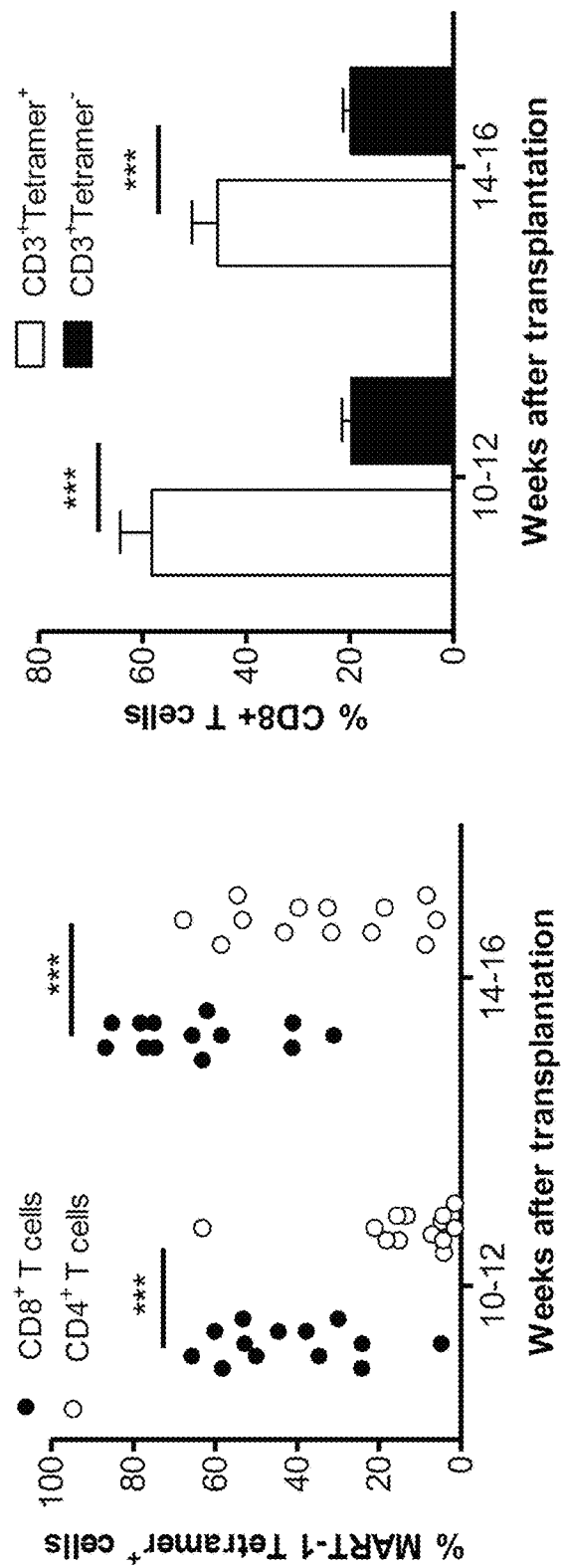

FIG. 66C. Generation of MART-1-specific T cells in humanized mice made by transplantation of human FTHY and TCR-engineered CD34$^+$ FLCs. Shown are percentages of MART-1 TCR$^+$ T cells in CD8$^+$ and CD4$^+$ T cell compartments (left) and percentages (mean±SEMs; n=13) of CD8$^+$ T cells in MART-1 TCR$^+$ and MART-1 TCR$^-$ T cell population (right).

Figure 66D:
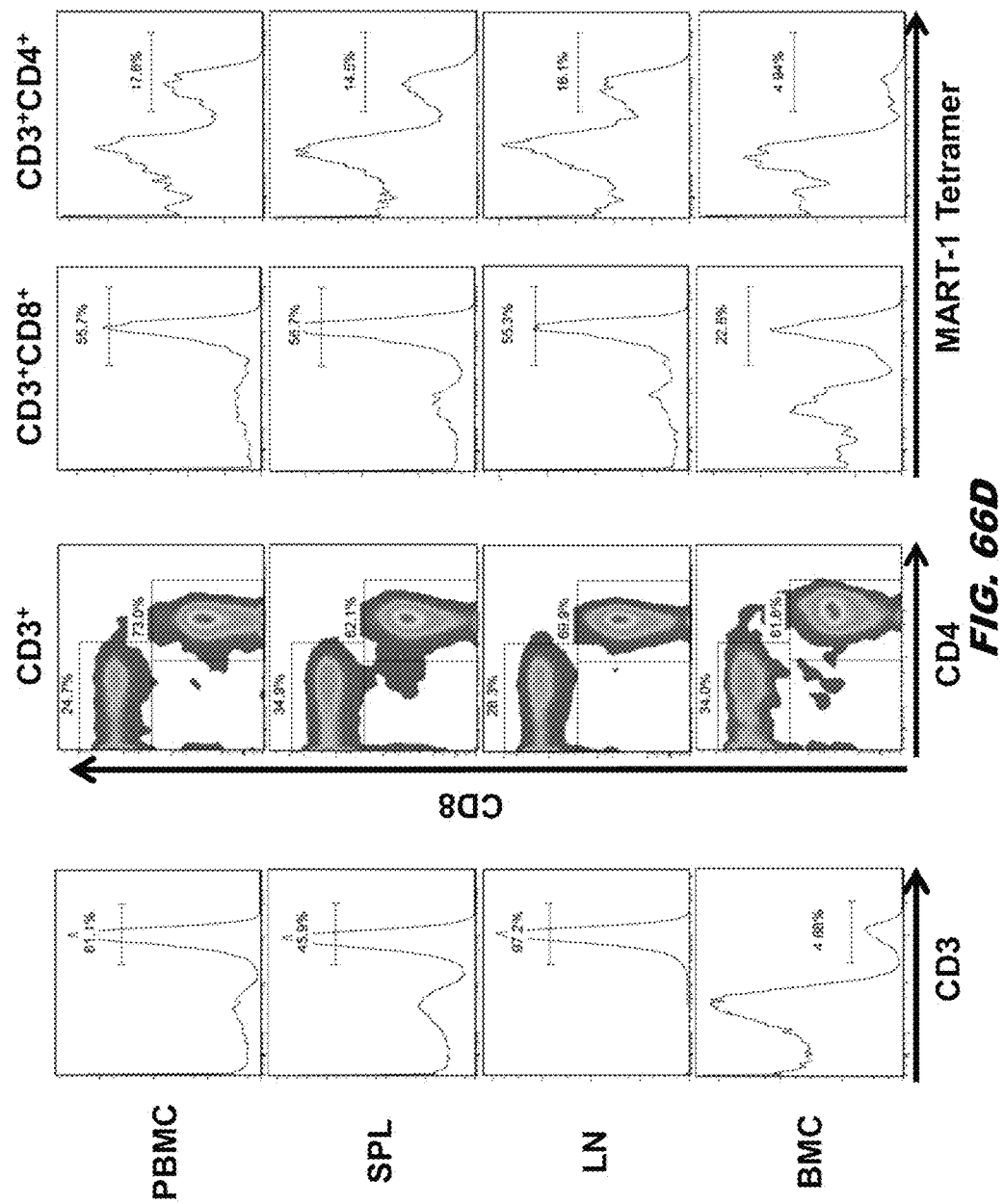

FIG. 66D. Generation of MART-1-specific T cells in humanized mice made by transplantation of human FTHY and TCR-engineered CD34$^+$ FLCs. FACS assessment of MART-1 TCR$^+$ T cells in CD8$^+$ and CD4$^+$ T cells from the indicated tissues at week 22.

Figure 66E:
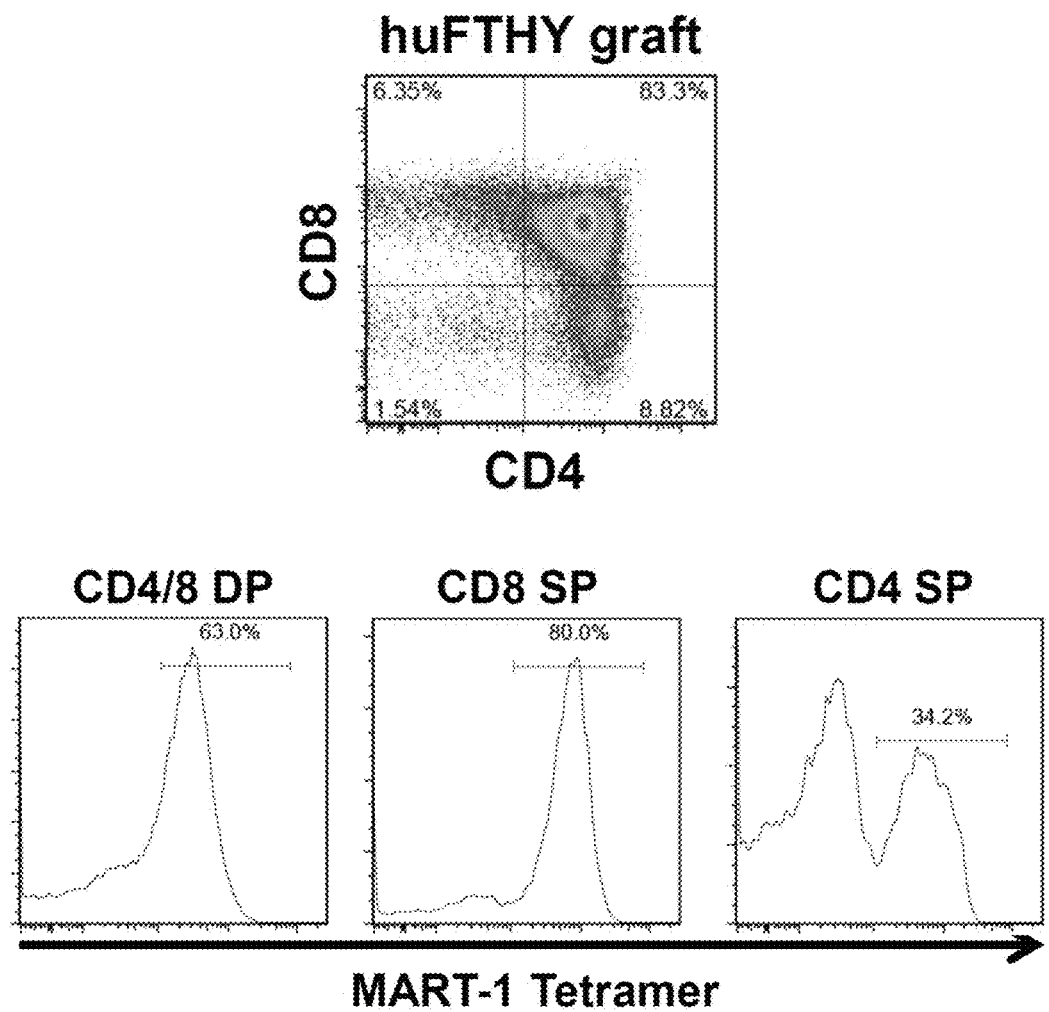

FIG. 66E. Generation of MART-1-specific T cells in humanized mice made by transplantation of human FTHY and TCR-engineered CD34$^+$ FLCs. FACS assessment of MART-1 TCR$^+$ T cells in CD4$^+$CD8$^+$ (DP), CD8SP and CD4SP human thymocytes. ***, p<0.001.

FIGS. 67A-F. MART-1 TCR$^+$ CD8, but not CD4, T cells show specific responses in humanized mice following MART-1 peptide immunization. Hu-mice were immunized with MART-1 peptide or PBS as control 15 weeks after humanization, and CD8 (FIGS. 67A-C) and CD4 (FIGS. 67D-E) T cell responses were assessed by flow cytometry 1 week prior to (before) and 3 weeks after immunization. (FIGS. 67A, D) Percentages of tetramer$^+$ cells in peripheral blood CD8 (FIG. 67A) and CD4 (FIG. 67D) T cells (mean±SEM; n=3). (FIG. 67B, E) Expression of CD45RA and CCR7 on tetramer$^+$ vs. tetramer$^-$ CD8 (FIG. 67B) and CD4 (FIG. 67E) T cells (mean±SEMs; n=7). Left, representative staining profiles of the cells prepared before (top) and after (bottom) immunization; Right, percentages of T cell subsets in tetramer+(top) and tetramer– (bottom) T cells prepared before and after immunization. Naïve, CD45RA$^+$ CCR7$^+$ naïve T cells; EM, CD45RA$^-$CCR7$^-$ effector memory T cells; CM, CD45RA$^-$ CCR7$^+$ central memory T cells; EM/RA, CD45RA$^+$CCR7$^-$ effector memory T cells. (FIG. 67C, F) Percentages of IFN-γ producing tetramer$^+$ CD8 (FIG. 67C) and CD4 (FIG. 67F) T cells prepared before and after immunization (mean±SEMs; n=5). *, p<0.05; , P<0.01; *, P<0.001; n.s., not significant.

FIGS. 68A-B. In vitro expansion and cytotoxicity of MART-1 TCR$^+$ T cells isolated from humanized mice. (FIG. 68A) Tetramer$^+$ T cells were purified from spleen and bone marrow of hu-mice and their cytotoxicity against Mel 624 (HLA-A2$^+$MART-1$^+$), Mel 888 (HLA-A2$^-$MART-1$^+$), Mel A375 (HLA-A2$^+$MART-1$^-$) melanoma cells was measured after a short period (5 days) of in vitro stimulation with anti-huCD3/CD28 microbeads. (FIG. 68B) In vitro expansion of tetramer$^+$ T cells in the presence of OTK3, rhIL-12 and irradiated feeder cells (protocol is detailed in online methods). Tetramer$^+$ T cells from 3 representative hu-mice are shown and data are presented as fold of expansion in cell numbers.

Figure 68C:
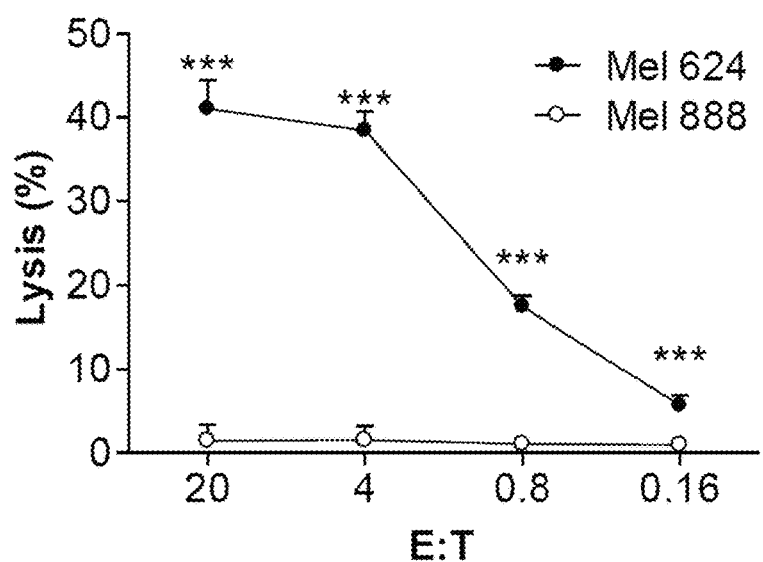
Figure 68C:
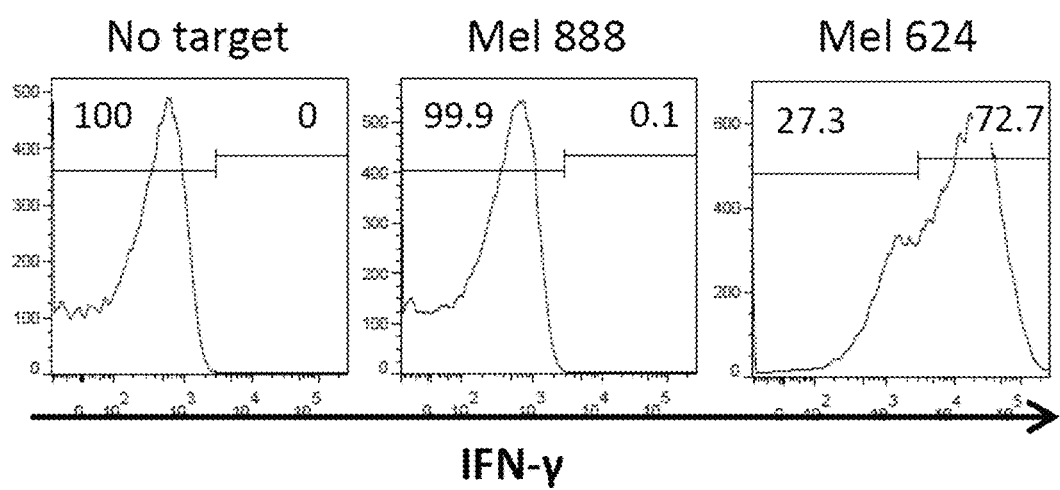
Figure 68D:
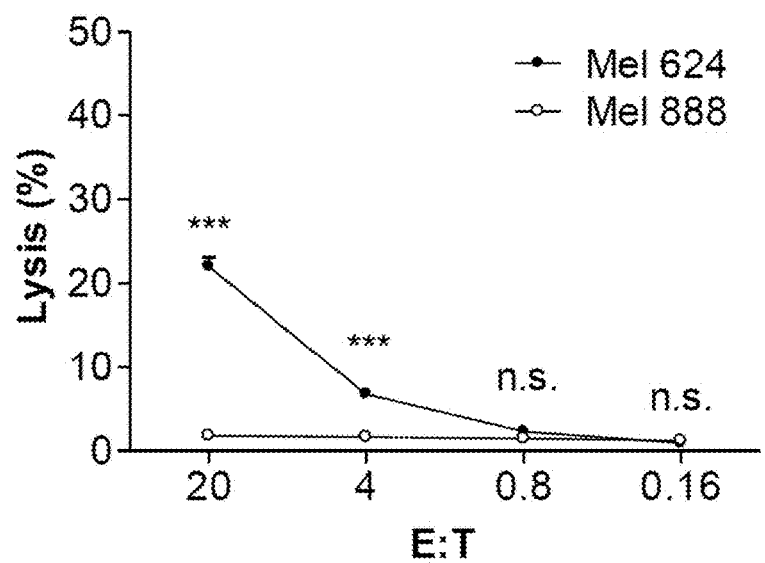
Figure 68D:
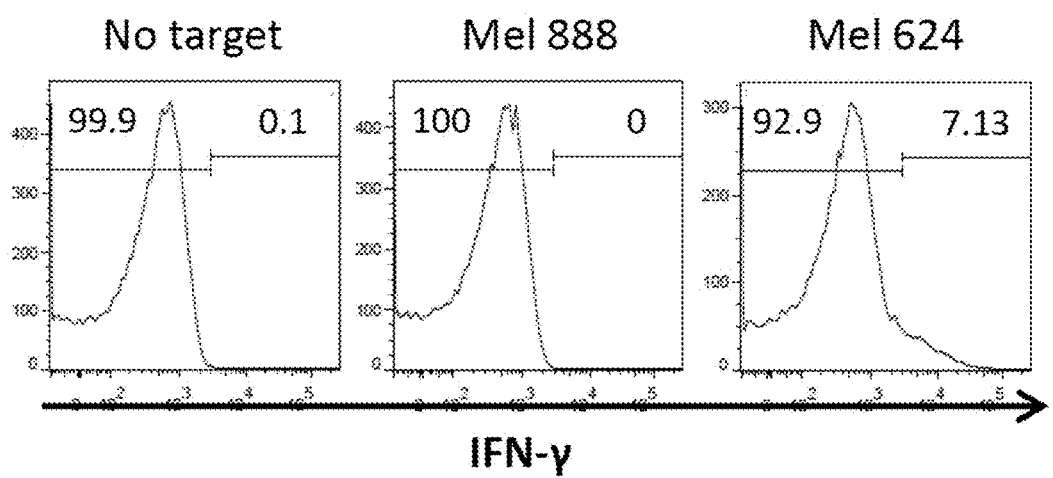

FIGS. 68C-D. In vitro expansion and cytotoxicity of MART-1 TCR$^+$ T cells isolated from humanized mice. Tetramer$^+$ CD8 (FIG. 68C) and CD4 (FIG. 68D) T cells were sorted from in vitro expanded tetramer$^+$ cells (shown in (FIG. 68B) were examined for cytotoxicity against melanoma cells using $^{51}$Cr release assay (left panel) and for IFN-γ production after co-cultured with melanoma cells by flow cytometry (right panel). *, P<0.05; , P<0.01; *, P<0.001; n.s., not significant.

Figure 69A:
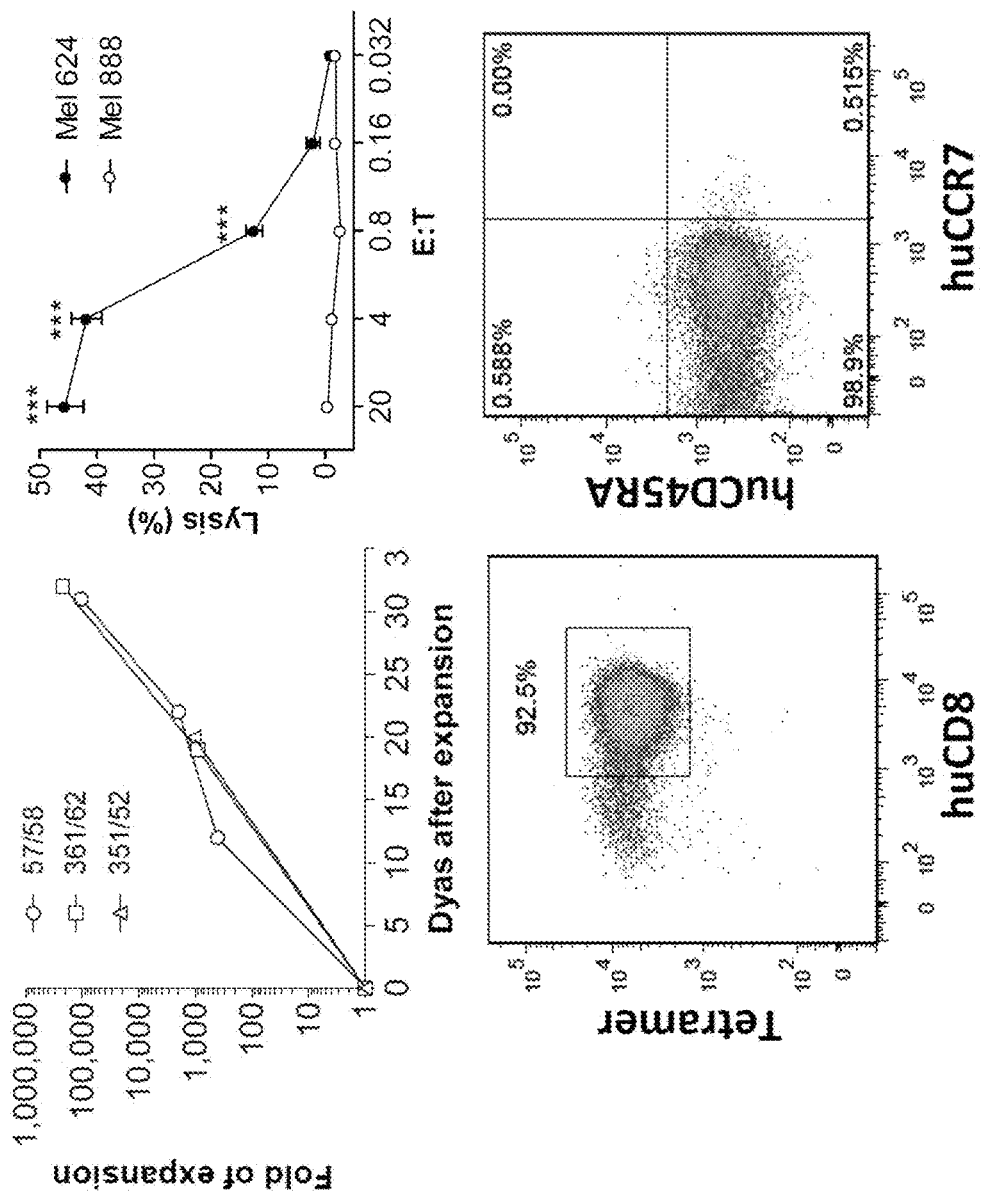

FIG. 69A. Antitumor effect by in vitro expanded MART-1-specific human CD8 T cells from humanized mice. Tetramer$^+$ CD8 T cells were purified from hu-mice (n=3) and cultured in T cell expansion media (see FIG. 68B). Data shown are cellularity at the indicated time points (left panel), expression of MART-1-specific TCR, CD8, CD45RA and CCR7 on expanded cells (middle panel), and cytotoxicity against melanoma cells (right panel) of the expanded cells.

Figure 69B:
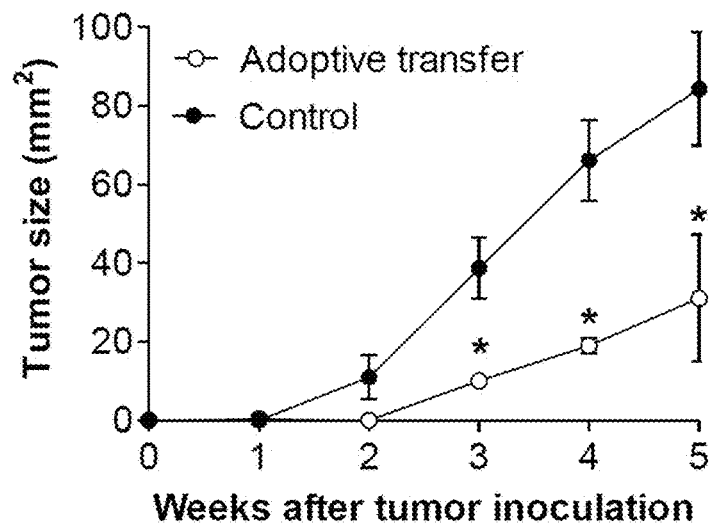
Figure 69B:
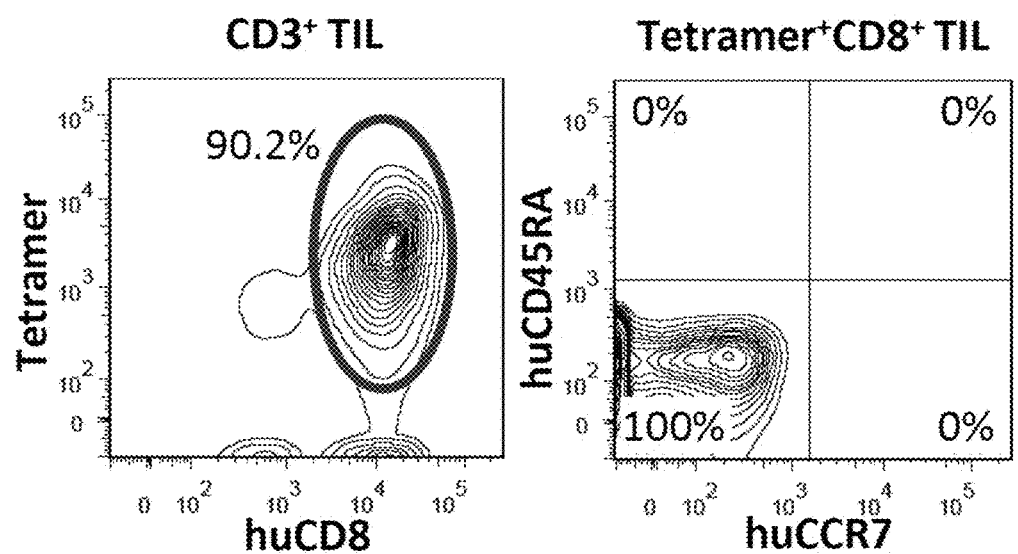

FIG. 69B. Antitumor effect by in vitro expanded MART-1-specific human CD8 T cells from humanized mice. Left panel, tumor burden in mice receiving 1×10$^6$ of Mel 624 (HLA-A2$^+$MART-1$^+$; s.c.) cells with or without (control) adoptive transfer of in vitro-expanded tetramer$^+$ CD8 T cells (1×10$^7$ per mouse; n=5 per group); Right panel, phenotypic analysis of TILs from mice 5 weeks after receiving adoptive transfer of in vitro-expanded tetramer$^+$ CD8 T cells.

Figure 69C:
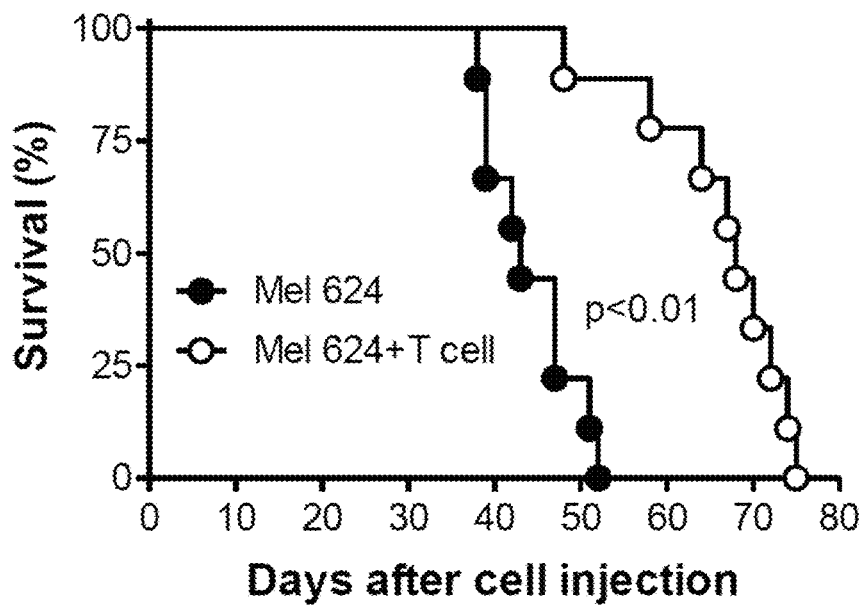

FIG. 69C. Antitumor effect by in vitro expanded MART-1-specific human CD8 T cells from humanized mice. Survival of mice that received 2×10$^5$ Mel 624 cells (i.v.) with or without adoptive transfer of 1×10$^7$ in vitro-expanded tetramer$^+$ CD8 T cells (n=9 per group).

Figure 69D:
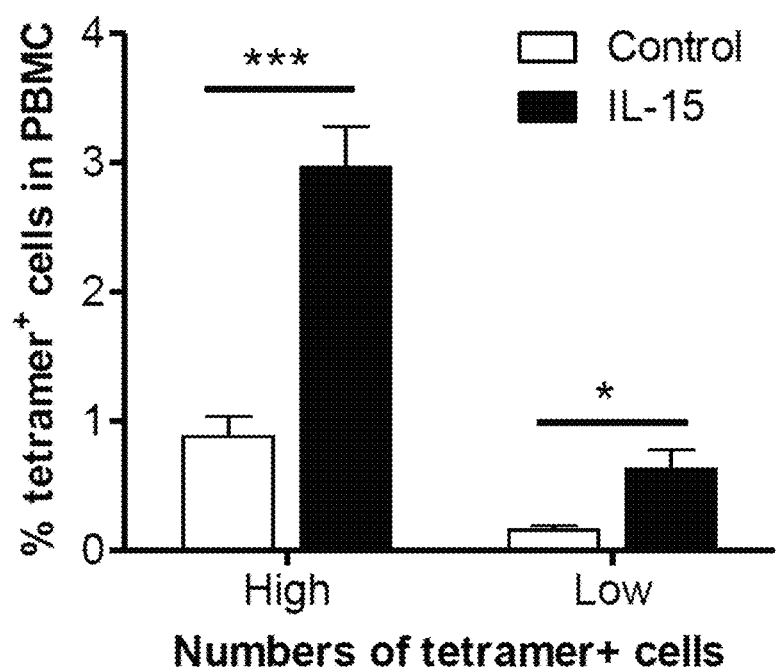

FIG. 69D. Antitumor effect by in vitro expanded MART-1-specific human CD8 T cells from humanized mice. Survival of adoptively transferred tetramer$^+$ CD8 T cells in mice with or without IL-15 treatment at day 7 post-cell transfer (High, 1×10$^7$/mouse; Low, 5×10$^6$/mouse; n=6 per group).

Figure 69E:
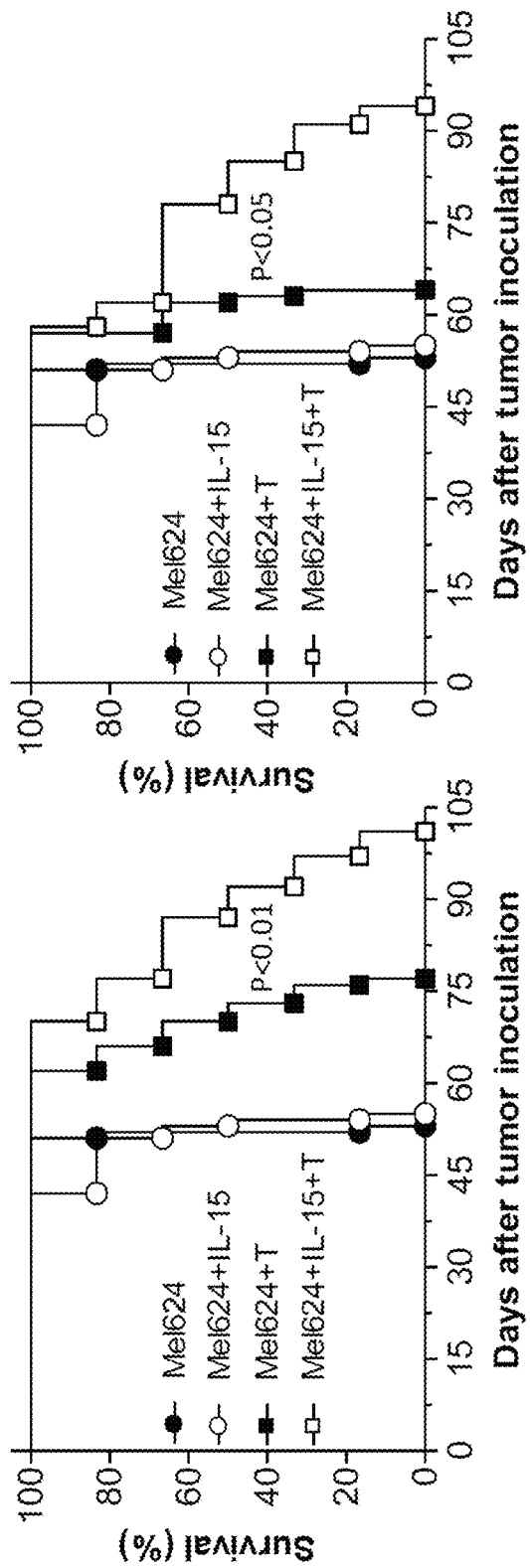

FIG. 69E. Antitumor effect by in vitro expanded MART-1-specific human CD8 T cells from humanized mice. Survival of mice that received 2×10$^5$ Mel 624 cells (i.v.) alone or together with 1×10$^7$ (left) or 5×10$^6$ (right) in vitro-expanded tetramer$^+$ CD8 T cells with or without IL-15 treatment (n=6 per group). *, P<0.05; , P<0.01; *, P<0.001.

Figure 70:
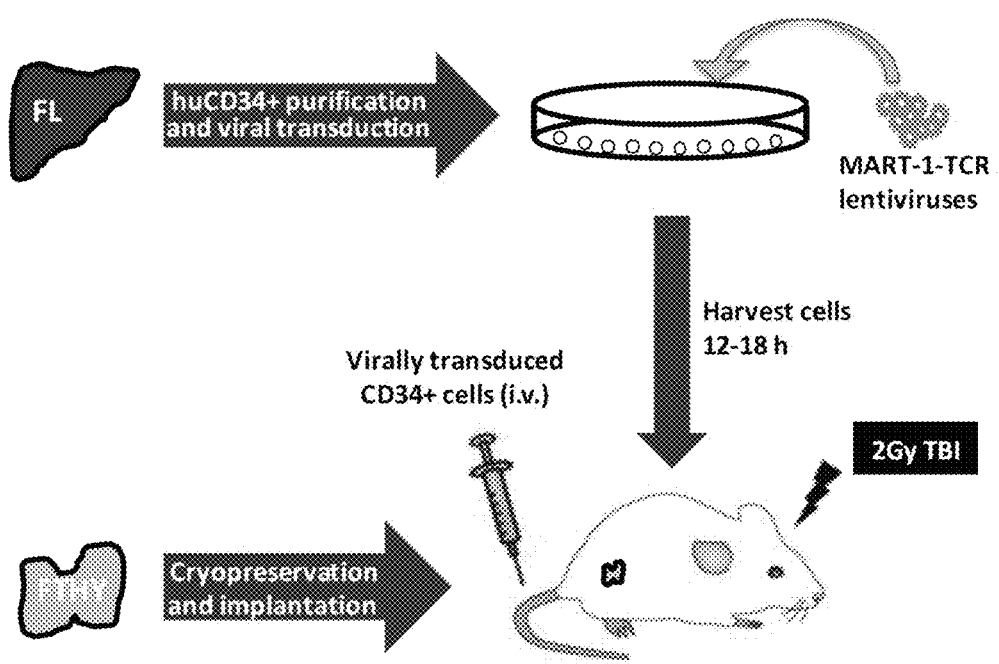

FIG. 70 is a schematic preparation of the humanized mouse model with human T cells expressing transgenic TCR specific MART-1.

FIGS. 71A-C shows cryopreservation treatment of human fetal thymic tissues significantly improve human T cell development from intravenously injected CD34+ cells in humanized mice. Sublethally-irradiated NSG mice were transplanted with fresh or cryopreservation-treated human fetal thymic tissue (under the renal capsule) together with human CD34+ FLCs (i.v.) that were transduced with GFP lentiviral viruses. (FIG. 71A) Schematic preparation of the GFP-transgenic hu-mice. (FIG. 71B) Percentages of GFP+ cells in peripheral blood human B and T cells at the indicated times (mean±SEMs; left) and FACS profile showing GFP+ cells in human thymocytes from the thymic graft (at week 26; right) from hu-mice receiving fresh human thymic grafts. (FIG. 71C) Percentages of GFP+ cells in peripheral human B and T cells at the indicated times (mean±SEMs; left) and FACS profile showing GFP+ cells in human thymocytes from the thymic graft (at week 26; right) from hu-mice receiving cryopreservation treated human thymic grafts. N=5 per group.

Figure 72A:
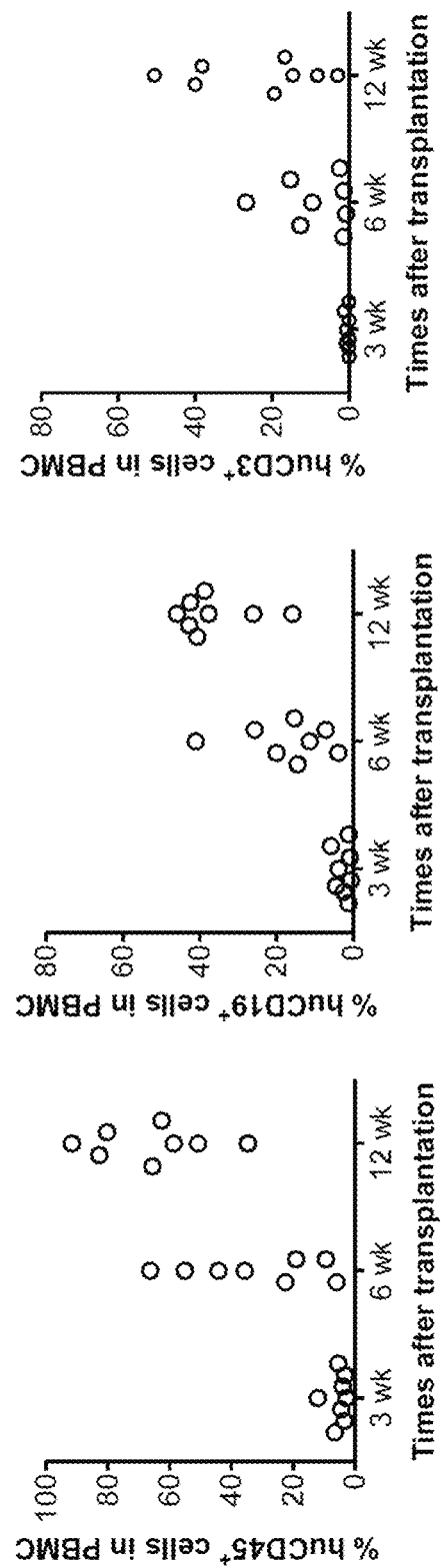
Figure 72B:
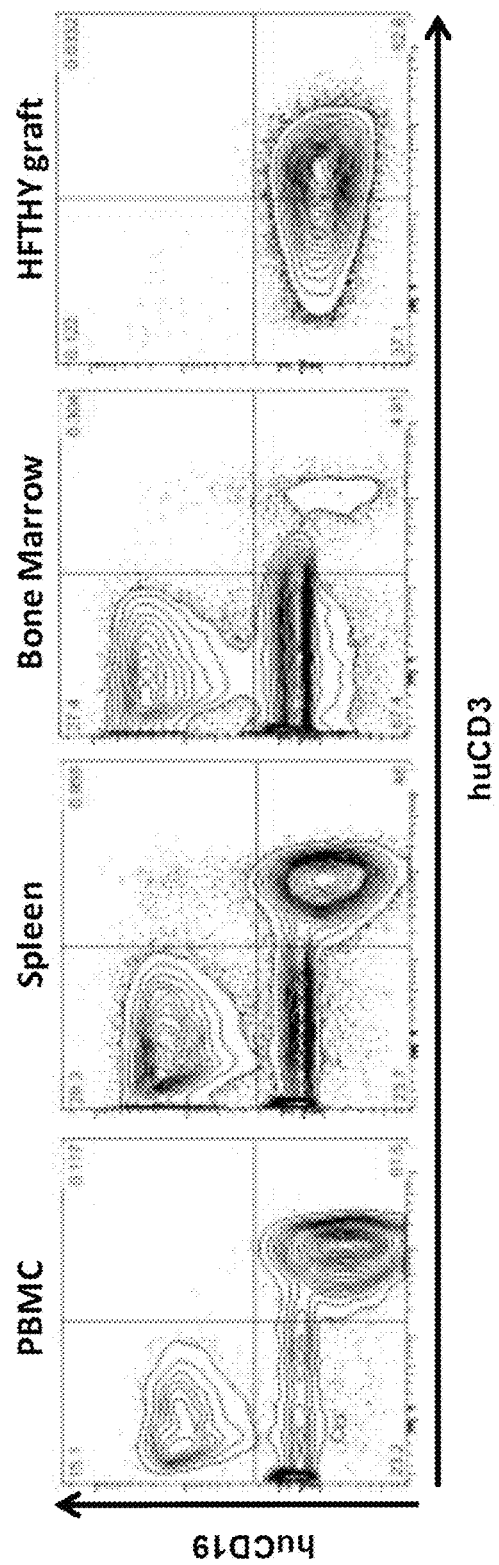

FIGS. 72A-B shows human lymphohematopoietic cell reconstitution in humanized mice. Graphs showing summary of flow cytometry data (FIG. 72A). Flow cytometric profiles (FIG. 72B) showing multilineages of human lymphohematopoietic cell reconstitution in different tissues prepared from a representative hu-mouse 22 weeks after transplantation of FTHY and CD34+ FLCs virally-transduced with MART-1-specific TCR gene.

FIGS. 73A-B shows CD4 T cells express a lower level of MART-1-specific TCR than CD8 T cells. (FIG. 73A) Representative flow cytometric profiles showing reconstitution of MART-1-specific TCR+ cells in peripheral blood CD8+ and CD8– (i.e., CD4+ confirmed by staining with anti-CD4 mAb) and fluorescence intensity of MART-1 tetramer staining 14 weeks after humanization. (FIG. 73B) Median fluorescence intensity (MFI; mean±SEMs; n=6) of MART tetramer staining in CD8+ and CD4+ T cells. ***, P<0.001.

Figure 74:
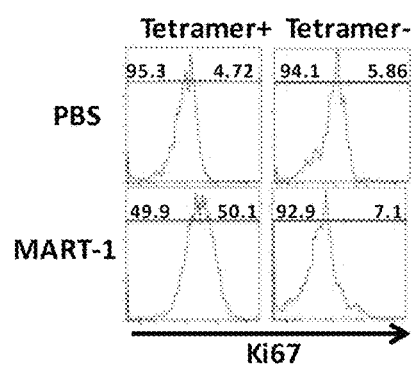
Figure 74:
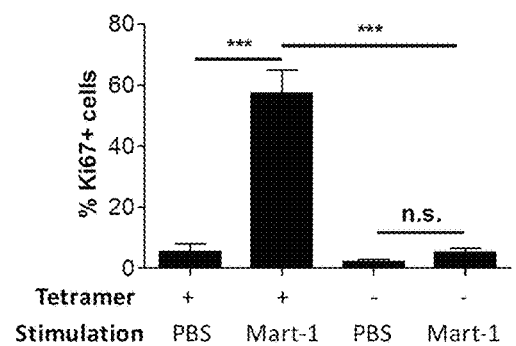
Figure 74:
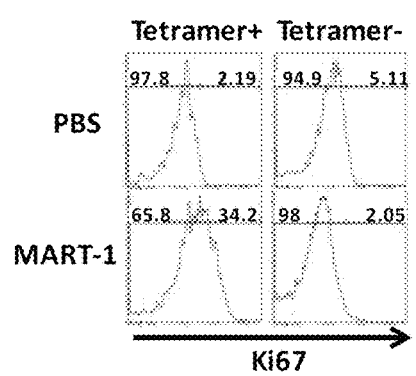
Figure 74:
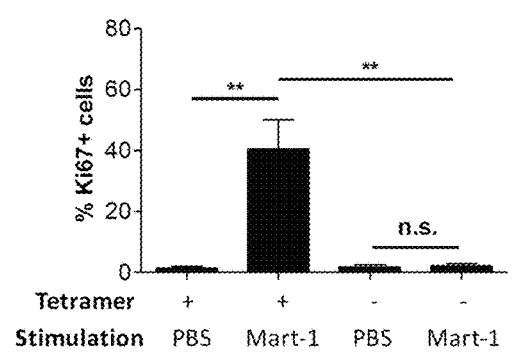

FIGS. 74A-B shows antigen specific response by both CD8 Tetramer+ T cells and CD4 Tetramer+ T cells in vitro. Spleen cells harvested from hu-mice were incubated with MART-1 peptides (10 μg/mL) or PBS as control for 3 days. Proliferation of CD8 (FIG. 74A) or CD4 (FIG. 74B) T cells was then determined by measuring Ki67 expression. N=7 per group. *, P<0.05; , P<0.01; *, P<0.001; n.s., not significant.

DETAILED DESCRIPTION

Type I diabetes (T1DM) results from the interplay of multigenic hereditary and poorly defined environmental factors. While HLA genotype is most strongly associated with disease[1-5], non-HLA-linked loci are clearly associated with T1DM risk[6-9]. Many of these loci are syntenic to non-MHC loci that contribute to autoimmunity in NOD mice[7], the model that most closely replicates the immunologic disorder in T1DM[10-12][13][3,14-18]. These include immunomodulatory genes, such as cytokines, costimulatory molecules and inhibitory molecules[7,6,19,20]. Defects in regulatory CD4 T cells[21-24] and NK/T cells[25,26] have been associated with both the murine and the human disease. Genetic studies have permitted analysis of mechanisms by which some of these genes promote autoimmunity in the NOD mouse model[6,7,19,27]. In humans with T1DM, however, the underlying defects arising from non-HLA-associated genes are largely undefined. Given that many of these loci contain immunoregulatory genes, it seems probable that intrinsic abnormalities in cells of the immune system, which originate from hematopoietic stem cells (HSCs), contribute to the development of autoimmunity. Indeed, abnormalities in T, B, NK, NKT and dendritic cells have been implicated in NOD mice and/or T1DM patients[25,27-35]. However, most of these studies involved analyses of T1DM patients after disease onset and do not distinguish cause from effects of disease or other (e.g. environmental) factors that precipitate disease. Thus, there is a need for models permitting the analysis of such defects in a controlled and prospective manner. In certain aspects, the invention provides development of a humanized mouse model allowing robust immune reconstitution from HSCs of T1DM patients can allow the identification of HSC-intrinsic, genetically determined abnormalities of the immune system that promote T1DM. The goal of this project is to develop such a model and to begin to explore HSC-intrinsic abnormalities in T cells associated with T1DM.

In certain aspects, the invention provides development of a humanized mouse model allowing robust immune reconstitution from HSCs of subject. In certain embodiments, the subjects are suffering from a disease or disorder, could allow the identification of HSC-intrinsic, genetically determined abnormalities of the immune system that promote the disease or disorder. In some embodiments, the disease or disorder is an immune disorder. In certain embodiments, the disease is HIV or AIDS. In other embodiments, the disease or disorder is autoimmune. In other embodiments, the disease or disorder is cancer.

"Humanized mouse" models have been developed. Human PBMC can populate immunodeficient mice[36], and human T cells can develop normally in human (HU) fetal thymus (THY) grafts implanted with a HSC source (fetal liver (LIV)) under the kidney capsule of immunodeficient mice[37]. However, there have been limitations to the immune analyses possible with these models, including the development of EBV-associated lymphproliferative disease in recipients of human PBMC[36,38] and a failure of T cells generated in HU THY/LIV grafts to populate the peripheral immune system at high levels or to function normally[37,39,40]. While improved immune function has been reported[41,42] with the use of NK cell-deficient, either class I-deficient or common gamma chain (γc) knockout NOD-SCID or RAG knockout mice as recipients of human HSCs[41-45], they require perinatal injection of HSCs, and only low numbers of human thymocytes populate the murine thymus.

The combination of human HSC injection and human fetal THY/LIV implantation under the kidney capsule has allowed high levels of human immune reconstitution, with large numbers (the order of $10^8$) of normal human thymocytes within the grafts and high levels of peripheral reconstitution of human T cells, B cells, immunoglobulins, and both myeloid and plasmacytoid dendritic cells[46,47]. Spontaneous rejection of xenografts was achieved in a humanized mouse model[46,47] and both T cell and antibody responses were elicited by protein immunization. This model has recently been reproduced with responses demonstrated to immunization with EBV[48]. Implantation of a human fetal THY in this model allows optimal homing, expansion and development of human thymocyte progenitors; once T cells develop and migrate to the periphery, the presence of reconstituted lymphoid tissues and human (syngeneic) APC populations in the periphery promotes expansion, survival and function of these T cells. Functional and phenotypically normal regulatory T cells (Tregs) are also generated in these grafts. Evidence indicates that these Tregs are rendered functional by interactions with the same HLA/peptide complexes as those present during positive selection in the thymus. Thymic epithelial cell MHC/peptide complexes positively select Tregs[49-51] and mouse data indicate that encounter with MHC[52] and with cognate antigen[53] in the periphery allows regulatory T cells to acquire and maintain full function.

Following emigration from the thymus, peripheral T cells are in a dynamic state in which T cell loss is counterbalanced by "homeostatic" expansion of naïve and memory T cells[54], maintaining a remarkably stable size T cell pool size[55,56]. Naïve T cells undergoing this type of expansion convert their phenotype permanently to that of memory T cells without specific antigen encounter[57-63], and can acquire certain effector functions, such as cytokine production[64,65]. Events during life, such as the decline in thymic function with age, clonal expansion due to infection and lymphopenia due to viral infections or therapeutic interventions are counterbalanced by these homeostatic processes[54]. T cell homeostatic expansion has been shown to require the same self MHC/peptide complexes as those present in the thymus during positive selection[54,58,66-71] [63,67,72-74] as well as cytokines such as IL-7 and IL-15[54,72,75-79]. Moreover, MHC/peptide complexes in the periphery play an important role in "tuning" T conventional cells to limit their autoimmune potential[52].

Abnormalities in lymphopenia-driven expansion have been implicated in the pathogenesis of T1DM in NOD mice and humans. One model to explain the immune defect in NOD mice involves increased apoptosis of peripheral T cells in association with decreased expression of anti-apoptotic molecules by T cells, resulting in lymphopenia, IL-21 production, and IL-21-driven T cell activation and expansion[80]. The breakdown in self-tolerance reflects in part the ability of autoreactive T cell clones to compete and survive in this environment due to their affinity for self antigens[54,80-82]. Indeed, several human autoimmune diseases[83-89], including T1DM[90,91], have been associated with lymphopenia and T1DM onset can follow viral infections that induce lymphopenia[54].

Defects in Treg numbers and function have been reported in T1DM patients and in NOD mice[22-24,92-97]. Moreover, transfer of Tregs[98,99] can reverse autoimmunity in NOD mice. However, Treg defects have not been borne up by all studies. In some, NOD mice have been found to have conserved Treg numbers and function[100,101], even with increasing age and disease onset[99], and some human studies have shown Treg conservation in T1DM patients[102]. Some of these discrepant data can be explained by the sole use of the CD25 marker to identify CD4$^+$ Treg in earlier studies, since this marker also identifies activated T cells[99,101,102]. More recent studies indicate that an insufficiency of Tregs at the site of inflammation in the pancreas rather than in lymphoid tissues and a relative resistance of effector cells to regulation may characterize the final stages of disease development in the NOD model[101]. However, studies in humans with T1DM have been limited to the analysis of peripheral blood samples, and much remains to be learned about whether or not primary defects in human Treg exist and are genetically programmed in T1DM patients.

Additionally, defects in NKT cells have been described in the periphery[25,30,31,103,104] and thymus[105,106] of NOD mice and in the blood of T1DM patients[26,92,101]. While decreases in NKT cell numbers have not been seen in all studies of T1DM patients[107,108], defective activation and cytokine production by these cells, including both IFN-γ[32,92,103] and IL-4[92,106,109] has been implicated in disease pathogenesis. Increasing the numbers of NKT cells[110,111] as well as in vivo activation of existing NKT cells[112-114] can reverse autoimmunity in NOD mice. A genetic basis for the abnormality in NKT cell function in these animals is indicated by its reversal by breeding to the NK complex, which contains the Idd6 locus, onto the NOD background[115].

In certain aspects, the invention provides a humanized mouse model and methods to examine possible defects in development, peripheral survival or peripheral "tuning"[52] of Tregs developing from HSC of T1DM patients. The instant model provides an opportunity to examine both the role of genetically programmed intrathymic and peripheral defects in the development of Treg and NKT cells.

In certain aspects, the invention provides a method of generating large numbers of diverse, functional, naïve T cells in mice using bone marrow cells from adult donors. The method involves using cryopreserved and thawed human fetal thymic tissue sharing HLA alleles with CD34+ cells from an adult patient bone marrow donor. The fetal thymus is implanted under the kidney capsule and the CD34+ cells are injected i.v. into any suitable mouse such as, but not limited to NOD-scid-common gamma chain knockout (NSG) immunodeficient mice, a NOD/Shi-scid/IL-2Rγnull (NOG) mouse, or any other mouse with a suitable genotype. Because of the HLA sharing between the thymus and the antigen-presenting cells generated from the adult patient donor, the T cells that are generated are able to function optimally with the antigen-presenting cells of the same adult donor. In certain embodiments, anti-CD2 antibody is given to the mice, combined with the cryopreservation and thawing of the thymus graft, so that T cells preexisting in the graft will not attack the adult bone marrow donor cells or the recipient mouse. T cells that develop in the fetal thymus graft from the injected adult bone marrow CD34+ cells are tolerant of the CD34+ cell donor and the mouse, most likely because these both generate antigen-presenting cells that contribute to tolerance induction in the thymus. It has been demonstrated that the T cells that populate the periphery of the mice receiving the thymus and adult CD34+ cell graft are functional and tolerant. Moreover, compared to the adult bone marrow donor, the T cell immune system in the reconstituted mice has been rejuvenated i.e. the percentage of antigen-inexperienced "naïve-type" T cells is greatly increased.

The availability of a large number of naïve T cells for infusion back to the original marrow donor has numerous therapeutic applications in patients with thymic insufficiency due to advanced age, extensive chemo/radiotherapy treatment, T cell-depleted hematopoietic cell transplantation, immunosuppressive drug treatment, graft-vs-host disease, or HIV infection.

In certain aspects the invention provides methods of using the cells therapeutically, including but not limited to T-cells, for T cell reconstitution/immunotherapy of patients.

In certain aspects, the invention provides therapeutic methods of adoptive transfer of the immune cells generated by the humanized mouse model of the invention. Provided herein are references which describe adoptive transfer methods for treatment of various diseases or disorders, the contents of which references are hereby incorporated by reference in their entireties: P. J. Ammolia, G. Muccioli-Casadei, H. Huls, S. Adams, A. Durett, A. Gee, E. Yvon, H. Weiss, M. Cobbold, H. B. Gaspar, C. Rooney, I. Kuehnle, V. Ghetie, J. Schindler, R. Krance, H. E. Heslop, P. Veys, E. Vitetta, and M. K. Brenner. Adoptive immunotherapy with allodepleted donor T-cells improves immune reconstitution after haploidentical stem cell transplantation. *Blood* 108 (6):1797-1808, 2006; H. E. Heslop, K. S. Slobod, M. A. Pule, G. A. Hale, A. Rousseau, C. A. Smith, C. M. Bollard, H. Liu, M. F. Wu, R. J. Rochester, P. J. Ammolia, J. L. Hurwitz, M. K. Brenner, and C. M. Rooney. Long-term outcome of EBV-specific T-cell infusions to prevent or treat EBV-related lymphoproliferative disease in transplant recipients. *Blood* 115 (5):925-935, 2010; P. J. Hanley, C. R. Cruz, B. Savoldo, A. M. Leen, M. Stanojevic, M. Khalil, W. Decker, J. J. Molldrem, H. Liu, A. P. Gee, C. M. Rooney, H. E. Heslop, G. Dotti, M. K. Brenner, E. J. Shpall, and C. M. Bollard. Functionally active virus-specific T cells that target CMV, adenovirus, and EBV can be expanded from naive T-cell populations in cord blood and will target a range of viral epitopes. *Blood* 114 (9):1958-1967, 2009; A. M. Leen, A. Christin, G. D. Myers, H. Liu, C. R. Cruz, P. J. Hanley, A. A. Kennedy-Nasser, K. S. Leung, A. P. Gee, R. A. Krance, M. K. Brenner, H. E. Heslop, C. M. Rooney, and C. M. Bollard. Cytotoxic T lymphocyte therapy with donor T cells prevents and treats adenovirus and Epstein-Barr virus infections after haploidentical and matched unrelated stem cell transplantation. *Blood* 114 (19):4283-4292, 2009; C. M. Bollard, S. Gottschalk, A. M. Leen, H. Weiss, K. C. Straathof, G. Carrum, M. Khalil, M. F. Wu, M. H. Huls, C. C. Chang, M. V. Gresik, A. P. Gee, M. K. Brenner, C. M. Rooney, and H. E. Heslop. Complete responses of relapsed lymphoma following genetic modification of tumor-antigen presenting cells and T-lymphocyte transfer. *Blood* 110 (8): 2838-2845, 2007; C. Quintarelli, J. F. Vera, B. Savoldo, G. M. Giordano Attianese, M. Pule, A. E. Foster, H. E. Heslop, C. M. Rooney, M. K. Brenner, and G. Dotti. Co-expression of cytokine and suicide genes to enhance the activity and safety of tumor-specific cytotoxic T lymphocytes. *Blood* 110 (8):2793-2802, 2007; B. Savoldo, J. A. Goss, M. M. Hammer, L. Zhang, T. Lopez, A. P. Gee, Y. F. Lin, R. E. Quiros-Tejeira, P. Reinke, S. Schubert, S. Gottschalk, M. J. Finegold, M. K. Brenner, C. M. Rooney, and H. E. Heslop. Treatment of solid organ transplant recipients with autologous Epstein Barr virus-specific cytotoxic T lymphocytes (CTLs). *Blood* 108 (9):2942-2949, 2006; A. M. Leen, G. D. Myers, U. Sili, M. H. Huls, H. Weiss, K. S. Leung, G. Carrum, R. A. Krance, C. C. Chang, J. J. Molldrem, A. P. Gee, M. K. Brenner, H. E. Heslop, C. M. Rooney, and C. M. Bollard. Monoculture-derived T lymphocytes specific for multiple viruses expand and produce clinically relevant effects in immunocompromised individuals. *Nat Med* 12 (10):1160-1166, 2006; Y. Cui, H. Zhang, J. Meadors, R. Poon, M. Guimond, and C. L. Mackall. Harnessing the physiology of lymphopenia to support adoptive immunotherapy in lymphoreplete hosts. *Blood* 114 (18):3831-3840, 2009; G. Brestrich, S. Zwinger, A. Fischer, M. Schmuck, A. Rohmhild, M. H. Hammer, A. Kurtz, L. Uharek, C. Knosalla, H. Lehmkuhl, H. D. Volk, and P. Reinke. Adoptive T-cell therapy of a lung transplanted patient with severe CMV disease and resistance to antiviral therapy. *Am J Transplant* 9 (7):1679-1684, 2009; K. P. Micklethwaite, L. Clancy, U. Sandher, A. M. Hansen, E. Blyth, V. Antonenas, M. M. Sartor, K. F. Bradstock, and D. J. Gottlieb. Prophylactic infusion of cytomegalovirus-specific cytotoxic T lymphocytes stimulated with Ad5f35 pp 65 gene-modified dendritic cells after allogeneic hemopoietic stem cell transplantation. *Blood* 112 (10):3974-3981, 2008; B. G. Till, M. C. Jensen, J. Wang, E. Y. Chen, B. L. Wood, H. A. Greisman, X. Qian, S. E. James, A. Raubitschek, S. J. Forman, A. K. Gopal, J. M. Pagel, C. G. Lindgren, P. D. Greenberg, S. R. Riddell, and O. W. Press. Adoptive immunotherapy for indolent non-Hodgkin lymphoma and mantle cell lymphoma using genetically modified autologous CD20-specific T cells. *Blood* 112 (6):2261-2271, 2008; G. Parmiani, A. De Filippo, L. Novellino, and C. Castelli. Unique human tumor antigens: immunobiology and use in clinical trials. *J Immunol* 178 (4):1975-1979, 2007; J. J. Sussman, R. Parihar, K. Winstead, and F. D. Finkelman. Prolonged culture of vaccine-primed lymphocytes results in decreased antitumor killing and change in cytokine secretion. *Cancer Res.* 64 (24):9124-9130, 2004.

The invention provides a method of treating or preventing a disease, for example but not limited to cancer, or an immunodeficiency, in a subject. An embodiment of the method comprises administering to the subject a composition comprising autologous T cells, isolated from the humanized mouse model, in an amount effective to treat the disease or immunodeficiency, wherein the autologous T cells are not ex vivo-expanded, cultured or activated. In certain embodiments, the invention provides a method of treating cancer in a subject, who optionally has undergone lymphodepleting chemotherapy, the method comprising administering to the subject a composition comprising autologous T cells isolated from the instant mouse model, including but not limited to, NKT, in an amount effective to treat cancer. Skilled artisans can readily determine the dose and regimen for administering cells isolated from the instant humanized mouse model, so as to achieve a therapeutic effect.

According to one aspect of the present invention, antigen-specific adoptive T-cell immunotherapy is provided by obtaining T-cells from the mouse model, wherein the T cells are expanded in vivo in the mouse model, and not ex-vivo, in the presence of the specific antigen against which the therapy is directed, and returning the expanded T-cells into the patient.

According to another aspect, the current invention provides a method for the generation of preparations of T-cells that are specific for at least one target antigen. Such preparation can be used in adoptive transfer for medical purposes, particularly in the treatment of infectious diseases, cancer and other diseases where antigen-specific T-cells are of benefit to the subject. The method according to the invention comprises the steps of making a humanized mouse model as described, exposing the mouse model to an antigen of interest, yielding a population of antigen specific T-cells, isolating the T-cell population from the mouse, and administering the isolated T-cells to the bone marrow donor, in an amount sufficient to cause therapeutic effect.

The isolation step may be carried out by any suitable method, and by way of example, may comprise sedimentation of the cells by centrifugation or other means to concentrate the cell preparation, so as to facilitate the application of the cell preparation to a patient, for example by injection.

According to one aspect of the invention, a method is provided, whereby one or more target antigens or peptide fragments thereof are administered to the mouse. Such target antigen presence, for example in soluble form as peptides or protein fragments, or complexed to carrier structures, can stimulate the immune system of the humanized mouse model to produce immune cells against the target antigens.

In certain aspects, the invention provides methods for treatment of diseases or disorders, for example but not limited to specific infections or cancers, comprising administering human T cells, in non-limiting example these are cells isolated from the periphery plus or minus the thymus of the claimed mouse model. Depending on the specific application, the cells used in the therapeutic methods may include transfer of specific cell populations, or the whole repertoire of T cells. In certain aspects, the invention provides methods for reconstitution of immune system of subjects in need thereof, for example but not limited to subjects whose thymus is not functioning well, comprising administering human T cells, in non-limiting example these are cells isolated from the periphery of the mouse model. In certain embodiments, the cells used in the adoptive transfer methods are T-cells derived from the mouse model. In certain embodiments, the T-cells are isolated and purified. In certain embodiments, the T cells which are infused by adoptive transfer are CD8+ T-cells. In other embodiments, the cells which are infused by adoptive transfer comprise, consist essentially of, or consist, the whole repertoire of T cells, including naïve T-cells. In certain embodiments, the cells used in the adoptive transfer methods are comprised in a therapeutic composition suitable for administering to human subjects.

The availability of a large number of naïve T cells for infusion back to the original marrow donor has numerous therapeutic applications in patients with thymic insufficiency due to advanced age, extensive chemo/radiotherapy treatment, T cell-depleted hematopoietic cell transplantation, immunosuppressive drug treatment, graft-vs-host disease, or HIV infection.

In certain aspects, the methods include immunization with specific antigens, whereby the mice could also provide T cells recognizing specific antigens to which the marrow donor/patient is unable to amount an effective immune response. In non-limiting examples, cancer patients, in whom tumor-specific T cells are tolerized by the tumor itself, can be infused with T-cells obtained from the instant mouse model, wherein the mouse was reconstituted with CD34+ cells from the cancer patient, and the mouse was exposed to antigens from the patient's cancer.

In another embodiments, immunosuppressed patients who have developed lymphoproliferative diseases caused by EBV, for example but not limited to e.g. post-transplant lymphoproliferative disease, can be infused with T-cells obtained from the instant mouse model. In certain embodiments, the mouse model is immunized with EBV antigens.

In another embodiment, immunosuppressed patients and/or patients with HIV infection who develop opportunistic infections, for example but not limited to CMV disease, aspergillosis, or any other viral, bacterial or fungal infection, can be infused with T-cells obtained from the instant mouse model. In certain embodiments, the mouse model is immunized with CMV antigens.

In certain embodiments, the adult donor CD34+ cells could be genetically modified to be made resistant to viruses that persist in the adult patient who will receive the T cells produced in the mice. Non-limiting examples of such modification include knockdown or mutation of CCR5 and/or CXCR4 in CD34+ cells from HIV-infected patient will make the new T cells produced in the mouse model resistant to HIV infection when they are returned to the patient.

In addition to expanding T cells with desired specificities by immunization of the mice, T cell differentiation for particular desired functions could also be directed in the mouse model. In a non-limiting example, the mice could be exposed to donor antigens or patient autoantigens in a manner that is conducive, for example via particular APCs, cytokines, to the differentiation of regulatory T cells in order to treat/prevent graft rejection/GVHD or autoimmune disease, respectively.

In other embodiments, the mice could also be used to generate an a priori tolerant immune system to an allograft donor, or an HCT recipient, in situations where organ, or hematopoietic cell, transplantation involves the use of recipient, or donor HCT graft, T cell depletion. For example, a patient could receive exhaustive in vivo T cell depletion as part of a non-myeloablative regimen for allogeneic HCT for the purpose of mixed chimerism/tolerance induction to an organ from the same donor. While, or even before mixed chimerism is being generated in the patient, CD34+ cells from both the donor and the patient could be reconstituting T cells that are mutually tolerant of one another in the mice. These could be infused to achieve rapid immune reconstitution of the adult recipient, whose thymus is not functioning well due to age and/or conditioning therapy.

In certain aspects, the invention provides a mouse model, where the mouse has received i.v. infusion of CD34+ cells from a donor and recipient, thereby the reconstituted immune system shows mixed chimerism and the reconstituted T-cells are tolerant to both recipient and donor tissues and/or cells.

In one aspect, the invention provides a non-human animal that is a recipient of CD34+ cells from a donor and tissue from a thymus which has been previously depleted of CD34+ cells, e.g., by cryopreservation and thawing, so that the non-human animal produces efficiently the in vivo development of a large pool of autologous, polyclonal, diverse and naïve T cells.

Mixed chimerism as described provides advantage in bone marrow transplantation, organ or tissue transplantation.

Example 1

The genetic predisposition to Type I diabetes (T1DM) can be associated with T cell-intrinsic abnormalities in the function of regulatory cells and in homeostatic expansion. Abnormalities in regulatory T cell function have been implicated in the NOD mouse model and in T1DM patients. Lymphopenia and increased "homeostatic" expansion have also been implicated in the development of autoimmunity in NOD mice. However, models allowing the analysis of these phenomena have not previously been available for human T cells. The invention provides a humanized mouse model in which robust peripheral reconstitution with human antigen-presenting cells (APCs) in combination with a human thymus graft allows the optimal development, peripheral survival and function of human T cells, including Treg. Moreover, it has been demonstrated that thymic epithelial cells co-implanted in thymus grafts can influence thymocyte selection and tolerance.

In certain aspects, the invention provides methods to reaggregate human thymus transplant model allowing human thymopoiesis in HLA-defined human thymus grafts. These studies can extend the humanized mouse model; instead of implanting intact fetal thymus tissue, CD45-negative thymic stromal cells cryopreserved from HLA-typed human fetal thymic tissue can be implanted under the kidney capsule of NOD-SCID mice. Without being bound by theory, thymi bearing common diabetes-susceptibility HLA alleles can support the thymopoiesis of T cells from i.v.-injected CD34+ cells from normal control and Type 1 diabetic subjects sharing these alleles. Alternative approaches include injection of intact human thymic tissue with thymic epithelial cells derived from HLA-transgenic NOD mice or adenoviral transduction of genes encoding diabetes susceptibility alleles into thymus grafts.

In certain aspects, the invention provides methods to compare peripheral survival, homeostatic expansion, phenotypic conversion and self-tolerance of conventional T cells derived from CD34 cells of T1DM versus normal controls. It can be determined whether or not T cells from T1DM patients show increased lymphopenia-driven expansion in association with loss of tolerance to "self" antigens of the thymus donor. It can be determined whether or not intrinsic abnormalities in homeostasis characterize T cells in T1DM patients.

In certain aspects, the invention provides methods to compare numbers, function and peripheral phenotypic conversion of regulatory T cells derived from CD34 cells of T1DM versus normal controls. Tregs and NKT cells derived from stem cells of T1DM patients may show defects. These studies can identify intrinsic abnormalities in regulatory cells from T1DM patients and their thymic versus post-thymic origin.

In certain embodiments, bone marrow can be collected from HLA-typed T1DM patients and normal volunteers. A 5-6 ml BM aspirate can provide sufficient CD34 cells (about $1.25 \times 10^6$) to transplant 10-12 NOD-SCID mice. HLA-transgenic NOD mice are available, and can be made by methods known in the art.

Provided herewith are data supporting the approach in which allogeneic human thymi can be used to support thymopoiesis from HSC of T1DM patients and controls. In certain embodiments are provided: 1) the development of a humanized mouse model allowing detailed analysis of human conventional and regulatory T cell development, function and homeostasis; 2) a variation on this model involving human T cell development in a xenogeneic thymus. The data obtained through these studies indicate that in certain embodiments a model involving human thymus grafts sharing MHC molecules with HSC donors can be essential for optimal human Treg development and function and T cell homeostasis; 3) an additional xenogeneic thymic transplantation model demonstrating that thymic epithelial cell implantation into thymic grafts can promote normal Treg and conventional T cell development and function.

Humanized Mouse Model for Assessing Human Immune Responses.

Figure 1:
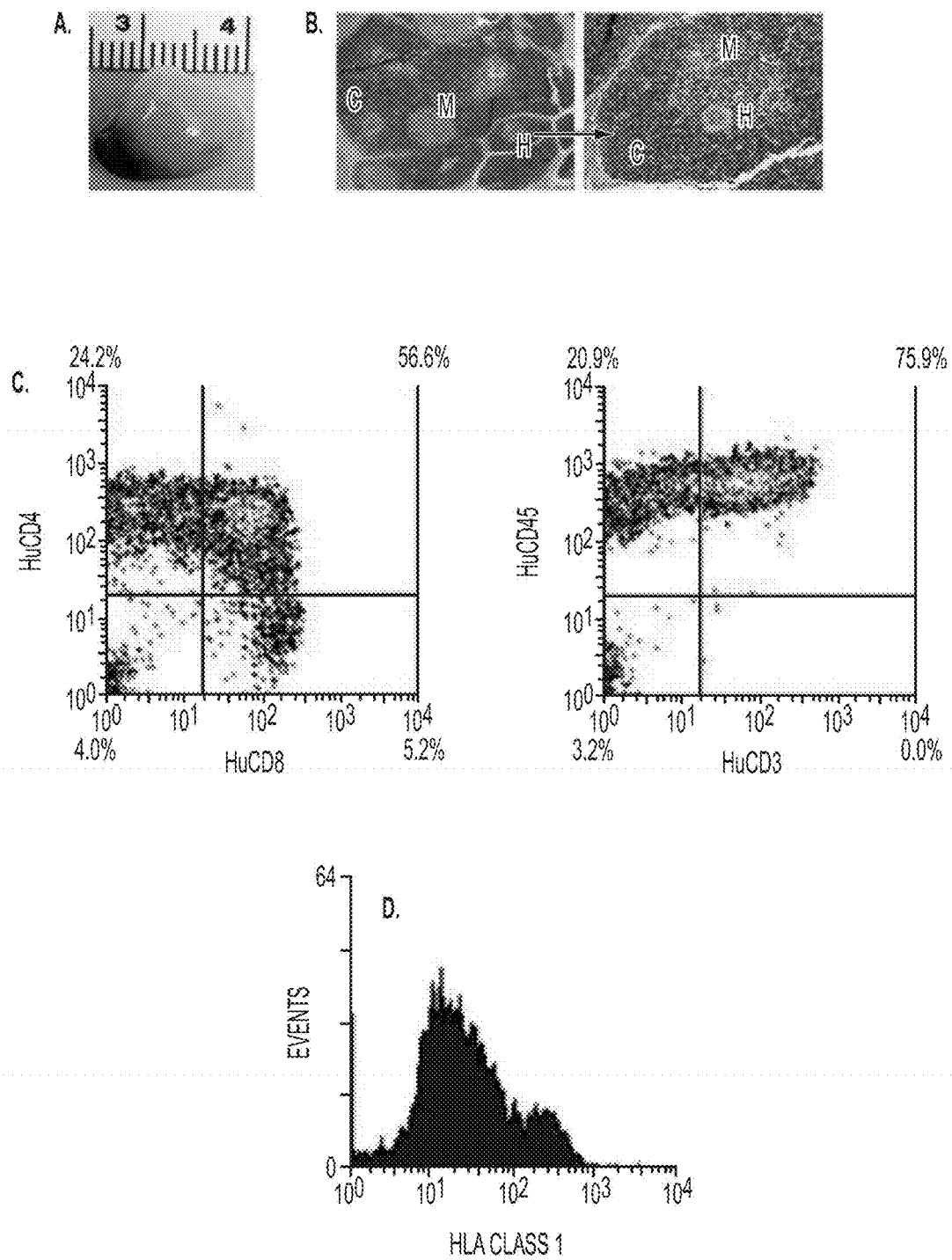
FIGS. 1A-D. Normal human thymopoiesis in long-term human thymus grafts implanted under the kidney capsule of NOD-SCID mice. Typical results are shown for THY/LIV grafts 20 weeks post-implantation.
Figure 2:
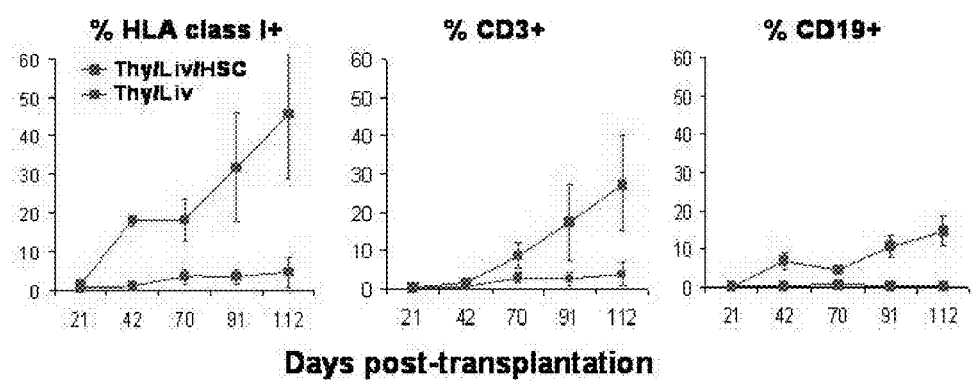
FIG. 2. Increased human chimerism in PBMC of NOD-SCID mice receiving human FL CD34 cell i.v. in addition to THY/LIV grafts under the kidney capsule from the same donor. The time course for human PBMC reconstitution is shown for groups receiving THY/LIV grafts alone (Thy/Liv, green line) or with i.v. injection of CD34 cells (Thy/Liv/HSC, red Line).
Figure 3:
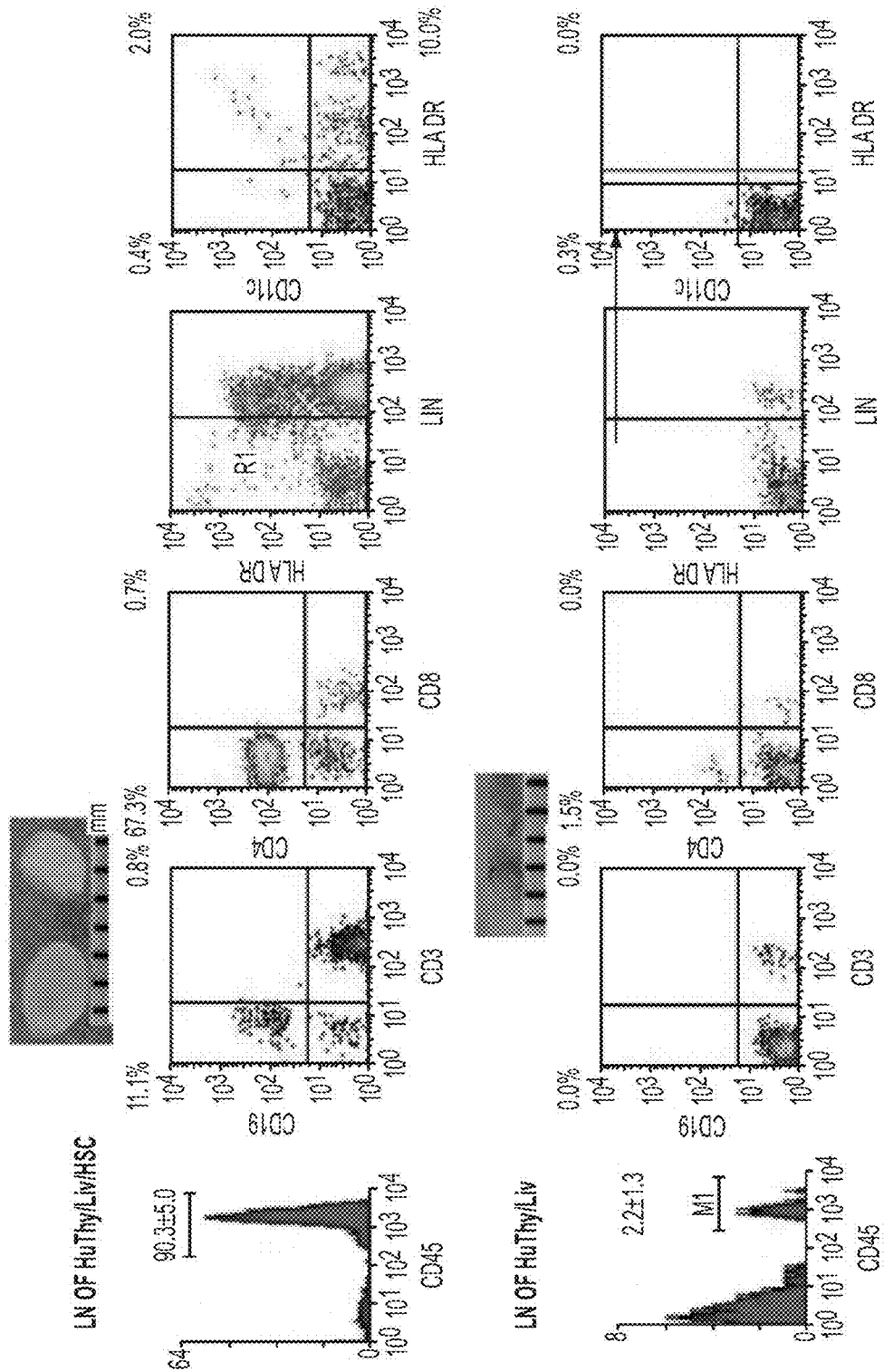
FIG. 3. Increased repopulation of NOD-SCID mouse lymph nodes with human T, B and dendritic cells (DCs) in recipients of i.v. CD34 cells in addition to THY/LIV grafts. Lymph nodes were anylized 25 weeks after implantation of fetal human THY/LIV grafts with (HuThy/Liv/HSC) or without (HuThy/Liv) i.v. injection of CD34 cells from the same fetal liver. Photographs show the gross appearance of the lymph nodes, which were markedly increased in size in the animals that received CD34 cells i.v. The panels on the far right show CD11c expression on gated HLA-DR+, Lin-lymph node cells, demonstrating the presence of DCs in the animals that received i.v. CD34 cells.
Figure 4:
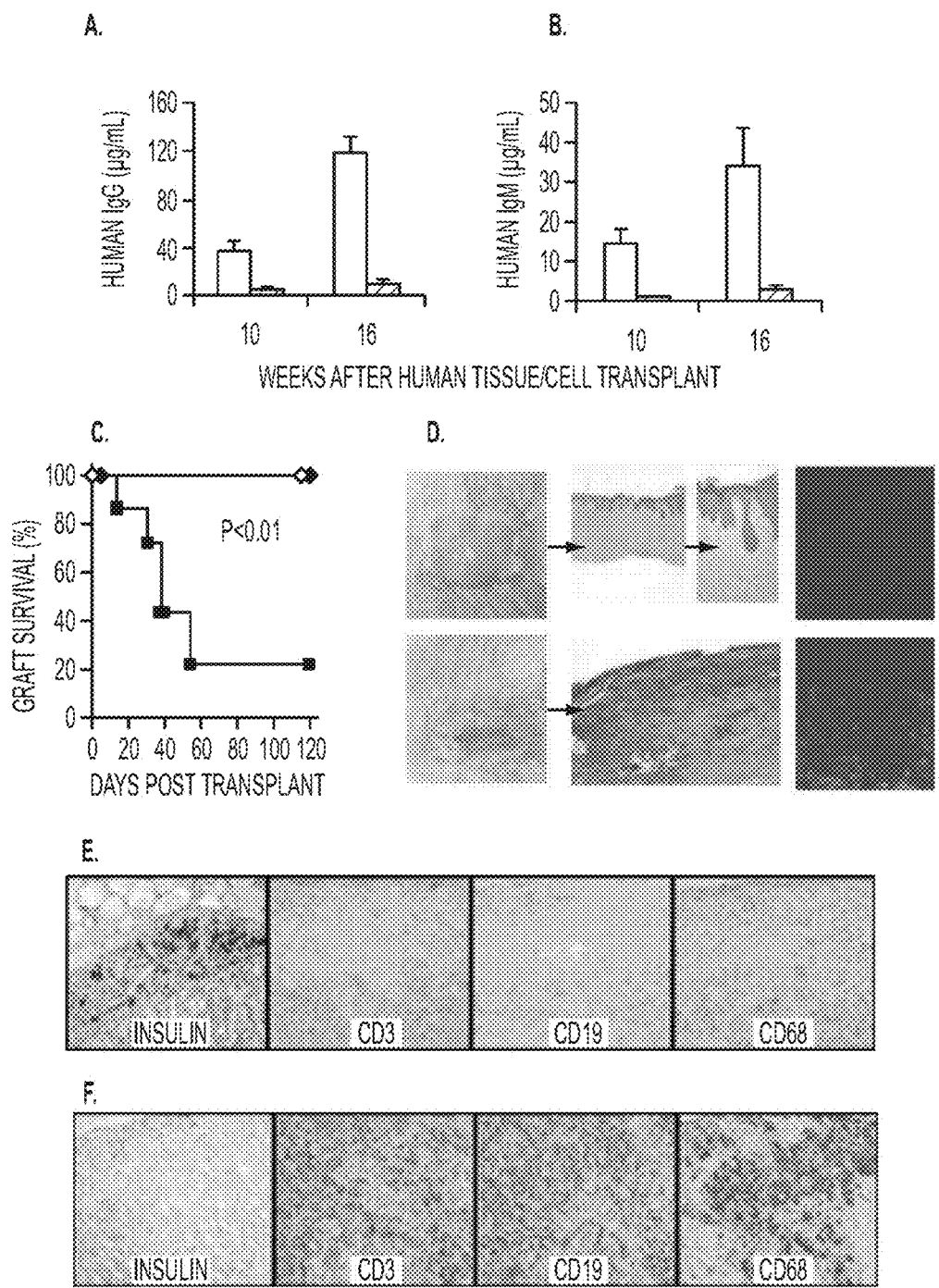
FIGS. 4A-F. Serum levels of human IgG (FIG. 4A) and IgM (FIG. 4B) in mice receiving Thy/Liv/HSC (□) or Thy/Liv alone (■) at the indicated times after human tissue/cell transplantation.

Implantation of fetal human thymus (THY) along with fetal liver (LIV) tissue fragments under the mouse kidney capsule achieves normal human thymopoiesis and T cell development in immunodeficient mice[116] (FIG. 1). While human T cells developing in these mice showed strong allogeneic and xenogeneic mixed lymphocyte responses (MLRs), they were incapable of rejecting porcine skin xenografts[46,117]. Since post-thymic T cell contact with self-peptide MHC ligands maintains the antigen reactivity of mature T cells[118] and HSC-derived APC promote antigen-specific T cell responses[119], without being bound by theory, the paucity of peripheral human APC can limit the in vivo immune responses of human T cells that develop in human thymus grafts in THY/LIV-grafted mice. Since i.v.-administration of human HSC to immunodeficient mice permits high levels of non-T cell human immune reconstitution[120-129], improved T cell reconstitution and function can be achieved by adding CD34 cell transplantation i.v. in NOD-SCID recipients of human THY/LIV grafts. NOD-SCID mice received 1.5-3 Gy TBI followed by transplantation of fetal human THY/LIV tissue under the kidney capsule either alone or with CD34+ fetal liver cells (FLC; $1 \times 10^5$) i.v. The i.v.-addition of $CD34^+$ HSC significantly improved human hematopoietic repopulation and lymphopoiesis (FIG. 2). Although functional human thymopoiesis (i.e., CD3' T cell development) was detected in both groups, significant repopulation with $CD19^+$ B cells and myeloid lineages was only seen in THY/LIV/CD34+ FLC-transplanted mice (FIG. 2). Moreover, the recipient lymph nodes from THY/LIV/$CD34^+$ FLC-transplanted, but not THY/LIV-transplanted mice were markedly enlarged (to a size resembling immunocompetent mouse lymph nodes) compared to the rudimentary nodes in control NOD-SCID. The former were populated with human CD3+ T, CD19+ B, and Lin−class II+ myeloid and plasmacytoid dendritic cells (FIG. 3 and[47]). THY/LIV/CD34+ FLC-transplanted mice also had significantly increased serum levels of human Ig (FIG. 4A,B). These mice showed markedly improved human immune responses in vivo as demonstrated by the ability to reject porcine skin (FIG. 4C,D) and islet (FIG. 4E,F) xenografts. This study was the first to demonstrate rejection of xenografts in humanized immunodeficient mice without the injection of pre-activated human T cells.

Antigen-specific human T cell and antibody responses were assessed in human Thy/Liv/CD34+ FLC-transplanted (i.e. "humanized") NOD-SCID mice. As shown in FIG. 5A, T cells from DNP-KLH-immunized but not control humanized mice proliferated in response to KLH in vitro. Germinal centers were detected in the secondary lymphoid tissues of immunized humanized mice (FIG. 5B). DNP-specific IgGs (mainly IgG1 and IgG2) were detected in the immunized, but not control, humanized mice (FIG. 5C). Thus, the human immune system developing in these mice can mediate specific T and B cell responses in vivo. The improved T cell function achieved by the i.v.-administration of human CD34 cells in recipients of human THY/LIV grafts suggests that interactions with human APC in the periphery promote immune function of human T cells emerging from the human thymus graft. This improvement in function can reflect improved T cell-APC interactions when adhesion receptors, cytokines, etc., are homologous rather than xenogeneic (i.e. murine).

Human Treg function and T cell homeostatic expansion are improved by development in a human compared to a xenogeneic thymus graft: High levels of normal human thymopoiesis (FIG. 6) with a diverse repertoire (FIG. 7) can also occur in swine (SW) thymic xenografts implanted with HU FL, resulting in xenogeneic tolerance[117] (FIG. 8). I.V. injection of human CD34+ FLC into SW/HU THY/LIV-grafted NOD/SCID mice (referred to as SW/HU mice) increases human hematopoiesis and T cell repopulation to comparable levels to mice receiving HU/HU THY/LIV plus human CD34+ FLC (referred to henceforth as HU/HU mice) (FIG. 9). In HU/HU mice, the human APC in the periphery and the thymic epithelium are from the same donor, while in the SW/HU mice the thymic epithelium is xenogeneic to the human T cells and to the human APC in the periphery (Table 1). Previous experience in a pig-to-immunocompetent mouse (thymectomized, T cell depleted to permit xenogeneic thymic engraftment) model demonstrated that xenogeneic thymic epithelium was entirely responsible for positive selection of xenogeneic T cells, with no contribution from the recipient MHC[130-132]. Recipient APCs populating the thymic xenografts contributed to negative selection, resulting in deletional tolerance to donor and recipient antigens[132-135]. Without being bound by theory, a similar situation can prevail in the SW/HU model. Human APCs are present in these porcine thymic grafts (FIG. 6C)[117] and, without being bound by theory, can play an important role in negative selection of (human) self-reactive thymocytes.

Figure 10:
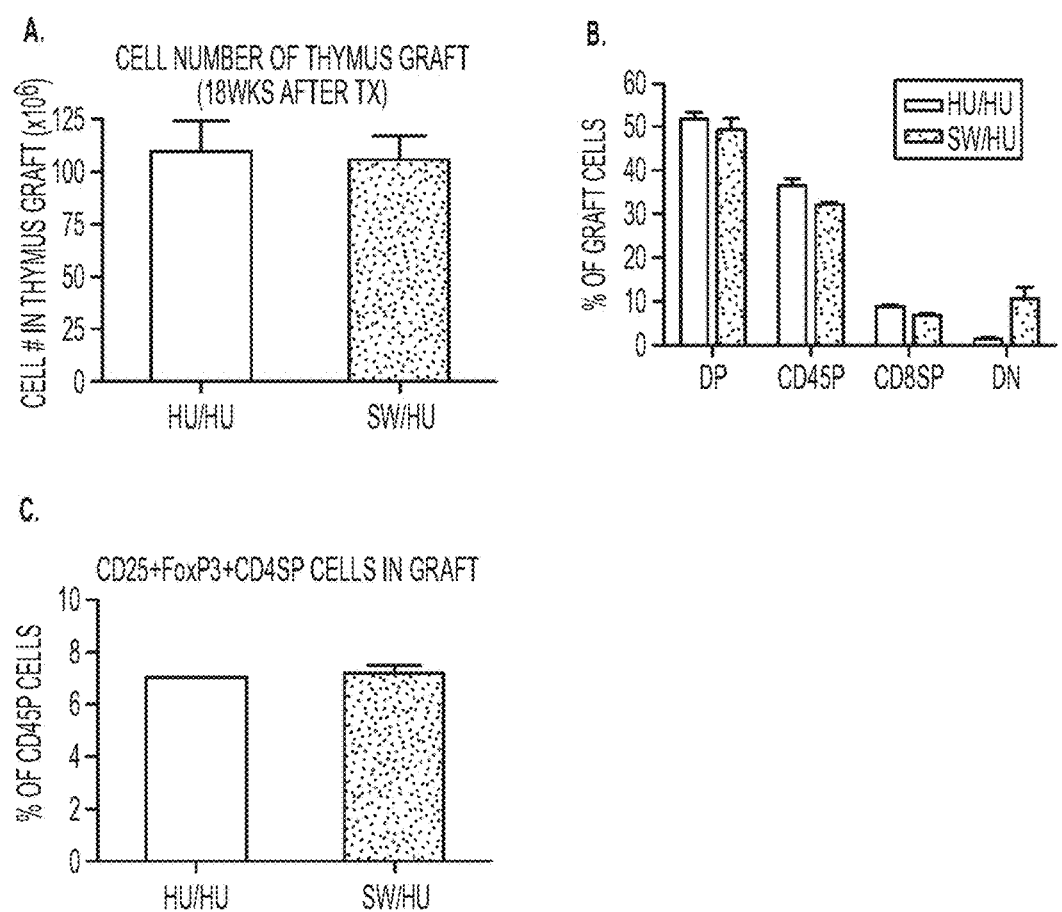

Similar thymocyte numbers and normal subset distributions were detected in SW/HU and HU/HU grafts (FIG. 10). Human Treg are generated in both HU/HU and SW/HU grafts, with similar numbers of FoxP3+ cells among CD4 SP thymocytes (FIG. 11), with similar phenotypes: largely CD45RA+CD45RO+HLA-DR$^{lo}$. While similar percentages of human FoxP3+CD127$^{-/low}$, CD25+ cells were detected in the periphery of SW/HU and HU/HU mice (FIG. 12), some significant phenotypic differences were observed between their phenotypes. As shown in FIG. 13, most CD4+CD25$^{hi}$ cells in normal human PBMC are FoxP3+ Treg that are CD45RA+CD45RO− "memory-type" Treg[136,137], and a high proportion express HLA-DR. Among PBMC of HU/HU mice analyzed 18 weeks after thymus grafting, most CD4+CD25$^{hi}$ cells also expressed FoxP3 (FIG. 13, middle panel), but a high percentage of these expressed both CD45RA and CD45RO, and many also expressed HLA-DR. The CD45RA+/CD45RO+ phenotype may indicate cells in transition to the "memory" phenotype in these animals that are much younger than normal adult human donors. In contrast, most CD4+CD25$^{hi}$ PBMC from SW/HU mice also expressed FoxP3 but still expressed the CD45RA+/CD45RO− "naïve" phenotype, and very few of them expressed HLA-DR (FIG. 13, bottom panel and FIG. 14). HLA-DR+ Treg reportedly have greater suppressive function than their HLA-DR− counterparts[138]. These data indicate that Treg developing in SW/HU grafts may undergo less post-thymic stimulation than those derived from HU/HU grafts, which encounter the same MHC in both the thymus and the periphery.

Peripheral Treg isolated (FIG. 15) from SW/HU mice showed reduced suppressive activity compared to those from HU/HU mice, which suppressed MLR responses as effectively as CD25+CD4+ cells from normal human PBMC (FIG. 16). Treg CD45RO and HLA-DR expression varied directly with the level of suppressive activity for cells derived from individual SW/HU mice (FIGS. 16 and 17). Together, the data indicate that HLA-DR expression and conversion to the memory phenotype are markers of peripheral activation or "tuning" of Treg that is optimized by peripheral encounter with the same MHC antigens as those involved in thymic positive selection. Consistently, peripheral expansion of murine Treg has been shown to be promoted by the positively selecting MHC/peptide complex[139].

To compare lymphopenia-driven expansion between human T cells generated in SW versus autologous HU THY grafts, naïve CFSE-labeled naïve T cells (FIG. 18) were adoptively transferred from SW/HU and HU/HU mice into mice reconstituted with human APC but lacking T cells ("HU-APC mice"; NOD-SCID mice that had received human FL CD34+ cells i.v. without a THY graft, FIG. 19). As shown in FIG. 20, a substantial proportion of these T cells proliferated and converted to the CD45RA−CD45RO+ phenotype after adoptive transfer into the T cell-deficient hosts. While the amount of division was similar for T cells from SW/HU and HU/HU mice, conversion to the "memory" phenotype was more extensive for T cells from HU/HU compared to SW/HU mice. Moreover, the number of T cells recovered in the adoptive recipients correlated with the levels of human hematopoietic reconstitution in the adoptive HU-APC recipients prior to transfer (FIG. 21), indicating that human APC supported expansion and/or survival of human T cells. Consistent with this interpretation, human T cells could not be recovered following adoptive transfer to unreconstituted NOD-SCID adoptive recipients (FIG. 21). Importantly, for adoptive recipients with similar levels of human hematopoietic reconstitution, the recovery of transferred T cells was reduced when the T cells were generated in SW compared to HU THY grafts (FIG. 21), These data establish the utility of the adoptive transfer model for the analysis of lymphopenia-driven expansion of human T cells. The data demonstrate for the first time that human, like murine, naïve T cells, undergo lymphpenia-driven expansion and convert to the memory phenotype in so doing. The data indicate that expression of the same MHC as that present in the positively selecting thymic environment may promote the survival and/or expansion of human T cells in a lymphopenic environment, as has been demonstrated for mice[54,58,66-71].

Implantation of Autologous Thymic Epithelial Cells Affects T Cell Selection in Thymus Grafts.

Normal, immunocompetent mice that are thymectomized (ATX), then treated with T cell depleting mAbs, permit engraftment, growth and function of fetal porcine (FP) THY tissue grafted under the recipient kidney capsule[133] (FIG. 22). The pig THY replaces the host THY, permitting peripheral T cell reconstitution[132,133,140] and donor-specific xenograft tolerance is achieved[133,134]. Murine T cells entering the periphery are functional and clear opportunistic infections[141]. Both porcine and murine APC present in FP THY grafts mediate intrathymic negative selection[132-135], while positive selection is mediated exclusively by porcine donor MHC[130-132].

While the FP THY/LIV-grafted ATX mice generally show excellent health, a large portion (>60%) of FP THY/LIV-grafted nude mice develop multi-organ autoimmune disease[135]. While ATX FP THY/LIV-grafted mice have residual host thymus-derived T cells in the periphery, nude mice lack a pre-existing CD4 pool, including Tregs. Adoptive transfers from FP THY/LIV-grafted nude mice to secondary BALB/c nude recipients revealed that autoimmune disease was induced by $CD25^-$ splenocytes from FP THY/LIV-grafted nude mice. Furthermore, $CD25^+CD4^+$ cells from FP THY/LIV-grafted nude mice showed impaired ability to suppress disease in secondary recipients compared to cells from normal BALB/c mice. Thus, autoimmunity in T cell-deficient nude mice after grafting with FP THY/LIV may reflect impaired suppression of anti-host immunity by Treg and increased autoreactivity among $CD25^-$ $CD4^+$ cells.

The addition of recipient thymic epithelial cells (TEC) to porcine thymic xenografts can positively select Treg on mouse thymic epithelium[49,51,142] that can suppress autoimmunity by encounter with the same antigens in the periphery. Moreover, "ectopic" production of organ-specific proteins by the murine thymic epithelium[51,143-146] can delete tissue-specific $CD25^-$ T cells in a xenogeneic thymus. The effect of injecting BALB/c recipient-type TEC [obtained by collagenase/dispase/DNase digestion and negative selection (with anti-CD45-MACS beads)] into FP THY grafts was therefore evaluated. As shown in FIG. 23, spleen cells from FP THY/LIV-grafted nude mice in which BALB/c TEC had been implanted induced less wasting syndrome in BALB/c nude mouse adoptive recipients, and spleen cells from these animals partially suppressed the wasting syndrome induced by splenocytes from mice grafted with FP THY/LIV without BALB/c TEC. Two-color fluorescent staining of the THY grafts that were injected with murine TEC clearly showed the long-term persistence of murine TEC in the FP THYgrafts of these animals (FIG. 24). These studies establish that injection of isolated thymic epithelial cells can impact the selection of conventional T cells and Treg.

Experimental Design and Methods

In certain aspects, the invention provides methods to develop a reaggregate human thymus transplant model allowing human thymopoiesis in HLA-defined human thymus grafts. These studies can extend the humanized mouse model; instead of implanting intact fetal THY tissue, CD45-negative thymic stromal cells cryopreserved from HLA-typed human fetal thymic tissue can be implanted under the kidney capsule of NOD-SCID mice. Without being bound by theory, thymi bearing common diabetes-susceptibility HLA alleles can support the thymopoiesis of T cells from i.v. injected CD34+ cells from normal control and T1DM subjects sharing these alleles.

NOD-SCID mice receiving HU THY/LIV grafts and CD34 cells i.v. from the same donor reconstitute normal human thymocyte, T cell, B cell and APC populations, develop secondary lymphoid organs and demonstrate T cell and antibody responses to immunization. Moreover, normal percentages of Treg are generated. While this model can be used to examine hematopoietic stem cell (HSC)-dependent T cells derived from T1DM HSC, the fetal THY donors would be allogeneic to the T1DM HSC donors. Since peripheral survival, lymphopenia-driven expansion, Treg function are optimized by interactions with peripheral MHC-peptide complexes encountered during selection in the thymus, it can be advantageous if THY grafts shared HLA alleles with the T1DM and normal bone marrow donors. This can be accomplished if previously HLA-typed, frozen THY tissue can be utilized selectively with HLA-typed volunteer donor HSC. Certain common class II HLA alleles are strongly associated with T1DM and are expected to be present in these patients. These include HLA-DRB1*03-DQB1*0201 (DR3), DRB1*04-DQB1*0302 (DR4) and DQA1*0301, DQB1*0302 (DQ8)[1-5]. Fortunately these alleles are also common in the general population, 30-50% of which has HLA-DR4 and/or DR3[1,147,148]. Therefore, it will not be difficult to obtain fetal tissue and normal control CD34 cells expressing one or both of these alleles, which will also be expressed by most T1DM patients. Additionally, certain class I HLA alleles are extremely common (e.g. HLA-A2 is present in about 30% of caucasians), making the selection of T1DM patients, normal controls and fetal THY donors sharing a single class I allele feasible.

In certain aspects, the invention provides methods to reaggregate thymic organ cultures, in which thymic stromal cells are cultured and depleted of APC, then implanted under the kidney capsule, are an established tool for studying the influence on thymopoiesis of thymic epithelial cells[51,149]. The adaptation of this technique to cryopreserved human thymic stromal cells can allow one to ensure matching of HLA alleles between thymic and CD34 cell donors. Seventeen to twenty gestational week human fetal tissue can be obtained from Advanced BIoscience Resources, Alameda, Calif., as described[46,47]. A small piece of FL can be used for HLA genotyping. $CD34^+$ cells can be purified from the FL using MACS as described[46] and cryopreserved. One half of the thymic tissue can be implanted under the kidney capsules of 2 Gy-irradiated NOD-SCID mice that will receive $2 \times 10^5$ cryopreserved and thawed CD34 cells from the FL of the same donor i.v. on the following day. The remaining half of the thymus can be cut into small pieces and digested at 37° C. in IMDM containing 0.2 mg/ml collagenase, 0.2 mg/ml dispase I. 2% FCS, 25 mM HEPES, and 25 µg/ml DNAse I, followed by incubation in 5 mM EDTA. After washing, thymic stromal cells can be isolated over a discontinuous Percoll gradient as described[51,149], then further depleted of $CD45^+$ cells using MACS, washed and resuspended to $10^6$ cells/µl for cryopreservation or resuspended as a slurry and placed in drops of 0.2-0.4 µl containing 0.5-1× $10^6$ stromal cells onto 0.45 µm Millipore nylon membranes supported by Gelfoam sponges in 6-well plates containing 3 ml IMDM and 10% FCS for 48 hours. One solidified reaggregate retrieved from each filter can be grafted under the kidney capsule as described[51,149]. Two hundred thousand $CD34^+$ cells from FL of the same donor can be thawed and injected i.v at the time of stromal cell implantation.

Groups of 2 Gy-irradiated NOD-SCID mice can receive either reaggregates formed from fresh thymic stromal cells or from stromal cells that are cryopreserved and thawed the next day, along with thawed CD34 cells i.v. The animals can be followed for human T cell and APC reconstitution beginning 4 weeks after implantation and every two weeks thereafter. They can be euthanized 18 weeks after implantation, their grafts compared for total cellularity, and thymocyte subsets and peripheral lymphoid reconstitution can be compared. Thus, T cell reconstitution achieved with intact thymus, fresh thymic stromal cells and cyropreserved and thawed thymic stromal cells can be compared. Without being bound by theory, high levels of human thymopoiesis can be achieved using reaggregate cultures from fresh or cryopreserved thymic stromal cells.

The advantage of using cryopreserved thymic stromal cells is that it enables one to accumulate a "bank" of HLA-typed cells for use with CD34 cells from T1DM patients and controls sharing HLA alleles, including HLA-DR3, DR4 and DQ8. T cells can then encounter at least some of the same HLA-peptide complexes involved in positive selection in the periphery, which can optimize T cell survival, function, homeostatic expansion and regulation. Reaggregate thymic cultures and/or grafts have been successfully produced from mouse[51,149] and human THY tissue[150]. However, without being bound by theory, cryopreservation can compromise the ability of thymic stromal cells to generate reaggregate organs. In this case, the cryopreservation and thawing procedures can be optimized. The effect of co-implanting CD34 cells into the "standing drop" in vitro or at the time of implantation under the kidney capsule to promote development of thymic architecture and overcome the requirement for thymocyte progenitor trafficking to the reaggregate graft in vivo can also be evaluated. Other parameters to vary if necessary include the size of the "standing drop" placed on each filter or the number of reaggregates implanted and hence the size of the thymic graft, as well as gestational age. An alternative approach can involve implantation of intact HLA-typed human thymic tissue with co-implantation of TEC derived from HLA-transgenic NOD mice expressing relevant diabetes susceptibility alleles that are shared by the CD34 cell donors. Implanted TEC show long-term survival in thymic xenografts and influence thymic selection (FIGS. 22-24). Since murine TEC are capable of selecting human thymocytes[41,42], without being bound by theory, co-implanted HLA-transgenic TEC can positively select human thymocytes on the relevant HLA molecules. Another alternative is to inject cryopreserved human TEC bearing the relevant HLA alleles into intact human thymus grafts. Finally, one can transduce human thymus grafts with HLA genes by injecting adenoviral vectors containing DNA encoding these HLA molecules as performed successfully in the native thymus by Mathis et al[151-154]. Thus, through one of these approaches, without being bound by theory, one can successfully generate a model in which thymopoieisis of CD34 cells from HLA-typed normal and T1DM donors will occur in the context of shared HLA alleles.

Based on the marked growth of fetal thymi and large numbers of thymocytes (typically $2$-$3\times10^8$ per graft) and high levels of peripheral reconstitution observed in previous studies (see FIGS. 1-3; one typically obtains $15$-$30\times10^6$ purified human T cells from the spleen and lymph nodes of one HU/HU mouse), without being bound by theory, one can obtain sufficient numbers of thymic and peripheral T cells for the studies herein. However, if lower levels of T cell reconstitution are achieved with the reaggregate THY grafts, NOD-SCID-γc knockout mice can be utilized instead of conventional NOD-SCID mice. The lack of NK cells NOD-SCID-γc mice can permit higher levels of human immune reconstitution in the presence of relatively low levels of thymopoiesis. While high levels of human T cell reconstitution have been achieved in NOD-SCID mice in the model, γc knockout mice can be advantageous in models involving lower levels of human thymopoiesis[41,42].

In certain aspects, the invention provides a mouse model as described and methods to compare peripheral survival, homeostatic expansion, phenotypic conversion and self-tolerance of conventional T cells derived from CD34 cells of T1DM versus normal controls. It can be determined whether or not T cells from T1DM patients show increased lymphopenia-driven expansion in association with loss of tolerance to "self" antigens of the thymus donor. It can be determined whether or not intrinsic abnormalities in homeostasis characterize T cells in T1DM patients.

As shown in FIGS. 1-3, combined human THY and HSC transplantation in NOD-SCID mice results in high levels of human multilineage hematopoiesis. This model can be modified to assure sharing of class-I and -II HLA alleles between the thymic stroma and the CD34 cells from T1DM patients and controls. Autoimmune pathogenesis in NOD mice can involve increased apoptosis of peripheral T cells, resulting in lymphopenia[54,80]. Human autoimmune diseases[83-89], including T1DM[90] have also been associated with lymphopenia. Without being bound by theory, T cells derived from HSC of T1DM patients exhibit reduced survival and increased lymphopenia-driven expansion and activation compared to those from HSC of normal controls. Humanized mice sharing class-I and -II alleles in the thymus and periphery can be prepared using the best regimen developed. Instead of FL CD34 cells, the animals can receive $10^5$ MACS-purified bone marrow CD34 cells from HLA-typed T1DM patients or normal controls (with a negative family history for T1DM) sharing the same HLA alleles with the fetal THY donor (Table 2). 10-12 NOD-SCID mice can be reconstituted with CD34 cells from one marrow aspirate, given that about $1.25\times10^6$ CD34 cells are aspirated in a single 5-6 ml pull. Beginning at 4 weeks post-transplantation, the peripheral blood of the animals can be monitored biweekly for human CD3, CD19, and CD14$^+$ cells as described[46,47]. When ≥5% human CD3$^+$ T cells are present in the peripheral blood, the mice can be utilized for further studies as described herein.

Human thymocyte subsets and splenic and lymph node (LN) T cells can be enumerated. The lymphoid tissues of recipients of CD34 cells from T1DM patients can be hypocellular compared to controls in association with decreased expression of anti-apoptotic proteins in memory T cells, as reported in the NOD mouse model[80]. On the other hand, these abnormalities in the NOD model can be an effect of disease, rather than a cause. The model can provide an opportunity to address whether or not there are primary abnormalities in homeostasis of T cells derived from HSC of T1DM patients. Absolute numbers of memory and naïve-type CD4 and CD8 cells can be enumerated by multi-color FCM including mAbs to CD8α, CD8β, CD45RA, CD45RO, CD95, CD27, CCR7 and CD62L. Possible results include increased numbers of double positive (RO$^+$ RA$^+$) T cells in animals reconstituted with T1DM HSC, as reported in T1DM patients[91,155,156], or reduced numbers of "clonally deviated" CD4−CD8αα+ thymocytes and T cells from T1DM HSC. Defects in production of clonally deviated cells are genetically encoded in the NOD background[157]. Activation markers, including HLA-DR, CD69 and CD25 on CD4 and CD8 T cells, can also be examined. T cell HLA-DR expression is elevated in association with recent-onset T1DM[158]. All of these data can be analyzed in relation to the level of human APC reconstitution, including B cells and lymphoid and myeloid DC subsets.

Decreased expression of the anti-apoptotic molecules Bcl-xL and Bcl-2 in memory-type T cells has been associated with increased T cell turnover and homeostatic expansion in NOD mice[80]. Therefore, apoptosis (using annexin and AAD) and the expression of anti-apoptotic proteins (using permeabilized cells) can be measured among peripheral T cell subsets defined by naïve and memory markers, using multicolor FCM. To assess replicative history, T cell receptor excision circles (TREC) and telomere length analyses can be performed on sorted naïve-type and memory-type CD4 and CD8 cells using qPCR as described[159,160].

Abnormalities of homeostasis in T cells derived from T1DM patients can be so severe that sufficient numbers of T cells cannot be obtained from reconstituted mice to permit performance of all of the above studies. While it is preferable to obtain data from individual reconstituted NOD-SCID mice, if necessary, lymphocytes from multiple animals reconstituted with the same CD34 cells can be pooled. Also, γc knockout NOD-SCID mice can be used if needed to enhance human immune reconstitution.

Peripheral survival of human T cells derived from normal versus T1DM CD34 cells can be compared by removing the THY graft by nephrectomy as has been previously described[161] and monitoring the decay of naïve- and memory-type T cells. Additionally, BrDU labeling studies can be performed as described[80] in both euthymic and graftectomized animals to assess peripheral T cell expansion in vivo.

The function of T cells derived from T1DM and control HSCs can be compared following in vivo immunization with hepatitis B vaccine and tetanus toxoid. In vitro assays of T cell proliferation and antibody responses can be assessed. Proliferative responses to global T cell stimulation (with anti-CD28 and anti-CD3 Dynal beads) and alloresponses to third party and both the thymus donor and autologous (CD34 cell donor) APCs can be compared using DCs from FL or bone marrow CD34 cells. Effective functional DC generation has been established from thawed cryopreserved human FL CD34 cells with GM-CSF and SCF on Day 0, adding TNF-α on Day 3 and using IL-4, GM-CSF and TNF-α from Day 6 onward. Since one does not expect to have sufficient CD34 cells from T1DM and normal control bone marrow donors for cryopreservation for subsequent DC generation (they can generally all be used to reconstitute mice), DC from these donors can be generated from peripheral blood monocytes as has been described previously[162]. T and B cell responses can be comparable for both Type-1 diabetic patients and normals, but that tolerance to the MHC of the HSC and/or the THY donor can be compromised in T1DM HSC-derived T cells.

Figure 19:
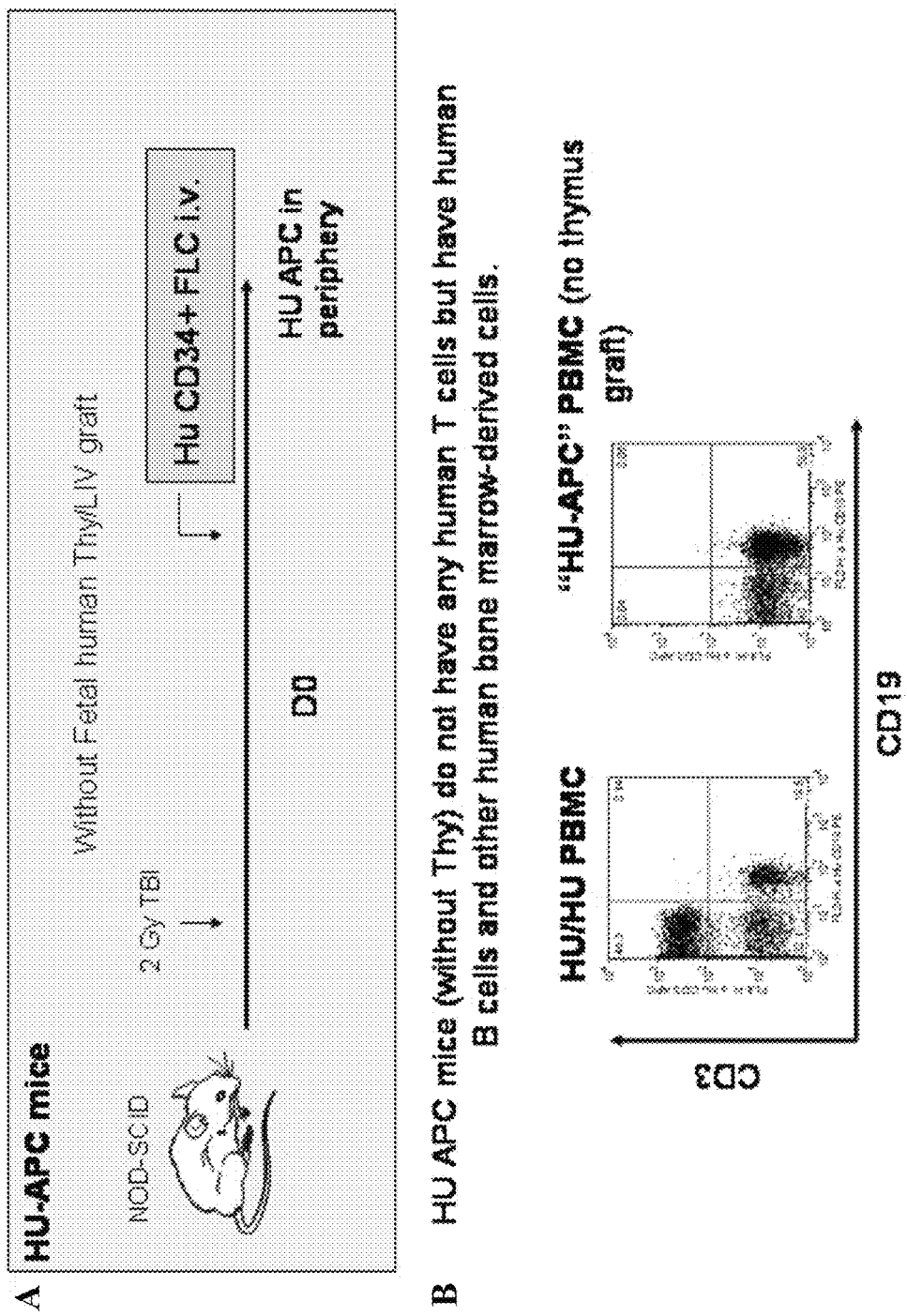

Adoptive transfer can be used to compare homeostatic expansion and survival of T cells derived from T1DM patients and controls. Lymphopenia-driven expansion and apoptosis can be greater for T1DM HSC-derived than control HSC-derived T cells. T cells generated in HU THY grafts can be adoptively transferred into secondary NOD-SCID mouse recipients whose peripheral APC populations have been reconstituted with FLC from the same CD34 donor as the THY without a fetal THY graft (HU-APC mice). These animals reconstitute human APC but not T cells (FIG. 19). They are "empty" of T cells and their APC express the same HLA antigens as those that mediated positive selection in the original THY graft. This model has been used to measure lymphopenia-driven expansion of T cells following adoptive transfer (FIGS. 18-21). Naïve CD4 and CD8 single positive (SP) thymocytes can be adoptively transferred from the grafts into secondary HU-APC recipients. Separate aliquots can be undepleted or depleted (by MACS sorting) of CD25+ cells, allowing comparison of responses to lymphopenia in the presence or absence of Treg. Lymphopenia-driven expansion of Treg can be specifically compared. Without being bound by theory, these mature single positive thymocytes will have undergone intrathymic selection but not have been subjected to post-thymic selection. They can be CFSE labeled and adoptively transferred ($10^6$ cells per recipient) into HU-APC mice. At timed intervals thereafter, the HU-APC recipients will be euthanized. T cells can be enumerated, and the level of T cell CFSE dilution as well as expression of CCD45RA and CD45RO, CD25 (vs FoxP3 to distinguish CD25+ Tregs), CD69, and apoptosis (using Annexin V and AAD) can be examined on human CD4 and CD8 cells. While lymphopenia-driven expansion is not normally associated with upregulation of the activation markers CD25 and CD69[60], T cell abnormalities from T1DM patients may involve autoantigen-driven activation with upregulation of these markers, in association with lymphopenia-driven expansion. Intracellular staining for IFN-γ and TNF-α, can indicate whether increased effector function is generated from homeostatically expanding T cells from T1DM HSC. If any such abnormalities are observed, analyses of human IL-21, IL-7, IL-15 and their receptors can be performed in the adoptive recipients to address the etiology of these abnormalities.

Tolerance in vitro in the T cells that have undergone homeostatic expansion, can be examined using the strategy described herein. Without being bound by theory, increased lymphopenia-driven expansion in T cells from diabetic patients can result in enrichment for self-reactive T cells with highest affinity and hence loss of tolerance to self. In this case "self" can include the TEC and FL CD34 cell donor, as well as the HSC donor for the original TEC-grafted animal.

The HLA type of the normal versus the T1DM CD34 cells can invariably differ, so the degree of sharing of HLA and of cross reactivity between each HSC and THY donor can differ. This can result in differences in the degree to which, for example, the HLA expressed in the periphery is capable of supporting homeostatic expansion of T cells. For this reason, the adoptive transfer studies can utilize SP thymocytes that have not undergone post-thymic selection. Also, THY donors who share ONLY the same HLA alleles with both HSC donors (the T1DM patient and their normal control) can be utilized. Moreover, these studies can be performed with HSC from at least 5 T1DM and 5 controls to help to compensate for inter-individual variations.

In certain aspects, the invention provides a mouse model and methods to compare numbers, function and peripheral phenotypic conversion of regulatory T cells derived from CD34 cells of T1DM versus normal controls. Tregs and NKT cells derived from stem cells of T1DM patients can show defects. These studies can identify intrinsic abnormalities in regulatory cells from T1DM patients and their thymic versus post-thymic origin.

While controversial[100-102], defects in Treg numbers[92] and function[22-24] have been reported in T1DM patients and in NOD mice[93-97]. Additionally, defects in NKT cells have been described in the periphery[30,31,103,104] and thymus[105] of NOD mice and in the peripheral blood of humans with T1DM[101]. Adoptive transfer or overexpression of NKT cells[110] or transfer of Tregs[98] can reverse autoimmunity in NOD mice. Both an insufficiency of Tregs at the site of inflammation in the pancreas and a relative resistance of effector cells to regulation seem to characterize the final stages of disease development in the NOD model[101]. However, studies in humans with T1DM were limited to the analysis of peripheral blood samples, and it is not known whether these defects in human Treg develop as a consequence of illness or are pathogenic for the disease and genetically programmed in T1DM patients. Without being bound by theory, T1DM patients can exhibit defects in Treg development, peripheral survival or peripheral "tuning"[52] to render them fully functional. The model provides an opportunity to examine both the role of intrathymic and peripheral defects in the development of Treg and NKT cells.

All of these studies can utilize the model developed to assure sharing of diabetogenic HLA molecules between the selecting thymus and the CD34$^+$ HSC used. Such sharing can allow interactions with the same MHC/peptide complexes on peripheral APC by Tregs selected on these complexes in the THY graft. Since Tregs show specificity for MHC/peptide complexes that select them in the thymus[51] and peripheral interactions with MHC/peptide complexes promote functionality of Tregs[52,53], HLA sharing between the thymus and the peripheral human APC is likely of considerable importance.

Analyses of Treg:

Numbers of CD127$^{-/lo}$FoxP3$^+$CD4$^+$CD8$^-$ Treg in thymi of NOD-SCID mice grafted with human HLA-DR3, DR4 or DQ8+ thymic tissue and CD34+ cells from normal individuals or T1DM patients can be compared. Using multicolor FCM, the phenotype of these cells can be compared. Without being bound by theory, similar to thymic Tregs presented in FIG. 11, these cells can be largely CD45RA$^+$CD45RO$^+$ HLA-DR$^{-/lo}$. Based on work in the NOD model, it is likely that the proportion of Tregs in the thymus may be reduced in recipients of HSC from T1DM patients compared to controls.

The numbers of CD127$^{-/lo}$FoxP3$^+$CD4$^+$CD8$^-$ Treg can be compared in the peripheral lymphoid tissues (LN and spleen) of the above animals. Using multicolor FCM, the naïve/memory phenotype and HLA-DR expression of these cells can be compared. It is expected that, as in FIG. 13, Treg derived from HSC of normal donors can include CD45RA$^+$CD45RO$^-$ and CD45RA$^-$CD45RO$^+$ subsets, with an HLA-DR$^+$ subset. DR$^+$ cells express the highest levels of FoxP3[138], and the studies herein (FIG. 13) indicate they may have interacted with the same MHC-peptide complexes in the periphery as those encountered in the thymus, promoting optimal suppressive activity[52]. If Treg from T1DM HSC have an intrinsic defect in function, they may not be able to acquire the CD45RA$^-$CD45RO$^+$ and HLA-DR$^+$ phenotype associated with full suppressive activity.

The suppressive function of flow sorted CD127$^{-/lo}$CD25$^+$CD4$^+$CD8$^-$ Treg from the thymus and peripheral lymphoid tissues of HU/HU mice reconstituted with CD34 cells from T1DM patients and normal controls can be compared. Graded numbers of Treg can be added to MLRs containing the following combinations of responder and stimulator cells: 1) CD25$^-$CD4$^+$ T cells sorted from the peripheral lymphoid tissues of humanized mice and stimulated with allogeneic PBMC; 2) CD25$^-$CD4$^+$ T cells sorted from the peripheral lymphoid tissues of humanized mice and stimulated with DCs derived from autologous PBMC (from the CD34 cell donor) as described[162]; 3) CD25$^-$CD4$^+$ T cells sorted from the peripheral lymphoid tissues of the humanized mice and stimulated with DCs derived from frozen FL-derived CD34 cells from the THY donor. Functional DCs from FL CD34 cells can be reliably generated. The ability of thymic and peripheral Treg from T1DM patients and normal controls to suppress allogeneic responses and responses to "autoantigens" expressed by the thymus and HSC donors can be compared. Since T cells derived from T1DM patients and normal controls can encounter the same shared HLA-DR antigens in the thymus and periphery, any observed differences in regulatory function cannot be attributed to failure of such encounters. Any reduction in regulatory function observed for Tregs from T1DM HSC can be interpreted in the context of phenotypic data from studies described in the preceding paragraph. The comparison of thymic and peripheral Tregs can allow determination of whether defects in Treg function in T1DM patients are manifested during thymic or post-thymic development.

Both IL-10 and TGF-β have been implicated as important effector cytokines for Treg function[163-165]. TGF-β also plays an important role in the expansion and peripheral generation of Treg, at least in part by induction of FoxP3 expression[36,163,166-170]. Studies in NOD mice have demonstrated a decreasing capacity of Treg from older animals to produce IL-10[97] and the development of diabetes is associated with a sudden decline in membrane-bound TGF-β expression by Treg[94]. If defects in suppressive function are identified in Treg from T1DM patients, sorted CD127$^{-/lo}$CD25$^+$CD4$^+$CD8$^-$ Treg from the thymus and periphery of humanized mice can be stimulated with anti-CD28/anti-CD3 Dynal beads with IL-2[171] and cytokine mRNAs and protein can be measured.

Adoptive Transfer Studies:

To compare lymphopenia-driven expansion of naïve CD127$^{-/lo}$CD25$^+$CD4$^+$CD8$^-$ Tregs derived from HSC of T1DM patients versus normal controls, CFSE-labeled "naïve" thymic Tregs can be adoptively transferred from each group into secondary HU-APC mice as described herein. If studies described herein demonstrate increased autoreactivity and/or lymphopenia-driven expansion when SP thymocytes depleted of CD25$^+$ cells are adoptively transferred, the ability of positively selected thymic Tregs to suppress autoimmunity and/or lymphopenia-driven activation in co-transfer studies can be addressed.

Analyses of NKT Cells:

Reduced numbers and defective function of invariant NKT cells have been reported in T1DM patients[92]. The model provides an opportunity to determine whether this defect is intrinsic to the HSC of T1DM patients and whether or not it reflects defects in thymic development of this cell subset. Multicolor FCM can be used to quantify invariant chain-expressing Vα24$^+$Vβ11$^+$ and Vα24JαQ CD4$^-$CD8$^-$ and CD4$^+$CD8$^-$ cells in the thymus and periphery. Since defects in IFN-γ production by invariant NKT cells from T1DM patients have been reported[92], these cells can be stimulated with PMA/ionophore as described[92] and intracellular levels of IFN-γ and IL-4 in NKT cells derived from T1DM patients and normals using multicolor FCM can be compared. These studies can elucidate the HSC and thymic origin of defects in NKT cells in T1DM patients.

The studies described herein can determine definitively whether or not T cells derived from HSC of T1DM patients have genetically-programmed intrinsic defects in T cell regulation and homeostasis, resolving the controversy on the role of such defects in T1DM pathogenesis. Depending on the results, future studies can involve gene expression profiling of T cells from T1DM and normal HSC, studies of adaptive Treg development, and examination of the role of APCs and other HSC-derived cells in autoimmunity. The model can allow evaluation of novel approaches, including genetic manipulation, to interrupting disease pathogenesis.

Volunteer Type 1 diabetic patients and normal control volunteers over the age of 18 who do not have coagulation or bleeding disorders or immunodeficiency can be included in the study. All volunteers can be screened by HLA typing and those with common diabetes-associated class II HLA alleles and common class I alleles can be selected for inclusion in the study.

TABLE 1

Description of "Hu/HU" and "Sw/Hu" reconstituted NOD/SCID mice

| Group | Thymic Epithelium | Fetal Liver | HSC i.v. | APC in periphery |
|---|---|---|---|---|
| Hu/Hu | Human | Human (same as thymus donor) | Human (same as thymus donor) | Human (same as thymus donor) |
| Sw/Hu | Pig | Human (xenogeneic to thymus donor) | Human (xenogeneic to thymus donor) | Human (xenogeneic to thymus donor) |

TABLE 2

Groups of mice to be prepared for comparison of T cells from HSC of T1DM vs normal control HSC sharing HLA alleles with fetal thymus donor

| Group | Thymic Epithelium | HSC i.v.: Bone marrow CD34 cells |
|---|---|---|
| 1 | Human fetus | Control with class I and Class II allele shared with thymic epipthelium |
| 2 | Same as Group 1 | T1DM sharing same class I and class II alleles with thymus and Group 1 donor |

REFERENCE LIST FOR EXAMPLE 1

1. Emery L M, Babu S, Bugawan T L, Norris J M, Erlich H A, Eisenbarth G S, Rewers M. Newborn HLA-DR,DQ genotype screening: age- and ethnicity-specific type 1 diabetes risk estimates. Pediatr Diabetes. 2005; 6:136-144.
2. Barker J M, Barriga K J, Yu L, Miao D, Erlich H A, Norris J M, Eisenbarth G S, Rewers M. Prediction of autoantibody positivity and progression to type 1 diabetes: Diabetes Autoimmunity Study in the Young (DAISY). J Clin Endocrinol Metab. 2004; 89:3896-3902.
3. Kent S C, Chen Y, Bregoli L, Clemmings S M, Kenyon N S, Ricordi C, Hering B J, Hafler D A. Expanded T cells from pancreatic lymph nodes of type 1 diabetic subjects recognize an insulin epitope. Nature. 2005; 435:224-228.
4. Mannering S I, Harrison L C, Williamson N A, Morris J S, Thearle D J, Jensen K P, Kay T W, Rossjohn J, Falk B A, Nepom G T, Purcell A W. The insulin A-chain epitope recognized by human T cells is posttranslationally modified. J Exp Med. 2005; 202:1191-1197.
5. Suri A, Walters J J, Gross M L, Unanue E R. Natural peptides selected by diabetogenic DQ8 and murine I-A (g7) molecules show common sequence specificity. J Clin Invest. 2005; 115:2268-2276.
6. Ueda H, Howson J M, Esposito L, Heward J, Snook H, Chamberlain G, Rainbow D B, Hunter K M, Smith A N, Di Genova G, Herr M H, Dahlman I, Payne F, Smyth D, Lowe C, Twells R C, Howlett S, Healy B, Nutland S, Rance H E, Everett V, Smink L J, Lam A C, Cordell H J, Walker N M, Bordin C, Hulme J, Motzo C, Cucca F, Hess J F, Metzker M L, Rogers J, Gregory S, Allahabadia A, Nithiyananthan R, Tuomilehto-Wolf E, Tuomilehto J, Bingley P, Gillespie K M, Undlien D E, Ronningen K S, Guja C, Ionescu-Tirgoviste C, Savage D A, Maxwell A P, Carson D J, Patterson C C, Franklyn J A, Clayton D G, Peterson L B, Wicker L S, Todd J A, Gough S C. Association of the T-cell regulatory gene CTLA4 with susceptibility to autoimmune disease. Nature. 2003; 423: 506-511.
7. Wicker L S, Clark J, Fraser H I, Garner V E, Gonzalez-Munoz A, Healy B, Howlett S, Hunter K, Rainbow D, Rosa R L, Smink L J, Todd J A, Peterson L B. Type 1 diabetes genes and pathways shared by humans and NOD mice. J. Autoimmun. 2005; 25 Suppl:29-33.
8. Smyth D J, Cooper J D, Bailey R, Field S, Burren O, Smink L J, Guja C, Ionescu-Tirgoviste C, Widmer B, Dunger D B, Savage D A, Walker N M, Clayton D G, Todd J A. A genome-wide association study of nonsynonymous SNPs identifies a type 1 diabetes locus in the interferon-induced helicase (IFIH1) region. Nat Genet. 2006; 38:617-619.
9. Steck A K, Bugawan T L, Valdes A M, Emery L M, Blair A, Norris J M, Redondo M J, Babu S R, Erlich H A, Eisenbarth G S, Rewers M J. Association of non-HLA genes with type 1 diabetes autoimmunity. Diabetes. 2005; 54:2482-2486.
10. Atkinson M A, Leiter E H. The NOD mouse model of type 1 diabetes: As good as it gets? Nature Med. 1999; 5:601-604.
11. Shoda L K, Young D L, Ramanujan S, Whiting C C, Atkinson M A, Bluestone J A, Eisenbarth G S, Mathis D, Rossini A A, Campbell S E, Kahn R, Kreuwel H T. A comprehensive review of interventions in the NOD mouse and implications for translation. Immunity. 2005; 23:115-126.
12. Yoshida K, Kikutani H. Genetic and immunological basis of autoimmune diabetes in the NOD mouse. Rev Immunogenet. 2000; 2:140-146.
13. McDevitt H O. The role of MHC class II molecules in susceptibility and resistance to autoimmunity. Curr Opin Immunol. 1998; 10:677-681.
14. Nakayama M, Abiru N, Moriyama H, Babaya N, Liu E, Miao D, Yu L, Wegmann D R, Hutton J C, Elliott J F, Eisenbarth G S. Prime role for an insulin epitope in the development of type 1 diabetes in NOD mice. Nature. 2005; 435:220-223.
15. Liu C P, Jiang K, Wu C H, Lee W H, Lin W J. Detection of glutamic acid decarboxylase-activated T cells with I-Ag7 tetramers. Proc Natl Acad Sci USA. 2000; 97:14596-14601.
16. Reijonen H, Mallone R, Heninger A K, Laughlin E M, Kochik S A, Falk B, Kwok W W, Greenbaum C, Nepom G T. GAD65-Specific CD4+ T-Cells with High Antigen Avidity Are Prevalent in Peripheral Blood of Patients With Type 1 Diabetes. Diabetes. 2004; 53:1987-1994.
17. Yu B, Gauthier L, Hausmann D H, Wucherpfennig K W. Binding of conserved islet peptides by human and murine MHC class II molecules associated with susceptibility to type I diabetes. Eur J Immunol. 2000; 30:2497-2506.
18. Chao C C, McDevitt H O. Identification of immunogenic epitopes of GAD 65 presented by Ag7 in non-obese diabetic mice. Immunogenetics. 1997; 46:29-34.
19. Vijayakrishnan L, Slavik J M, Illes Z, Greenwald R J, Rainbow D, Greve B, Peterson L B, Hafler D A, Freeman G J, Sharpe A H, Wicker L S, Kuchroo V K. An autoimmune disease-associated CTLA-4 splice variant lacking the B7 binding domain signals negatively in T cells. Immunity. 2004; 20:563-575.
20. Barker J M. Type 1 diabetes associated autoimmunity: Natural History, Genetic Associations and Screening. J Clin Endocrinol Metab. 2006.
21. Rogner U C, Lepault F, Gagnerault M C, Vallois D, Morin J, Avner P, Boitard C. The Diabetes Type 1 Locus Idd6 Modulates Activity of CD4+CD25+ Regulatory T-Cells. Diabetes. 2006; 55:186-192.
22. Arif S, Tree T I, Astill T P, Tremble J M, Bishop A J, Dayan C M, Roep B O, Peakman M. Autoreactive T cell responses show proinflammatory polarization in diabetes but a regulatory phenotype in health. J Clin Invest. 2004; 113:451-463.
23. Lindley S, Dayan C M, Bishop A, Roep B O, Peakman M, Tree T I. Defective Suppressor Function in CD4+ CD25+ T-Cells From Patients With Type 1 Diabetes. Diabetes. 2005; 54:92-99.
24. Brusko T M, Wasserfall C H, Clare-Salzler M J, Schatz D A, Atkinson M A. Functional defects and the influence of age on the frequency of CD4+ CD25+ T-cells in type 1 diabetes. Diabetes. 2005; 54:1407-1414.
25. Esteban L M, Tsoutsman T, Jordan M A, Roach D, Poulton L D, Brooks A, Naidenko O V, Sidobre S, Godfrey D I, Baxter A G. Genetic control of NKT cell numbers maps to major diabetes and lupus Loci. J Immunol. 2003; 171:2873-2878.
26. Wilson S B, Kent S C, Patton K T, Orban T, Jackson R A, Exley M, Porcelli S, Schatz D A, Atkinson M A, Balk S P, Strominger J L, Hafler D A. Extreme Th1 bias of invariant Vα24JαQ T cells in type 1 diabetes. Nature. 1998; 391:177-181.
27. Zucchelli S, Holler P, Yamagata T, Roy M, Benoist C, Mathis D. Defective central tolerance induction in NOD mice: genomics and genetics. Immunity. 2005; 22:385-396.
28. Nikolic T, Bunk M, Drexhage H A, Leenen P J. Bone marrow precursors of nonobese diabetic mice develop into defective macrophage-like dendritic cells in vitro. J Immunol. 2004; 173:4342-4351.
29. Rodacki M, Svoren B, Butty V, Besse W, Laffel L, Benoist C, Mathis D. Altered natural killer cells in type 1 diabetic patients. Diabetes. 2007; 56:177-185.
30. Baxter A G, Kinder S J, Hammond K J, Scollay R, Godfrey D I. Association between alphabetaTCR+CD4− CD8− T-cell deficiency and IDDM in NOD/Lt mice. Diabetes. 1997; 46:572-582.
31. Falcone M, Yeung B, Tucker L, Rodriguez E, Sarvetnick N. A defect in interleukin 12-induced activation and interferon gamma secretion of peripheral natural killer T cells in nonobese diabetic mice suggests new pathogenic mechanisms for insulin-dependent diabetes mellitus. J Exp Med. 1999; 190:963-972.
32. Wilson S B, Delovitch T L. Regulatory Lymphocytes: Janus-like role of regulatory iNKT cells in autoimmune disease and tumour immunity. Nat Rev Immunol. 2003; 3:211-222.
33. Townsend S E, Goodnow C C. Abortive proliferation of rare T cells induced by direct or indirect antigen presentation by rare B cells in vivo. J Exp Med. 1998; 187: 1611-1621.
34. Greeley S A, Katsumata M, Yu L, Eisenbarth G S, Moore D J, Goodarzi H, Barker C F, Naji A, Noorchashm H. Elimination of maternally transmitted autoantibodies prevents diabetes in nonobese diabetic mice. Nat Med. 2002; 8:399-402.
35. Hussain S, Salojin K V, Delovitch T L. Hyperresponsiveness, Resistance to B-Cell Receptor-Dependent Activation-Induced Cell Death, and Accumulation of Hyperactivated B-Cells in Islets Is Associated With the Onset of Insulitis but not Type 1 Diabetes. Diabetes. 2004; 53:2003-2011.
36. Mosier D E, Gulizia R J, Baird S M, Wilson D B. Transfer of a functional human immune system to mice with severe combined immunodeficiency. Nature. 1988; 335:256-259.
37. McCune J M, Namikawa R, Kaneshima H, Shultz L D, Lieberman M, Weissman I L. The SCID-hu mouse: Murine model for the analysis of human hematolymphoid differentiation and function. Science. 1988; 241:1632-1639.
38. Wagar E J, Cromwell M A, Shultz L D, Woda B A, Sullivan J L, Hesselton R M, Greiner D L. Regulation of human cell engraftment and development of EBV-related lymphoproliferative disorders in Hu-PBL-scid mice. J Immunol. 2000; 165:518-527.
39. Sawada T, DellaPelle A, Seebach J D, Sachs D H, COLVIN R B, Iacomini J. Human cell-mediated rejection of porcine xenografts in an immunodeficient mouse model. Transplantation. 1997; 63:1331-1338.
40. Alegre M-L, Peterson L J, Jeyarajah D R, Weiser M, Bluestone J A, Thistlewaite J R. Severe combined immunodeficient mice engrafted with human splenocytes have functional human T cells and reject human allografts. J Immunol. 1994; 153:2738-2749.
41. Ishikawa F, Yasukawa M, Lyons B, Yoshida S, Miyamoto T, Yoshimoto G, Watanabe T, Akashi K, Shultz L D, Harada M. Development of functional human blood and immune systems in NOD/SCID/IL2 receptor {gamma} chain(null) mice. Blood. 2005; 106:1565-1573.
42. Traggiai E, Chicha L, Mazzucchelli L, Bronz L, Piffaretti J C, Lanzavecchia A, Manz M G. Development of a human adaptive immune system in cord blood cell-transplanted mice. Science. 2004; 304:104-107.
43. Kollet O, Peled A, Byk T, Ben-Hur H, Greiner D, Shultz L, Lapidot T. β2 microglobulin-deficient (B2mnull) NOD/SCID mice are excellent recipients for studying human stem cell function. Blood. 2000; 95:3102-3105.
44. Shultz L D, Lyons B L, Burzenski L M, Gott B, Chen X, Chaleff S, Kotb M, Gillies S D, King M, Mangada J, Greiner D L, Handgretinger R. Human lymphoid and myeloid cell development in NOD/LtSz-scid IL2R gamma null mice engrafted with mobilized human hemopoietic stem cells. J Immunol. 2005; 174:6477-6489.
45. Macchiarini F, Manz M G, Palucka A K, Shultz L D. Humanized mice: are we there yet? J Exp Med. 2005; 202:1307-1311.
46. Lan P, Wang L, Diouf B, Eguchi H, Su H, Bronson R, Sachs D H, Sykes M, Yang Y G. Induction of human T cell tolerance to porcine xenoantigens through mixed hematopoietic chimerism. Blood. 2004; 103:3964-3969.
47. Lan P, Tonomura N, Shimizu A, Wang S, Yang Y G. Reconstitution of a functional human immune system in immunodeficient mice through combined human fetal thymus/liver and CD34+ cell transplantation. Blood. 2006; 108:487-492.
48. Melkus M W, Estes J D, Padgett-Thomas A, Gatlin J, Denton P W, Othieno F A, Wege A K, Haase A T, Garcia J V. Humanized mice mount specific adaptive and innate immune responses to EBV and TSST-1. Nat Med. 2006; 12:1316-1322.

49. Bensinger S J, Bandeira A, Jordan M S, Caton A J, Laufer T M. Major histocompatibility complex class II-positive cortical epithelium mediates the selection of CD4(+)25(+) immunoregulatory T cells. J Exp Med. 2001; 194:427-438.
50. Baldwin T A, Hogquist K A, Jameson S C. The fourth way? Harnessing aggressive tendencies in the thymus. J Immunol. 2004; 173:6515-6520.
51. Aschenbrenner K, D'Cruz L M, Vollmann E H, Hinterberger M, Emmerich J, Swee L K, Rolink A, Klein L. Selection of Foxp3(+) regulatory T cells specific for self antigen expressed and presented by Aire(+) medullary thymic epithelial cells. Nat Immunol. 2007; 8:351-358.
52. Bhandoola A, Tai X, Eckhaus M, Auchincloss H, Mason K, Rubin S A, Carbone K M, Grossman Z, Rosenberg A S, Singer A. Peripheral Expression of Self-MHC-II Influences the Reactivity and Self-Tolerance of Mature CD4(+) T Cells. Evidence from a Lymphopenic T Cell Model. Immunity. 2002; 17:425.
53. Samy E T, Setiady Y Y, Ohno K, Pramoonjago P, Sharp C, Tung K S. The role of physiological self-antigen in the acquisition and maintenance of regulatory T-cell function. Immunol Rev. 2006; 212:170-184.
54. Marleau A M, Sarvetnick N. T cell homeostasis in tolerance and immunity. J Leukoc Biol. 2005; 78:575-584.
55. Tanchot C, Rosado M M, Agenes F, Freitas A A, Rocha B. Lymphocyte homeostasis. Semin Immunol. 1997; 9:331-337.
56. Berzins S P, Boyd R L, Miller J F A P. The role of the thymus and recent thymic migrants in the maintenance of the adult peripheral lymphocyte pool. J Exp Med. 1998; 187:1839-1848.
57. Tough D F, Sprent J. Turnover of naive- and memory-phenotype T cells. J Exp Med. 1994; 179:1127-1135.
58. Goldrath A W, Bevan M J. Low-affinity ligands for the TCR drive proliferation of mature CD8+ T cells in lymphopenic hosts. Immunity. 1999; 11:183-90.
59. Goldrath A W, Bogatzki L Y, Bevan M J. Naive T Cells Transiently Acquire a Memory-like Phenotype during Homeostasis-driven Proliferation. J Exp Med. 2000; 192:557-564.
60. Murali-Krishna K, Ahmed R. Cutting edge: naive T cells masquerading as memory cells. J Immunol. 2000; 165:1733-1737.
61. Cho B K, Rao V P, Ge Q, Eisen F I N, Chen J. Homeostasis-stimulated Proliferation Drives Naive T Cells to Differentiate Directly into Memory T Cells. J Exp Med. 2000; 192:549-556.
62. Tanchot C, Le Campion A, Martin B, Leaument S, Dautigny N, Lucas B. Conversion of naive T cells to a memory-like phenotype in lymphopenic hosts is not related to a homeostatic mechanism that fills the peripheral naive T cell pool. J Immunol. 2002; 168:5042-5046.
63. Min B, McHugh R, Sempowski G D, Mackall C, Foucras G, Paul W E. Neonates support lymphopenia-induced proliferation. Immunity. 2003; 18:131-140.
64. Goldrath A W, Luckey C J, Park R, Benoist C, Mathis D. The molecular program induced in T cells undergoing homeostatic proliferation. Proc Natl Acad Sci USA. 2004; 101:16885-16890.
65. Gudmundsdottir H, Turka L A. A closer look at homeostatic proliferation of CD4(+) T cells: costimulatory requirements and role in memory formation. J Immunol. 2001; 167:3699-3707.
66. Le Campion A, Bourgeois C, Lambolez F, Martin B, Leaument S, Dautigny N, Tanchot C, Penit C, Lucas B. Naive T cells proliferate strongly in neonatal mice in response to self-peptide/self-MHC complexes. Proc Natl Acad Sci USA. 2002; 99:4538-4543.
67. Kieper W C, Jameson S C. Homeostatic expansion and phenotypic conversion of naive T cells in response to self peptide/MHC ligands. Proc Natl Acad Sci USA. 1999; 96:13306-13311.
68. Brocker T. Survival of mature CD4 T lymphocytes is dependent on major histocompatibility complex class II-expressing dendritic cells. J Exp Med. 1997; 186:1223-1232.
69. Boursalian T E, Bottomly K. Survival of naiveCD4 T cells: Roles of restricting versus selecting MHC class II and cytokine milieu. J Immunol. 1999; 162:3795-3801.
70. Viret C, Wong F S, Janeway Jr. C A. Designing and maintaining the mature TCR repertoire: the continuum of self-peptide: self-MHC complex recognition. Immunity. 1999; 10:559-568.
71. Ernst B, Lee D-S, Chang J M, Sprent J, Surh C D. The peptide ligands mediating positive selection in the thymus control T cell survival and homeostatic proliferation in the periphery. Immunity. 1999; 11:173-181.
72. Schuler T, Hammerling G J, Arnold B. Cutting Edge: IL-7-dependent homeostatic proliferation of CD8+ T cells in neonatal mice allows the generation of long-lived natural memory T cells. J. Immunol. 2004; 172:15-19.
73. Takeda S, Rodewald H-R, Arakawa H, Bluethmann H, Shimizu T. MHC class II molecules are not required for survival of newly generated CD4+ T cells, but affect their long-term life span. Immunity. 1997; 5:217-228.
74. Kirberg J, Berns A, Von Boehmer H. Peripheral T cell survival requires continual ligation of the T cell receptor to major histocompatibility complex-encoded molecules. J Exp Med. 1997; 186:1269-1275.
75. Goldrath A W, Sivakumar P V, Glaccum M, Kennedy M K, Bevan M J, Benoist C, Mathis D, Butz E A. Cytokine requirements for acute and basal homeostatic proliferation of naive and memory CD8+ T cells. J Exp Med. 2002; 195:1515-1522.
76. Schluns K S, Kieper W C, Jameson S C, LEFRANCOIS L. Interleukin-7 mediates the homeostasis of naive and memory CD8 T cells in vivo. Nat Immunol. 2000; 1:426-432.
77. Tan J T, Ernst B, Kieper W C, LeRoy E, Sprent J, Surh C D. Interleukin (IL)-15 and IL-7 jointly regulate homeostatic proliferation of memory phenotype CD8+ cells but are not required for memory phenotype CD4+ cells. J Exp Med. 2002; 195:1523-1532.
78. Becker T C, Wherry E J, Boone D, Murali-Krishna K, Antia R, Ma A, Ahmed R. Interleukin 15 is required for proliferative renewal of virus-specific memory CD8 T cells. J Exp Med. 2002; 195:1541-1548.
79. Kieper W C, Tan J T, Bondi-Boyd B, Gapin L, Sprent J, Ceredig R, Surh C D. Overexpression of interleukin (IL)-7 leads to IL-15-independent generation of memory phenotype CD8+ T cells. J Exp Med. 2002; 195:1533-1539.
80. King C, Ilic A, Koelsch K, Sarvetnick N. Homeostatic expansion of T cells during immune insufficiency generates autoimmunity. Cell. 2004; 117:265-277.
81. Almeida A R, Borghans J A, Freitas A A. T cell homeostasis: thymus regeneration and peripheral T cell restoration in mice with a reduced fraction of competent precursors. J Exp Med. 2001; 194:591-599.
82. La Gruta N L, Driel I R, Gleeson P A. Peripheral T cell expansion in lymphopenic mice results in a restricted T cell repertoire. Eur J Immunol. 2000; 30:3380-3386.

83. Mirzayan M J, Schmidt R E, Witte T. Prognostic parameters for flare in systemic lupus erythematosus. Rheumatology (Oxford). 2000; 39:1316-1319.
84. Kirtava Z, Blomberg J, Bredberg A, Henriksson G, Jacobsson L, Manthorpe R. CD4+ T-lymphocytopenia without HIV infection: increased prevalence among patients with primary Sjogren's syndrome. Clin Exp Rheumatol. 1995; 13:609-616.
85. Kaye B R. Rheumatologic manifestations of HIV infections. Clin Rev Allergy Immunol. 1996; 14:385-416.
86. Gerli R, Paganelli R, Cossarizza A, Muscat C, Piccolo G, Barbieri D, Mariotti S, Monti D, Bistoni O, Raiola E, Venanzi F M, Bertotto A, Franceschi C. Long-term immunologic effects of thymectomy in patients with myasthenia gravis. J Allergy Clin Immunol. 1999; 103:865-872.
87. Koetz K, Bryl E, Spickschen K, O'Fallon W M, Goronzy J J, Weyand C M. T cell homeostasis in patients with rheumatoid arthritis. Proc Natl Acad Sci USA. 2000; 97:9203-9208.
88. Goronzy J J, Weyand C M. Aging, autoimmunity and arthritis: T-cell senescence and contraction of T-cell repertoire diversity—catalysts of autoimmunity and chronic inflammation. Arthritis Res Ther. 2003; 5:225-234.
89. Goronzy J J, Weyand C M. T-cell regulation in rheumatoid arthritis. Curr Opin Rheumatol. 2004; 16:212-217.
90. Kaaba S A, Al Harbi S A. Abnormal lymphocyte subsets in Kuwaiti patients with type-1 insulin-dependent diabetes mellitus and their first-degree relatives. Immunol Lett. 1995; 47:209-213.
91. Peakman M, Warnock T, Vats A, McNab G L, Underhill J, Donaldson P T, Vergani D. Lymphocyte subset abnormalities, autoantibodies and their relationship with HLA DR types in children with type 1 (insulin-dependent) diabetes and their first degree relatives. Diabetologia. 1994; 37:155-165.
92. Kukreja A, Cost G, Marker J, Zhang C, Sun Z, Lin-Su K, Ten S, Sanz M, Exley M, Wilson B, Porcelli S, Maclaren N. Multiple immuno-regulatory defects in type-1 diabetes. J Clin Invest. 2002; 109:131-140.
93. Brode S, Raine T, Zaccone P, Cooke A. Cyclophosphamide-induced type-1 diabetes in the NOD mouse is associated with a reduction of CD4+CD25+Foxp3+ regulatory T cells. J Immunol. 2006; 177:6603-6612.
94. Gregg R K, Jain R, Schoenleber S J, Divekar R, Bell J J, Lee H H, Yu P, Zaghouani H. A sudden decline in active membrane-bound TGF-beta impairs both T regulatory cell function and protection against autoimmune diabetes. J Immunol. 2004; 173:7308-7316.
95. You S, Belghith M, Cobbold S, Alyanakian M A, Gouarin C, Barriot S, Garcia C, Waldmann H, Bach J F, Chatenoud L. Autoimmune diabetes onset results from qualitative rather than quantitative age-dependent changes in pathogenic T-cells. Diabetes. 2005; 54:1415-1422.
96. Pop S M, Wong C P, Culton D A, Clarke S H, Tisch R. Single cell analysis shows decreasing FoxP3 and TGF-beta1 coexpressing CD4+CD25+ regulatory T cells during autoimmune diabetes. J Exp Med. 2005; 201:1333-1346.
97. Gregori S, Giarratana N, Smiroldo S, Adorini L. Dynamics of pathogenic and suppressor T cells in autoimmune diabetes development. J Immunol. 2003; 171:4040-4047.
98. Tang Q, Henriksen K J, Bi M, Finger E B, Szot G, Ye J, Masteller E L, McDevitt H, Bonyhadi M, Bluestone J A. In Vitro-expanded Antigen-specific Regulatory T Cells Suppress Autoimmune Diabetes. J Exp Med. 2004; 199: 1455-1465.
99. Mellanby R J, Thomas D, Phillips J M, Cooke A. Diabetes in non-obese diabetic mice is not associated with quantitative changes in CD4+ CD25+ Foxp3+ regulatory T cells. Immunology. 2007; 121:15-28.
100. Berzins S P, Venanzi E S, Benoist C, Mathis D. T-cell compartments of prediabetic NOD mice. Diabetes. 2003; 52:327-334.
101. Tang Q, Bluestone J A. Regulatory T-cell physiology and application to treat autoimmunity. Immunol Rev. 2006; 212:217-237.
102. Brusko T, Wasserfall C, McGrail K, Schatz R, Viener H L, Schatz D, Haller M, Rockell J, Gottlieb P, Clare-Salzler M, Atkinson M. No Alterations in the Frequency of FOXP3+ Regulatory T-Cells in Type 1 Diabetes. Diabetes. 2007; 56:604-612.
103. Falcone M, Yeung B, Tucker L, Rodriguez E, Sarvetnick N. A defect in interleukin 12-induced activation and interferon γ secretion of peripheral natural killer T cells in nonobese diabetic mice suggests new pathogenic mechanisms for insulin-dependent diabetes mellitus. J Exp Med. 1999; 190:963-972.
104. Grose S. Critics slam Russian trial to test pig pancreas for diabetics. Nat Med. 2007; 13:390-391.
105. Godfrey D I, Kinder S J, Silvera P, Baxter A G. Flow cytometric study of T cell development in NOD mice reveals a deficiency in alphabetaTCR+CDR−CD8− thymocytes. J Autoimmun. 1997; 10:279-285.
106. Gombert J M, Herbelin A, Tancrede-Bohin E, Dy M, Carnaud C, Bach J F. Early quantitative and functional deficiency of NK1+-like thymocytes in the NOD mouse. Eur J Immunol. 1996; 26:2989-2998.
107. Lee P T, Putnam A, Benlagha K, Teyton L, Gottlieb A, Bendelac A. Testing the NKT cell hypothesis of human IDDM pathogenesis. J Clin Invest. 2002; 110:793-800.
108. Oikawa Y, Shimada A, Yamada S, Motohashi Y, Nakagawa Y, Irie J, Maruyama T, Saruta T. High frequency of valpha24(+) vbeta11(+) T-cells observed in type 1 diabetes. Diabetes Care. 2002; 25:1818-1823.
109. Mi Q S, Ly D, Zucker P, McGarry M, Delovitch T L. Interleukin-4 but not interleukin-10 protects against spontaneous and recurrent type 1 diabetes by activated CD1d-restricted invariant natural killer T-cells. Diabetes. 2004; 53:1303-1310.
110. Lehuen A, Lantz O, Beaudoin L, Laloux V, Carnaud C, Bendelac A, Bach J F, Monteiro R C. Overexpression of natural killer T cells protects Valpha14-Jalpha281 transgenic nonobese diabetic mice against diabetes. J Exp Med. 1998; 188:1831-1839.
111. Duarte N, Stenstrom M, Campino S, Bergman M L, Lundholm M, Holmberg D, Cardell S L. Prevention of diabetes in nonobese diabetic mice mediated by CD1d-restricted nonclassical NKT cells. J Immunol. 2004; 173: 3112-3118.
112. Hong S, Wilson M T, Serizawa I, Wu L, Singh N, Naidenko O V, Miura T, Haba T, Scherer D C, Wei J, Kronenberg M, Koezuka Y, Van Kaer L. The natural killer T-cell ligand alpha-galactosylceramide prevents autoimmune diabetes in non-obese diabetic mice. Nat Med. 2001; 7:1052-1056.
113. Sharif S, Arreaza G A, Zucker P, Mi Q S, Sondhi J, Naidenko O V, Kronenberg M, Koezuka Y, Delovitch T L, Gombert J M, Leite-De-Moraes M, Gouarin C, Zhu R, Hameg A, Nakayama T, Taniguchi M, Lepault F, Lehuen A, Bach J F, Herbelin A. Activation of natural killer T cells by alpha-galactosylceramide treatment prevents the onset and recurrence of autoimmune Type 1 diabetes. Nat Med. 2001; 7:1057-1062.

114. Chen Y G, Choisy-Rossi C M, Holl T M, Chapman H D, Besra G S, Porcelli S A, Shaffer D J, Roopenian D, Wilson S B, Serreze D V. Activated NKT cells inhibit autoimmune diabetes through tolerogenic recruitment of dendritic cells to pancreatic lymph nodes. J Immunol. 2005; 174:1196-1204.
115. Carnaud C, Gombert J, Donnars O, Garchon H, Herbelin A. Protection against diabetes and improved NK/NKT cell performance in NOD.NK1.1 mice congenic at the NK complex. J Immunol. 2001; 166:2404-2411.
116. Namikawa R, Weilbaecher K N, Kaneshima H, Yee E J, McCune J M. Long-term human hematopoiesis in the SCID-hu mouse. J Exp Med. 1990; 172:1055-1063.
117. Nikolic B, Gardner J P, Scadden D T, Arm J S, Sachs D H, Sykes M. Normal development in porcine thymus grafts and specific tolerance of human T cells to porcine donor MHC. J Immunol. 1999; 162:3402-3407.
118. Stefanova I, I, Dorfman J R, Germain R N. Self-recognition promotes the foreign antigen sensitivity of naive T lymphocytes. Nature. 2002; 420:429-434.
119. Liu Y J. Dendritic cell subsets and lineages, and their functions in innate and adaptive immunity. Cell. 2001; 106:259-262.
120. Wang J C Y, Doedens M, Dick J E. Primitive human hematopoietic cells are enriched in cord blood compared with adult bone marrow or mobilized peripheral blood as measured by the quantitative in vivo SCID-repopulating cell assay. Blood. 1997; 89:3919-3924.
121. Dao M A, Shah A J, Crooks G M, Nolta J A. Engraftment and retroviral marking of CD34+ and CD34+CD38– human hematopoietic progenitors assessed in immune-deficient mice. Blood. 1998; 91:1243-1255.
122. Bhatia M, Bonnet D, Murdoch B, Gan O I, Dick J E. A newly discovered class of human hematopoietic cells with SCID-repopulating activity. Nature Med. 1998; 4:1038-1045.
123. van der Loo J C M, Hanenberg H, Cooper R J, Luo F-Y, Lazaridis E N, Williams D A. Nonobese diabetic/severe combined immunodeficiency (NOD/SCID) mouse as a model system to study the engraftment and mobilization of human peripheral blood stem cells. Blood. 1998; 92:2556-2570.
124. Gothot A, van der Loo J C M, Clapp W, Srour W F. Cell cycle-related changes in repopulating capacity of human mobilized peripheral blood CD34+ cells in non-obese/severe combined immune-deficient mice. Blood. 1998; 92:2641-2649.
125. Dao M A, Nolta J A. Immunodeficient mice as models of human hematopioetic stem cell engraftment. Curr Opin Immunol. 1999; 11:532-538.
126. Peled A, Kollet O, Ponomaryov T, Petit I, Franzita S, Grabovsky V, Slav M M, Nagler A, Lider O, Alon R, Zipor D, Lapidot T. The chemokine SDF-1 activates the integrins LFA-1, VLA-4, and VLA-5 on immature human CD34+ cells: role in transendothelial/stromal migration and engraftment of NOD/SCID mice. Blood. 2000; 95:3289-3296.
127. Angelopoulou M, Novelli E, Grove J E, Rinder H M, Civin C, Cheng L, Krause D S. Cotransplantation of human mesenchymal stem cells enhances human myelopoiesis and megakaryocytopoiesis in NOD/SCID mice. Exp Hematol. 2003; 31:413-420.
128. Matsumura T, Kametani Y, Ando K, Hirano Y, Katano I, Ito R, Shiina M, Tsukamoto H, Saito Y, Tokuda Y, Kato S, Ito M, Motoyoshi K, Habu S. Functional CD5+ B cells develop predominantly in the spleen of NOD/SCID/common gamma chain(null) (NOG) mice transplanted either with human umbilical cord blood, bone marrow, or mobilized peripheral blood CD34+ cells. Exp Hematol. 2003; 31:789-797.
129. Palucka A K, Gatlin J, Blanck J P, Melkus M W, Clayton S, Ueno H, Kraus E T, Cravens P, Bennett L, Padgett-Thomas A, Marches F, Islas-Ohlmayer M, Garcia J V, Banchereau J. Human dendritic cell subsets in NOD/SCID mice engrafted with CD34+ hematopoietic progenitors. Blood. 2003; 102:3302-3310.
130. Zhao Y, Rodriguez-Barbosa J I, Zhao G, Shaffer J, Arm J S, Sykes M. Maturation and function of mouse T cells with a transgenic TCR positively selected by highly disparate xenogeneic porcine MHC. Cell Mol Biol. 2000; 47:217-228.
131. Zhao Y, Swenson K, Sergio J J, Sykes M. Pig MHC mediates positive selection of mouse CD4+ T cells with a mouse MHC-restricted TCR in pig thymus grafts. J Immunol. 1998; 161:1320-1326.
132. Zhao Y, Sergio J J, Swenson K A, Arm J S, Sachs D H, Sykes M. Positive and negative selection of functional mouse CD4 cells by porcine MHC in pig thymus grafts. J Immunol. 1997; 159:2100-2107.
133. Lee L A, Gritsch H A, Sergio J J, Arm J S, Glaser R M, Sablinski T, Sachs D H, Sykes M. Specific tolerance across a discordant xenogeneic transplantation barrier. Proc Natl Acad Sci USA. 1994; 91:10864-10867.
134. Zhao Y, Swenson K, Sergio J J, Arm J S, Sachs D H, Sykes M Skin graft tolerance across a discordant xenogeneic barrier. Nature Med. 1996; 2:1211-1216.
135. Zhao Y, Rodriguez-Barbosa J I, Shimizu A, Swenson K, Sachs D H, Sykes M. Despite efficient intrathymic negative selection of host-reactive T cells, autoimmune disease may develop in porcine thymus-grafted athymic mice: Evidence for failure of regulatory mechanisms suppressing autoimmunity. Transplantation. 2002; 75:1832-1840.
136. Cupedo T, Nagasawa M, Weijer K, Blom B, Spits H. Development and activation of regulatory T cells in the human fetus. Eur J Immunol. 2005; 35:383-390.
137. Seddiki N, Santner-Nanan B, Tangye S G, Alexander S I, Solomon M, Lee S, Nanan R, Saint Groth B F. Persistence of naive CD45RA+ regulatory T cells in adult life. Blood. 2006; 107:2830-2838.
138. Baecher-Allan C, Wolf E, Hafler D A. MHC class II expression identifies functionally distinct human regulatory T cells. J Immunol. 2006; 176:4622-4631.
139. Cozzo C, Larkin J, III, Caton A J. Self-peptides drive the peripheral expansion of CD4+CD25+ regulatory T cells. J Immunol. 2003; 171:5678-5682.
140. Zhao Y, Rodriguez-Barbosa J I, Swenson K, Zhao G, Arm J S, Sachs D H, Sykes M. Highly disparate xenogeneic skin graft tolerance induction by fetal pig thymus in thymectomized mice: Conditioning requirements and the role of co-implantation of fetal pig liver. Transplantation. 2001; 72:1608-1615.
141. Zhao Y, Fishman J A, Sergio J J, Oliveros J L, Pearson D A, Szot G L, Wilkinson R A, Arm J S, Sachs D H, Sykes M. Immune restoration by fetal pig thymus grafts in T cell-depleted, thymectomized mice. J Immunol. 1997; 158:1641-1649.
142. Jordan M S, Boesteanu A, Reed A J, Petrone A L, Holenbeck A E, Lerman M A, Naji A, Caton A J. Thymic selection of CD4+CD25+ regulatory T cells induced by an agonist self-peptide. Nat Immunol. 2001; 2:301-306.
143. Derbinski J, Schulte A, Kyewski B, Klein L. Promiscuous gene expression in medullary thymic epithelial cells mirrors the peripheral self. Nat Immunol. 2001; 2:1032-1039.

144. Anderson M S, Venanzi E S, Klein L, Chen Z, Berzins S P, Turley S J, Von Boehmer H, Bronson R, Dierich A, Benoist C, Mathis D. Projection of an immunological self shadow within the thymus by the aire protein. Science. 2002; 298:1395-1401.
145. Gotter J, Brors B, Hergenhahn M, Kyewski B. Medullary Epithelial Cells of the Human Thymus Express a Highly Diverse Selection of Tissue-specific Genes Colocalized in Chromosomal Clusters. J Exp Med. 2004; 199:155-166.
146. Kyewski B, Derbinski J. Self-representation in the thymus: an extended view. Nat Rev Immunol. 2004; 4:688-698.
147. Petrone A, Battelino T, Krzisnik C, Bugawan T, Erlich H, Di Mario U, Pozzilli P, Buzzetti R. Similar incidence of type 1 diabetes in two ethnically different populations (Italy and Slovenia) is sustained by similar HLA susceptible/protective haplotype frequencies. Tissue Antigens. 2002; 60:244-253.
148. Petrone A, Bugawan T L, Mesturino C A, Nistico L, Galgani A, Giorgi G, Cascino I, Erlich H A, Di Mario U, Buzzetti R. The distribution of HLA class II susceptible/protective haplotypes could partially explain the low incidence of type 1 diabetes in continental Italy (Lazio region). Tissue Antigens. 2001; 58:385-394.
149. Rodewald H R, Paul S, Haller C, Bluethmann H, Blum C. Thymus medulla consisting of epithelial islets each derived from a single progenitor. Nature. 2001; 414:763-768.
150. Martinez-Caceres E, Jaleco A C, Res P, Noteboom E, Weijer K, Spits H. Characterization of CD34+ thymic stromal cells located in the subcapsular cortex of the human thymus. Exp Hematol. 1998; 26:588-596.
151. Rooke R, Waltzinger C, Benoist C, Mathis D. Positive selection of thymocytes induced by gene transfer: MHC class II-mediated selection of CD8 lineage cells. Int Immunol. 1999; 11:1595-1600.
152. Nakano N, Rooke R, Benoist C, Mathis D. Positive selection of T cells induced by viral delivery of neopeptides to the thymus. Science. 1997; 275:678-683.
153. Rooke R, Waltzinger C, Benoist C, Mathis D. Targeted complementation of MHC class II deficiency by intrathymic delivery of recombinant adenoviruses. Immunity. 1997; 7:123-134.
154. Rooke R, Benoist C, Mathis D. Intrathymic delivery of MHC genes using recombinant adenoviruses. Methods Mol Biol. 2000; 134:69-79.
155. Smerdon R A, Peakman M, Hussain M J, Alviggi L, Watkins P J, Leslie R D, Vergani D. Increase in simultaneous coexpression of naive and memory lymphocyte markers at diagnosis of IDDM. Diabetes. 1993; 42:127-133.
156. Petersen L D, Duinkerken G, Bruining G J, van Lier R A, de Vries R R, Roep B O. Increased numbers of in vivo activated T cells in patients with recent onset insulin-dependent diabetes mellitus. J Autoimmun. 1996; 9:731-737.
157. Holler P D, Yamagata T, Jiang W, Feuerer M, Benoist C, Mathis D. The same genomic region conditions clonal deletion and clonal deviation to the CD8 {alpha} {alpha} and regulatory T cell lineages in NOD versus C57BL/6 mice. Proc Natl Acad Sci USA. 2007; 104:7187-7192.
158. Hehmke B, Michaelis D, Gens E, Laube F, Kohnert K D. Aberrant activation of CD8+ T-cell and CD8+ T-cell subsets in patients with newly diagnosed IDDM. Diabetes. 1995; 44:1414-1419.
159. Zippelius A, Pittet M J, Batard P, Rufer N, De Smedt M, Guillaume P, Ellefsen K, Valmori D, Lienard D, Plum J, MACDONALD H R, Speiser D E, Cerottini J C, Romero P. Thymic selection generates a large T cell pool recognizing a self-peptide in humans. J Exp Med. 2002; 195:485-494.
160. Wolf D, Rumpold H, Koppelstatter C, Gastl G A, Steurer M, Mayer G, Gunsilius E, Tilg H, Wolf A M. Telomere length of in vivo expanded CD4(+)CD25 (+) regulatory T-cells is preserved in cancer patients. Cancer Immunol Immunother. 2006; 55:1198-1208.
161. Rodriguez-Barbosa J I, Zhao Y, Ezquerra A, Zhao G, Sachs D H, Sykes M. Murine CD4 T cells selected in a highly disparate xenogeneic porcine thymus graft do not show rapid decay in the absence of selecting MHC in the periphery. J Immunol. 2002; 169:6697-6710.
162. Rubio M T, Means T K, Chakraverty R, Shaffer J, Fudaba Y, Chittenden M, Luster A D, Sykes M. Maturation of human monocyte-derived dendritic cells (MoDCs) in the presence of prostaglandin E2 optimizes CD4 and CD8 T cell-mediated responses to protein antigens: role of PGE2 in chemokine and cytokine expression by MoDCs. Int Immunol. 2005; 17:1561-1572.
163. Huber S, Schramm C, Lehr H A, Mann A, Schmitt S, Becker C, Protschka M, Galle P R, Neurath M F, Blessing M. Cutting edge: TGF-beta signaling is required for the in vivo expansion and immunosuppressive capacity of regulatory CD4+CD25+ T cells. J Immunol. 2004; 173:6526-6531.
164. Zheng S G, Gray J D, Ohtsuka K, Yamagiwa S, Horwitz D A. Generation ex vivo of TGF-beta-producing regulatory T cells from CD4+CD25− precursors. J Immunol. 2002; 169:4183-4189.
165. Nakamura K, Kitani A, Fuss I, Pedersen A, Harada N, Nawata H, Strober W. TGF-beta1 plays an important role in the mechanism of CD4+CD25+ regulatory T cell activity in both humans and mice. J Immunol. 2004; 172:834-842.
166. Chen W, Jin W, Hardegen N, Lei K J, Li L, Marinos N, McGrady G, Wahl S M. Conversion of peripheral CD4+ CD25− naive T cells to CD4+CD25+ regulatory T cells by TGF-beta induction of transcription factor Foxp3. J Exp Med. 2003; 198:1875-1886.
167. Peng Y, Laouar Y, Li M O, Green E A, Flavell R A. TGF-{beta} regulates in vivo expansion of Foxp3-expressing CD4+CD25+ regulatory T cells responsible for protection against diabetes. Proc Natl Acad Sci USA. 2004; 101:4572-4577.
168. Fu S, Zhang N, Yopp A C, Chen D, Mao M, Chen D, Zhang H, Ding Y, Bromberg J S. TGF-beta induces Foxp3+ T-regulatory cells from CD4+ CD25− precursors. Am J Transplant. 2004; 4:1614-1627.
169. Marie J C, Letterio J J, Gavin M, Rudensky A Y. TGF-{beta} 1 maintains suppressor function and Foxp3 expression in CD4+CD25+ regulatory T cells. J Exp Med. 2005; 201:1061-1067.
170. Bettelli E, Carrier Y, Gao W, Korn T, Strom T B, Oukka M, Weiner H L, Kuchroo V K. Reciprocal developmental pathways for the generation of pathogenic effector TH17 and regulatory T cells. Nature. 2006; 441:235-238.
171. Porter D L, Levine B L, Bunin N, Stadtmauer E A, Luger S M, Goldstein S, Loren A, Phillips J, Nasta S, Perl A, Schuster S, Tsai D, Sohal A, Veloso E, Emerson S, June C H. A phase 1 trial of donor lymphocyte infusions expanded and activated ex vivo via CD3/CD28 costimulation. Blood. 2006; 107:1325-1331.

Example 2: "Mini Me" Mouse: A Model for Immune Rejuvenation and Individualized Analysis of Immune Pathogenesis in Adult Humans Many autoimmune diseases are mediated by autoreactive T cells. Genetic factors contribute substantially to susceptibility to autoimmunity. While HLA genotype is most strongly linked with autoimmune diseases[1-4], recently-defined non-HLA-linked genes collectively confer substantial risk[3-10]. Similar loci contribute to autoimmunity in non-obese diabetic (NOD) mice[8] and its human counterpart, Type 1 diabetes mellitus (T1DM)[11]. These loci include immunomodulatory genes, such as cytokines, costimulatory and inhibitory molecules[8, 12, 13]. Defects in regulatory CD4 T cells[14-16] NK/T cells[17-19], APCs[20, 21] and T effector cells[22] have been associated with both murine and human T1DM and other autoimmune diseases[2, 23, 24]. Genetic studies have permitted analysis of mechanisms by which some of these genes promote autoimmunity in NOD mice[8, 12]. In humans with autoimmune diseases, however, the underlying defects arising from non-HLA-associated genes are largely undefined. Given that many of these loci contain immunoregulatory genes, it seems probable that intrinsic abnormalities in the cells of the immune system, which originate from hematopoietic stem cells (HSCs), contribute to the development of autoimmunity, as disease susceptibility is transferred via hematopoietic stem cells in both NOD mice[25] and humans[26]. Most clinical studies involve analyses of patients after disease onset and cannot distinguish cause from effects of the disease, its treatment or precipitating environmental factors, precluding determination of the genetically-determined, HSC-intrinsic immunoregulatory abnormalities that confer disease susceptibility.

"Humanized mouse" models have been developed. Human peripheral blood mononuclear cells (PBMC) can populate immunodeficient mice[27] and human T cells develop in human fetal thymus (THY) grafts implanted with fetal liver under the kidney capsule[28]. Recently, it was shown that the combination of intravenous human HSC infusion with human fetal thymus and liver (THY/LIV) grafts under the kidney capsule allows human immune reconstitution with high levels of peripheral human T cells, B cells, immunoglobulins, and both myeloid and plasmacytoid dendritic cells[29]. Strong antigen-specific immune responses are observed in vivo[29-31], including class-switched antibody responses. Normal thymic development of regulatory T cells (Tregs) with suppressive function has been demonstrated. Furthermore, this model also allowed the demonstration of homeostatic peripheral expansion of human T cells[32].

In order to study the role of genetically determined HSC-intrinsic abnormalities in human autoimmune disease pathogenesis, it will be necessary to achieve human peripheral T cell reconstitution and immune function with adult HSCs obtained from a patient with autoimmunity. However, these cells are not available in large quantities, and adult human HSCs do not engraft as well as fetal CD34+ cells in immunodeficient mice[33]. Furthermore, allogeneic HSCs can be rejected by allogeneic thymocytes pre-existing within a fetal thymus graft.

The invention provides the development of a new humanized mouse model using cryopreserved/thawed human fetal thymus tissue that can support the generation and peripheral reconstitution with T cells and APCs from small numbers of adult, allogeneic bone marrow CD34+ cells. A rejuvenated immune system is generated from HSCs from adult bone marrow aspirates. This "Mini Me" mouse can allow the identification of HSC-intrinsic immune abnormalities predisposing to autoimmunity, individualized evaluation of immunotherapeutic strategies and can achieve immune reconstitution in adults with thymic insufficiency.

Overcoming the Immune Barrier Imposed by Mature T Cells in Fetal Thymus Grafts:

To assess human immune reconstitution from adult HSCs in immunodeficient mice grafted with allogeneic fetal human thymus tissue, CD34+ cells were isolated from discarded human bone marrow infusion filters and given i.v. to sublethally irradiated nonobese diabetic-severe combined immunodeficient (NOD/SCID) mice receiving fetal THY transplantation. Recipients of untreated fetal human THY grafts showed low percentages of peripheral T cells during the first weeks after transplantation, which eventually disappeared, indicating that these cells emigrated from the graft and non-T cells did not reconstitute from injected allogeneic CD34+ cells. Moreover, some long-term (>20 weeks) animals have developed a GVHD-like wasting syndrome. The thymocytes pre-existing in the THY grafts can reject the allogeneic CD34+ cells and expand to attack recipient tissues, thereby preventing immune reconstitution and causing GVHD, respectively. Methods for depleting thymocytes pre-existing within the graft were tested in an effort to prevent these phenomena.

Fetal thymus organ culture (FTOC) with 2'-deoxyguanosine (dGuo) has been shown to deplete thymocytes while preserving the stromal elements[34] that can become recolonized and support thymopoiesis[35]. NOD/SCID mice received allogeneic adult CD34+ cells in addition to fetal THY tissue that had been cultured for 7 or 21 days in the presence of dGuo. Control animals received fetal liver CD34+ cells from the donor of the dGuo-treated thymic tissue. Mice that received $5 \times 10^5$ adult CD34+ cells without a THY graft reconstituted an average of 20% human PBMCs by Week 10 (FIG. 25A), but CD3+ cells were undetectable (FIG. 25C). In mice that received 7 day dGuo-cultured THY tissue plus allogeneic CD34+ cells, CD3+ levels averaging ~7% of PBMC were detectable by 6 weeks post-transplantation (FIG. 25C), but CD19+ cells did not appear (FIG. 25B), indicating that mature T cells escaping dGuo depletion rejected the infused allogeneic CD34+ cells and demonstrating that resident cells within the THY graft do not achieve multilineage reconstitution or maximally reconstitute the peripheral T cell pool (FIG. 25C).

Successful thymic engraftment with human thymopoiesis as well as peripheral CD19+ cell reconstitution occurred after intravenous infusion of $5 \times 10^5$ allogeneic adult CD34+ cells in combination with a 21-day dGuo-cultured THY graft, with an average of ~25% human CD3+ cells among PBMC at 20 weeks (FIG. 25C). Thus, progenitors derived from peripherally-infused allogeneic adult CD34+ cells can populate dGuo-treated thymi, where they undergo thymopoiesis, and emigrate to the periphery. Control recipients of dGuo-treated fetal thymus tissue with $4 \times 10^5$ autologous fetal liver CD34+ cells instead of allogeneic adult marrow CD34+ cells had ~35% human peripheral blood CD3+ PBMC by 14 weeks (FIG. 25C), indicating that T cell reconstitution was more efficient after injection of autologous fetal CD34+ cells vs. allogeneic adult CD34+ cells.

While both groups of mice receiving 21-day FTOC grafts exhibited high levels of long-term peripheral B cell reconstitution (FIG. 25B), the infusion of fewer than $5 \times 10^5$ adult CD34+ cells did not allow successful engraftment and B cell reconstitution. Since only limited HSC numbers are available through volunteer bone marrow aspiration, NOD/SCID/IL2 receptor γ chain$^{null}$ (NSG) mice were used, which lack NK cells and are more permissive for engraftment of human HSC[36], for the ensuing experiments.

The irradiation of THY grafts to deplete preexisting thymocytes was next evaluated. NSG mice received 7 Gy irradiated thymic tissue in combination with $3 \times 10^5$ adult CD34+ cells, with or without anti-human CD2 mAb i.p. Both groups of mice showed excellent B cell and monocyte reconstitution from the allogeneic adult CD34+ cells, demonstrating that rejection by graft T cells was prevented. However, these mice generated only very low numbers of peripheral T cells by 20 weeks and grafts were barely visible upon laparotomy, indicating that thymic irradiation impairs thymic growth and/or function.

Cryopreserved/Thawed Fetal THY Grafts Allow Peripheral Reconstitution of T Cells and Multiple Hematopoietic Lineages from Allogeneic, Adult Human Hematopoietic Stem Cells in NSG Mice.

Figure 26:
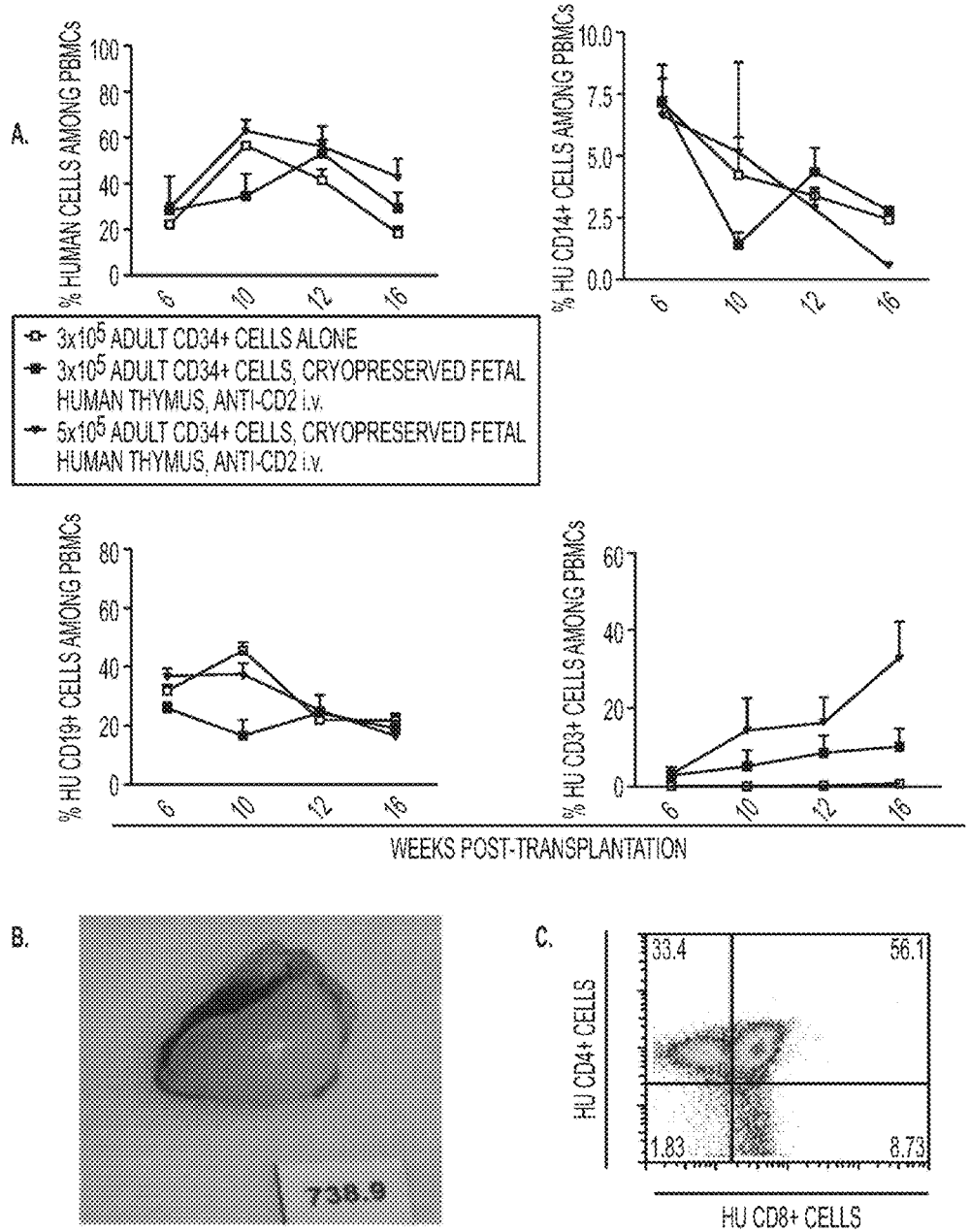

Transplantation of cryopreserved[37, 38] thymus tissue can restore immune function in mice[37, 38]. Cryopreservation of human fetal THY tissue can deplete thymocytes without impairing growth potential. Groups of sublethally irradiated NSG mice received cryopreserved/thawed fetal human THY grafts plus $3-5 \times 10^5$ allogeneic, adult HSCs i.v. and two doses of anti-CD2 mAb. As shown in FIG. 26, all mice achieved human B cell and monocyte chimerism by 6 weeks. In contrast to recipients of HSCs alone, mice that received cryopreserved/thawed THY grafts generated peripheral T cells, which appeared by 6 weeks and peaked at ~10% and ~30% of PBMC 16 weeks post-transplantation in mice infused with $3 \times 10^5$ or $5 \times 10^5$ CD34+ cells, respectively. THY grafts from recipients of CD34+ cells were markedly enlarged 20 weeks post-transplantation and showed robust human thymopoiesis, with a majority of CD4/CD8 double positive human thymocytes (FIGS. 26B-C), as previously observed with fetal CD34+ cells[31].

Control animals that received cryopreserved THY with or without anti-CD2 mAb, but without i.v. CD34+ cells, did not repopulate significant human T cells in the periphery. Thus, pre-existing graft thymocytes were depleted by cryopreservation and intravenous injection of CD34+ cells was necessary for human T cell reconstitution.

None of the long-term animals in this study that received a cryopreserved/thawed THY plus anti-CD2 mAb developed wasting syndrome, consistent with the hypothesis that the syndrome is due to graft-vs.-host reactivity of pre-existing mature T cells emigrating from the thymus graft.

Human Immune Reconstitution from a Bedside Bone Marrow Aspirate from Control and T1DM Volunteers.

The reconstitution capabilities of adult CD34+ cells isolated from a bedside bone marrow aspirate were next evaluated. An aspiration of 15 ml bone marrow yielded $3.6 \times 10^5$ and $2.7 \times 10^6$ CD34+ cells from a healthy control and T1DM patient volunteer, respectively. Sublethally irradiated NSG mice received $1.8 \times 10^5$ adult CD34+ cells each in addition to a cryopreserved/thawed human fetal thymus graft and anti-human CD2 mAb. Control irradiated NSG mice received CD34+ cells without thymic tissue. Human chimerism was detectable from Week 6 on and peaked at ~25%-80% by 20 weeks (FIG. 27). Mice that received a THY graft in addition to i.v. CD34+ cells from the control and T1DM volunteers developed peak CD3+ cell levels between ~50% and ~90%, while control NSG mice had minimal T cell reconstitution. CD19+ cells and CD14+ cells also recovered from the HSCs from both the T1DM and control volunteer (FIG. 27). Similar results were obtained in a repeat experiment, in which 6 NSG mice were reconstituted with $2 \times 10^5$ CD34+ cells from a single T1DM volunteer aspirate.

T Cell Function, Self Tolerance and Treg Development from T1DM and Control Adult CD34 Cells.

T cell function was assessed by transplanting allogeneic and xenogeneic (pig) skin to THY-grafted mice that received adult CD34+ cells. As shown in FIG. 28A, these mice rapidly rejected allogeneic human and xenogeneic pig skin grafts. To assess T cell alloreactivity and self-tolerance of T cells generated from adult CD34+ cells of T1DM and normal volunteers, a mixed lymphocyte reaction (MLR) was performed using purified T cells isolated from the spleens and lymph nodes. As shown in FIG. 28B, T cells from mice reconstituted from T1DM and control subjects showed self-tolerance along with strong alloresponses in MLR. Of note, fresh adult donor T cells and T cells from mice that received CD34+ cells from the same healthy control bone marrow donor showed similar, robust responses to the allogeneic stimulator and similar self-tolerance. Thus, immune responsiveness and self tolerance of the adult volunteer were recapitulated in the "Mini Me" mouse.

Studies have indicated that Treg numbers are reduced in the blood of T1DM patients compared to non-diabetic controls[39]. Natural Tregs were quantified in thymus grafts and the periphery of reconstituted mice. As shown in FIG. 28C, CD25highFoxP3+ natural Tregs among CD4+CD8- thymocytes were present in similar numbers and proportions in human thymic grafts reconstituted from control and T1DM volunteers. Moreover, similar proportions of Tregs were detected in the peripheral immune system of both groups of reconstituted mice (FIG. 28D).

Rejuvenated T Cell Phenotype in the "Mini Me" Mouse.

At 20 weeks post-transplantation, spectratyping analysis was performed on CD4 and CD8 SP thymocytes of mice reconstituted from T1DM CD34 cells and a normal volunteer (FIG. 29A). In both populations from thymic grafts reconstituted by T1DM or control volunteers, the human T cells showed a diverse repertoire, with utilization of all 11 BV families analyzed and a near normal CDR3 length distribution for all of them. The mean Hamming distance for all analyzed BV families was 21.2, indicating similar T cell polyclonality to that in 20 normal control peripheral blood CD4 subsets. Comparison of T cells in the blood of the adult control volunteer CD34 cell donor revealed a marked increase in the proportion of naïve-type CD45RA+ CD45RO- CD4, CD8 and Treg subsets in the "Mini Me" mouse reconstituted from the same donor (FIG. 29B,C). Thus, a rejuvenated version of the adult donor's immune system is generated in the "Mini Me" mouse.

It is demonstrated here that adult, bone marrow-derived CD34+ cells can reconstitute sublethally irradiated NSG mice grafted with cryopreserved/thawed allogeneic thymus tissue. This reconstitution involves multiple hematopoietic lineages, including T cells, B cells and myeloid cells. In contrast to irradiation or 7-day dGuo-treatment, cryopreserving/thawing the fetal thymus tissue plus administration of anti-CD2 mAb successfully depletes mature T cells from the thymus graft, prevents the rejection of allogeneic CD34+ cells, prevents late-onset wasting syndrome and preserves thymic function. Under such conditions, thymopoiesis, growth of the thymus graft and reconstitution of a functional, diverse and rejuvenated immune system is achieved that recapitulates the self-tolerance of the adult donors. While fetal liver fragments were included in the humanized mouse model upon which our studies are based[29, 31], it was found that these fragments are not required, as progenitors from infused CD34+ cells can populate the human thymic grafts.

While in vivo thymopoiesis and peripheral reconstitution from dGuo-treated human thymi are demonstrated, peripheral T cell reconstitution from infused adult CD34+ cells was slow when thymi were treated with dGuo for a sufficient time period (21 days) to prevent rejection of allogeneic CD34+ cells. Human thymic tissue cultured for several weeks in dGuo has been used to achieve T cell reconstitution in patients with complete DiGeorge syndrome[40]. Given that T cell recovery is slow in these children[40], the results indicate cryopreservation of the thymic tissue as an approach to more rapid T cell recovery while preventing GVHD.

Cryopreservation of fetal thymus tissue permits accumulation of a "bank" of HLA-typed tissue for use with adult CD34+ cells from patients and controls sharing class II alleles associated with autoimmune diseases. These alleles are relatively common in the general population[41]. The use of NSG mice allows the engraftment of relatively small numbers of allogeneic adult HSC, so that multiple mice (up to 15) can be reconstituted from CD34+ cells isolated from a 15 ml bone marrow aspirate of an adult volunteer.

Immune reconstitution from adult bone marrow CD34+ cells in NSG mice allows in vivo analysis of HSC-intrinsic immune defects associated with the development of autoimmune diseases. It provides an immune system unaltered by disease and allows comparison of normal controls versus patients in a controlled and prospective manner. Human studies have previously been limited to the analysis of peripheral blood samples, and it has been difficult to distinguish cause from effect of the disease. Defects in Treg numbers and function have been reported for T1DM[15, 16, 39, 42], systemic lupus erythematosus[43] and rheumatoid arthritis[44]. However, Treg defects have not been borne up by all studies and NOD mice have been found to have conserved Treg numbers and function[45, 46]. Some human studies have shown Treg conservation in T1DM patients[47]. Thus far, no gross abnormalities have been observed in the T cell populations generated from T1DM patients CD34 cells, which generate Tregs in similar proportions as healthy control CD34 cell donors. Thus, the studies rule out a genetically programmed reduction in the ability to generate Tregs from T1DM hematopoietic stem cells. Further studies in the model can allow in-depth assessment of the myriad of immunoregulatory abnormalities that have been implicated in T1DM, along with an understanding of the genetic polymorphisms that may confer them.

For T1DM, immunopathological findings in animal models such as the NOD mouse mimic human disease[48] to some extent, but have also led to misconceptions and erroneous extrapolations[48, 49]. While rejection of allogeneic islets has been modeled in a diabetic humanized mouse model[50], sensitized, disease-associated PBMC were transferred from individuals who had already developed T1DM, precluding analysis of fundamental cell-intrinsic immunoregulatory defects underlying immune pathogenesis. HLA-transgenic immunocompetent mice have provided insight into the pathogenesis of autoimmune diseases such as rheumatoid arthritis[51], multiple sclerosis[52], celiac disease[53], T1DM[54-56] and spontaneous diabetes has been described[57]. However, none of these models permit analyses of human HSC-intrinsic, genetically determined immune abnormalities initiating autoimmune pathogenesis. In contrast, the combined administration of i.v. CD34+ cells and fetal THY tissue in immunodeficient mice allows recovery of normal T cell function, T-B interactions, class-switched antibody responses, along with the development of secondary lymphoid organs with normal structural features and both plasmacytoid and myeloid dendritic cells[29-31]. Since Tregs develop normally and T cell homeostasis can be studied in this model[32], it can allow assessment of underlying immune regulatory abnormalities in cells derived from HSCs of patients with autoimmune diseases. Furthermore, this "Mini Me" model can also allow the analysis of individual responsiveness of an adult marrow donor to immunotherapy. In addition, the reconstitution of multiple mice with naïve T cells with a diverse repertoire derived from adult HSCs can provide patients with thymic insufficiency, such as cancer patients, hematopoietic cell transplant recipients or HIV patients, with a source of functional, self-tolerant T cells for adoptive transfer. The mice can be immunized with tumor antigens or viral proteins to generate desired specific immune responses, as responses to protein antigens develop in mice receiving human THY and CD34 cell grafts[30]. Additionally, the mice can generate large numbers of autologous Tregs with desired specificities for the treatment of patients with autoimmune disease, GVHD or allografts. The specific tolerance to CD34 cell donor "self" antigens and the absence of GVHD in the studies most likely reflects intrathymic deletion due to the presence of APCs from the human HSC donor and the murine recipient, respectively, in the human thymus graft, as the presence of both human donor and murine recipient class II$^{high}$ APCs in thymic xenografts in immunodeficient mice has been previously demonstrated[58].

The invention provides a model that permits the development of multilineage peripheral human hematopoietic cells from adult HSCs. The "Mini Me" mouse provides a "clean slate" immune system, unaltered by disease or its treatment, for the analysis of intrinsic defects in immunoregulation associated with autoimmune disorders and of genetically-controlled responses to immunotherapies. These mice also have therapeutic potential as a source of polyclonal, naïve or activated T cells with desired specificities and properties for use in patients.

Materials and Methods

Animals and Human Tissues and Cells.

Nonobese diabetic-severe combined immunodeficient (NOD/SCID) and NOD/SCID/IL2 receptor γ chain$^{null}$ (NSG) mice were obtained from Jackson Laboratory (Bar Harbor, Me.), and housed in a specific pathogen-free microisolator environment. Human fetal thymus and liver tissues of gestational age 17 to 20 weeks were obtained from Advanced Biosciences Resource (Alameda, Calif.). Fragments of fetal thymus tissue were cryopreserved in 10% DMSO and 90% human AB serum (Atlanta Biologicals, Lawrenceville, Ga.), irradiated or cultured, depending on the experimental design. CD34+ cells were isolated from a 15 ml bone marrow aspirate, or from discarded human bone marrow filters, or from fetal human liver tissue using a magnetic-activated cell sorter (MACS) separation system with anti-human CD34+ microbeads (Miltenyi Biotec, Auburn, Calif.).

Fetal Thymus Organ Culture.

Human fetal thymus culture was performed as previously published[34]. Briefly, thymus fragments were placed on 0.8 μm isopore membrane filters (Millipore, Billerica, Mass.) on 1 cm$^2$ Gelfoam sponges (Pharmacia & Upjohn Co, NY). To eliminate endogenous thymocytes, organ cultures were grown in the presence of 1.35 mM 2'-deoxyguanosine (Sigma-Aldrich, St. Louis, Mo.) in Dulbecco's modified Eagle medium (DMEM, Sigma-Aldrich, St. Louis, Mo.) at 37° C. for 7 or 21 days.

Human Tissue Transplantation.

NOD/SCID and NSG mice were conditioned with sub-lethal (2.5 Gy) total-body irradiation. Thawed, irradiated or cultured human fetal thymus fragments measuring about 1 mm$^3$ were implanted underneath the recipient kidney capsule. Within 24 hours of fetal thymus organ transplantation, 1-5×10$^5$ human CD34+ cells were injected intravenously into the mice. Some recipients were treated intravenously with anti-human CD2 mAb (BTI 322; 100 μg/mouse) on Days 0 and 7.

Skin Grafting.

Split thickness (2.3 mm) skin samples from a MHC miniature pig and an allogeneic human donor were grafted on the lateral thoracic wall 39 weeks after human tissue transplantation Skin grafts were evaluated daily from day 7 onward to 4 weeks and then at least one inspection every third day thereafter. Grafts were defined as rejected when less than 10% of the graft remained viable.

Flow Cytometry (FCM).

Levels of human hematopoietic cells in transplanted mice were assessed by four-color flow cytometry. Mice were tail bled at regular intervals after transplantation to obtain peripheral blood mononuclear cells (PBMC), which were prepared with histopaque-1077 (Sigma-Aldrich, St. Louis, Mo.). Flourochrome-labelled mAbs, purchased from BD Pharmingen (San Diego, Calif.), were used in different combinations: anti-mouse CD45, anti-mouse Ter119, anti-human CD4, anti-human CD8, anti-human CD14, anti-human CD19, anti-human CD45, anti-human CD3, anti-human CD45RA, anti-human CD45RO, anti-human CD127, anti-human FoxP3, anti-human CD25 and isotype control mAbs. FCM analysis was performed using a FACScalibur, FACScanto or LSRII (BD Mountain View, Calif.), and analysis was carried out by FLOWJO software (TreeStar, San Carlos, Calif.). Dead cells were excluded from the analysis by gating out low forward scatter and high propidium iodide (PI)—retaining cells. Murine erythroid cells were excluded from the analysis of human chimerism by gating out mouse Ter119+ cells.

Mixed Lymphocyte Reactions.

Splenocytes and lymph nodes were harvested from humanized mice and mononuclear cell suspensions were isolated by ficoll separation. Human T cells were enriched by depletion of mouse cells using anti-mouse CD45 and Ter-119 microbeads (Miltenyi Biotec, Auburn, Calif.) followed by T cell purification using the Pan T cell isolation kit II (Miltenyi Biotec, Auburn, Calif.) according to the manufacturer's instructions. Purity was >90%. Responder T cells (10$^5$ per well) were cultured with irradiated human allogeneic PBMCs (3000 rad, 10$^5$ cells per well) as stimulators for 5 days and proliferation was measured via [$^3$H] thymidine incorporation as has been previously described[59]. Data are shown as mean [$^3$H] thymidine incorporation in triplicate cultures.

Spectratyping.

Total RNA was extracted directly from 1 to 2×10$^4$ CD4 or CD8 single positive thymocytes (purity >80%), reverse transcribed and single-strand cDNA synthesis was performed as described[60]. Amplification reactions were performed using a TCR β chain constant region primer and individual variable region primers as described[60]. Products were then used in run-off reactions with a Cβ-specific FAM-labeled primer (Integrated DNA Technologies, Coralville, Iowa) as described[60]. The labelled products were then used to determine the length distribution of the TCR β-chain length. The size and area of the peaks corresponding to the DNA products were determined using an ABI 3100 Genetic Analyzer (Applied Biosystems, Foster City, Calif.) and analyzed using Applied Biosystems Genotyper 3.7 NT. Hamming distances to assess the quantitative difference between the experimental and reference β-chain length distributions of peripheral blood CD4 T cells in normal humans were calculated as described[60].

Statistical Analysis.

Statistical analysis and comparisons were performed with PRISM software version 4.0 (GraphPad, San Diego, Calif.). Data in bar graphs are expressed as mean±SEM. Student's t-test for parametric data sets, or Mann-Whitney test for nonparametric data sets were used to compare groups. A p value less than 0.05 was considered to be statistically significant.

Human CD34+ Cell Isolation and Fetal Thymus Preparation for Humanized Mice.

Human Tissue:

Human fetal thymus tissue was ordered from a commercial source, eg. Stem-ex or Advanced Bioscience Resources.

Media:

Bone Marrow Medium (500 ml Media199, 5 ml HEPES, 5 ml DNAse, 40 μl gentamycin), MACS buffer (500 ml PBS, 5 g BSA, 2 ml 0.5M EDTA-degas for 30 minutes)

Material:

sterile scissors and forceps, sterile 6 ml syringe, sterile 10 cm petri dish, 50 ml falcon tubes, Histopaque-1077, 40 μm cell stainer, human AB serum and DMSO if cryopreserving, CD34+ MACS isolation kit. All procedures have to be performed under sterile conditions.

Preparation of Fetal Thymus Tissue:

1. Cut fetal thymus tissue in ~1-2 mm3 big pieces with sterile scissors. 2. Keep fetal thymic tissue in culture media on ice for immediate subcapsular transplantation or cryopreserve in 1.5 ml sterile cryopreservation tubes using 90% human AB serum and 10% DMSO. Move tubes quickly to the cell freezer and start freezing process. 3. After freezing, move tubes with fetal thymus tissue to a −80° C. freezer. If not transplanted within one week, store tissue pieces in liquid nitrogen. 4. For thawing, remove tubes from liquid nitrogen and place in 37° C. waterbath. As soon as ice has started to melt, remove tubes and transfer content into 50 ml conical containing bone marrow media. After 5 minutes, transfer thymus pieces into a new 50 ml conical containing fresh bone marrow media in order to dilute the DMSO. Repeat dilution step after 5 minutes. 5. Place thymic pieces in media on ice for immediate subcapsular transplantation.

Preparation of Fetal Liver CD34+ Cells:

1. Put fetal liver in a 10 cm sterile petri dish and smash it gently in bone marrow media with a sterile plunger of a 3 or 6 ml syringe. Transfer cell suspension into 50 ml conicals through a 40 μm cell strainer. 2. Place cell suspension slowly and gently onto 20 ml of Histopaque 1.077 of a new 50 ml tube. Be careful not to disrupt the gradient layer. 3. Transfer tubes to centrifuge holder, balance holders and centrifuge at 1400-1500 rpm for 30 min at room temperature with BRAKE OFF. 4 After centrifugation, collect buffy coats and filter again through a cell strainer. Mix well with new bone marrow media to prevent gradient re-formation. 5 Centrifuge tubes for 5 minutes at 2000 rpm with brake on. 6. Decant supernatant and collect pellet. 7. Proceed with CD34+ enrichment using the MACS Human CD34+ isolation kit (130-046-702) instructions. Confirm purity by FACS, wash in BM media. 8. Cryopreserve in 90% human AB serum and 10% DMSO or inject 100-400,000 CD34+ cells per mouse i.v. in BM media. Mice must have received 2-2.5 Gy TBI at least 8 h in advance.

REFERENCE LIST FOR EXAMPLE 2

1. Suri, A., Walters, J. J., Gross, M. L., & Unanue, E. R. Natural peptides selected by diabetogenic DQ8 and murine I-A(g7) molecules show common sequence specificity. *J. Clin. Invest* 115, 2268-2276 (2005).
2. Goronzy, J. J. & Weyand, C. M. Developments in the scientific understanding of rheumatoid arthritis. *Arthritis Res Ther* 11, 249 (2009).
3. Danska, J. S. & Poussier, P. After the GWAS rush: nuggets of insight into the pathogenesis of autoimmune disease. *Semin Immunol* 21, 313-317 (2009).
4. Svejgaard, A. The immunogenetics of multiple sclerosis. *Immunogenetics* 60, 275-286 (2008).
5. Ueda, H. et al. Association of the T-cell regulatory gene CTLA4 with susceptibility to autoimmune disease. *Nature* 423, 506-511 (2003).
6. Smyth, D. J. et al. A genome-wide association study of nonsynonymous SNPs identifies a type 1 diabetes locus in the interferon-induced helicase (IFIH1) region. *Nat. Genet.* 38, 617-619 (2006).
7. Steck, A. K. et al. Association of non-HLA genes with type 1 diabetes autoimmunity. *Diabetes* 54, 2482-2486 (2005).
8. Wicker, L. S. et al. Type 1 diabetes genes and pathways shared by humans and NOD mice. *J. Autoimmun.* 25 Suppl, 29-33 (2005).
9. Jakkula, E. et al. Genome-wide association study in a high-risk isolate for multiple sclerosis reveals associated variants in STAT3 gene. *Am J Hum Genet* 86, 285-291 (2010).
10. Coenen, M. J. et al. Common and different genetic background for rheumatoid arthritis and coeliac disease. *Hum Mol Genet* 18, 4195-4203 (2009).
11. Atkinson, M. A. & Leiter, E. H. The NOD mouse model of type 1 diabetes: As good as it gets? *Nature Med.* 5, 601-604 (1999).
12. Vijayakrishnan, L. et al. An autoimmune disease-associated CTLA-4 splice variant lacking the B7 binding domain signals negatively in T cells. *Immunity* 20, 563-575 (2004).
13. Barker, J. M. Type 1 diabetes associated autoimmunity: Natural History, Genetic Associations and Screening. *J Clin Endocrinol. Metab* (2006).
14. Rogner, U. C. et al. The Diabetes Type 1 Locus Idd6 Modulates Activity of CD4+CD25+ Regulatory T-Cells. *Diabetes* 55, 186-192 (2006).
15. Arif, S. et al. Autoreactive T cell responses show proinflammatory polarization in diabetes but a regulatory phenotype in health. *J Clin Invest* 113, 451-463 (2004).
16. Lindley, S. et al. Defective Suppressor Function in CD4+CD25+ T-Cells From Patients With Type 1 Diabetes. *Diabetes* 54, 92-99 (2005).
17. Esteban, L. M. et al. Genetic control of NKT cell numbers maps to major diabetes and lupus Loci. *J Immunol* 171, 2873-2878 (2003).
18. Wilson, S. B. et al. Extreme Th1 bias of invariant Vα24JαQ T cells in type 1 diabetes. *Nature* 391, 177-181 (1998).
19. Rodacki, M. et al. Altered natural killer cells in type 1 diabetic patients. *Diabetes* 56, 177-185 (2007).
20. Jin, Y. et al. APC dysfunction is correlated with defective suppression of T cell proliferation in human type 1 diabetes. *Clin Immunol* 130, 272-279 (2009).
21. Alard, P. et al. Deficiency in NOD Antigen-Presenting Cell Function May Be Responsible for Suboptimal CD4+ CD25+ T-Cell-Mediated Regulation and Type 1 Diabetes Development in NOD Mice. *Diabetes* 55, 2098-2105 (2006).
22. D'Alise, A. M. et al. The defect in T-cell regulation in NOD mice is an effect on the T-cell effectors. *Proc. Natl. Acad. Sci. U.S.A.* 105, 19857-19862 (2008).
23. Crispin, J. C. et al. Pathogenesis of human systemic lupus erythematosus: recent advances. *Trends Mol Med* 16, 47-57 (2010).
24. Venken, K., Hellings, N., Liblau, R., & Stinissen, P. Disturbed regulatory T cell homeostasis in multiple sclerosis. *Trends Mol Med* 16, 58-68 (2010).
25. Serreze, D. V., Leiter, E. H., Worthen, S. M., & Shultz, L. D. NOD marrow stem cells adoptively transfer diabetes to resistant (NOD×NON)F1 mice. *Diabetes* 37, 252-255 (1988).
26. Lampeter, E. F., McCann, S. R., & Kolb, H. Transfer of diabetes type 1 by bone-marrow transplantation. *Lancet* 351, 568-569 (1998).
27. Mosier, D. E., Gulizia, R. J., Baird, S. M., & Wilson, D. B. Transfer of a functional human immune system to mice with severe combined immunodeficiency. *Nature* 335, 256-259 (1988).
28. McCune, J. M. et al. The SCID-hu mouse: Murine model for the analysis of human hematolymphoid differentiation and function. *Science* 241, 1632-1639 (1988).
29. Lan, P., Tonomura, N., Shimizu, A., Wang, S., & Yang, Y. G. Reconstitution of a functional human immune system in immunodeficient mice through combined human fetal thymus/liver and CD34+ cell transplantation. *Blood* 108, 487-492 (2006).
30. Tonomura, N., Habiro, K., Shimizu, A., Sykes, M., & Yang, Y. G. Antigen-specific human T-cell responses and T cell-dependent production of human antibodies in a humanized mouse model. *Blood* 111, 4293-4296 (2008).
31. Lan, P. et al. Induction of human T cell tolerance to porcine xenoantigens through mixed hematopoietic chimerism. *Blood* 103, 3964-3969 (2004).
32. Onoe, T. et al. Homeostatic expansion and phenotypic conversion of human T cells depend on peripheral interactions with APC. *J Immunol* (2010).
33. Lepus, C. M. et al. Comparison of human fetal liver, umbilical cord blood, and adult blood hematopoietic stem cell engraftment in NOD-scid/common gamma chain–/–, Balb/c-Rag1–/–common gamma chain–/–, and C.B-17-scid/bg immunodeficient mice. *Hum Immunol* 70, 790-802 (2009).
34. Jenkinson, E. J. & Anderson, G. Fetal thymic organ cultures. *Curr. Opin. Immunol.* 6, 293-297 (1994).
35. Jenkinson, E. J., Franchi, L. L., Kingston, R., & Owen, J. J. Effect of deoxyguanosine on lymphopoiesis in the developing thymus rudiment in vitro: application in the production of chimeric thymus rudiments. *Eur J Immunol* 12, 583-587 (1982).
36. Shultz, L. D., Ishikawa, F., & Greiner, D. L. Humanized mice in translational biomedical research. *Nat Rev Immunol* 7, 118-130 (2007).
37. Cacheiro, L. H., Glover, P. L., & Perkins, E. H. Restoration of immune competence with cryopreserved thymus. *Transplantation* 40, 110-112 (1985).
38. Cheers, C., Leuchars, E., Davies, A. J., & Wallis, V. Restoration of thymectomized irradiated mice by frozen and stored thymus grafts. *Transplantation* 10, 505-511 (1970).

39. Kukreja, A. et al. Multiple immuno-regulatory defects in type-1 diabetes. *J Clin Invest* 109, 131-140 (2002).
40. Davis, C. M. et al. Normalization of the peripheral blood T cell receptor V beta repertoire after cultured postnatal human thymic transplantation in DiGeorge syndrome. *J Clin Immunol* 17, 167-175 (1997).
41. Barker, J. M. et al. Two single nucleotide polymorphisms identify the highest-risk diabetes HLA genotype: potential for rapid screening. *Diabetes* 57, 3152-3155 (2008).
42. Brusko, T. M., Wasserfall, C. H., Clare-Salzler, M. J., Schatz, D. A., & Atkinson, M. A. Functional defects and the influence of age on the frequency of CD4+ CD25+ T-cells in type 1 diabetes. *Diabetes* 54, 1407-1414 (2005).
43. Bonelli, M. et al. Phenotypic and functional analysis of CD4+CD25−FoxP3+ T cells in patients with systemic lupus erythematosus. *J Immunol* 182, 1689-1695 (2009).
44. Flores-Borja, F., Jury, E. C., Mauri, C., & Ehrenstein, M. R. Defects in CTLA-4 are associated with abnormal regulatory T cell function in rheumatoid arthritis. *Proc Natl Acad Sci USA* 105, 19396-19401 (2008).
45. Berzins, S. P., Venanzi, E. S., Benoist, C., & Mathis, D. T-cell compartments of prediabetic NOD mice. *Diabetes* 52, 327-334 (2003).
46. Tang, Q. & Bluestone, J. A. Regulatory T-cell physiology and application to treat autoimmunity. *Immunol Rev* 212, 217-237 (2006).
47. Brusko, T. et al. No Alterations in the Frequency of FOXP3+ Regulatory T-Cells in Type 1 Diabetes. *Diabetes* 56, 604-612 (2007).
48. von Herrath, M. & Nepom, G. T. Animal models of human type 1 diabetes. *Nat Immunol* 10, 129-132 (2009).
49. Roep, B. O. Are insights gained from NOD mice sufficient to guide clinical translation? Another inconvenient truth. *Ann N Y. Acad Sci* 1103, 1-10 (2007).
50. King, M. et al. Development of new-generation HU-PBMC-NOD/SCID mice to study human islet alloreactivity. *Ann N Y. Acad Sci* 1103, 90-93 (2007).
51. Taneja, V. & David, C. S. Role of HLA class II genes in susceptibility/resistance to inflammatory arthritis: studies with humanized mice. *Immunol Rev* 233, 62-78 (2010).
52. Lang, H. L. et al. A functional and structural basis for TCR cross-reactivity in multiple sclerosis. *Nat Immunol* 3, 940-943 (2002).
53. Black, K. E., Murray, J. A., & David, C. S. HLA-DQ determines the response to exogenous wheat proteins: a model of gluten sensitivity in transgenic knockout mice. *J Immunol* 169, 5595-5600 (2002).
54. Serreze, D. V., Niens, M., Kulik, J., & DiLorenzo, T. P. Bridging mice to men: using HLA transgenic mice to enhance the future prediction and prevention of autoimmune type 1 diabetes in humans. *Methods Mol Biol* 602, 119-134 (2010).
55. King, M., Pearson, T., Rossini, A. A., Shultz, L. D., & Greiner, D. L. Humanized mice for the study of type 1 diabetes and beta cell function. *Ann N Y. Acad Sci* 1150, 46-53 (2008).
56. Gregersen, J. W., Holmes, S., & Fugger, L. Humanized animal models for autoimmune diseases. *Tissue Antigens* 63, 383-394 (2004).
57. Wen, L., Chen, N. Y., Tang, J., Sherwin, R., & Wong, F. S. The regulatory role of DR4 in a spontaneous diabetes DQ8 transgenic model. *J Clin Invest* 107, 871-880 (2001).
58. Nikolic, B. et al. Normal development in porcine thymus grafts and specific tolerance of human T cells to porcine donor MHC. *J. Immunol.* 162, 3402-3407 (1999).
59. Kraus, A. B. et al. Early host CD8 T-cell recovery and sensitized anti-donor IL-2-producing and cytolytic T-cell responses associated with marrow graft rejection following nonmyeloablative bone marrow transplantation. *Exp. Hematol.* 31, 609-621 (2003).
60. Wu, H. D. et al. The lymphocytic infiltration in calcific aortic stenosis predominantly consists of clonally expanded T cells. *J. Immunol.* 178, 5329-5339 (2007).

Example 3

Intrinsic abnormalities in cells of the immune system, including T, B, NK, NKT and dendritic cells (DC), have been implicated in autoimmune pathogenesis in NOD mice and/or Type 1 diabetes mellitus (T1DM). However, most human studies cannot distinguish cause from effects of the disease, since they involve analyses of T1DM patients after disease onset. A new humanized mouse model has been developed as described herein that can permit the analysis of such defects in a controlled and prospective manner.

A humanized mouse model was described in which NOD/SCID mice are reconstituted with a functional human immune system by transplanting human fetal thymus and liver tissue in addition to an i.v. infusion of human CD34+ fetal liver cells. These mice show peripheral reconstitution of multilineage human hematopoietic cells, including B, T and DCs, develop normal sized lymphoid tissues and demonstrate strong antigen-specific immune responses in vivo. Normal thymic development was demonstrated of regulatory T cells and showed Treg function and conversion to an "activated" phenotype in the periphery. This model also allows the examination of homeostatic peripheral expansion of human T cells, for which an appropriate in vivo model has been lacking so far. Adoptive transfer of autologous T cells from humanized mice to T cell-deficient humanized mice demonstrated two distinct proliferative responses in vivo in a lymphopenic setting. Human naïve CD4 and CD8 T cells that undergo rapid proliferation acquire a memory-like phenotype and the ability to rapidly produce IFN-γ, while those undergoing slow proliferation retain naïve phenotypic and functional characteristics. Recovery of both populations depends on the level of human non-T cell chimerism in the periphery of recipient humanized mice.

This invention provides the establishment of a humanized mouse model using cryopreserved/thawed human fetal thymus tissue that can support the generation and population of the NOD/SCIDcommon gamma chain knockout mouse periphery with T cells and APCs from small numbers of adult, allogeneic bone marrow CD34+ cells. Bone marrow CD34+ cells from T1DM patients and healthy controls can be injected into mice receiving fetal human thymus grafts that express T1DM-associated HLA-class II alleles and HLA-A0201. This model can allow the comparison of peripheral survival, homeostatic expansion, phenotypic conversion as well as self-tolerance of conventional and regulatory T cells derived from CD34+ cells of T1DM versus normal controls. It is possible that hematopoietic stem cells from T1DM patients can show intrinsic abnormalities that contribute to autoimmunity.

Type 1 diabetes mellitus is caused by autoimmune destruction of the insulin-producing β cells. While poorly defined environmental factors play an import role in the development of autoimmunity, genetic factors substantially contribute to disease susceptibility.

The HLA genotype is most strongly linked with T1DM. However, non-HLA-linked loci clearly also contribute to autoimmunity risk. Many of these loci contain immunoregulatory genes. Therefore, without being bound by theory, intrinsic abnormalities in the cells of the immune system, which originate from hematopoietic stem cells (HSCs), can contribute to the development of autoimmunity. While the NOD mouse model has permitted genetic studies to analyze mechanisms by which some of these genes promote autoimmunity, clinical studies involve analyses of patients after disease onset and cannot distinguish cause from effects of the disease, its treatment or environmental factors that precipitate. Thus, there is a need for models that permit the analysis of human immunologic defects in a controlled and prospective manner Herein is presented a humanized mouse model that permits the development of multilineage peripheral human hematopoietic cells in sublethally irradiated NOD/SCID/IL2 receptor γ chain null (NSG) mice from adult, allogeneic bone marrow CD34+ cells administered in low numbers. This model can make it possible to compare T cells and other immune cells derived from CD34+ cells of normal controls versus patients with autoimmune disease in a controlled and prospective manner.

Many "humanized mouse" models have been developed. Human peripheral blood mononuclear cells (PBMC) can populate immunodeficient mice and human T cells develop in human fetal thymus (THY) grafts implanted with fetal liver under the kidney capsule. It was shown that the combination of intravenous fetal CD34+ cell infusion with human fetal thymus and liver (THY/LIV) grafts under the kidney capsule allows human immune reconstitution with high levels of peripheral human T cells, B cells, immunoglobulins, and both myeloid and plasmacytoid dendritic cells. These mice develop normal-sized lymphoid tissues and demonstrate strong antigen-specific immune responses in vivo, including robust class-switched antibody responses following protein immunization. Furthermore, normal thymic development of regulatory T cells (Treg) has been demonstrated with Treg function and conversion to an "activated" phenotype in the periphery. This model also allows the examination of peripheral homeostatic expansion of human T cells, for which an appropriate in vivo model has been lacking so far.

Adult, bone marrow-derived CD34+ cells can reconstitute sublethally irradiated NSG mice grafted with cryopreserved/thawed allogeneic thymus tissue and reconstitute multiple peripheral hematopoietic cell lineages, including T cells. In contrast to irradiation or 7-day dGuo-treatment, cryopreserving/thawing the fetal thymus tissue plus anti-CD2 mAb successfully depletes mature intrathymic T cells, prevents the rejection of allogeneic CD34+ cells and preserves thymic function. Bone marrow CD34+ cells from patients with autoimmune disease and healthy controls can therefore be injected into mice receiving fetal human thymus grafts that express disease-associated HLA-class II alleles. Using low numbers of aspirated bone marrow cells, this model can allow the identification of HSC-intrinsic immune abnormalities in patients with autoimmune diseases.

Example 4

In certain aspects, the invention provides methods to develop a reaggregate human thymus transplant model allowing human thymopoiesis in HLA-defined human thymus grafts. In this example, instead of implanting intact fetal thymus tissue, CD45-negative thymic stromal cells cryopreserved from HLA-typed human fetal thymic tissue can be implanted under the kidney capsule of NOD-SCID mice. Thymi bearing common diabetes-susceptibility HLA alleles can support the thymopoiesis of T cells from i.v.-injected CD34+ cells from normal control and Type 1 diabetic subjects sharing these alleles. Alternative approaches include injection of intact human thymic tissue with thymic epithelial cells derived from HLA-transgenic NOD mice or adenoviral transduction of genes encoding diabetes susceptibility alleles into thymus grafts.

In certain aspects, the invention provides a mouse model and methods to compare peripheral survival, homeostatic expansion, phenotypic conversion and self-tolerance of conventional T cells derived from CD34 cells of T1DM versus normal controls. It can be determined whether or not T cells from T1DM patients show increased lymphopenia-driven expansion in association with loss of tolerance to "self" antigens of the thymus donor. It can be determined whether or not intrinsic abnormalities in homeostasis characterize T cells in T1DM patients.

In certain aspects, the invention provides methods to compare numbers, function and peripheral phenotypic conversion of regulatory T cells derived from CD34 cells of T1DM versus normal controls. Tregs and NKT cells derived from stem cells of T1DM patients can show defects. These studies can identify intrinsic abnormalities in regulatory cells from T1DM patients and their thymic versus post-thymic origin.

Various regimens were evaluated for engraftment of fetal human thymus grafts NOD.scid mice that would allow human thymopoiesis from allogeneic CD34+ cells.

CD34 Cell Isolation from Human Bone Marrow Filters:

Before performing bone marrow harvests on normal and Type 1 diabetic donors for the studies, it was necessary to establish a model for human thymopoiesis in NOD-SCID mice receiving adult CD34$^+$ cells and allogeneic fetal thymic tissue. As a source of adult CD34+ cells for these studies, discarded bone marrow filters from the Massachusetts General Hospital Bone Marrow Transplant Unit were used. From each filter, 5-25×10$^6$ normal donor CD34$^+$ cells were isolated per filter using MACS beads. Flow cytometric analyses revealed ~90% purity. These cells were cryopreserved for use in these studies.

Fetal Thymus Organ Cultures:

Human fetal thymus tissue was obtained from Advanced Bioscience, California. To prevent rejection of allogeneic CD34 cell-derived thymocytes by mature T cells residing in the fetal thymus graft, culture in the presence of 1.35M dGuo was evaluated. The percentages of CD4 and CD8 single positive cells in the thymus were reduced from 43% and 14% to 3.4% and 2.1%, respectively, after 10 days of culture. In comparison, after culture for a similar period without dGuo, the proportion of CD4 and CD8 single positive cells was 20.1% and 13.3%, respectively. However, fetal thymus organ culture with dGuo for even 20 days did not completely deplete all mature thymocytes.

Human T Cell Reconstitution from dGuo-Treated Human Fetal Thymus Grafts:

NOD/SCID mice received 2.5 Gy TBI one day prior to the transplantation of human fetal thymus that had been cultured for 20 days in the presence of dGuo. Successful thymic engraftment with human thymopoiesis occurred after intravenous infusion of allogeneic adult CD34$^+$ cells: Human CD3+ cells were detectable in peripheral blood of all mice 20 weeks after transplantation, representing an average of ~25% of PBMC. Age-matched control mice that received either fresh or dGuo-treated human fetal thymus tissue but no CD34+ cells did not have detectable human CD3$^+$ cells in the blood at any time point after transplantation. These results demonstrate that stem cells and mature T cells residing in the thymus graft are not able to sustain sufficient thymopoiesis to generate a peripheral human T cell pool and that additional CD34+ cell infusion is essential. The studies demonstrate that thymocytes in dGuo-treated fetal thymus tissue do not reject thymocyte progenitors from allogeneic CD34 cells. Moreover, it has been shown that progenitors derived from peripherally-infused CD34+ cells can populate the dGuo-treated thymi, where they undergo thymopoiesis.

Another age-matched control group that received dGuo-treated fetal thymus tissue also received i.v. infusion of CD34+ cells isolated from the liver of the same fetal donor instead of allogeneic adult marrow-derived CD34+ cells. After infusion of these syngeneic fetal CD34+ cells, peripheral blood CD3+ reconstitution was detectable by 14 weeks after transplantation with CD3+ cells, to an average of ~35% of PBMC. Thus, reconstitution of human peripheral CD3+ cells appears to be more rapid after injection of autologous fetal CD34+ cells comparison to that achieved with allogeneic CD34+ cells obtained from adults.

The data indicate that the T cell reconstitution achieved with grafts that were cultured with dGuo for 20 days, with i.v. administration of CD34+ cells, can be slower than that achieved with fresh fetal thymus grafts co-implanted with fetal liver fragments and i.v. fetal liver-derived CD34+ cells from the same donor. In such studies, high levels of CD3+ cells were detectable in the peripheral blood within 9 weeks of transplantation.

In an attempt to accelerate the reconstitution of human CD3+ T cells, another group was established with human fetal thymus grafts that had been cultured for only 7 days in the presence of dGuo. Although CD3+ levels averaging ~7% of PBMC were detectable within 6 weeks after transplantation, these levels declined over the ensuing weeks. By 20 weeks after transplantation, CD3+ T cell levels in the blood averaged <5%. Furthermore, no CD19+ cells were detectable at any time point, in contrast to results achieved with 20-day dGuo-cultured thymus and i.v. CD34 cells, in which multilineage human leukocyte reconstitution from the injected CD34 cells was observed. These results indicate that the infused allogeneic CD34+ cells may have been rejected by mature T cells that were not depleted by dGuo treatment in the 7-day dGuo-treated thymus grafts. Thus, it is concluded that the longer dGuo culture period is required to eliminate mature thymocytes from fetal thymus grafts and thereby to permit survival and function of allogeneic CD34+ cells and their progeny.

Human T Cell Reconstitution with Other Regimens:

Experiments investigate further ways of achieving allogeneic CD34 cell engraftment and thymopoiesis in human fetal thymus grafts. Groups of NOD-SCID mice have received human fetal thymus grafts that had been cryopreserved before transplantation. Cryopreservation of fetal thymus tissue has been shown in other of the studies to decrease the number of thymocytes in porcine thymus grafts, leading to more rapid repopulation by human CD34 cell-derived progenitors. As an alternative approach, one group of mice received human fetal thymus tissue that had been irradiated with 7 Gy before transplantation. In another group, the efficacy was tested of co-culturing dGuo-cultured fetal thymus tissue with CD34+ cells in a "hanging drop" culture prior to implantation, in order to overcome the requirement for thymocyte progenitor trafficking to the graft in vivo.

OP9-DL1 Co-Culture:

Another approach to promoting human thymopoiesis might be to expand T cell progenitors by co-culture of CD34 cells with OP9-DL1 cells before adding them to allogeneic "hanging drop" or reaggregate thymus cultures. Using the OP9-DL1 cell line, a protocol has been worked out to enable in vitro differentiation from human adult CD34+ cells to pre-T cells. After 28 days of co-culture of $5 \times 10^5$ CD34+ cells per well on a monolayer of OP9-DL1 cells, a total of $4 \times 10^5$ cells were obtained, 67% of which were double positive for the pre-T cell markers CD1a and CD7. However, due to the high number of CD34+ cells needed per well, this approach can be impractical for these purposes, as the number of CD34+ obtained from diabetic patients and healthy controls via bone marrow aspiration is limited.

Additionally, there can be an evaluation of reaggregate thymus cultures with and without CD45+ cell depletion using MACS beads. After culture with CD34+ cells, these reaggregate tissues can be transplanted into irradiated NOD-.scid mice.

The regimen that allows the highest and most rapid reconstitution of human CD3+ cells will be chosen. CD34 cells from bone marrow aspirates from diabetic patients as well as healthy volunteers can be transfused to ~10 NOD-SCID mice. Fetal thymus tissue bearing common diabetes-susceptibility HLA alleles can be transplanted underneath the kidney capsule of these mice. After reconstitution with human T cells, analyses of T cells, T regs and NKT cells can be possible.

Example 5

Human T cell reconstitution from dGuo-treated human fetal thymus grafts: NOD/SCID mice received 2.5 Gy TBI one day prior to the transplantation of human fetal thymus that had been cultured for 20 days in the presence of dGuo (Table 3). Successful thymic engraftment with human thymopoiesis occurred after intravenous infusion of $5 \times 10^5$ allogeneic adult CD34+ cells: Human CD3+ cells were detectable in peripheral blood of all mice 20 weeks after transplantation, representing an average of ~25% of PBMC. Age-matched control mice that received either fresh or dGuo-treated human fetal thymus tissue but no CD34+ cells did not have detectable human CD3+ cells in the blood at any time point after transplantation. These results demonstrate that stem cells and mature T cells residing in the thymus graft are not able to sustain sufficient thymopoiesis to generate a peripheral human T cell pool and that additional CD34+ cell infusion is essential. The studies also demonstrated that thymocytes pre-existing in the 20-day dGuo-treated fetal thymus tissue did not reject thymocyte progenitors from allogeneic CD34 cells. Moreover, the data show that progenitors derived from peripherally-infused CD34+ cells can populate the dGuo-treated thymi, where they undergo thymopoiesis.

Another age-matched control group that received dGuo-treated fetal thymus tissue received i.v. infusion of $4 \times 10^5$ CD34+ cells isolated from the liver of the same fetal donor instead of allogeneic adult marrow-derived CD34+ cells. After infusion of these syngeneic fetal CD34+ cells, peripheral blood CD3+ reconstitution was detectable by 14 weeks after transplantation with CD3+ cells, to an average of ~35% of PBMC. Thus, reconstitution of human peripheral CD3+ cells appears to be more efficient after injection of autologous fetal CD34+ cells in comparison to that achieved with allogeneic CD34+ cells obtained from adults.

The data indicate that the T cell reconstitution achieved with grafts that were cultured with dGuo for 20 days, with i.v. administration of CD34+ cells, can be slower than that achieved with fresh fetal thymus grafts co-implanted with fetal liver fragments and i.v. fetal liver-derived CD34+ cells from the same donor, as previously published. In those studies, high levels of CD3+ cells were detectable in the peripheral blood within 9 weeks of transplantation.

In an attempt to accelerate the reconstitution of human CD3+ T cells, another group was established with human fetal thymus grafts that had been cultured for only 7 days in the presence of dGuo. Although CD3+ levels averaging ~7% of PBMC were detectable within 6 weeks after transplantation, these levels declined over the ensuing weeks. By 20 weeks after transplantation, CD3+ T cell levels in the blood averaged <5%. Furthermore, no CD19+ cells were detectable at any time point, in contrast to results achieved with 20-day dGuo-cultured thymus and i.v. CD34 cells, in which multi-lineage human leukocyte reconstitution from the injected CD34 cells was observed. These results indicate that the infused allogeneic CD34+ cells may have been rejected by mature T cells that were not depleted by dGuo treatment in the 7-day dGuo-treated thymus grafts. Thus, it was concluded that the longer dGuo culture period is required to eliminate mature thymocytes from fetal thymus grafts and thereby to permit survival and function of allogeneic CD34+ cells and their progeny.

TABLE 3

Experimental Groups for Fetal Thymus Organ Culture Experiments

| Exp Group | Autologous fetal liver CD34+ cells | Adult BM-derived CD34+ cells | Untreated Thy TX | dGuo-treated THY for 20 days | dGuo-treated Thy for 7 days |
|---|---|---|---|---|---|
| A | — | $5 \times 10^5$ | − | − | − |
| B | — | — | + | − | − |
| C | — | — | − | + | − |
| D | $4 \times 10^5$ | — | − | + | − |
| E | — | $5 \times 10^5$ | − | + | − |
| F | — | $5 \times 10^5$ | − | − | + |

Cryopreservation and irradiation of fetal human thymus tissue: Cryopreservation of fetal thymus tissue has been shown in other of the studies to decrease the number of thymocytes in porcine thymus grafts, leading to more rapid repopulation by human CD34 cell-derived progenitors. Therefore groups of NOD-SCID mice received human fetal thymus grafts that had been cryopreserved prior to transplantation (Table 4). As an alternative approach, one group of mice received human fetal thymus tissue that had been irradiated with 7 Gy before transplantation and a control group received untreated, fresh fetal human thymus tissue. All animals received 2.5 Gy TBI and $2.5 \times 10^5$ adult CD34+ cells i.v. This number of cells was found to be sufficient to achieve high levels of multilineage human reconstitution when fetal human liver-derived CD34+ cells were used. A control group in this experiment received $2 \times 10^5$ autologous fetal liver-derived CD34+ cells. This control group achieved robust multilineage human T, B and myeloid reconstitution, as is typically seen in this model.

Human hematopoietic reconstitution in all recipients of adult bone marrow-derived CD34+ cells was very low during the 16 weeks of post-transplant follow-up: In NOD-SCID mice that received untreated human thymus tissue, the percentage of human cells among PBMC averaged about 10% by Week 6, with only minor fluctuations up until Week 16 post-transplant. Remarkably, by 6 weeks after transplantation, T cell levels in these mice already averaged about 7% among PBMC, peaking at an average level of ~12.5% at 10 weeks and declining to an average of ~2.3% 16 weeks post-transplant. In contrast, B cell levels in these animals never reached levels greater than ~2% among PBMC during the follow-up period. These results indicate that the T cells that appeared in the periphery early after transplantation were derived from thymocytes that were present within the fetal thymus graft at the time of transplantation and which subsequently emigrated into the periphery. Since the CD34 cell donor was allogeneic to these thymocytes, the failure to demonstrate multilineage chimerism indicates that the CD34 cell graft was rejected by these T cells. Furthermore, mature T cells and/or progenitor cells present in the transplanted graft were not able to sustain long-term thymopoiesis, as demonstrated by the low percentage of peripheral CD3+ cells at 16 weeks post-transplantation.

In contrast to these results in recipients of untreated thymus grafts, human cell B and T cell levels were never greater than about 1% after transplantation in mice that received irradiated thymus grafts, demonstrating that irradiation with 7 Gy successfully depleted thymocytes carried in the graft. However, the failure to achieve non-T cell reconstitution in these mice suggested that the number of ($2.5 \times 10^5$) adult CD34+ cells given might be too low to achieve robust multilineage human hematopoietic reconstitution.

In the same experiment, the group that received cryopreserved fetal thymus tissue had no detectable T cells in the periphery up to 8 weeks post-transplantation, but demonstrated about 3.5 and 5% human T cells among PBMC at 10 and 12 weeks, respectively. These data demonstrate that cryopreservation successfully depleted pre-existing mature thymocytes. The low but gradually increasing T cell reconstitution that began at 10 weeks post-transplant indicates that progenitors in the thymus may have been preserved despite cryopreservation. Since significant B cell chimerism was not detected at any time in the post-transplant observation period, it seems less likely that the late T cell reconstitution was derived from the adult CD34 cells given.

Figure 36:
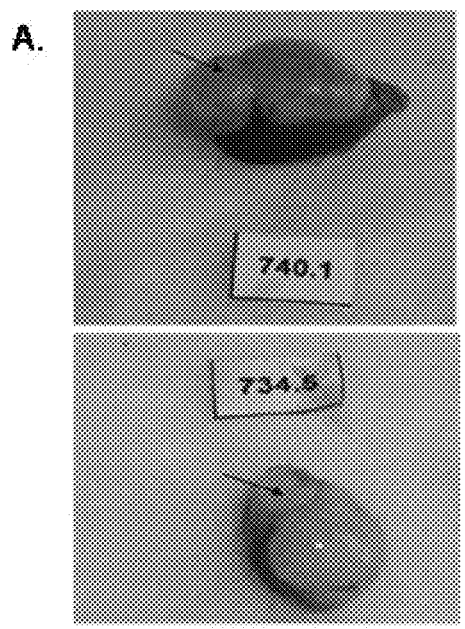
Figure 36:
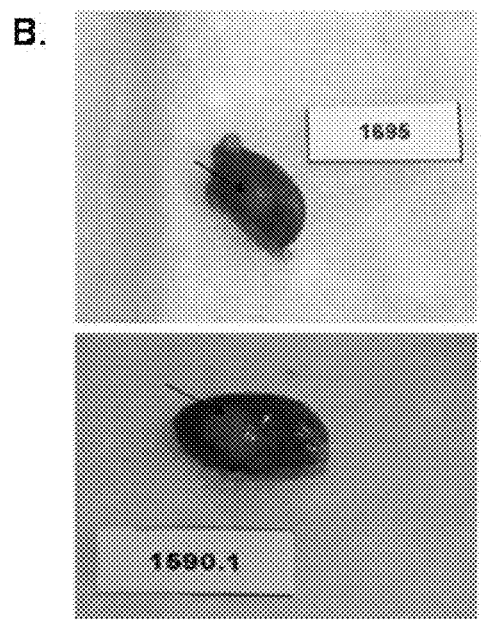

Comparison of the appearance of the human thymus grafts of the above 3 groups of mice proved to be informative (FIG. 36). Recipients of untreated human thymus grafts and of cyropreserved thymus grafts both had abundant, viable thymic tissue under the kidney capsule at the time of sacrifice 20 weeks post-transplantation (FIG. 36A). In contrast, recipients of irradiated thymic tissue had barely visible thymi under the kidney capsule at this time (FIG. 36B). These data indicate that irradiation had either eliminated the capacity of thymic epithelial cells to divide and hence for the grafts to grow and/or eliminated thymocyte progenitors from the graft. If the former explanation is correct, then the presence of robust thymopoiesis without peripheral T cell reconstitution in the recipients of untreated or cryopreserved thymic grafts may reflect early repopulation of these grafts by progenitors from the initial adult CD34 cell graft, with failure of these T cells to survive once they migrate to the periphery, due to the absence of human APCs. Studies that were performed suggest that human APCs in the periphery are critical for the survival of human T cells developing in human thymus grafts.

TABLE 4

Experimental Groups for Cryopreservation and Irradiation of the Thymus Graft

| Exp Group | Autologous fetal liver CD34+ cells | Adult BM-derived CD34+ cells | Untreated Thy TX | Cryo-preserved Thy TX | 7 Gy Irradiated Thy TX |
|---|---|---|---|---|---|
| A | $2 \times 10^5$ | — | + | − | − |
| B | — | $2.5 \times 10^5$ | − | − | − |
| C | — | $2.5 \times 10^5$ | + | − | − |

TABLE 4-continued

Experimental Groups for Cryopreservation
and Irradiation of the Thymus Graft

| Exp Group | Autologous fetal liver CD34+ cells | Adult BM-derived CD34+ cells | Untreated Thy TX | Cryo-preserved Thy TX | 7 Gy Irradiated Thy TX |
|---|---|---|---|---|---|
| D | — | $2.5 \times 10^5$ | — | + | — |
| E | — | $2.5 \times 10^5$ | — | — | + |

Human cell reconstitution in NOD.scid-IL2R-gamma$^{null}$ mice: Because adult bone marrow CD34 cells appeared to be less effective than fetal liver CD34 cells at achieving multilineage human hematopioetic reconstitution in NOD-scid mice, ways of improving the efficiency of adult CD34 cells was sought in achieving this outcome. NOD-SCID-common gamma chain knockout mice (NSG mice) were evaluated as potentially more permissive recipients of adult CD34 cells, since these mice lack NK cells and optimal human cell engraftment has been reported in other models. Since both cryopreservation as well as irradiation of the thymus successfully depleted intrathymic alloreactive T cells in the experiments described, these regimens were tested in NSG mice. Furthermore, two doses were added of monoclonal anti-human CD2 antibody (BTI 322, 100 μg) to the protocol at day 0 and 7 to enhance depletion of thymus graft-derived T cells (Table 5).

Groups of 2.5 Gy irradiated NSG mice received $3 \times 10^5$ adult bone marrow-derived CD34+ cells alone or in addition to fetal human thymic tissue that had been cryopreserved or 7 Gy irradiated. One group of animals received $5 \times 10^5$ adult bone marrow-derived CD34+ cells in addition to cryopreserved human fetal thymus tissue, while controls received either cryopreserved thymic tissue alone or along with BTI 322.

Remarkably, approximately 25% human cells were already detectable among PBMC at 6 weeks post-transplantation in NSG mice that received 3 or $5 \times 10^5$ adult human bone marrow CD34+ cells either alone or along with cryopreserved human fetal thymus tissue (FIG. 37). Peak human cell levels (~60 to 75% of PBMC) were detectable at 8 weeks, thereafter averaging ~30 to 60%. Human CD19+ cells were detectable at high levels starting at 6 weeks post-transplant at about 30% and peaked at 8 weeks at ~55% of PBMC. In NSG mice that received cryopreserved human fetal thymus tissue, T cells were detectable in the periphery by week 6 post-transplantation (~3% of PBMC) and increased to peaks of ~10% and ~30% in mice that received $3 \times 10^5$ or $5 \times 10^5$ adult human CD34+ cells, respectively (FIG. 37). In contrast, no human T cells (<1% among PBMC) were detectable in NSG mice that did not receive a human fetal thymus graft or in mice that received thymic grafts that were 7 Gy irradiated. These results confirm that 7 Gy thymic irradiation impairs thymic growth and/or function and does not allow thymopoiesis following transplantation in the model of the invention. Controls that received cryopreserved human fetal thymus tissue with or without BTI 322, but without i.v. CD34 cells, did not generate significant human T cells in the periphery. This result demonstrates that intrathymic progenitors and mature thymocytes were adequately depleted by cryopreservation and/or that the injection of intravenous CD34+ cells, with the attendant human APC repopulation, is necessary to support high levels of peripheral human T cell reconstitution.

TABLE 5

Experimental Groups for NSG Mice Experiments

| Exp Group | Adult BM-derived CD34+ cells | BTI 322 i.v. | Cryopreserved Thy TX | 7 GY Irradiated Thy TX |
|---|---|---|---|---|
| A | $3 \times 10^5$ | — | — | — |
| B | — | — | + | — |
| C | — | + | + | — |
| D | $3 \times 10^5$ | + | + | — |
| E | $3 \times 10^5$ | + | — | + |
| F | $5 \times 10^5$ | + | + | — |

Studies are currently underway to determine whether or not treatment with anti-CD2 mAB (BTI 322) is needed in this model. Importantly, a humanized mouse model has been established provided for here that successfully allows human thymopoiesis from low numbers of adult bone marrow CD34+ cells in allogeneic human fetal thymus grafts that have been cryopreserved prior to transplantation.

The regimen that allows the highest and most rapid reconstitution of human CD3+ cells will be chosen. The experimental design is shown in FIG. 38. CD34 cells from bone marrow aspirates from diabetic patients as well as healthy volunteers can be transfused to ~10 NSG mice. A bank of fetal human thymus tissue that is HLA typed has been accumulated. Fetal thymus tissue bearing common diabetes-susceptibility HLA class II alleles can be transplanted underneath the kidney capsule of these mice. In addition to HLA class II, there is a PCR-based assay for the common HLA class I allele A201. This allows matching of the diabetes susceptibility class II alleles between thymic graft and CD34+ cell donor, and also bone marrow donors and thymic grafts that share HLA-A201, which is present in about 30% of caucasians. After reconstitution with human T cells, comparisons at the level of reconstitution of naïve- and memory-type T cells, Tregs and NKT cells can be done. Adoptive transfers can be performed to compare T cell homeostatic expansion and survival between T cells derived from CD34 cells of T1DM patients versus normal volunteers. Comparison of Treg function and susceptibility of effector T cells to Tregs in vitro can be done.

Peripheral survival can be compared with homeostatic expansion, phenotypic conversion and self-tolerance of conventional T cells derived from CD34 cells of T1DM versus normal controls. Determination of whether or not T cells from T1DM patients show increased lymphopenia-driven expansion in association with loss of tolerance to "self" antigens of the thymus donor can be done. Determination of whether or not intrinsic abnormalities in homeostasis characterize T cells in T1DM patients can be done.

Autoimmune pathogenesis in NOD mice can involve increased apoptosis of peripheral T cells, resulting in lymphopenia. Human autoimmune diseases, including T1DM have also been associated with lymphopenia. T cells derived from HSC of T1DM patients exhibit reduced survival and increased lymphopenia-driven expansion and activation compared to those from HSC of normal controls.

Human thymocyte subsets and splenic and lymph node (LN) T cells can be enumerated. The lymphoid tissues of recipients of CD34 cells from T1DM patients can be hypocellular compared to controls in association with decreased expression of anti-apoptotic proteins in memory T cells, as reported in the NOD mouse model. On the other hand, these abnormalities in the NOD model can be an effect of disease, rather than a cause. The model can provide an opportunity to address whether or not there are primary abnormalities in homeostasis of T cells derived from HSC of T1DM patients. Absolute numbers of memory and naïve-type CD4 and CD8 cells can be enumerated by multi-color FCM including mAbs to CD8α, CD8β, CD45RA, CD45RO, CD95, CD27, CCR7 and CD62L. Results include increased numbers of double positive (RO$^+$ RA$^+$) T cells in animals reconstituted with T1DM HSC, as reported in T1DM patients, or reduced numbers of "clonally deviated" CD4–CD8αα+ thymocytes and T cells from T1DM HSC. Defects in production of clonally deviated cells are genetically encoded in the NOD background. Examination of activation markers, including HLA-DR, CD69 and CD25 on CD4 and CD8 T cells can be done. T cell HLA-DR expression is elevated in association with recent-onset T1DM. All of these data can be compared in relation to the level of human APC reconstitution, including B cells and lymphoid and myeloid DC subsets.

Adoptive transfer can be used to compare homeostatic expansion and survival of T cells derived from T1DM patients and controls. Lymphopenia-driven expansion and apoptosis may be greater for T1DM HSC-derived than control HSC-derived T cells. T cells generated in HU THY grafts can be adoptively transferred into secondary NOD-SCID mouse recipients whose peripheral APC populations have been reconstituted with FLC from the same CD34 donor as the THY without a fetal THY graft (HU-APC mice). These animals reconstitute human APC but not T cells. They are "empty" of T cells and their APC express the same HLA antigens as those that mediated positive selection in the original THY graft. This model has been used to measure lymphopenia-driven expansion of T cells following adoptive transfer. Adoptive transfer of naive CD4 and CD8 single positive (SP) thymocytes from the grafts into secondary HU-APC recipients can be accomplished. Separate aliquots can be undepleted or depleted (by MACS sorting) of CD25$^+$ cells, allowing comparison of responses to lymphopenia in the presence or absence of Treg. Lymphopenia-driven expansion of Treg can be specifically compared. Without being bound by theory, these mature single positive thymocytes may have undergone intrathymic selection but not have been subjected to post-thymic selection. They can be CFSE labeled and adoptively transferred (10$^6$ cells per recipient) into HU-APC mice. At timed intervals thereafter, the HU-APC recipients can be euthanized. T cells can be enumerated, and the level of T cell CFSE dilution as well as expression of CCD45RA and CD45RO, CD25 (vs FoxP3 to distinguish CD25+ Tregs), CD69, and apoptosis (using Annexin V and AAD) can be examined on human CD4 and CD8 cells. While lymphopenia-driven expansion is not normally associated with upregulation of the activation markers CD25 and CD69, T cell abnormalities from T1DM patients can involve autoantigen-driven activation with upregulation of these markers, in association with lymphopenia-driven expansion. Intracellular staining for IFN-γ and TNF-α, can address the possibility that increased effector function is generated from homeostatically expanding T cells from T1DM HSC. If any such abnormalities are observed, analyses of human IL-21, IL-7, IL-15 and their receptors can be performed in the adoptive recipients to address the etiology of these abnormalities.

Comparison of numbers, function and peripheral phenotypic conversion of regulatory T cells derived from CD34 cells of T1DM versus normal controls. Tregs and NKT cells derived from stem cells of T1DM patients can show defects. These studies can identify intrinsic abnormalities in regulatory cells from T1DM patients and their thymic versus post-thymic origin.

T1DM patients exhibit defects in Treg development, peripheral survival, susceptibility of effector cells to regulation or peripheral "tuning" of Tregs to render them fully functional. The model provides an opportunity to examine both the role of intrathymic and peripheral defects in the development of Treg.

Comparison of numbers of CD127$^{-/lo}$FoxP3$^+$CD4$^+$CD8$^-$ Treg in thymi as well as peripheral lymphoid tissues (LN and spleen) of NSG mice grafted with human HLA-DR3, DR4 or DQ8+ thymic tissue and CD34+ cells from normal individuals or T1DM patients. If Treg from T1DM HSC have an intrinsic defect in function, they may not be able to acquire the CD45RA$^-$CD45RO$^+$ and HLA-DR$^+$ phenotype associated with full suppressive activity.

Regulatory function can be compared of titrated numbers of Tregs from the thymus and periphery of recipients of normal vs T1DM CD34+ HSCs added to autologous and allogeneic CD25− CD4 T cells.

Susceptibility of effector cells (CD25− CD4 cells stimulated with anti-CD3 and anti-CD28) derived from normal vs T1DM CD34+ HSCs to suppression by Treg can be compared. CD25high CD4 cells from the same third party and from both CD34 cell donors can be titrated into cultures containing CD25− CD4 T cells derived from normal vs T1DM CD34 cells stimulated with anti-CD3 and anti-CD28.

Analyses of NKT cells: Reduced numbers and defective function of invariant NKT cells have been reported in T1DM patients. The model provides an opportunity to determine whether this defect is intrinsic to the HSC of T1DM patients and whether or not it reflects defects in thymic development of this cell subset. Multicolor FCM can be used to quantify invariant chain-expressing Vα24$^+$Vβ11$^+$ and Vα24JαQ CD4$^-$CD8$^-$ and CD4$^+$CD8$^-$ cells in the thymus and periphery.

Example 6

Various regimens were evaluated for engraftment of fetal human thymus grafts in NOD.scid mice that would allow human thymopoiesis from allogeneic CD34+ cells.

CD34 Cell Isolation from Human Bone Marrow Filters:

Before performing bone marrow harvests on normal and Type 1 diabetic donors for these studies, it was necessary to establish a model for human thymopoiesis in NOD.scid mice receiving adult CD34$^+$ cells and allogeneic fetal thymic tissue. As a source of adult CD34+ cells for these studies, discarded bone marrow filters were used. From each filter, 5-25×10$^6$ normal donor CD34$^+$ cells were isolated using MACS beads. Flow cytometric analyses revealed ~90% purity. These cells were cryopreserved.

Fetal Thymus Organ Cultures:

Human fetal thymus tissue was obtained. To prevent rejection of allogeneic CD34 cell-derived thymocytes by mature T cells residing in the fetal thymus graft, culture in the presence of 1.35M dGuo was evaluated. The percentages of CD4 and CD8 single positive cells in the thymus were reduced from 43% and 14% to 3.4% and 2.1%, respectively, after 10 days of culture. In comparison, after culture for a similar period without dGuo, the proportion of CD4 and CD8 single positive cells was 20.1% and 13.3%, respectively. However, fetal thymus organ culture with dGuo for even 20 days did not completely deplete all mature thymocytes.

Human T Cell Reconstitution from dGuo-Treated Human Fetal Thymus Grafts:

NOD.scid mice received 2.5 Gy TBI one day prior to the transplantation of human fetal thymus that had been cultured for 20 days in the presence of dGuo (Table 6). Successful thymic engraftment with human thymopoiesis occurred after intravenous infusion of 5×10⁵ allogeneic adult CD34⁺ cells: Human CD3+ cells were detectable in peripheral blood of all mice 20 weeks after transplantation, representing an average of ~25% of PBMC. Age-matched control mice that received either fresh or dGuo-treated human fetal thymus tissue but no CD34+ cells did not have detectable human CD3⁺ cells in the blood at any time point after transplantation. These results demonstrate that stem cells and mature T cells residing in the thymus graft are not able to sustain sufficient thymopoiesis to generate a peripheral human T cell pool and that additional CD34⁺ cell infusion is essential. The studies also demonstrated that thymocytes pre-existing in the 20-day dGuo-treated fetal thymus tissue did not reject thymocyte progenitors from allogeneic CD34 cells. Moreover, the data show that progenitors derived from peripherally-infused CD34+ cells can populate the dGuo-treated thymi, where they undergo thymopoiesis.

Another age-matched control group that received dGuo-treated fetal thymus tissue received i.v. infusion of 4×10⁵ CD34+ cells isolated from the liver of the same fetal donor instead of allogeneic adult marrow-derived CD34+ cells. After infusion of these syngeneic fetal CD34+ cells, peripheral blood CD3+ reconstitution was detectable by 14 weeks after transplantation with CD3+ cells, to an average of ~35% of PBMC. Thus, reconstitution of human peripheral CD3+ cells appears to be more efficient after injection of autologous fetal CD34+ cells in comparison to that achieved with allogeneic CD34+ cells obtained from adults.

In an attempt to accelerate the reconstitution of human CD3+ T cells, another group was established with human fetal thymus grafts that had been cultured for only 7 days in the presence of dGuo. Although CD3+ levels averaging ~7% of PBMC were detectable within 6 weeks after transplantation, these levels declined over the ensuing weeks. By 20 weeks after transplantation, CD3+ T cell levels in the blood averaged <5%. Furthermore, no CD19⁺ cells were detectable at any time point, in contrast to results achieved with 20-day dGuo-cultured thymus and i.v. CD34 cells, in which multilineage human leukocyte reconstitution from the injected CD34 cells was observed. These results indicate that the infused allogeneic CD34⁺ cells may have been rejected by mature T cells that were not depleted by dGuo treatment in the 7-day dGuo-treated thymus grafts. Thus, it was concluded that the longer dGuo culture period is required to eliminate mature thymocytes from fetal thymus grafts and thereby to permit survival and function of allogeneic CD34+ cells and their progeny.

Cryopreservation and Irradiation of Fetal Human Thymus Tissue:

Cryopreservation of fetal thymus tissue has been shown in studies to decrease the number of thymocytes in porcine thymus grafts, leading to more rapid repopulation by human CD34 cell-derived progenitors. Therefore groups of NOD-.scid mice received human fetal thymus grafts that had been cryopreserved prior to transplantation (Table 7). As an alternative approach, one group of mice received human fetal thymus tissue that had been irradiated with 7 Gy before transplantation and a control group received untreated, fresh fetal human thymus tissue. All animals received 2.5 Gy TBI and 2.5×10⁵ adult CD34+ cells i.v. A control group in this experiment received 2×10⁵ autologous fetal liver-derived CD34+ cells.

This control group achieved robust multilineage human T, B and myeloid reconstitution, as is typically seen in this model.

TABLE 6

Experimental Groups for Fetal Thymus Organ Culture Experiments

| Exp Group | Autologous fetal liver CD34+ cells | Adult BM-derived CD34+ cells | Untreated Thy TX | dGuo-treated THY for 20 days | dGuo-treated Thy for 7 days |
|---|---|---|---|---|---|
| A | — | 5 × 10⁵ | — | — | — |
| B | — | — | + | — | — |
| C | — | — | — | + | — |
| D | 4 × 10⁵ | — | — | + | — |
| E | — | 5 × 10⁵ | — | + | — |
| F | — | 5 × 10⁵ | — | — | + |

Human hematopoietic reconstitution in all recipients of adult bone marrow-derived CD34+ cells was very low during the 16 weeks of post-transplant follow-up: In NOD-.scid mice that received untreated human thymus tissue, the percentage of human cells among PBMC averaged about 10% by Week 6, with only minor fluctuations up until Week 16 post-transplant. Remarkably, by 6 weeks after transplantation, T cell levels in these mice already averaged about 7% among PBMC, peaking at an average level of ~12.5% at 10 weeks and declining to an average of ~2.3% 16 weeks post-transplant. In contrast, B cell levels in these animals never reached levels greater than ~2% among PBMC during the follow-up period. These results indicate that the T cells that appeared in the periphery early after transplantation were derived from thymocytes that were present within the fetal thymus graft at the time of transplantation and which subsequently emigrated into the periphery. Since the CD34 cell donor was allogeneic to these thymocytes, the failure to demonstrate multilineage chimerism suggests that the CD34 cell graft was rejected by these T cells. Furthermore, mature T cells and/or progenitor cells present in the transplanted graft were not able to sustain long-term thymopoiesis, as demonstrated by the low percentage of peripheral CD3+ cells at 16 weeks post-transplantation.

In contrast to these results in recipients of untreated thymus grafts, human cell B and T cell levels were never greater than about 1% after transplantation in mice that received irradiated thymus grafts, demonstrating that irradiation with 7 Gy successfully depleted thymocytes carried in the graft. However, the failure to achieve non-T cell reconstitution in these mice indicated that the number of (2.5×10⁵) adult CD34+ cells given can be too low to achieve robust multilineage human hematopoietic reconstitution.

In the same experiment, the group that received cryopreserved fetal thymus tissue had no detectable T cells in the periphery up to 8 weeks post-transplantation, but demonstrated about 3.5 and 5% human T cells among PBMC at 10 and 12 weeks, respectively. These data demonstrate that cryopreservation successfully depleted pre-existing mature thymocytes. The low but gradually increasing T cell reconstitution that began at 10 weeks post-transplant indicates that progenitors in the thymus may have been preserved despite cryopreservation. Since significant B cell chimerism was not detected at any time in the post-transplant observation period, it seems less likely that the late T cell reconstitution was derived from the adult CD34 cells given. Comparison of the appearance of the human thymus grafts of the above 3 groups of mice proved to be informative: Recipients of untreated human thymus grafts and of cyropreserved thymus grafts both had abundant, viable thymic tissue under the kidney capsule at the time of sacrifice 20 weeks post-transplantation. In contrast, recipients of irradiated thymic tissue had barely visible thymi under the kidney capsule at this time. These data indicate that irradiation had either eliminated the capacity of thymic epithelial cells to divide and hence for the grafts to grow and/or eliminated thymocyte progenitors from the graft. If the former explanation is correct, then the presence of robust thymopoiesis without peripheral T cell reconstitution in the recipients of untreated or cryopreserved thymic grafts can reflect early repopulation of these grafts by progenitors from the initial adult CD34 cell graft, with failure of these T cells to survive once they migrate to the periphery, due to the absence of human APCs. Other studies indicate that human APCs in the periphery are critical for the survival of human T cells developing in human thymus grafts.

TABLE 7

Experimental Groups for Crypreservation and Irradiation of the Thymus Graft

| Exp Group | Autologous fetal liver CD34+ cells | Adult BM-derived CD34+ cells | Untreated Thy TX | Cryo-preserved Thy TX | 7 Gy Irradiated Thy TX |
|---|---|---|---|---|---|
| A | $2 \times 10^5$ | — | + | − | − |
| B | — | $2.5 \times 10^5$ | − | − | − |
| C | — | $2.5 \times 10^5$ | + | − | − |
| D | — | $2.5 \times 10^5$ | − | + | − |
| E | — | $2.5 \times 10^5$ | − | − | + |

Human cell reconstitution in NOD.scid-IL2R-gamma$^{null}$ mice: Because adult bone marrow CD34 cells appeared to be less effective than fetal liver CD34 cells at achieving multilineage human hematopoietic reconstitution in NOD.scid mice, ways to improve the efficiency of adult CD34 cells were sought in achieving this outcome. NOD-SCID-common gamma chain knockout mice (NSG mice) were evaluated as potentially more permissive recipients of adult CD34 cells, since these mice lack NK cells and optimal human cell engraftment has been reported in other models. Since both cryopreservation as well as irradiation of the thymus successfully depleted intrathymic alloreactive T cells in the experiments described above, these regimens were tested in NSG mice. Furthermore, two doses were added of monoclonal anti-human CD2 antibody (BTI 322, 100 µg) to the protocol at day 0 and 7 to enhance depletion of thymus graft-derived T cells (Table 8).

Groups of 2.5 Gy irradiated NSG mice received $3 \times 10^5$ adult bone marrow-derived CD34+ cells alone or in addition to fetal human thymic tissue that had been cryopreserved or 7 Gy irradiated. One group of animals received $5 \times 10^5$ adult bone marrow-derived CD34+ cells in addition to cryopreserved human fetal thymus tissue, while controls received either cryopreserved thymic tissue alone or along with BTI 322. Remarkably, approximately 25% human cells were already detectable among PBMC at 6 weeks post-transplantation in NSG mice that received 3 or $5 \times 10^5$ adult human bone marrow CD34+ cells either alone or along with cryopreserved human fetal thymus tissue. Peak human cell levels (~60 to 75% of PBMC) were detectable at 8 weeks, thereafter averaging ~30 to 60%. Human CD19+ cells were detectable at high levels starting at 6 weeks post-transplant at about 30% and peaked at 8 weeks at ~55% of PBMC. In NSG mice that received cryopreserved human fetal thymus tissue, T cells were detectable in the periphery by week 6 post-transplantation (~3% of PBMC) and increased to peaks of ~10% and ~30% in mice that received $3 \times 10^5$ or $5 \times 10^5$ adult human CD34+ cells, respectively. In contrast, no human T cells (<1% among PBMC) were detectable in NSG mice that did not receive a human fetal thymus graft or in mice that received thymic grafts that were 7 Gy irradiated. These results confirm that 7 Gy thymic irradiation impairs thymic growth and/or function and does not allow thymopoiesis following transplantation in our model. Controls that received cryopreserved human fetal thymus tissue with or without BTI 322, but without i.v. CD34 cells, did not generate significant human T cells in the periphery.

This result demonstrates that intrathymic progenitors and mature thymocytes were adequately depleted by cryopreservation and/or that the injection of intravenous CD34+ cells, with the attendant human APC repopulation, is necessary to support high levels of peripheral human T cell reconstitution.

TABLE 8

Experimental Groups for NSG Mice Experiments

| Exp Group | Adult BM-derived CD34+ cells | BTI 322 i.v. | Cryopreserved Thy TX | 7 GY Irradiated Thy TX |
|---|---|---|---|---|
| A | $3 \times 10^5$ | − | − | − |
| B | — | − | + | − |
| C | — | + | + | − |
| D | $3 \times 10^5$ | + | + | − |
| E | $3 \times 10^5$ | + | − | + |
| F | $5 \times 10^5$ | + | + | − |

Human cell reconstitution from a bedside aspirate: Volunteers were recruited for this study and HLA class II typing in addition to a PCR-based assay for the common HLA class I allele A201 was performed. This allows not only matching of the diabetes susceptibility class II alleles between thymic graft and CD34+ cell donor, but also bone marrow donors and thymic grafts that share HLA-A201, which is present in about 30% of Caucasians. A bank of HLA-typed fetal human thymus tissue has been accumulated. Following the successful multilineage reconstitution in NSG mice as described above, the regimen was tested with adult CD34+ cells isolated from a bedside bone marrow aspirate. A 15 ml bone marrow aspirate enabled the isolation of $3.6 \times 10^5$ and $2.7 \times 10^6$ CD34+ cells from a healthy control and diabetic patient, respectively. 2.5 Gy irradiated NSG mice received $1.8 \times 10^5$ adult CD34+ cells each in addition to a cryopreserved/thawed human fetal thymus graft and anti-CD2 mAb. A control group of irradiated NSG mice received CD34+ cells without a thymus transplant. Human cells were detectable from Week 6 on and peaked 20 weeks after transplantation with levels ranging between ~25% and ~80% (FIG. 27). CD19+ cells reconstituted, though at relatively low levels (<20%), possibly due to the low number ($1.8 \times 10^5$) of adult CD34+ cells that were injected per mouse. The aim is to inject $>2 \times 10^5$ CD34+ cells in future experiments, and this has been done in a repeat experiment that showed more robust B cell and monocyte reconstitution. Nevertheless, experimental animals that received a fetal thymus graft in addition to an i.v. infusion of adult CD34+ cells had peak CD3+ cell levels of ~50-90%, while the control NSG mice reconstituted minimal CD3+ levels post-transplantation (FIG. 27). Twenty weeks post-transplantation, MLR assays were performed with purified T cells isolated from the spleen and lymph nodes of these mice. While all mice showed self-tolerance, strong allo-responses were observed (FIG. 28B). T cells isolated from the mice that received CD34+ cells from the healthy control showed similar allo-responses to T cells that were enriched from the blood of the human control donor. Furthermore, normal development was demonstrated of Tregs in these mice. Comparison of concurrent samples from the normal control donor blood and cells from the humanized mice reconstituted with CD34 cells from that donor revealed a rejuvenated T cell (including Treg) phenotype in the reconstituted mice, with predominantly naïve CD45RA+CD45RO−CD62L+ positive cells. A comparison of the percentage of CD25+CD127−FoxP3+ cells among CD4+ cells as well as the percentage of memory versus naïve CD4+ T cells revealed no difference between mice reconstituted with T1DM CD34+ cells versus HSCs from the healthy control.

A humanized mouse model has been established that successfully allows human thymopoiesis from low numbers of adult bone marrow CD34+ cells in allogeneic human fetal thymus grafts that have been cryopreserved prior to transplantation. The newly generated T cells show similar functionality and self-tolerance as those in the adult CD34+ cell donor, but the immune phenotype is rejuvenated. This new-generation humanized mouse model can allow safe, controlled and prospective analysis of hematopoietic stem cell-intrinsic immunoregulatory defects predisposing to T1DM or other autoimmune diseases. Another group of NSG mice have been reconstituted that received 2×10^5 adult CD34+ cells from a bedside aspirate.

After reconstitution with human T cells, comparison of the level of reconstitution of naïve- and memory-type T cells, Tregs and NKT cells can be done. Adoptive transfers can be performed to compare T cell homeostatic expansion and survival between T cells derived from CD34 cells of T1DM patients versus normal volunteers as described herein. Comparison of Treg function and susceptibility of effector T cells to Tregs in vitro can be done.

Comparison of peripheral survival, homeostatic expansion, phenotypic conversion and self-tolerance of conventional T cells derived from CD34 cells of T1DM versus normal controls. Determination of whether or not T cells from T1DM patients show increased lymphopenia-driven expansion in association with loss of tolerance to "self" antigens of the thymus donor can be done. Determination of whether or not intrinsic abnormalities in homeostasis characterize T cells in T1DM patients can be done.

The numbers, function and peripheral phenotypic conversion of regulatory T cells derived from CD34 cells of T1DM versus normal controls can be compared. Tregs and NKT cells derived from stem cells of T1DM patients can show defects. These studies can identify intrinsic abnormalities in regulatory cells from T1DM patients and their thymic versus post-thymic origin.

A new-generation humanized mouse model has been developed that allows safe, controlled and prospective analysis of hematopoietic stem cell-intrinsic immunoregulatory defects predisposing to autoimmune diseases, and of individual responsiveness to immunotherapeutic agents.

Following reconstitution of the humanized mice with human T cells, comparison of the level of reconstitution of naïve- and memory-type T cells, Tregs and NKT cells can be done. Adoptive transfers can be performed to compare T cell homeostatic expansion and survival between T cells derived from CD34 cells of T1DM patients versus normal volunteers. A study of whether or not T cells from T1DM patients show increased lymphopenia-driven expansion in association with loss of tolerance to "self" antigens of the thymus donor can be done. This can determine whether or not intrinsic abnormalities in homeostasis characterize T cells in T1DM patients. Furthermore, Treg function can be compared and susceptibility of effector T cells to Tregs in vitro and the study should help identify intrinsic abnormalities in regulatory cells from T1DM patients and their thymic versus post-thymic origin.

Example 7: Immunocompetence of T Cells in Mixed Chimeras

Early studies of mixed chimerism to achieve allograft tolerance[41] were based, in part, on the observation that mixed allogeneic chimeras were more immunocompetent than fully allogeneic chimeras when complete MHC barriers were traversed[42,43]. This immunocompetence reflects the role of the MHC of the thymic epithelium in positively selecting T cells, resulting in a repertoire that preferentially recognizes peptide antigens in the context of host MHC[42]. Recipient APCs are present in the periphery of mixed chimeras but not in fully allogeneic chimeras, resulting in superior immune responses in the mixed chimeras[42-44]. Nevertheless, these studies may have influenced by the choice of antigenic systems studied, as other models, including xenogeneic thymus transplantation, demonstrate that T cells selected on the MHC of one thymus (in this case, porcine) can mount vigorous MHC-restricted immune responses in the context of a completely different (recipient) MHC[45,46]. Such animals cleared opportunistic infections, despite the absence of cells expressing thymic MHC in the periphery[45]. Likewise, humans with congenital thymic aplasia receiving extensively HLA-mismatched allogeneic thymic transplants that reconstitute their T cell pool, show robust host-restricted T cell responses[47]. In the xenogeneic system, it was demonstrated very clearly that recipient MHC does not participate in positive selection in the thymus[45,46,48]. Based on these observations and spectratyping analyses of human T cells developing in porcine thymus grafts[49], it was concluded that the diverse T cell repertoire selected in the xenogeneic thymus permits robust immune responses restricted by recipient (xenogeneic) MHC present on APCs. Studies described herein have demonstrated the ability of human APCs in the periphery to promote the survival of human T cells positively selected in a porcine thymus graft, albeit less effectively than they promote survival of human T cells positively selected in human thymic grafts. Thus, mixed xenogeneic chimeras can be capable of generating immune responses in the context of donor, in addition to recipient, MHC, since donor APC's are present in the periphery.

Despite the above reasons to expect T cell immunocompetence in mixed xenogeneic chimeras, studies in mixed allogeneic chimeras have raised a concern about using fully MHC-mismatched donors. In mice achieving mixed chimerism with fully MHC-mismatched allogeneic donors, viral infection with LCMV resulted in clearance of infected recipient cells, while infected donor cells persisted as a viral reservoir that resulted in illness in the animals[50]. This phenomenon was avoided by the sharing of recipient MHC antigens on the donor hematopietic cells, due to exquisite host MHC restriction of anti-viral CTL activity[44,50]. Such MHC sharing is not possible in mixed xenogeneic chimeras unless the pigs are engineered to express HLA alleles. HLA transgenic pigs have already been generated[27,51-53], and the studies can determine their necessity for the approach in this invention.

Humanized mice allowing assessment of immune tolerance at multiple levels provide a powerful pre-clinical tool. The excellent immune function in the humanized mouse model allows important questions regarding both the innate and adaptive immune systems to be addressed to determine what further genetic modifications of porcine source animals could help to advance this therapeutic approach. Many pathogens, especially viruses, show species specificity in their range of infection. Thus, whether xenogeneic cells can serve as a reservoir of infection with human pathogens that can cause chronic infection cannot be predicted a priori and needs to be examined for relevant pathogens and specifically in the pig→human combination.

Provided herein are models that permit analysis of the function of a human immune system in the presence of porcine mixed xenogeneic chimerism. The studies make use of the new, humanized mouse model along with porcine cytokine transgenes in order to address such questions. While observations are extended about immune function from allogeneic mixed chimerism models in mice, certain cell-cell molecular interactions are ineffective in xenogeneic combinations[54-58]. Therefore the ability of mixed chimerism to induce tolerance among the same components of the immune system as those tolerized in allogeneic models needs to be tested in the species combination of interest. It has been observed that induction of mixed chimerism tolerizes B cells and NK cells in a xenogeneic combination, rat→mouse. The use of the humanized mouse model provided here and pig cytokine Tg mice, along with human cytokine vectors, to address the question of NK cell tolerance and B cell tolerance in the pig human combination is innovative. Provided herein are methods to tolerizing these cells to xenografts.

Xenograft Rejection by Human T Cells in Humanized Mice.

Figure 39:
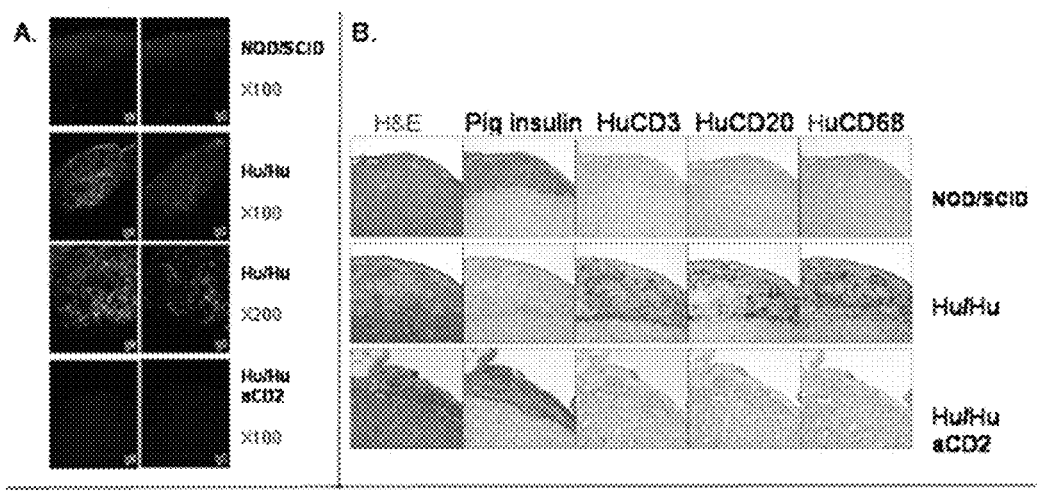

Provided here is a humanized mouse model involving implantation of fetal human thymus (THY) and liver (LIV) grafts under the kidney capsule of NOD/SCID mice along with i.v. injection of $CD34^+$ fetal liver cells (FLC) from the same fetal liver. Such animals show multilineage human leukocyte reconstitution, including T,B,dendritic cells (DCs) and monocytes and develop structured lymphoid tissues. Spontaneous islet xenograft rejection occurred in these "HU" mice[4], as shown in FIG. 39. Porcine islet xenografts survived long-term in control NOD/SCID mice, but were completely rejected in HU mice (FIG. 39A). Grafts from the humanized NOD/SCID mice lost all insulin-producing cells and were intensely infiltrated with human T cells, B cells and macrophages (FIG. 39A), with deposition of human antibodies (FIG. 39B). Graft rejection, including infiltration by human B cells and macrophages, was completely prevented by depletion of human T cells with anti-human CD2 mAb (BTI322) (FIG. 39), demonstrating that human T cells play a critical role in porcine islet xenograft rejection and are required for graft infiltration by human B cells and macrophages. Thus, induction of T cell tolerance can be key to overcoming rejection of pig islet xenografts.

It has been shown that porcine thymus transplantation induces robust xenograft tolerance in T cell-depleted, thymectomized mice[62,63]. This approach also promotes acceptance of porcine αGal KO kidney xenografts in NHPs[11]. Moreover, SW THY xenotransplantation leads to specific tolerance of human T cells that develop in SW THY grafts[64]. The ability of porcine thymus grafts to induce human T cell tolerance in humanized mice with pre-established human immune systems was assessed. Porcine fetal THY grafts were transplanted under the opposite kidney capsule of HU mice after human T cell reconstitution was achieved, by approximately 10-14 weeks. To prevent rejection of SW THY grafts by pre-existing human T cells, HU mice were injected with anti-CD2 mAb BTI322. Because BTI322 mediated efficient human T cell depletion only in peripheral lymphoid tissues but not in the thymus, HU THY grafts were removed (by nephrectomy) at the time of SW THY implantation. Long-term survival of SW THY grafts was seen in all BTI322-treated HU/HU mice, but not in untreated control HU mice. Furthermore, human T cell reconstitution occurred in BTI322-treated, graftectomized HU mice 9-12 weeks after SW THY transplantation, reflecting normal human thymopoiesis in the SW grafts[5]. Thus, thymic graftectomy and anti-CD2 treatment overcomes the human anti-pig T cell barrier in humanized mice. This regimen can be used in Aim 2 to achieve SW mixed chimerism in established HU mice to assess tolerance of pre-existing xenoreactive Nab-producing cells.

TABLE 9

Donor-specific skin graft tolerance in pig-human mixed chimeras prepared in pig cytokine transgenic NOD-SCID mice as described previously.

| Group | Transplants | Skin graft survival (day) | |
|---|---|---|---|
| | | SLA-matched skin | 3rd party pig skin |
| A (n = 8) | pBMT | >111-120 | >111-120 |
| B (n = 4) | pBMT+ HuThy/Liv/HSC | >120 (n = 3), >40* | 14, 38, 55, >40* |
| C (n = 3) | HuThy/Liv/HSC | 14, 38, >120** | 38, 31, >120** |

*Died on day 40 with surviving skin grafts
**With severe mononuclear cell infiltration on histology
Control animals (unreconstituted animals receiving pig BMT alone) and long-term humanized mice (human THY/LIV/CD34 cell-grafted mice with human immune systems) that did or did not receive pig BMT were grafted with donor SLA-matched and third party pig skin. Non-reconstituted controls failed to reject both types of grafts. Humanized mice without pig BMT rejected both types of porcine grafts. Mixed pig-human chimeras accepted skin from the donor-type pig and rejected third-party SLA-mismatched skin.

Induction of Antigen-Specific T Cell and Antibody Responses in HU Mice.

Antigen-specific human responses were assessed in HU mice immunized with 2,4-Dinitrophenyl hapten-Keyhole Limpet Hemocyanin (DNP-KLH) in Complete Freunds Adjuvant (CFA) 14 weeks post-transplant and boosted 3 weeks later with DNP-KLH in IFA. CFSE proliferation assays revealed human T cell responses in DNP-KLH-immunized HU mice but not PBS (in adjuvant)-injected controls[3], with comparable proliferation to mitogen in both groups. Germinal centers were observed in the secondary lymphoid tissues and DNP-specific IgGs (mainly human IgG1 and IgG2, some IgG3) were detected in the DNP-KLH-immunized HU mice[65]. T cell-dependent antigen-specific immune responses, including class switching suggesting effective T-B cell cooperation, were thus demonstrated in HU mice.

To assess responses to immunization with protein antigens and pathogens, HU/HU mice were immunized with tetanus toxoid (TT) and proliferative responses to TT and to a neoantigen (chicken IgG) were measured 4 weeks later, 3 weeks after boosting. Blocking HLA-specific mAbs to assess MHC restriction of such responses were identified. Responses of splenocytes depleted of mouse WBCs and erythrocytes, with antigen added, and of purified human T cells with antigen-pulsed autologous human FLC-derived DCs, were compared. In both instances, human T cells from HU/HU mice showed robust responses to recall antigen (FIG. 40 shows results of stimulation with FLC-derived DCs) that were blocked by anti-human class II mAbs, demonstrating that they were HLA-restricted. No in vitro responses to neoantigen were detected (FIG. 40).

Anti-Pig Natural Antibodies Develop in HU Mice:

Sera from 3 of 4 mice collected 7-13 weeks after HU THY-CD34 cell transplantation contained cytotoxic NAbs against porcine targets. This observation is used to assess the ability of porcine mixed chimerism to tolerize human anti-pig NAb-producing cells in HU mice.

Explore the Ability of Mixed Xenogeneic Chimerism to Induce Natural Antibody-Producing B Cell Tolerance in the Pig-Human Species Combination.

Studies during the currently funded period have demonstrated that humanized mice produce cytotoxic natural antibodies (NAb) against the pig. The impact of mixed chimerism induction on pre-existing and newly developing human anti-pig Nab can be assessed. Human anti-pig non-Gal Nab-producing cells can be identified.

Examine the Impact of Mixed Chimerism Induced at the Time of Human Thymus Grafting/CD34 Cell Administration on NAb Formation.

Anti-pig NAb levels can be compared in HU and HU-SW mixed chimeric humanized mice when porcine BMT is performed at the same time as HU THY/CD34 grafting. These studies can allow at the effect of mixed chimerism on the de novo development of non-Gal anti-pig Nabs to be studied. Both cytotoxicity assays and indirect flow cytometry (FCM) can be performed as has been previously described[70,71,103]. FCM can allow identification of Nab isotype. Human anti-pig Nabs of both IgM and IgG classes have been detected in normal human serum[104-109]. In the case of HU mice, the xenoantibodies may have mainly non-Gal specificity, since the mouse is Gal+ and either tolerance to Gal or absorption of any anti-Gal Nab on mouse tissues would therefore be expected. To determine whether human anti-pig NAb tolerance, if observed in HU-SW mice, is specific for the donor pig or is broad, a comparison of reactivity to SLA$^{dd}$ donor and third party YUC porcine cells can be done.

Compare Immune Responses in Humanized Mice with and without Porcine Mixed Xenogeneic Chimerism.

Humanized mice demonstrate robust immune responses, with excellent T cell proliferative and antibody responses following protein immunization[2-4] (FIG. 40).

Comparison of Immune Responses to Immunogens Among Human T Cells Generated in HU Mice and HU-SW Mixed Chimeras (10 Per Group).

Humanized mice can be created as described above in pig hematopoietic cytokine Tg NRG recipients and porcine BMCs can be administered on the same day as human THY/CD34 implantation/administration[1]. Control HU mice will not receive porcine BMCs. The kinetics of human CD3, CD4 and CD8 reconstitution, as well as human B cells and monocytes, can be monitored in the peripheral blood beginning at 3 weeks post-implantation. Reconstitution of porcine cells of various lineages can also be monitored. Total human and porcine IgG and IgM levels can be measured by ELISA. When an average of >5% human T cells are detected in WBCs of all groups, 5 animals per group can be immunized as in FIG. 40, using CFA and tetanus toxoid (TT) followed by a boost 3 weeks later with Incomplete Freund's Adjuvant (IFA) and TT. Control animals (5 per group) will receive adjuvants alone. The animals can be euthanized one week after the boost and proliferative responses of purified T cells to TT presented by DCs prepared from the original FLC donor and to DCs prepared from a porcine donor SLA-matched dd animal can be assessed. Techniques have been established for preparing human DCs from FL CD34 cells (see FIG. 40) and for preparing porcine DCs from PBMCs[118,119]. Blocking anti-pig and human class II mAbs can be added to confirm the human or pig MHC restriction of any observed responses. Similar studies can be performed using immunization with DNP-KLH as described[3]. In addition to measuring T cell proliferative responses, sera can be tested by both human- and pig-specific ELISA for class-switched antibody responses to KLH.

All in vitro analyses can also include assessments of reactivity to the porcine donor SLA, third party pig, NOD mice, the human donor and third party human in order to assess allo- and xenoreactivity and tolerance.

HU-SW chimeras may show tolerance to the donor pig and human[1] and to the recipient mouse (similar to pig thymus-grafted SW/HU mice in FIG. 43), with robust responses to non-donor pig and human, whereas the HU mice may be tolerant only to the human donor and mouse recipient and not to the pig (as in HU/HU mice in FIG. 43).

REFERENCES FOR EXAMPLE 7

1. Xu Y, Yang Y G, Ohdan H, Ryan D, Harper D, Wu C, Kruger-Grey H S, Thall A D, Awwad M, and Sykes M. Characterization of anti-Gal antibody-producing cells of baboons and humans. Transplantation 81 (6):940-948, 2006. PMID: 16570021, PMCID not available
2. Lan P, Tonomura N, Shimizu A, Wang S and Yang Y G. Reconstitution of a functional human immune system in immunodeficient mice through combined human fetal thymus/liver and CD34+ cell transplantation. Blood 108 (2): 487-492, 2006. PMID: 16410443, PMCID not available.
3. Ide K, Wang H, Liu J, Wang X, Asahara T, Sykes M, Yang Y G, Ohdan H. Role for CD47-SIRPα signaling in xenograft rejection by macrophages. Proc Natl Acad Sci USA 2007; 104(12):5062-6. PMCID: PMC1829264
4. Wang H, Madariaga M L, Wang S, Oldenborg P-A, Yang Y G. Lack of CD47 on Non-hematopoietic Cells Induces Split Macrophage Tolerance to CD47null Cells. Proc Natl Acad Sci USA 2007; 104:13744-13749. PMID: 17699632, PMCID not available
5. Yang Y G and Sykes M. Xenotransplantation—Current Status and a Perspective on the Future. Nat. Rev. Immunol. 2007; 7(7):519-531. PMID: 17571072, PMCID not available
6. Yang Y G and Sykes M. Tolerance in xenotransplantation. Curr Opin Transplant. 2007. 12:169-175. PMID and PMCID not available.
7. Kawahara T, Rodriguez-Barbosa J I, Zhao Y, Zhao G, and Sykes M. Global Unresponsiveness as a Mechanism of Natural Killer Cell Tolerance in Mixed Xenogeneic Chimeras. Am J Transplant 2007: 7:2090-2097. PMID: 17640313, PMCID not available
8. Tonomura N, Habiro K, Shimizu A, Sykes M, Yang Y G. Antigen specific human T cell responses and T cell-dependent production of human antibodies in a humanized mouse model. Blood 2008 111:4293-4296. PMCID: PMC2288728
9. Tonomura N, Shimizu A, Wang S, Yamada K, Tchipashvili V, Weir G C, Yang Y G. Pig islet xenograft rejection in a mouse model with an established human immune system. Xenotransplantation 2008; 15:129-135. PMID: 18447886 PMCID not available
10. Shimizu I, Fudaba Y, Shimizu A, Yang, Y G, and Sykes M. Comparison of human T cell repertoire generated in xenogeneic porcine and human thymus grafts. Transplantation 2008: 86:601-610. PMCID: PMC2680689
11. Haspot F, Bardwell P D, Zhao G, and Sykes M. High antigen levels do not preclude B cell tolerance induction with alpha1,3Gal via mixed chimerism. Xenotransplantation 2008: 15:313-320. PMCID: PMC2633101

12. Fudaba Y, Onoe T, Chittenden M, Shimizu A, Shaffer J, Bronson R, Sykes M. Defective regulatory and effector T cell function predispose to autoimmunity following xenogeneic thymic transplantation. J Immunol 2008: 181: 7649-7659 PMCID: PMC2673578
13. Habiro K, Sykes M, Yang Y G. Thymic xenotransplantation induces human T cell tolerance to porcine xenoantigens in humanized mice with an established human immune system. Am J Transplant. 2009: 9:6:1324-1329 PMCID: PMC2752337
14. Onoe T, Chittenden M, Zhao G, Yang Y-G, and Sykes M. Phenotypic conversion, survival, and/or homeostatic expansion of human T cells in vivo depends on peripheral interactions with human antigen-presenting cells. J Immunol 2010: 184:12:6756-6765. PMID: 20483739 PMCID not yet available
15. Wang Y, Wang H, Wang S, Fu Y, Yang Y G. Survival and function of CD47-deficient thymic grafts in mice. Xenotransplantation 2010; 17:160-165. PMID: 20522249 PMCID not yet available
16. Yang Y G. CD47 in xenograft rejection and tolerance induction. Xenotransplantation 2010 (In press).

Example 8

Figure 45:
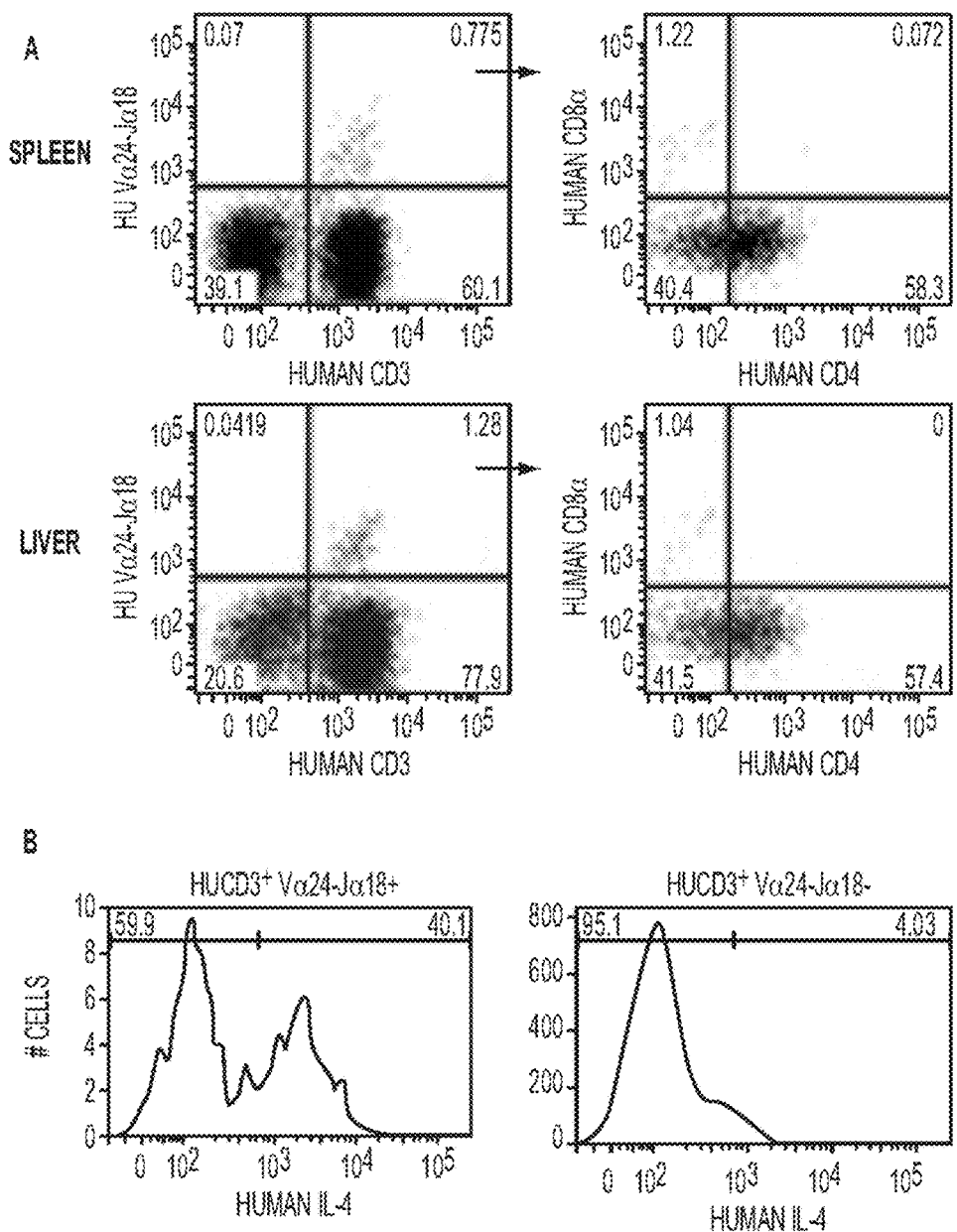

Provided herein are methods make a leukemia model, and methods to evaluate the anti-tumor effect of RLI in mixed chimeric hu-mice. Three groups of hu-mice can be prepared (Table 10): Group A, mixed allogeneic hu-mouse chimeras without leukemia (non-leukemic RLI and non-RLI recipients. These groups can confirm the efficacy of RLI in eliminating chimerism); Group B, mixed allogeneic hu-mouse chimeras with leukemia (leukemic RLI recipients and non-RLI controls); and Group C, hu-mice with functional human immune systems (RLI donors). Each recipient group can contain at least 10 animals To establish mixed hu-mouse chimeras (Group A; Table 10), NSG mice can be transplanted with magnetically isolated fetal liver CD34+ cells from two different allogeneic donors who have differential expression of HLA-A*201 (HLA-A2+ and HLA-A2−), along with thymic tissue from the HLA-A2+ donor. HLA-A2 expression (tested by flow cytometry on fetal liver cell suspensions with A2-specific mAb [One Lambda, Inc.]) in these donors can allow the determination of mixed chimerism by flow cytometry. In other studies using this model, it has been established that cryopreserved/thawed fetal thymic tissue, along with injection of anti-CD2 mAb BTI-322 to deplete pre-existing T cells from the fetal thymus graft, permits robust human multilineage hematopoietic repopulation from allogeneic CD34 cells given i.v. and now routine use of cryopreserved thymus, anti-CD2 and frozen allogeneic CD34 cells is done in these studies. Thus, HLA typing of such tissue has been done and establishment of a small bank for use in studies requiring particular HLA alleles has been done. As shown in FIG. 45, data demonstrate that mixed chimerism can be induced in the hu-mouse model. Chimerism can be monitored following transplantation by measuring HLA-A2 expression on human CD14+ monocytes, CD19+ B cells and CD3+ T cells in peripheral blood as described[59]. These mice are expected to generate multi-lineage mixed chimerism with mutually tolerant T cell populations from both donors. Indeed, donor-specific tolerance was demonstrated in early studies of mixed xenogeneic chimerism induction with this model[54].

TABLE 10

Hu-mice to be prepared

| Group | A2+ fetal tissue | A2− fetal tissue |
|---|---|---|
| A: RLI recipients | Thy + CD34+ FLCs | CD34+ FLCs |
| B: Leukemic RLI recipients | Thy + MLL transduced CD34+ FLCs | CD34+ FLCs |
| C: RLI donors | Thy + CD34+ FLCs | None |

Mice with stable mixed chimerism can be used as recipients of RLI. RLI can be performed by injecting human splenocytes and lymph node cells (negatively selected with anti-mouse CD45 and Ter119 mAb-coated MACS beads to leave only human cells) from RLI donor hu-mice (Group C) to half of the mixed chimeric hu-mice (recipients) in groups A and B after leukemia has developed in at least half of the Group B mice as determined by WBC analysis as above. In initial studies, pooled human lymphocytes can be used from half as many RLI donors as recipients, but this number may be titrated up or down, depending on results of initial experiments. In this manner, the effect of RLI in animals with leukemia at stages that mimic both overt relapse and minimal residual disease can be assessed. Comparison of groups receiving or not receiving RLI can determine the extent to which RLI is protective against overt and subclinical established leukemias. If a protective effect of RLI is detected, addition of a control group that is reconstituted only from the HLA-A2+ donor and therefore is not chimeric can be done, and receives RLI, and a non-chimeric group receiving RLI plus allogeneic human lymphocytes. As in the mouse model, these groups can demonstrate tumor mortality that is similar to that of non-RLI-treated recipients, and therefore can demonstrate that rejection of an established graft is essential for the anti-tumor effect of RLI.

Evaluate the Ability of Enhancing iNKT Cell Reactivity with αGal-Cer Treatment to Augment the Anti-Tumor Effect of RLI.

Comparisons can include groups receiving no RLI, RLI alone, αGal-Cer alone and the combination of RLI and αGal-Cer. Studies in the mouse model have shown that αGal-Cer enhances the anti-tumor effect of RLI[31] and a similar dosing regimen to that employed in the mouse model can be utilized. It has been already demonstrated that hu-mice produce iNKT cells and that these produce IL-4 upon administration of αGal-Cer (FIG. 44).

Example 9: Methods to Generate Virus-Specific T Cells and Model of EBV-Induced Lymphoma Provided herein are methods of reconstituting individual human patient immune systems in mice. These methods can generate large numbers of naïve T cells with a broad repertoire of specificities. In certain embodiments, these methods can generate virus-specific T cell responses in these humanized mice to demonstrate the potential of this technology to provide protective T cells for patients who can't clear opportunistic viral reactivations and/or develop EBV-related lymphomas.

Many patients receiving bone marrow or solid organ transplants or infected with HIV-1 are afflicted with opportunistic infections from common viruses and bacteria that are present in most individuals. Because the T cell immune systems do not function normally in these patients and their own thymuses are unable to function to generate new T cells, these patients often succumb to complications of these infections or reject their grafts because their immunosuppression must be decreased in order to promote immunity to the infection. The thymus is the organ responsible for making T lymphocytes, which are needed to protect humans from attack by infectious organisms. As described herein, a method of generating a new, functioning immune system from individual human patients in mice has been developed. This is achieved by injecting bone marrow CD34+ hematopoietic stem cells (HSCs) into immunodeficient mice that also receive a fetal human thymus fragment under the kidney capsule. The thymus tissue is treated in a way that destroys its pre-existing T cells so that the patient HSCs are not rejected. These patient HSCs generate a human immune system in the immunodeficient mice, including T cells that develop in the thymus graft in large numbers. These T cells are functional and have a very diverse repertoire of rearranged T cell receptors, making them capable of recognizing a full panoply of foreign antigens. The T cells that repopulate the immune systems of these mice have the "naïve" phenotype, in marked contrast to the adult human donors, who have much more skewing toward the memory phenotype by middle age, meaning that their T cell compartment is filled up by a limited repertoire of T cells that often lack the ability to clear infections.

Many transplant patients, for example, but not limited to, bone marrow or organ transplant patients, and HIV patients have very poor thymic function and very few naïve T cells. As a result, their T cell repertoire consists of a narrowed range of recognition capabilities and they are incapable of clearing opportunistic infections. Among the common opportunistic infections in these patient groups are reactivated cytomegalovirus (CMV) and Epstein-Barr virus (EBV) infections. These CMV infections can be life-threatening and EBV reactivation can culminate in posttransplant lymphoproliferative disease (PTLD), which is fatal if not successfully treated. Infusion of CMV- or EBV-reactive T cells has been shown to be beneficial in such patients, but often these T cells are limited in number and are derived from allogeneic (non-self) donors, so they do not persist in large numbers and may provide only partial protection.

The method described herein of generating naïve T cell repertoires de novo in immunodeficient mice can provide large numbers of autologous (self-derived, so they are not rejected by the patient's immune system) pathogen-specific T cells after immunization. In certain embodiments, these "Individual Immune Response" (IIR) mice can be immunized with CMV and EBV antigens in order to generate large numbers of T cells with these specificities and to demonstrate that they can clear viral infections and EBV-related PTLD in the humanized mouse model. These data can demonstrate the potential to improve the treatment of opportunistic infections in immunocompromised humans using T cells generated in IIR mice.

Figure 28:
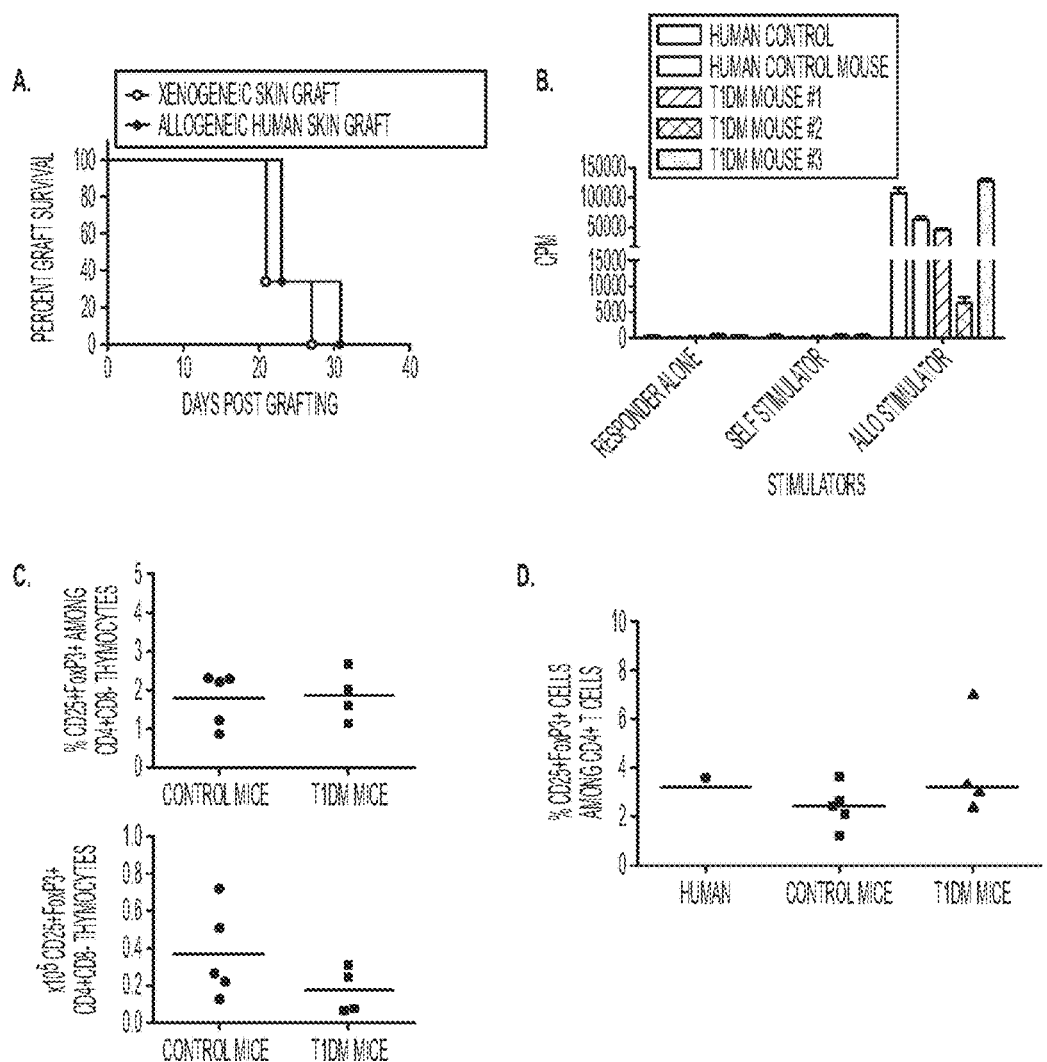
Figure 29:
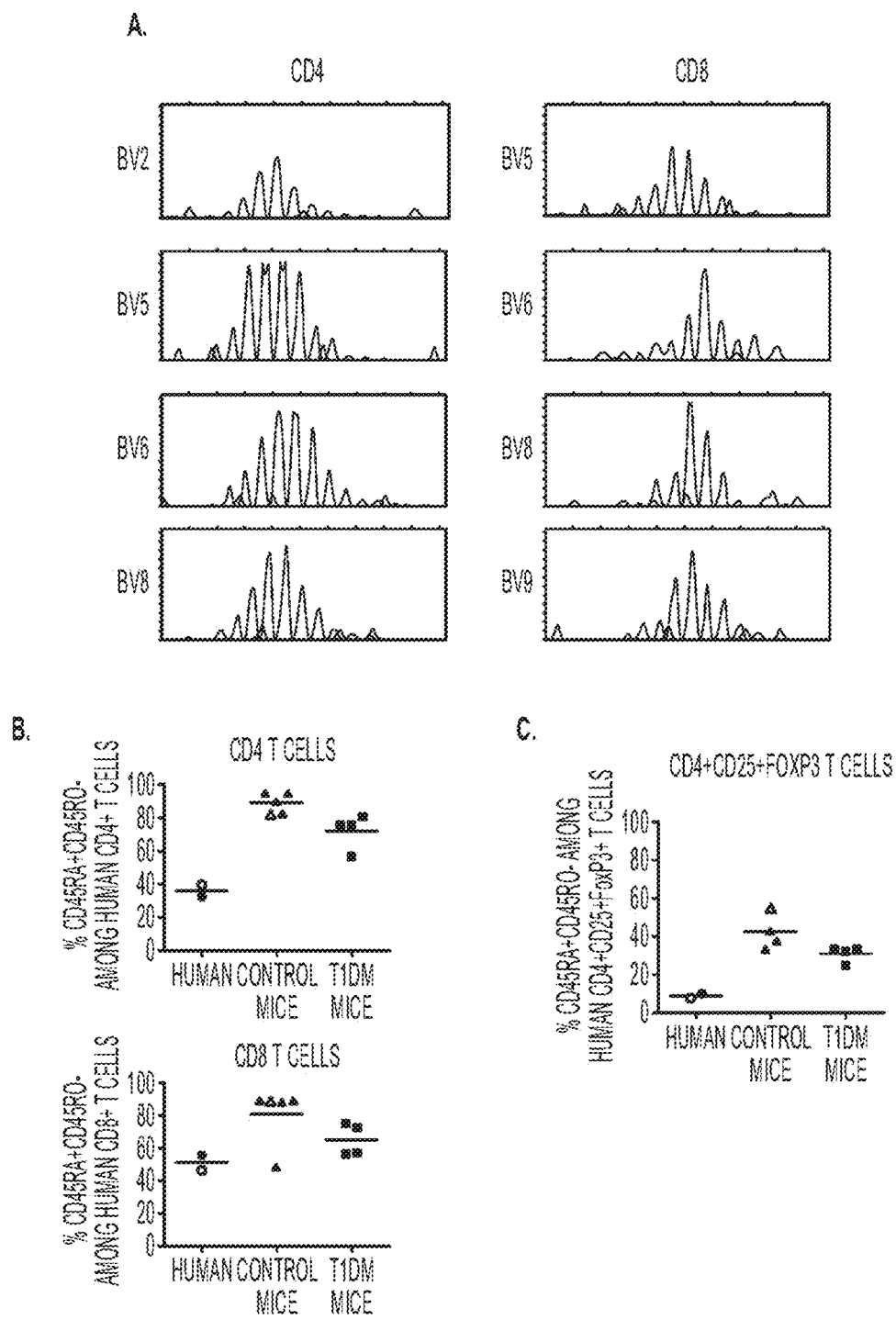

Experiments described herein demonstrated that robust human immune systems can be generated in immunodeficient mice using bedside aspirates of adult bone marrow from adult human volunteers (FIGS. 27, 28). This is referred to as the "Individualized Immune Response" (IIR) mouse model. Newly generated T cells are functional and self-tolerant (FIGS. 27, 28), have a diverse repertoire (FIG. 29) and include regulatory T cells in normal proportions. The immune phenotype of the adult CD34+ cell donor is rejuvenated compared to that of the adult donor (FIG. 29). These mice can be used for therapeutic purposes as a source of autologous naive T cells with a broad repertoire to improve immunocompetence in thymic insufficiency states (e.g. HIV-1 infection, post-hematopoietic cell transplantation, etc), and, because the humanized mice can be immunized with any antigens of interest, including but not limited to, any microbial antigen, can provide a source of antigen-specific T cells to treat refractory infections in these patients. Essentially unlimited numbers of these mice and hence of diverse, naïve autologous T cells, can be generated from patient bone marrow or mobilized peripheral blood HSCs.

These mice can be used to generate human T cells that respond to opportunistic viral reactivation diseases, protecting them from such diseases, for example but not limited to life-threatening CMV disease and EBV-related lymphomas. Humanized mice with adult human bone marrow-derived naïve T cells can be generated and immunized with suitable antigens, for example CMV or EBV antigens. Such antigens are known in the art and can be readily determined by a skilled artisan. These immune responses can be measured by quantifying the T cells recognizing these antigens and mounting protective responses. These T cells can be adoptively transferred to additional mice with immune systems from the same donors but lacking T cells, because they are not given a human thymus graft, to see if they can control CMV and EBV infections in the T cell-deficient mice.

Figure 46:
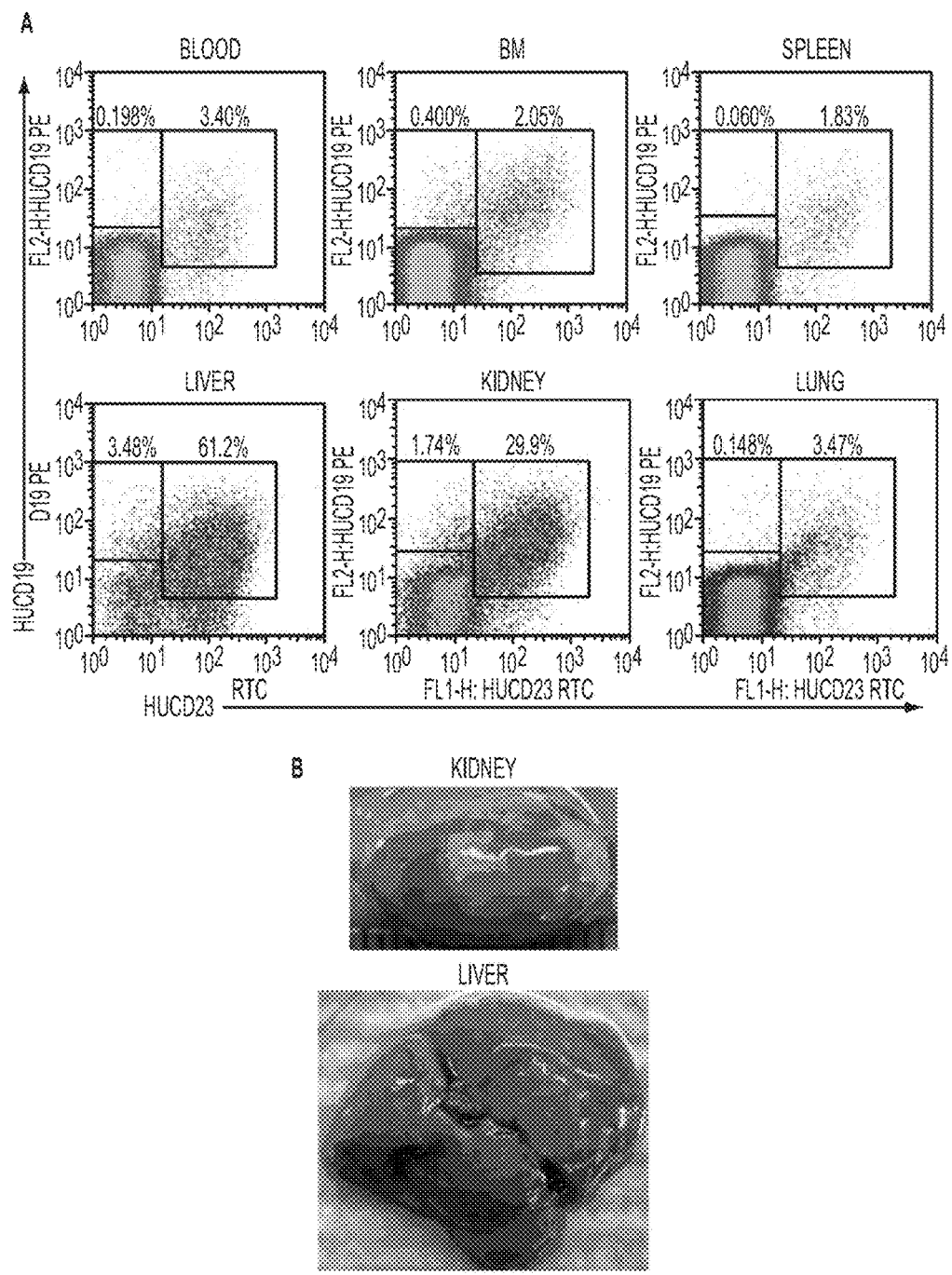

A model of EBV-induced lymphoma, resembling EBV-induced post-transplant lymphoproliferative disease, has been generated in the humanized mouse model (FIG. 46). This model of EBV-induced lymphoma can be used to assess the ability of adoptive transfer of T cells generated with EBV immunization in IIR mice to eliminate or reduce these tumors.

In a non-limiting embodiment, humanized mice with adult human bone marrow-derived naïve T cells (CD34+ cells from a first human donor) can be generated and immunized with EBV antigens. Such antigens are known in the art and can be readily determined by a skilled artisan. These immune responses can be measured by quantifying the T cells recognizing these antigens and mounting protective responses. These T cells can be adoptively transferred to mice with EBV-induced lymphoma, for example autologous EBV-induced lymphoma, to determine whether autologous T cells generated with EBV immunization in IIR mice eliminate or reduce these EBV-induced lymphoma/tumors.

Example 10: The Mini-Me Mouse: A Humanized Mouse Model to Study Cell-Intrinsic Immune Pathogenesis of Type 1 Diabetes In Type 1 diabetes (T1DM), multiple genetic determinants encoding HLA and immunomodulatory molecules create an immune system predisposed to autoimmune attack on pancreatic beta cells. T1DM susceptibility is transferred with hematopoietic stem cells (HSCs) in mouse and probably man, indicating that genetically programmed immune defects intrinsic to HSCs result in abnormal immune regulation or self-tolerance. In humans, it is difficult to distinguish whether any particular immunoregulatory abnormality causes disease or results from secondary immune effect of diabetes progression or treatment. To assess the HSC-determined immunoregulatory abnormalities associated with T1DM, a humanized mouse model that achieves multilineage human immune cell reconstitution was developed from a small number of adult CD34+ HSCs transplanted with allogeneic cryopreserved fetal thymic tissue into NOD/SCID/IL2RtUli (NSG) mice. NSG mice were reconstituted with HSCs aspirated from bone marrow of adult T1DM and control volunteers. The newly generated T cells are functional and self-tolerant, have a diverse repertoire and include regulatory T cells. The immune phenotype of these "Mini Me" mice is more naive or rejuvenated compared to the adult bone marrow donor. No gross differences were detected in the phenotype of T cell populations or in the numbers and phenotypes of regulatory T cells derived from HSCs of adult T1DM or control HSC donors. The Mini Me mouse permits comparison of immune phenotype and immunoregulatory function in control and T1DM prone immune systems in the absence of diabetes. This model can be used to determine whether immunoregulatory cell populations are inherently dysfunctional in the T1DM immune system.

Type 1 diabetes (T1DM) is an autoimmune disease that results from the interplay of multigenic hereditary and poorly defined environmental factors, and is caused by destruction of insulin-producing pancreatic $\beta$ cells. It accounts for 5-15% of all diabetes cases.

Genetics:

HLA-encoded T1DM susceptibility may account for ~50% of the inherited disease risk. Many non-HLA IDDM susceptibility genes, including immunomodulatory genes (e.g. cytokines (IL2/IL21), costimulatory (IL2R$\alpha$) and inhibitory molecules (CTLA-4)), are also genetically linked to T1DM.

Current animal models for T1DM include the NOD mouse and BB rat, which spontaneously develop diabetes. Models have given invaluable insights into disease, and NOD mice and humans share several susceptibility-related genes. Of more than 230 immune-interventional therapies developed in mice, very few have clinical significance in humans.

Humanized Mouse Models

Humanized mouse models are "mice engrafted with functional human cells, tissues or expressing human transgenes". They allow in vivo studies of human cell and tissue function and serve as a bridge between basic research and clinical translation.

Rationale for a Humanized Mouse Model to Study T1D:

T1D patients are studied after disease onset. Therefore these studies are unable to distinguish cause from effect of disease or other (environmental) factors. In mouse, the susceptibility to T1D can be transferred with hematopoietic stem cells (HSC). To assess HSC-determined immunoregulatory abnormalities associated with T1DM, a humanized mouse model that achieves multilineage human immune cell reconstitution was developed from adult CD34+ HSCs transplanted with allogeneic fetal thymus tissue into NOD/SCID/IL2Rg null mice. Without being bound by theory, genetic predisposition to Type 1 diabetes is associated with T cell-intrinsic abnormalities in the function of regulatory T cells, in responses of effector T cells to regulation and in T cell homeostasis.

Conclusions and future directions for the Mini Me model: Achieved multilineage reconstitution from a small number of adult CD34+ HSCs; B cell reconstitution and normal thymopoiesis of human T cells derived from adult; CD34+ HSCs lead to sustained T and B cell reconstitution in the mouse; T cells that develop in the human thymus have a more naïve or rejuvenated phenotype compared to the human donor; T cells are functional and self-tolerant; Similar numbers of "natural" T regulatory cells are produced by the thymic grafts, and present in peripheral blood of T1DM HSC compared to control HSC reconstituted Mini Me mice.

Immune reconstitution from adult bone marrow CD34+ cells in NSG mice allows in vivo analysis of HSC-intrinsic immune defects in a safe, controlled and prospective manner.

The Mini Me mouse provides a "clean slate" immune system, unaltered by disease or its treatment, for analysis of HSC-intrinsic defects in immunoregulation associated with Type 1 diabetes.

The development of a new humanized mouse model with multilineage human lymphohematopoietic cells involves the combined transplantation of human thymic tissue and peripheral injection of CD34+ cells. This mouse model has several advantages, such as high, sustained repopulation with multilineage human hematopoietic cells and strong immune responses in vivo and in vitro.

FIGS. 49 to 57 describe the development of the Mini Me mouse model, and present some of the results obtained using the Mini Me mouse model.

The following was done and observed: Successful multilineage human lymphohematopoietic cell reconstitution in NSG mice with $1.8 \times 10^5$ adult human CD34+ and cryopreserved, allogeneic human fetal thymus tissue plus 100 µg×2 anti-CD2 mAb i.v. Macroscopically profound increase of thymic grafts with normal phenotypic distribution of human thymocytes with majority of CD4+CD8+ double positive thymocytes. Generation of a rejuvenated version of the adult donor's immune system. Normal T cell function in vitro and in vivo plus self-tolerance in NSG mice reconstituted with THY grafts and allogeneic, adult CD34+ cells. Normal FoxP3+ Treg cell development in humanized mice with predominantly naive phenotype. Normal T cell polyclonality in NSG mice reconstituted with THY grafts and allogeneic, adult CD34+ cells. Similar numbers and proportions of Tregs in THY graft and PBL in NSG mice reconstituted from T1DM and healthy control Example 11: The "Mini Me" Mouse: A Humanized Mouse Model to Study Cell Intrinsic Pathogenesis of Type 1 Diabetes Type 1 diabetes mellitus is caused by autoimmune destruction of the insulin-producing $\beta$ cells. While poorly defined environmental factors play an important role in the development of autoimmunity, genetic factors substantially determine the susceptibility to autoimmune disease.

The HLA genotype is most strongly linked with T1DM, however, non-HLA-linked loci clearly also contribute to autoimmunity risk. Many of these loci contain immunoregulatory genes, therefore, without being bound by theory, intrinsic abnormalities in the cells of the immune system, which originate from hematopoietic stem cells (HSCs), can contribute to the development of autoimmunity. While the NOD mouse model has permitted genetic studies to analyze mechanisms by which some of these genes promote autoimmunity, clinical studies involve analyses of patients after disease onset and cannot distinguish cause from effects of the disease, its treatment, or environmental factors that precipitates the disease. The biobreeding rat and the NOD mouse have given invaluable insights into T1DM, but they have also led to misconceptions and erroneous extrapolations. Thus, there is a need for models that permit the analysis of human immunologic defects in a controlled and prospective manner.

Here, a new humanized mouse model that permits the development of multilineage peripheral human hematopoietic cells in sublethally irradiated NOD/SCID/IL2 receptor $\gamma$ chain null (NSG) mice from adult, allogeneic bone marrow CD34+ cells administered in low numbers is presented. This model can make it possible to compare T cells and other immune cells derived from CD34+ cells of normal controls versus patients with autoimmune disease in a controlled and prospective manner.

Humanized Mice

Many "humanized mouse" models have been developed. Human peripheral blood mononuclear cells (PBMC) can populate immunodeficient mice and human T cells develop in human fetal thymus (THY) grafts implanted with fetal liver under the kidney capsule. Recently, it has been shown that the combination of intravenous fetal CD34+ cell infusion with human fetal thymus and liver (THY/LIV) grafts under the kidney capsule allows human immune reconstitution with high levels of peripheral human T cells, B cells, immunoglobulins, and both myeloid and plasmacytoid dendritic cells. These mice develop normal-sized lymphoid tissues and demonstrate strong antigen-specific immune responses in vivo, including robust class-switched antibody responses following protein immunization. Furthermore, normal thymic development of regulatory T cells (Treg) has been demonstrated with Treg function and conversion to an "activated" phenotype in the periphery. This model also allows the examination of peripheral homeostatic expansion of human T cells, for which an appropriate in vivo model has been lacking so far.

FIGS. 58 to 66 describe the development of the Mini Me mouse model, and present some of the results obtained using the Mini Me mouse model.

Conclusions include the following: Sustained multilineage reconstitution was achieved by engraftment of a small number of adult human CD34+ cells in sublethally irradiated NSG mice grafted with allogeneic fetal thymus under the kidney capsule. Normal thymopoiesis of human T cells derived from adult CD34+ HSCs occurs in the fetal thymus graft, including production of a diverse repertoire of Vβ TCR and production of "natural" regulatory T cells. T cells and T regulatory cells have a more naïve or rejuvenated phenotype compared to the human donor. T cells are functional and self-tolerant.

The Mini Me mouse provides a "clean slate" immune system, unaltered by disease or its treatment, for analysis of HSC-intrinsic defects in immunoregulation associated with Type 1 diabetes.

Example 12

Provided herein are methods to develop a reaggregate human thymus transplant model allowing human thymopoiesis from adult CD34+ in HLA-defined human thymus grafts These studies can extend the humanized mouse model; instead of implanting intact fetal thymus tissue, CD45-negative thymic stromal cells cryopreserved from HLA-typed human fetal thymic tissue can be implanted under the kidney capsule of NOD-SCID mice. Thymi bearing common diabetes-susceptibility HLA alleles can support the thymopoiesis of T cells from i.v.-injected CD34+ cells from normal control and Type 1 diabetic subjects sharing these alleles. Alternative approaches include injection of intact human thymic tissue with thymic epithelial cells derived from HLA-transgenic NOD mice or adenoviral transduction of genes encoding diabetes susceptibility alleles into thymus grafts.

In previous years, evaluation of various regimens for engraftment of fetal human thymus grafts in NOD.scid and NOD.scid-IL2R-gamma$^{null}$ mice that can allow human thymopoiesis from allogeneic CD34+ cells was reported. In these experiments, whether deoxyguanosine treatment of human fetal thymus tissue for either 7 or 21 days or cryopreservation of the fetal thymus in prior to transplantation can sufficiently deplete resident thymocytes to allow multilineage reconstitution for adult allogeneic human CD34+ hematopoietic stem cells was tested. Results from these pilot experiments demonstrated that cryopreservation of the fetal thymus sufficiently depleted resident thymocytes and allowed both time for HLA typing of the tissue and multilineage reconstitution of human immune cells from adult CD34+ donors in NOD.scid-IL2R-gamma$^{null}$ mice. Observations from a compilation of multiple experiments using bedside bone marrow aspirates from healthy control and subjects with T1D will be briefly summarized herein.

Human Cell Reconstitution from a Bedside Aspirate

In a previous report, data from successful multilineage reconstitution of NSG mice transplanted with cryopreserved allogeneic human thymus and CD34+ cells isolated from bedside bone marrow aspirates of the first paired healthy control and T1D BM donor volunteers were described. In the past year, 20 individuals were recruited, of which 19 subjects have provided blood for DNA isolation and SNP-genotyping. For these studies, each paired BM donor group and fetal thymus graft are matched at common diabetes susceptibility loci HLA*A201, DRB*0302 and/or DQB*0301. Four additional pairs of healthy control and T1D bedside bone marrow aspirations that are matched at HLA*A201, DRB*0302 and/or DQB*0301 were successfully performed. HLA-typed, cryopreserved fetal thymus tissue is also being established and accumulated. Healthy controls recruited for BM aspiration that do not match T1D subjects enrolled in the study are drawn for experiments. From these individuals, 3 bone marrow aspirations were drawn.

A 10-15 ml bone marrow aspirate provides an average of $1.5 \times 10^6$ and $2.7 \times 10^6$ CD34+ cells at ~85-90% purity from a healthy control or T1D subject (n=5 for each group) respectively. The protocol was standardized to include 2Gy TBI 1 day prior to transplant, 2 injections of anti-CD2 monoclonal antibody at day 0 and day 7 post-transplant and injection of $2 \times 10^5$ adult BM-derived CD34+ cells. The development of human chimerism is monitored starting at 4 weeks post-transplant, continuing every 2 weeks up to 20 weeks post-transplant. Total human chimerism and lineage-specific chimerism among total PBMCs were compiled from four independent experiments (FIG. 55). As a control, irradiated NSG mice received CD34+ cells alone without a thymus transplant. Human cells were detectable as early as 4 weeks post-transplant and peaked at 12 weeks post-transplant at 37% and 43% in healthy control and T1D CD34+ cell-derived mice, respectively. In recipients of thymus grafts but not control recipients, human CD3+ cells were present in both healthy control and T1D CD34+ cell-derived mice by 8 weeks post-transplant (~8% of PBMCs) and increased to 38% and 24% in healthy control and T1D CD34+ cell-derived mice by 20 weeks post-transplant. Human B cell chimerism reached peak levels by 8 weeks post transplant with 10% and 17% CD19+ cells among PBMCs in healthy control and T1D CD34+ cell-derived mice respectively. Monocyte populations also peaked at 8 weeks post-transplant with 11% and 6.5% among PBMCs in healthy control and T1D CD34+ cell-derived mice. Animals receiving only CD34+ cells (no thymus graft; "CD34 only mice") developed human chimerism levels that peaked at 57% of PBMCs at the first observed timepoint 6 weeks post-transplant and declined steadily until 20 weeks post-transplant. Human cell populations in these mice were primarily composed of B cells, with a small increase in CD3+ cells appearing 14 weeks post-transplant. The T cells observed in CD34+ only mice likely developed in the mouse thymus. The native thymus of animals which received a thymic graft contained very few total thymocytes (ranging from 0.9-2.7×10⁶ cells over n=6 animals) compared to the number of thymocytes in the human thymus grafts (ranging from 0.3-43.1×10⁶ cells) in animals sacrificed 9 weeks post-transplant. Analysis of PBMC populations from CD34⁺ only injected NSGs compared to CD34⁺/Thy Tx animals revealed a decrease in the proportion of CD4⁺CD45RA⁺ naïve cells in the CD34⁺ only group (mean 8.5% compared to 55% for the CD34/Thy TX group). This observation indicates that a small number of human T cells develop in the mouse thymus and expand in the periphery of the CD34⁺ only animals at late timepoints.

Analysis of the human thymic grafts in long-term (22-25 weeks) NOD.scid-IL2R-gamma*null* mice demonstrated robust thymopoiesis from adult CD34⁺ cells (FIG. 54). There were normal proportions of CD4/CD8 double positive and single positive cells. Additionally, subgating the single positive CD4 and CD8 cells demonstrated a similar profile of CD45RA and CD45RO expression to that in thymic grafts of humanized mice made by transplantation of autologous fetal thymus and fetal liver-derived CD34⁺ cells. Although the mice reconstituted with cells derived from the T1D subjects trended toward decreased thymocyte numbers, there were no significant differences between animals reconstituted with T1D or healthy control CD34⁺ cell donors. More animals from multiple paired T1D and healthy control CD34⁺ cell donors can be added to these analyses to determine if thymopoiesis is less efficient from T1D derived CD34⁺ cells.

To determine if the T cells produced by the thymic graft had diverse TCR cell repertoires, single positive CD4 and CD8 thymocytes in NOD.scid-IL2R-gamma*null* mice reconstituted with CD34⁺ cells derived from control and T1D subjects were analyzed by spectratyping the beta chain of the TCR 20 weeks post-transplant (FIG. 65). These human T cells showed a diverse repertoire, with similar utilization of the BV families and a polyclonal CDR3 length distribution for each BV. The reconstituted repertoires resembled those of the average CD4 T cell repertoires of 12 healthy adults, with average Hamming distances for all analyzed BV families in each sample ranging from 14.2 to 26.2 with a mean of 20.6. The Hamming distance is the average of the distances of the observed TCR β-chain length distributions for each BV family from a polyclonal reference distribution. The Hamming distances found in the reconstituted thymocyte population is indicative of a typical T cell polyclonality as seen in healthy control peripheral blood leukocytes.

Thymic graft cryopreservation led to marked depletion of graft thymocytes (FIG. 55), which can contribute to the avoidance of rejection of allogeneic volunteer donor CD34 cells injected iv. In addition to multilineage reconstitution of human cells shown in FIG. 55 above, it was observed that none of the long-term animals that received cryopreserved/thawed THY plus anti-CD2 mAb developed wasting syndrome or other evidence of GVHD. However, one animal that was not injected with anti-CD2 mAb developed GVHD-like syndrome characterized by severe alopecia, skin inflammation, hunched posture and weight loss starting 22 weeks post-transplant. Without being bound by theory, the injection of anti-CD2 mAb can be important for depleting residual live thymocytes which remain in the fetal thymus graft after cryopreservation. To directly test whether treatment with anti-CD2 mAb is necessary for multilineage reconstitution and prevention of GVHD symptoms, NOD.scid-IL2R-gamma*null* mice were transplanted with cryopreserved fetal thymus and allogeneic fetal liver-derived CD34+ cells with and without injection of anti-CD2 mAb (FIG. 56). Anti-CD2 mAb was not required to prevent rejection of allogeneic donor stem cells, as no difference was seen in the level of human reconstitution up to 15 weeks post-transplant. Additionally, no differences were noted in the peripheral reconstitution by human CD3, CD19 and CD14 cells. All animals look healthy up to this timepoint, and the mice are continued to be monitored for signs of GVHD.

A humanized mouse model that successfully allows human thymopoiesis from a small number of adult bone marrow CD34⁺ cells in allogeneic human fetal thymus grafts has thus been established.

Provided herein are methods to compare peripheral survival, homeostatic expansion, phenotypic conversion and self-tolerance of conventional T cells derived from CD34⁺ cells of T1D versus normal controls using the model that was developed.

It can be determined whether or not T cells from T1DM patients show increased lymphopenia-driven expansion in association with loss of tolerance to "self" antigens of the thymus donor. It can also be determined whether or not intrinsic abnormalities in homeostasis characterize T cells in T1DM patients.

Phenotype of T Cells Derived from HSCs of T1D and Healthy Control Subjects.

Without being bound by theory, T cells derived from HSC of T1D subjects can exhibit reduced survival and increased lymphopenia-driven expansion and activation compared to those from the HSC of healthy controls. To address this, CD4 and CD8 cells were analyzed in peripheral blood and the expression of CD45RA and CD45RO as markers of naïve and memory T cells was compared (FIG. 57). The immune system in NSG mice reconstituted with adult CD34⁺ cells and transplanted with fetal thymus appeared to be rejuvenated, as a higher proportion of CD45RA⁺ naïve cells was detected compared to the peripheral blood of the HSC donor. Additionally, there was a significant decrease in the percentage of naïve cells in the immune systems generated from HSCs of T1D subjects compared to those in healthy controls. Without being bound by theory, this observation indicates that one or many genetic abnormalities in HSCs of T1D individuals drives expansion and activation of T effector cells. This indicates that this phenotype observed in T1D patients and the NOD mouse are not a consequence of the disease initiation or progression, since these animals have no overt autoimmune symptoms assessed by immunohistochemistry of the pancreas.

Assessing Self-Tolerance and Immune Response in NSG Mice Reconstituted with Adult CD34⁺ Cells and Fetal Thymus.

In a previous report, it was shown that T cells derived from mice transplanted with human CD34⁺ cells from healthy controls or T1D subjects with allogeneic fetal thymus were self-tolerant, but exhibited strong allo-responses in a mixed lymphocyte reaction. T cell reconstitution was evident at late timepoints (>30 weeks post-transplantation) in a separate experiment in which the fetal thymus was irradiated prior to transplantation, at late timepoints. It is shown that the human immune system in these animals is capable of recognizing allogeneic human tissue and xenogeneic pig tissue and rejecting it. Pig skin and human skin from an allogeneic donor (i.e. not the fetal donor and not the adult CD34⁺ cell donor) were grafted onto NSG mice reconstituted with HSCs from a healthy control subject (bone marrow filter recovered CD34+ cells) 30 weeks post-transplantation (FIG. 58A). Animals with human immune cells rejected the skin graft within 5 weeks, while naïve NSG animals accepted the human skin graft for more than 14 weeks without signs of rejection.

To determine if the human immune system in the NSG animal reconstituted by adult CD34$^+$ cells was capable of antigen-specific recall, animals derived from CD34$^+$ cells of a T1D subject were immunized with tetanus or sham immunized with PBS. They were boosted by a second immunization, and the human cells were purified from the spleen and peripheral blood. These cells were stimulated in vitro with tetanus toxoid protein, and proliferative response measured by tritiated thymidine incorporation (FIG. 58B). As a positive control the proliferative response of human PBMCs from an adult donor immunized for tetanus are shown. These data demonstrate that the immune system of these NSG mice is capable of mounting a recall response to specific antigen.

Provided herein are methods to compare the numbers, function and peripheral phenotypic conversion of regulatory T cells derived from CD34$^+$ cells of T1D versus healthy subjects in the mouse model developed.

Without being bound by theory, Tregs and NKT cells derived from stem cells of T1DM patients can show defects. These studies can identify intrinsic abnormalities in regulatory cells from T1DM patients and their thymic versus post-thymic origin.

Defects in Treg numbers and function have been reported in T1D patients and in NOD mice. In NOD mice, deficiency of Tregs at the site of inflammation in the pancreas and the relative resistance of effector cells to regulation are believed to contribute to the final stages of disease development. The model developed allows prospective analysis of genetically determined defects in Treg phenotype and function arising from a T1D prone immune system.

The thymic grafts of NSG animals transplanted with healthy control or T1D CD34$^+$ cells and fetal thymus were analyzed to determine if Tregs were developing in the thymic grafts. Percentages of CD4$^+$CD8$^-$CD25$^+$FoxP3$^+$ cells were similar in animals reconstituted with CD34$^+$ cells from T1D and healthy control subjects. However, total cell numbers of FoxP3$^+$ cells trended toward a decrease in the T1D CD34$^+$ cell derived mice compared to the healthy control-derived grafts (FIG. 59A). This trend reflects the tendency to overall lower total numbers of thymocytes recovered from grafts of mice reconstituted with CD34$^+$ cells derived from T1D subjects. Although the decrease in the absolute numbers of thymocytes did not reach significance, these data indicate that there may be a defect in thymopoiesis from T1D-derived progenitors. In a separate experiment, Helios was added as a marker for natural Tregs to the FCM panel. Animals reconstituted with control and T1D marrow had similar percentages of CD4$^+$CD8$^-$CD25$^+$CD127$^{lo}$FoxP3$^+$Helios$^+$ cells (FIG. 59B). In addition to the stains in the thymus, the presence of Tregs was also assayed in the periphery. It was found that the percentage of circulating Tregs in the peripheral blood of mice reconstituted with healthy control and T1D CD34$^+$ cells was similar to levels found in healthy adult volunteers (FIG. 59C).

Figure 60:
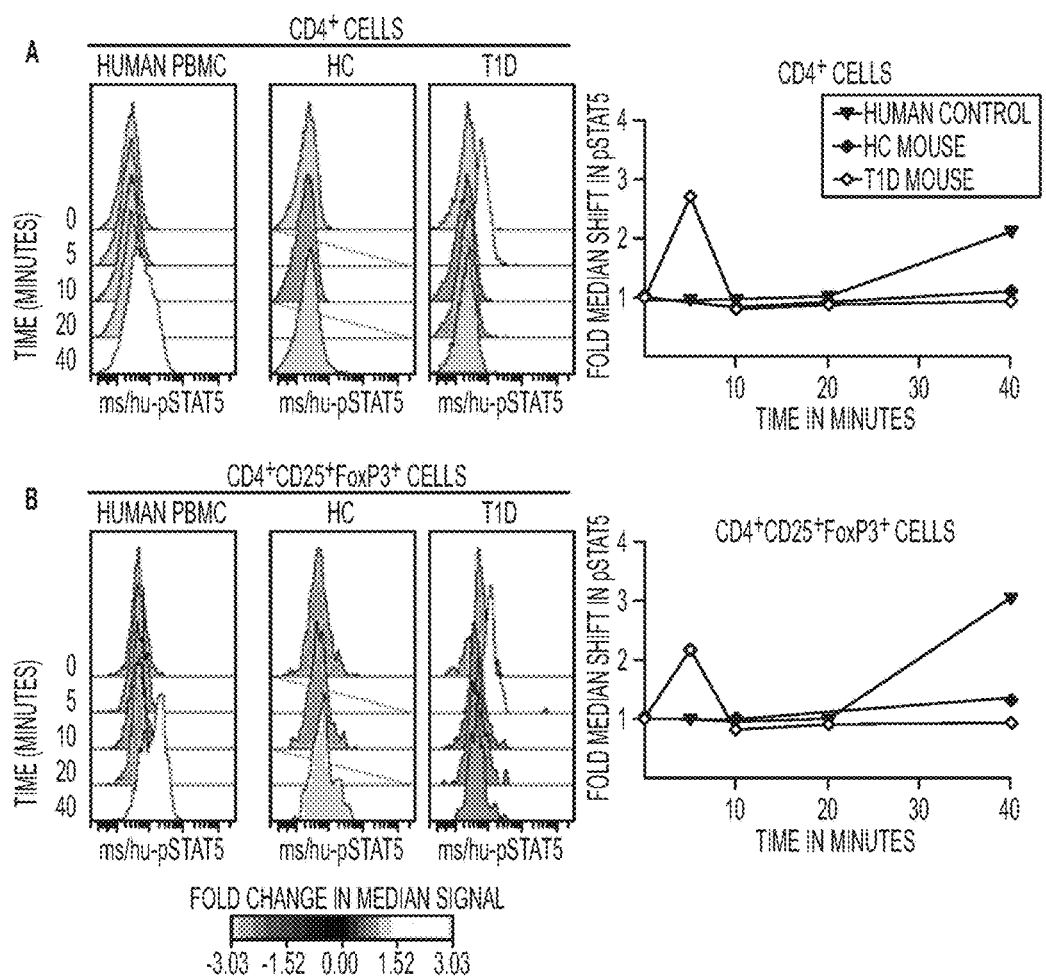

IL-2 is a susceptibility gene in the Idd3 locus. Stimulation of Tregs with IL-2 mediates activation of the transcription factor STAT5 and subsequent upregulation of FoxP3 gene transcript. This stimulation pathway affects Treg function and survival. To determine if there is a defect in IL-2 stimulated activation of STAT5 in Tregs derived from NSG animals reconstituted with T1D HSCs, a FCM protocol was designed to measure phosphorylation of STAT5 in cells stimulated with IL-2. The results (n=1 HC and T1D donor pair) indicate a possible defect in IL-2 signaling in T cells which develop from T1D-derived HSCs. Cells from the T1D CD34$^+$ cell-derived mouse showed an early shift in pSTAT5 median intensity and rapid return to baseline in both CD4$^+$ and Treg gated subsets compared to the adult human PBMC control (FIG. 60). This can reveal a genetically defined functional defect in Treg signaling for this T1D donor.

In summary, a humanized mouse model that successfully allows human thymopoiesis from low numbers of adult bone marrow CD34$^+$ cells in allogeneic human fetal thymus grafts that have been cryopreserved prior to transplantation was established. In this report, it is shown that the newly generated T cells in this model have similar functionality and self-tolerance as those in the adult CD34$^+$ cell donor, but the immune phenotype is rejuvenated. The protocol has been standardized for this new humanized mouse model, and investigation of the immune function of these animals at an earlier time-point, when monocytes, B and T cells are present (8-12 weeks post-transplant) will begin. Genetically determined defects in T cells that can explain the evolution of autoimmune attack in T1D subjects can be investigated.

All Type 1 diabetic patients can benefit from the understanding of stem cell-intrinsic abnormalities in T cell function that can be obtained from these studies.

The levels of reconstitution of naïve and memory-type T cells, Tregs and NKT cells from T1D and healthy control CD34$^+$ cells derived immune systems can be compared in the animal model. Through adoptive transfer of T cells in the model, T cell homeostatic expansion and survival can be compared between T cells derived from CD34$^+$ cells of T1D and healthy volunteers. The response of T1D and healthy control-derived immune systems in recall response can be compared after immunization with tetanus toxoid. Suppressive function of Tregs and susceptibility of effector cells to Tregs can be analyzed. Flow cytometry-based assays can be continued to monitor cell signaling within Tregs. The analysis of Treg signaling can be expanded to include activation of STAT3 downstream of IL-21 stimulation (another gene within the susceptibility locus Idd3). In addition, whether there is defective IL-2 stimulated upregulation of gene transcription of FoxP3, TGFβ and IL-10 in regulatory T cells derived from T1D donor HSCs can be addressed in the model. These studies can help to identify functional defects in effector and regulatory T cell populations that arise due to intrinsic-genetic defects and lend insight into how T1D evolves.

A new-generation humanized mouse model that allows safe, controlled and prospective analysis of hematopoietic stem cell-intrinsic immunoregulatory defects predisposing to autoimmune diseases, and of individual responsiveness to immunotherapeutic agents, has been developed. T cell populations that evolve from immune stem cells derived from T1D and healthy control volunteers can be investigated in this humanized mouse model.

REFERENCES FOR EXAMPLE 12

Danzl N, Kalscheuer H, Sykes M. The mini me mouse: a humanized mouse model to study cell intrinsic immune pathogenesis of type 1 diabetes. Presented at the 11$^{th}$ Annual Rachmiel Levine Symposium, Pasadena, Calif., March 2011.

Kalscheuer H, Danzl N, Onoe T, Faust T, Winchester R, Goland R, Greenberg E, Spitzer T R, Savage D G, Chio G, Tahara H, Yang Y G, and Sykes M. A model for immune rejuvenation and individualized in vivo analysis of human immune responsiveness. Science Translational Medicine, Submitted November 2011.

Oneo, T., Kalscheuer H., Danzl N., Chittenden M., Zhao G., Yang Y. G., Sykes M. Human natural regulatory T cell development, suppressive function and post thymic maturation in a humanized mouse model. Journal of Immunology, 2011 Oct. 1; 187(7): 3895-903.

Example 13: A Model for Immune Rejuvenation and Individualized In Vivo Analysis of Human Immune Responsiveness Immunodeficient mice receiving human fetal thymus grafts and fetal CD34+ cells i.v. generate robust human immune systems. Peripheral human antigen-presenting cells promote optimal function of T cells exported from the thymus grafts. However, to use humanized mice to study or treat human immune-mediated disorders, adult hematopoietic cells must populate allogeneic fetal thymus grafts while avoiding rejection by mature graft thymocytes. These obstacles have been overcome and it has been demonstrated that robust immune reconstitution in mice with hematopoietic stem cells (HSCs) aspirated from bone marrow of adults with Type 1 diabetes (T1D) and healthy control volunteers. Fetal thymic cryopreservation permits HLA typing and hence selection for shared alleles, while preventing allogeneic adult HSC rejection. Newly generated T cells are functional and self-tolerant, have a diverse repertoire and include Tregs. The immune phenotype of the adult CD34+ cell donor is rejuvenated. T1D and control HSCs generated similar numbers of natural Tregs intrathymically. However, peripheral T cells from T1D subjects showed increased proportions of activated/memory cells compared to controls, indicating HSC-intrinsic differences in T cell homeostasis. This "Individualized Immune Response (IIR)" mouse can allow personalized analysis of genetically-controlled immune dysregulation and responsiveness to immunotherapies and has potential therapeutic utility as a source of autologous T cells for the treatment of various immune disorders.

Human peripheral blood mononuclear cells (PBMC) can populate immunodeficient mice (1) and human T cells develop in human fetal thymus (THY) grafts implanted with fetal liver under the kidney capsule (2). The combination of intravenous human hematopoietic stem cell (HSC) infusion with human fetal thymus and liver (THY/LIV) grafts under the kidney capsule allows human immune reconstitution with high levels of peripheral human T cells, B cells, and both myeloid and plasmacytoid dendritic cells (3), with antigen-specific immune responses in vivo (3-5). Normal thymic development of regulatory T cells (Tregs) with suppressive function (6) and homeostatic peripheral expansion of human T cells occurs (7).

Humanized mice can be used for therapeutic purposes, as a source of naive T cells for the treatment of thymic insufficiency states, as a source of antigen-specific T cells following immunization, or as a source of regulatory cells in transplantation or autoimmune diseases. Humanized mice also have potential for analysis of the effects of autoimmunity-associated genetic polymorphisms on immune regulation. Recently-defined non-HLA-linked genes collectively confer substantial autoimmune disease risk (8-11). In humans with autoimmune diseases, however, underlying immunoregulatory defects arising from non-HLA-associated genes are largely undefined. Given that many of these loci contain immunoregulatory genes, such as cytokines, costimulatory and inhibitory molecules (8-11), intrinsic abnormalities in the cells of the immune system, which originate from hematopoietic stem cells (HSCs), likely contribute to the development of autoimmunity. Consistently, diabetes disease susceptibility is transferred via hematopoietic cells in NOD mice (12) and, without being bound by theory, in humans (13). However, studies of patients with disease cannot distinguish underlying causes from effects of disease evolution, disease treatment or precipitating environmental factors.

Fulfillment of the above therapeutic and basic research goals of humanized mice can require achievement of human immune reconstitution and function with adult HSCs obtained from patients. However, these cells are not available in large quantities from study volunteers, and adult HSCs engraft less efficiently than fetal CD34+ cells in immunodeficient mice (14). Furthermore, even if obtained in large quantities for therapeutic applications, adult HSCs can be rejected by allogeneic thymocytes pre-existing in fetal thymus grafts.

The development of a new humanized mouse model that supports robust peripheral reconstitution of T cells and APCs from small numbers of adult, allogeneic bone marrow CD34+ cells is presented. This "Individualized Immune Response (IIR)" mouse can be used to identify HSC-intrinsic immune abnormalities predisposing to autoimmunity and can have potential to provide immune reconstitution and immunotherapy for humans.

Results

Overcoming the Immune Barrier Imposed by Mature T Cells in Fetal Thymus Grafts.

To assess human immune reconstitution from adult HSCs in immunodeficient mice, CD34+ cells were isolated from discarded human bone marrow infusion filters and given i.v. to sublethally irradiated nonobese diabetic-severe combined immunodeficient (NOD/SCID) mice receiving fetal THY transplantation. Recipients of untreated fetal human THY grafts showed low peripheral T cell reconstitution during the first weeks after transplantation, which declined markedly over time, indicating that these cells emigrated from the graft (average CD3+ cell reconstitution 7.0%±8.22% of PBMC at 6 weeks, n=5 vs 2.34%±2.26% at 16 weeks post-transplantation). Non-T cells did not reconstitute from injected allogeneic CD34+ cells, indicating that these were rejected. Moreover, some long-term (>20 weeks) animals reconstituted with fetal human THY grafts and CD34+ cells have developed a late-onset graft-versus-host disease (GVHD)-like wasting syndrome. Without being bound by theory, thymocytes pre-existing in the THY grafts can reject allogeneic CD34+ cells and expand to attack recipient tissues, preventing immune reconstitution and causing xenogeneic GVHD, respectively. Methods for depleting graft thymocytes were therefore tested in an effort to prevent these phenomena.

Fetal thymus organ culture (FTOC) with 2'-deoxyguanosine (dGuo) depletes thymocytes while preserving stromal elements (15) that can support thymopoiesis (16). NOD/SCID mice received allogeneic adult CD34+ cells plus fetal THY tissue cultured for 7 or 21 days in the presence of dGuo. Control animals received fetal liver CD34+ cells from the thymic tissue donor. Mice that received $5\times10^5$ adult CD34+ cells without a THY graft reconstituted an average of 20% human PBMCs by Week 10 (FIG. 25A), but CD3+ cells were undetectable (FIG. 25C). In mice that received 7 day dGuo-cultured THY tissue plus allogeneic CD34+ cells, CD3+ levels averaging ~7% of PBMC were detectable by 6 weeks and subsequently declined (FIG. 25C), but CD19+ cells did not appear (FIG. 25B). Mature T cells escaping dGuo depletion apparently rejected the infused allogeneic CD34+ cells. Cells within the THY grafts did not achieve human non-T cell reconstitution or a high level of T cell reconstitution (FIG. 25C).

In contrast, successful thymic engraftment with human thymopoiesis as well as peripheral CD19+ cell reconstitution occurred after intravenous infusion of $5 \times 10^5$ allogeneic adult CD34+ cells with a 21-day dGuo-cultured THY graft, (average ~25% human CD3+ cells among PBMC at 20 weeks, FIG. 25B,C). Thus, progenitors derived from peripherally-infused allogeneic adult CD34+ cells populated dGuo-treated thymi, underwent thymopoiesis, and emigrated to the periphery. Control recipients of dGuo-treated fetal thymus tissue with $4 \times 10^5$ autologous fetal liver CD34+ cells instead of allogeneic adult marrow CD34+ cells showed more rapid T cell reconstitution (FIG. 25C) than was achieved with allogeneic adult CD34+ cells.

While the above recipients of 21-day FTOC grafts exhibited high levels of long-term human chimerism (FIG. 25), a lower dose of adult CD34+ cells did not achieve robust immune reconstitution (average 3.89%±9.89% human cells in PBMC at 20 weeks in recipients of $2 \times 10^5$ CD34+ cells, n=9). Only limited HSCs are available through volunteer bone marrow aspiration. Therefore, NOD/SCID/IL2 receptor γ chain$^{null}$ (NSG) mice, which lack NK cells and are more permissive for engraftment of human HSCs (17), were used for the ensuing experiments.

Irradiation of THY grafts to deplete pre-existing thymocytes was also evaluated. NSG mice receiving 7 Gy irradiated THY plus $3 \times 10^5$ adult CD34+ cells showed excellent B cell and monocyte reconstitution, but low numbers of peripheral T cells by 20 weeks. THY grafts were barely visible upon laparotomy (FIG. 63), indicating that thymic irradiation impairs thymic growth and/or function. T cells eventually reconstituted the periphery and thymic grafts were enlarged and cellular at the time of sacrifice >45 weeks post-implantation.

Cryopreserved/Thawed Fetal THY Grafts Allow Peripheral Reconstitution of T Cells and Multiple Hematopoietic Lineages from Allogeneic, Adult Human Hematopoietic Stem Cells.

Transplantation of cryopreserved/thawed mouse thymus tissue can restore immune function (18, 19). Since the studies above indicated that human fetal THY tissue contains viable, alloreactive and xenoreactive thymocytes, the ability of cryopreservation of intact fetal thymic tissue fragments to deplete these thymocytes was evaluated. As shown in FIG. 55, cryopreservation of thymic tissue indeed led to marked depletion (>2 to >3 logs) of all thymocyte subsets from fetal thymic tissue.

To test the utility of cryopreserved fetal thymic tissue, sublethally irradiated NSG mice received cryopreserved/thawed fetal human THY grafts plus $3\text{-}5 \times 10^5$ allogeneic, adult CD34+ cells i.v. To further assure depletion of T cells derived from pre-existing graft thymocytes, the mice received a depleting anti-human CD2 mAb. As shown in FIG. 26, all mice achieved human B cell and monocyte chimerism by 6 weeks. Unlike recipients of CD34+ cells alone, which showed minimal T cell reconstitution, recipients of cryopreserved/thawed THY grafts generated peripheral T cells, which appeared by 6 weeks and peaked at ~10% and ~30% of PBMC at 16 weeks following infusion with $3 \times 10^5$ or $5 \times 10^5$ CD34+ cells, respectively (FIG. 26A, lower right panel). While it took 20 weeks to achieve T cell reconstitution with 21-day dGuo-treated grafts, similar T cell levels were reconstituted by 10 weeks with cryopreserved/thawed THY grafts. At the time of animal sacrifice, these cryopreserved grafts were markedly enlarged, showing evidence of robust human thymopoiesis with predominant CD4/CD8 double positive thymocytes (FIG. 26B,C).

Control animals receiving cryopreserved THY grafts without i.v. CD34+ cells (with [n=5] or without [n=4] anti-CD2 mAb) did not repopulate significant human T cells or non-T cells in the periphery (0.46%±0.34% human cell reconstitution 20 weeks post-transplantation, n=9). Thus, the majority of pre-existing graft thymocytes were depleted by cryopreservation and administration of CD34+ cells was necessary for human T cell and non-T cell reconstitution. Additional control NSG animals receiving fresh thymic tissue with allogeneic CD34+ cells showed human T cells (mean 2.4% of PBMC) but no human chimerism in any other lineage by 5 weeks (<0.006%), whereas recipients of autologous CD34+ cells showed significant human T cell (mean 3.4%), B cell (mean 2.1%) and monocyte (mean 0.2%) reconstitution by this time. Thus, T cells from fresh thymic tissue implanted into NSG mice rejected allogeneic CD34+ cells.

None of the long-term animals that received cryopreserved/thawed THY plus anti-CD2 mAb developed wasting syndrome or other evidence of GVHD. Mouse class II+ cells were present in the long-term human THY grafts (FIG. 68), indicating that human thymocytes developing in the grafts from i.v. injected CD34+ cells are tolerized to the mouse recipient by negative selection. Without being bound by theory, the inclusion of anti-CD2 mAb was important for the prevention of a wasting syndrome induced by residual xenogeneic GVH-reactive mature T cells emigrating from fetal human thymus grafts. This was indicated by the development of a late-onset (at 22 weeks) GVHD-like syndrome (severe alopecia, skin inflammation, hunched posture and weight loss) in the only mouse that did not receive anti-CD2 mAb within a group of NSG mice receiving cryopreserved THY grafts (plus allogeneic CD34+ cells i.v.). However, anti-CD2 mAb was not required to prevent rejection of allogeneic donor stem cells, as no difference was seen in the level of human reconstitution by 15 weeks when groups of mice receiving cryopreserved thymic grafts and allogeneic CD34+ cells with or without anti-CD2 mAb treatment were compared (FIG. 56).

Human Immune Reconstitution from a Bedside Bone Marrow Aspirate from Control and T1D Volunteers.

Figure 61:
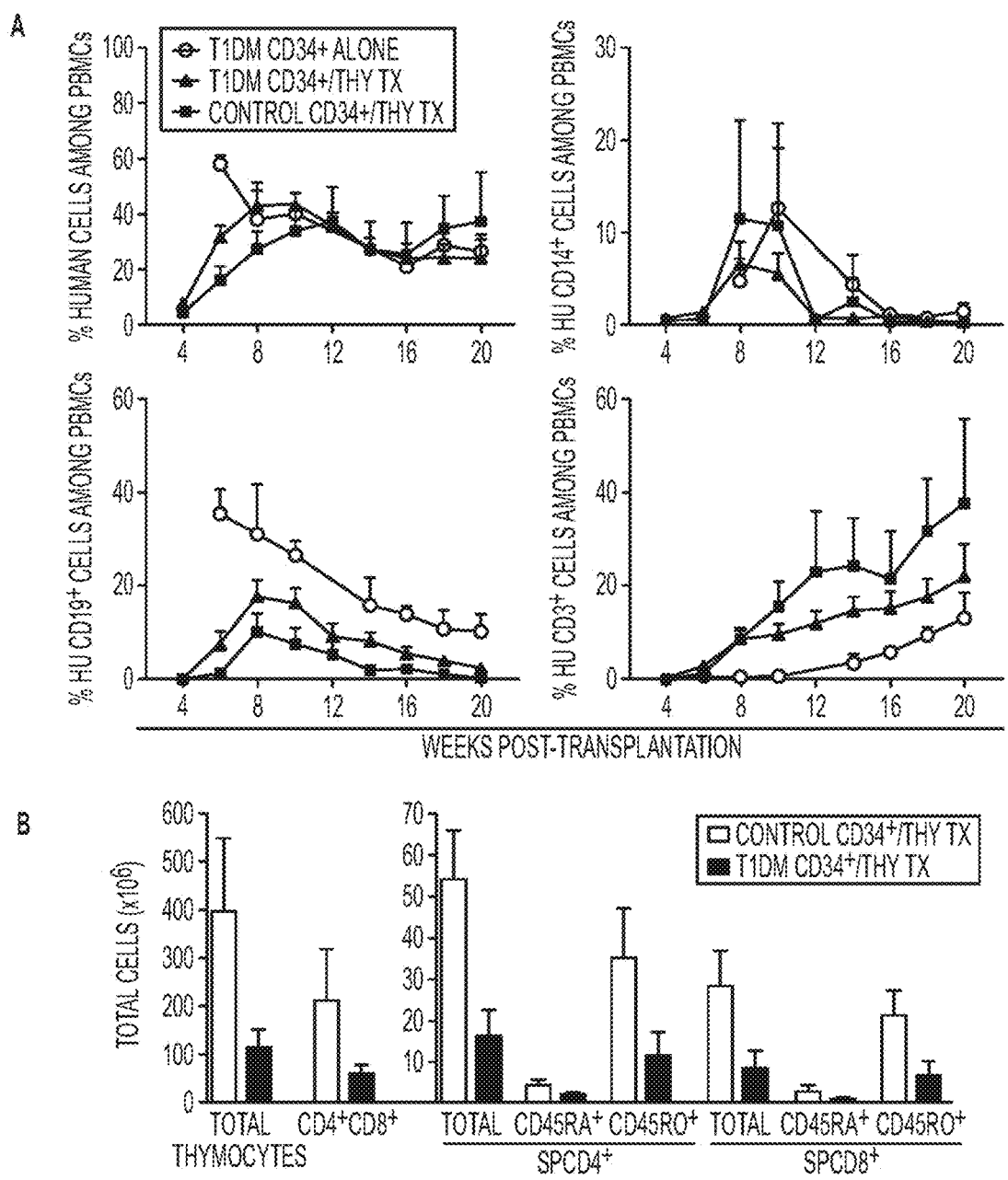

Reconstitution capabilities of adult CD34+ cells isolated from bedside bone marrow aspiration were next evaluated. An aspiration of 15 ml bone marrow yielded $3.6 \times 10^5$ and $2.7 \times 10^6$ CD34+ cells from an initial healthy control and T1D volunteer subject, respectively. Sublethally irradiated NSG mice received $1.8 \times 10^5$ adult CD34+ cells each plus a cryopreserved/thawed human fetal THY graft and anti-human CD2 mAb. Control irradiated mice received CD34+ cells without THY tissue. Human chimerism was detectable by Week 6 and peaked at ~25%-80%. Recipients of THY grafts plus i.v. CD34+ cells from the control and T1D volunteers developed substantial CD3+ cell levels by 8 weeks, while control mice (no THY graft) had markedly delayed T cell reconstitution (FIG. 61). CD19+ cells and CD14+ cells also developed from the HSCs of the T1D and control volunteers. Similar results were obtained in 3 additional experiments, in each of which 4-14 NSG mice were each reconstituted with $2\text{-}3 \times 10^5$ CD34+ cells from a single volunteer aspirate. Composite data from these experiments are presented in FIG. 61A. Splenic T cell reconstitution was also rapid and robust, with a mean of $2.47 \times 10^6$ (SEM $0.6 \times 10^6$) human CD3 cells per spleen in a group of 3 T1D cell-reconstituted mice and $10^6$ CD3 cells in a healthy control-reconstituted mouse spleen that were sacrificed at 9 weeks. FIG. 61B shows the robust thymopoiesis from adult CD34+ cells, including normal proportions of CD4/CD8 double positive and single positive cells and similar proportions of CD45RO+ and CD45RA+ cells among single positive thymocytes as was seen with fetal thymus and fetal CD34+ cells (6). Although thymocyte numbers tended to be lower in T1D compared to healthy control CD34 cell-reconstituted animals, no statistically significant differences were seen between the two groups.

T Cell Function and Self Tolerance in Mice Reconstituted with Volunteer Donor Bone Marrow CD34+ Cells.

T cell function was assessed by transplanting allogeneic human and xenogeneic (pig) skin to THY-grafted mice that received adult CD34+ cells. These mice rapidly rejected allogeneic human and xenogeneic pig skin grafts (FIG. 58A), while naive, untreated NSG mice accepted allogeneic human and xenogeneic skin grafts for the duration of follow-up (106 and 50 days, respectively) (FIG. 58A) with no infiltrates or evidence for rejection on histology of xenografts or allografts (FIG. 65).

To assess self-tolerance of T cells generated from adult CD34+ cells of T1D and healthy volunteers, mixed lymphocyte reactions (MLR) were performed using purified T cells isolated from the spleens and lymph nodes. T cells from mice reconstituted from T1D and control subjects showed self-tolerance along with strong responses to allogeneic human stimulators in MLR (FIG. 28B, Table 11). Notably, fresh adult donor T cells and T cells from a mouse reconstituted from the same healthy control bone marrow donor showed similar, robust responses to the allogeneic stimulator and similar self-tolerance. Thus, immune responsiveness and self-tolerance to the adult volunteer were recapitulated in these mice. Because they generate immune function from an individual adult bone marrow donor, these animals are referred to henceforth as "Individualized Immune Response [IIR]" mice.

The presence of Tregs was assessed in thymus grafts and the periphery of reconstituted mice. As shown in FIG. 59A, CD25highFoxP3+ Tregs were present among CD4+CD8− thymocytes of IIR mice. Analysis of CD4+CD8−CD25+ CD127lo thymocytes demonstrated that the majority of FoxP3+ cells were also Helios+, indicative of thymically-derived "natural" Tregs. Similar numbers and proportions of Tregs were detected in THY grafts reconstituted from control and T1D volunteers. Furthermore, while some studies have indicated that Treg numbers are reduced in the blood of T1D subjects compared to healthy controls (20), similar proportions of Tregs were detected in the peripheral blood of both groups of reconstituted mice (FIG. 59B).

Diverse TCR Cell Repertoire in Single Positive (SP) Thymocytes Derived from Adult Donor CD34+ Cells.

At 20 weeks post-transplantation, spectratyping analysis was performed on CD4 and CD8 SP thymocytes of mice reconstituted from T1D CD34+ cells and a normal volunteer (FIG. 29A). These human T cells showed a diverse repertoire, with similar utilization of the BV families and a polyclonal CDR3 length distribution for each BV. The reconstituted repertoires resembled those of the average CD4 T cell repertoires of 12 healthy adults, with average Hamming distances for all analyzed BV families in each sample ranging from 14.2 to 26.2, mean 20.6 (Table 12). This is indicative of typical T cell polyclonality as seen in healthy control PBL.

TABLE 12

Similarity of b-chain length distribution of experimentally reconstituted T-cell repertoires to a pooled CD4 T-cell reference repertoire of 12 healthy adults as measured by the Hamming distance for selected BV families

| Recons. Repertoire Sample Number | BV1 | BV2 | BV3 | BV4 | BV5 | BV5S1 | BV6a | BV6b | BV7 | BV8 | BV9 | BV11 | mHD* |
|---|---|---|---|---|---|---|---|---|---|---|---|---|---|
| 5683-CD4 | 16.1 | 29.6 | 29.9 | 19.9 | 36.2 | 17.8 | 12.3 | 15.0 | 13.8 | 31.9 | 19.3 | 29.0 | 22.6 |
| 5700-CD4 | 7.2 | 24.8 | 8.0 | 12.1 | 26.3 | 26.1 | 12.3 | 10.6 | 12.6 | 16.7 | 4.7 | 9.5 | 14.2 |
| 5700-CD8 | 21.3 | 17.7 | 35.1 | 15.6 | 19.3 | 11.0 | 22.1 | 20.4 | 23.2 | 15.0 | 15.4 | 43.8 | 21.7 |
| 3433-CD4 | 28.8 | 25.8 | 39.5 | 16.0 | 23.6 | 12.3 | 27.1 | 34.3 | 22.2 | 24.3 | 31.6 | 29.4 | 26.2 |
| 5195-CD4 | 12.7 | 28.4 | 32.9 | 18.3 | 21.3 | 28.6 | 17.4 | 35.2 | 12.8 | 19.1 | 20.9 | 44.7 | 24.4 |
| 5681-CD4 | 13.7 | 18.2 | 19.9 | 14.3 | 23.8 | 18.8 | 21.8 | 14.3 | 17.5 | 22.4 | 11.9 | 21.3 | 18.2 |
| 5685-CD8 | 17.1 | 19.6 | 11.0 | 13.8 | 21.3 | 17.7 | 20.0 | 12.7 | 15.1 | 14.8 | 12.9 | 23.1 | 16.6 |
| | | | | | | | | | | | | | 20.6 |

*mHD Hamming Distance is the average of the distances of the observed TCR β-chain length distributions for each BV family from a ployclonal reference distribution.

TABLE 11

Phenotype of T cells used in MLR assays in FIG. 28B

| % Human T Cells | T1DM #1 | T1DM #2 | T1DM #3 |
|---|---|---|---|
| CD3+ | 43.9 | 52.1 | 88.8 |
| CD3+CD44RA+RO− | 56.4 | 74.4 | 71.8 |
| CD3+CD45RA−RO+ | 5.45 | 7.2 | 5.35 |

Similar Treg Development from T1D and Control Bone Marrow CD34+ Cells.

Naïve Vs Memory T Cell Phenotype in IIR Mice.

The T cells populating the peripheral tissues of mice reconstituted from CD34+ bone marrow cells of healthy control and T1D volunteers included both "naïve"-type CD45RA+CD45RO− and "memory"-type CD45RA− CD45RO+ cells (FIG. 66A). Comparison of T cells in the blood of a control CD34+ cell donor revealed a marked increase in the proportion of naïve-type CD45RA+ CD45RO− CD4, CD8 and Treg subsets in the IIR mouse reconstituted from the same donor (FIG. 66A,B). Thus, a rejuvenated version of the adult donor's immune system is generated in IIR mice. As shown in FIG. 66C, the human thymus was necessary for this rejuvenation, as the proportion of naïve-type T cells in PBMC of recipients of CD34+ cells alone was markedly lower than that in mice that also received thymus grafts.

When the proportions of naïve-type and memory-type CD4 and CD8 T cells were compared in the blood of IIR mice generated simultaneously from T1D or healthy control donors, the T cells derived from T1D CD34+ cells showed significantly reduced proportions of naïve-type cells compared to those derived from healthy controls (FIG. 66A). Tregs derived from CD34+ cells of T1D donors tended more toward the "memory" phenotype than those from healthy controls, but this trend did not achieve statistical significance (FIG. 66B; p=0.07).

Discussion

It is demonstrated herein that adult, bone marrow-derived CD34+ cells can reconstitute NSG mice grafted with cryopreserved/thawed allogeneic thymus tissue, generating multiple hematopoietic lineages, including T cells, B cells and myeloid cells. Cryopreserving/thawing the fetal thymus plus administering anti-CD2 mAb depletes mature T cells from the graft, preventing rejection of allogeneic CD34+ cells and GVHD, while preserving thymic function. Thymopoiesis, growth of the thymus graft and reconstitution of a functional, diverse and rejuvenated immune system is achieved. Self-tolerance of the adult donors is recapitulated. While fetal liver fragments were included in the humanized mouse model upon which the studies are based (3, 5), these fragments are not required, as thymocyte progenitors from infused CD34+ cells populated the human thymic grafts in the current study.

While in vivo thymopoiesis and peripheral reconstitution were also achieved from dGuo-treated human thymi, T cell reconstitution from infused adult CD34+ cells was slow when thymi were dGuo-treated sufficiently long (21 days) to prevent rejection of allogeneic CD34+ cells. Slow T cell recovery has also been observed in patients with complete DiGeorge syndrome receiving thymic tissue cultured for several weeks in dGuo (21). The results indicate that cryopreservation of thymic tissue can support more rapid T cell recovery while preventing GVHD.

Cryopreservation of fetal thymus tissue permits HLA typing of tissue for use with adult CD34+ cells sharing HLA alleles, which is important for optimal immune function. The use of NSG mice allows the engraftment of relatively small numbers of allogeneic adult HSC, allowing reconstitution of multiple mice from a bedside bone marrow aspirate.

Immune reconstitution from adult bone marrow CD34+ cells of patients in NSG mice provides an immune system unaltered by disease, allowing comparison of individuals in a controlled and prospective manner. Human immune analyses are typically limited to peripheral blood samples, and underlying immune dysregulation cannot be distinguished from the ensuing cascade of inflammatory events that culminate in disease. Defects in Treg numbers and function have been reported for T1D (20, 22-24), systemic lupus erythematosus (25) and rheumatoid arthritis (26), but this has been controversial in T1D (27-29). No gross abnormalities were observed in the T cell populations generated from T1D subjects' CD34+ cells, which generated Tregs intrathymically in similar proportions as healthy control CD34+ cells. However, significantly reduced proportions of naïve-type T cells were observed in the blood of IIR mice generated from T1D compared to healthy control donors, indicating that abnormalities of T cell homeostasis, as described in NOD mice (30), can be a feature of T1D-derived HSCs. The model can allow assessment of genetically-programmed, HSC-intrinsic immunoregulatory abnormalities in T1D in relation to predisposing gene alleles.

HLA-transgenic immunocompetent mice have provided insight into the pathogenesis of autoimmune diseases such as rheumatoid arthritis (31), multiple sclerosis (32), celiac disease (33) and T1D (34-37). However, none of these models permit analyses of human HSC-intrinsic, genetically determined immune abnormalities that can contribute to autoimmune pathogenesis. In contrast, the combined administration of i.v. CD34+ cells and fetal THY tissue in immunodeficient mice generated functional human T cells, T-B interactions, class-switched antibody responses, with secondary lymphoid organs containing both plasmacytoid and myeloid dendritic cells (3-5). Since Tregs develop normally (6) and T cell homeostasis can be studied in this model (7), it can allow assessment of HSC-intrinsic immunoregulatory abnormalities associated with autoimmune diseases in HSC donors. The ability to HLA type the thymus before transplantation allows selection for thymi with disease-associated HLA alleles. Without being bound by theory, while transplantation of T1D HSCs does not cause autoimmune disease in NSG mice, further development of the model using HLA transgenic NSG mice can permit studies of autoimmune disease pathogenesis.

The "Individualized Immune Response" model can also allow the analysis of individual responsiveness of an adult marrow donor to immunotherapeutic agents. In addition, the reconstitution of multiple mice with naïve T cells with a diverse repertoire derived from adult HSCs can provide patients with thymic insufficiency due to immunosuppressants, chemotherapy, irradiation or HIV, with functional, self-tolerant T cells for adoptive transfer. Mice receiving human fetal THY and CD34+ cell grafts generate anti-HIV and other antigen-specific immune responses (4, 38), indicating the immunotherapeutic potential of this approach. The mice can also be used to generate large numbers of autologous Tregs with desired specificities for the treatment of patients with autoimmune disease, GVHD or organ allografts. The specific tolerance to CD34+ cell donor "self" antigens and the absence of GVHD in the studies most likely reflects intrathymic deletion due to the presence of APCs from the human HSC donor and the murine recipient, respectively, in the human thymus graft, as previously indicated in another thymic xenograft model (39).

In summary, a model that permits the development of multilineage peripheral human hematopoietic cells from adult HSCs has been established. The "Individualized Immune Response" mouse provides an immune system unaltered by disease or its treatment that can allow the analysis of intrinsic defects in immunoregulation associated with autoimmune disorders and of genetically-controlled responses to immunotherapies. These mice also have therapeutic potential as a source of polyclonal, naïve or activated T cells with desired specificities and properties for use in patients.

Materials and Methods

Animals and Human Tissues and Cells.

Nonobese diabetic-severe combined immunodeficient (NOD/SCID) and NOD/SCID/IL2 receptor γ chain$^{null}$ (NSG) mice were obtained from Jackson Laboratory (Bar Harbor, Me.), and housed in a specific pathogen-free microisolator environment. Human fetal thymus and liver tissues (gestational age 17-20 weeks) were obtained from Advanced Biosciences Resource (Alameda, Calif.). Fetal thymus fragments were cryopreserved in 10% DMSO and 90% human AB serum (Atlanta Biologicals, Lawrenceville, Ga.), irradiated or cultured, depending on the experimental design. CD34+ cells were isolated from a 15 ml bone marrow aspirate, or from discarded human bone marrow filters obtained from the Massachusetts General Hospital (MGH) Bone Marrow Processing Laboratory, or from fetal human liver tissue using a magnetic-activated cell sorter (MACS)

separation system with anti-human CD34+ microbeads (Miltenyi Biotec, Auburn, Calif.).

Fetal Thymus Organ Culture.

Human fetal thymus culture was performed as previously published (15). Briefly, thymus fragments were placed on 0.8 μm isopore membrane filters (Millipore, Billerica, Mass.) on 1 cm² Gelfoam sponges (Pharmacia & Upjohn Co, NY). To eliminate endogenous thymocytes, organ cultures were grown in the presence of 1.35 mM 2'-deoxyguanosine (Sigma-Aldrich, St. Louis, Mo.) in Dulbecco's modified Eagle medium (DMEM, Sigma-Aldrich, St. Louis, Mo.) at 37° C. for 7 or 21 days.

Human Tissue Transplantation.

Mice were conditioned with sublethal (2.5 Gy) total-body irradiation. Human fetal thymus fragments measuring about 1 mm³ were implanted underneath the recipient kidney capsule. Within 24 hours, 1-5×10⁵ human CD34+ cells were injected intravenously. Some recipients were treated intravenously with anti-human CD2 mAb (BTI322 (40); 100 μg) on Days 0 and 7.

Skin Grafting.

Split thickness (2.3 mm) skin samples from a MHC miniature pig and an allogeneic human donor were grafted on the lateral thoracic wall 39 weeks after human tissue transplantation. Skin grafts were evaluated daily from day 7 onward to 4 weeks and then at least one inspection every third day thereafter. Grafts were defined as rejected when less than 10% of the graft remained viable.

Flow Cytometry (FCM).

Levels of human hematopoietic cells in transplanted mice were assessed by four-color flow cytometry. Mice were tail bled at regular intervals after transplantation to obtain peripheral blood mononuclear cells (PBMC), which were prepared with Histopaque-1077 (Sigma-Aldrich, St. Louis, Mo.). Flourochrome-labelled mAbs, purchased from BD Pharmingen (San Diego, Calif.), were used in different combinations: anti-mouse CD45, anti-mouse Ter119, anti-human CD4, anti-human CD8, anti-human CD14, anti-human CD19, anti-human CD45, anti-human CD3, anti-human CD45RA, anti-human CD45RO, anti-human CD127, anti-human FoxP3, anti-human CD25 and isotype control mAbs. FCM analysis was performed using a FACSCalibur, FACSCanto or LSRII (BD Mountain View, Calif.), and analysis was carried out by FlowJo software (TreeStar, San Carlos, Calif.). Dead cells were excluded from the analysis by gating out low forward scatter and high propidium iodide (PI)-retaining cells. Murine erythroid cells were excluded by gating out mouse Ter119+ cells.

Mixed Lymphocyte Reactions.

Splenocytes and lymph nodes were harvested from humanized mice and mononuclear cell suspensions were isolated by Ficoll separation. Human T cells were enriched by depletion of mouse cells using anti-mouse CD45 and anti-Ter-119 microbeads (Miltenyi Biotec, Auburn, Calif.) followed by T cell purification using the Pan T cell isolation kit II (Miltenyi Biotec, Auburn, Calif.) according to the manufacturer's instructions. Purity was >90%. Responder T cells (10⁵ per well) were cultured with irradiated human allogeneic PBMCs (3000rad, 10⁵ cells per well) as stimulators for 5 days and proliferation was measured via [³H] thymidine incorporation as described (41). In self-stimulated control cultures, responder cells were incubated with autologous PBMCs from the same humanized mouse, depleted of mouse CD45+ and Ter119+ cells. Data are shown as mean [³H] thymidine incorporation in triplicate cultures.

Spectratyping.

Total RNA was extracted directly from 1 to 2×10⁴ CD4 or CD8 single positive thymocytes (purity >80%), reverse transcribed and single-strand cDNA synthesis was performed as described (42). Amplification reactions were performed using a TCR β-chain constant region primer and individual variable region primers as described (42). Products were then used in run-off reactions with a Cβ-specific FAM-labeled primer (Integrated DNA Technologies, Coralville, Iowa) as described (42). The labelled products were then used to determine the length distribution of the TCR β-chain length. The size and area of the peaks corresponding to the DNA products were determined using an ABI 3100 Genetic Analyzer (Applied Biosystems, Foster City, Calif.) and analyzed using Applied Biosystems Genotyper 3.7 NT. Hamming distances to assess the quantitative difference between the experimental and reference β-chain length distributions of peripheral blood CD4 T cells in normal humans were calculated as described (42).

Statistical Analysis.

Statistical analysis and comparisons were performed with GraphPad Prism version 4.0 (GraphPad Software, La Jolla, Calif.). Data in bar graphs are expressed as mean±SEM. Student's t-test for parametric data sets, or Mann-Whitney test for nonparametric data sets were used to compare groups. A p value less than 0.05 was considered to be statistically significant.

Immunohistochemistry.

Formalin fixed tissues were cut at 5 um for hematoxylin and eosin stain. For cytokeratin stain, frozen skin sections were fixed in 4% paraformaldehyde in PBS for 20 min, followed by permeabilization in 0.05% saponin/10 mM glycine/5% donkey serum/RPMI for 15 min and blocked with 5% dry milk in PBS, washed in 0.05% Tween in PBS and incubated with antihuman cytokeratin (MFN 116; Dako) overnight. Sections were washed and incubated with anti-mouse IgG (H+L) Alexa Fluor 488 and DAPI. For mouse MHCII stain, frozen sections were fixed in acetone at 4 C for 10 minutes, followed by permeabilization in 0.05% saponin/ 10 mM glycine/5% donkey serum/RPMI for 15 min and blocked with 10% egg white/0.05% BSA in PBS biotin block. Sections were stained with anti-mouse MHCII-biotin (M5/114.15.2; eBioscience) for 1 hour, washed and stained with streptavidin-Alexa Fluor 568 (Invitrogen). Images were acquired with an Axio Observer D1 microscope (Carl Zeiss, Inc.).

REFERENCE LIST FOR EXAMPLE 13

1. Mosier, D. E., R. J. Gulizia, S. M. Baird, and D. B. Wilson. 1988. Transfer of a functional human immune system to mice with severe combined immunodeficiency. *Nature* 335:256-259.
2. McCune, J. M., R. Namikawa, H. Kaneshima, L. D. Shultz, M. Lieberman, and I. L. Weissman. 1988. The SCID-hu mouse: Murine model for the analysis of human hematolymphoid differentiation and function. *Science* 241:1632-1639.
3. Lan, P., N. Tonomura, A. Shimizu, S. Wang, and Y. G. Yang. 2006. Reconstitution of a functional human immune system in immunodeficient mice through combined human fetal thymus/liver and CD34+ cell transplantation. *Blood* 108:487-492.
4. Tonomura, N., K. Habiro, A. Shimizu, M. Sykes, and Y. G. Yang. 2008. Antigen-specific human T-cell responses and T cell-dependent production of human antibodies in a humanized mouse model. *Blood* 111:4293-4296.

5. Lan, P., L. Wang, B. Diouf, H. Eguchi, H. Su, R. Bronson, D. H. Sachs, M. Sykes, and Y. G. Yang. 2004. Induction of human T cell tolerance to porcine xenoantigens through mixed hematopoietic chimerism. *Blood* 103:3964-3969.
6. Onoe, T., H. Kalscheuer, N. Danzl, M. Chittenden, G. Zhao, Y. G. Yang, and M. Sykes. 2011. Human natural regulatory T cell development, suppressive function, and postthymic maturation in a humanized mouse model. *J. Immunol.* 187:3895-3903.
7. Onoe, T., H. Kalscheuer, M. Chittenden, G. Zhao, Y.-G. Yang, and M. Sykes. 2010. Homeostatic expansion and phenotypic conversion of human T cells depend on peripheral interactions with APC. *J Immunol* 184:6756-6765.
8. Ueda, H., J. M. Howson, L. Esposito, J. Heward, H. Snook, G. Chamberlain, D. B. Rainbow, K. M. Hunter, A. N. Smith, G. Di Genova, M. H. Herr, I. Dahlman, F. Payne, D. Smyth, C. Lowe, R. C. Twells, S. Howlett, B. Healy, S. Nutland, H. E. Rance, V. Everett, L. J. Smink, A. C. Lam, H. J. Cordell, N. M. Walker, C. Bordin, J. Hulme, C. Motzo, F. Cucca, J. F. Hess, M. L. Metzker, J. Rogers, S. Gregory, A. Allahabadia, R. Nithiyananthan, E. Tuomilehto-Wolf, J. Tuomilehto, P. Bingley, K. M. Gillespie, D. E. Undlien, K. S. Ronningen, C. Guja, C. Ionescu-Tirgoviste, D. A. Savage, A. P. Maxwell, D. J. Carson, C. C. Patterson, J. A. Franklyn, D. G. Clayton, L. B. Peterson, L. S. Wicker, J. A. Todd, and S. C. Gough. 2003. Association of the T-cell regulatory gene CTLA4 with susceptibility to autoimmune disease. *Nature* 423: 506-511.
9. Steck, A. K., T. L. Bugawan, A. M. Valdes, L. M. Emery, A. Blair, J. M. Norris, M. J. Redondo, S. R. Babu, H. A. Erlich, G. S. Eisenbarth, and M. J. Rewers. 2005. Association of non-HLA genes with type 1 diabetes autoimmunity. *Diabetes* 54:2482-2486.
10. Svejgaard, A. 2008. The immunogenetics of multiple sclerosis. *Immunogenetics* 60:275-286.
11. Danska, J. S. and P. Poussier. 2009. After the GWAS rush: nuggets of insight into the pathogenesis of autoimmune disease. *Semin Immunol* 21:313-317.
12. Serreze, D. V., E. H. Leiter, S. M. Worthen, and L. D. Shultz. 1988. NOD marrow stem cells adoptively transfer diabetes to resistant (NOD×NON)F1 mice. *Diabetes* 37:252-255.
13. Lampeter, E. F., S. R. McCann, and H. Kolb. 1998. Transfer of diabetes type 1 by bone-marrow transplantation. *Lancet* 351:568-569.
14. Lepus, C. M., T. F. Gibson, S. A. Gerber, I. Kawikova, M. Szczepanik, J. Hossain, V. Ablamunits, N. Kirkiles-Smith, K. C. Herold, R. O. Donis, A. L. Bothwell, J. S. Pober, and M. J. Harding. 2009. Comparison of human fetal liver, umbilical cord blood, and adult blood hematopoietic stem cell engraftment in NOD-scid/gammac−/−, Balb/c-Rag1−/−gammac−/−, and C.B-17-scid/bg immunodeficient mice. *Hum Immunol* 70:790-802.
15. Jenkinson, E. J. and G. Anderson. 1994. Fetal thymic organ cultures. *Curr. Opin. Immunol.* 6:293-297.
16. Jenkinson, E. J., L. L. Franchi, R. Kingston, and J. J. Owen. 1982. Effect of deoxyguanosine on lymphopoiesis in the developing thymus rudiment in vitro: application in the production of chimeric thymus rudiments. *Eur J Immunol* 12:583-587.
17. Shultz, L. D., F. Ishikawa, and D. L. Greiner. 2007. Humanized mice in translational biomedical research. *Nat Rev Immunol* 7:118-130.
18. Cacheiro, L. H., P. L. Glover, and E. H. Perkins 1985. Restoration of immune competence with cryopreserved thymus. *Transplantation* 40:110-112.
19. Cheers, C., E. Leuchars, A. J. Davies, and V. Wallis. 1970. Restoration of thymectomized irradiated mice by frozen and stored thymus grafts. *Transplantation* 10:505-511.
20. Kukreja, A., G. Cost, J. Marker, C. Zhang, Z. Sun, K. Lin-Su, S. Ten, M. Sanz, M. Exley, B. Wilson, S. Porcelli, and N. Maclaren. 2002. Multiple immuno-regulatory defects in type-1 diabetes. *J Clin Invest* 109:131-140.
21. Davis, C. M., T. M. McLaughlin, T. J. Watson, R. H. Buckley, S. E. Schiff, L. P. Hale, B. F. Haynes, and M. L. Markert. 1997. Normalization of the peripheral blood T cell receptor V beta repertoire after cultured postnatal human thymic transplantation in DiGeorge syndrome. *J Clin Immunol* 17:167-175.
22. Arif, S., T. I. Tree, T. P. Astill, J. M. Tremble, A. J. Bishop, C. M. Dayan, B. O. Roep, and M. Peakman. 2004. Autoreactive T cell responses show proinflammatory polarization in diabetes but a regulatory phenotype in health. *J Clin Invest* 113:451-463.
23. Lindley, S., C. M. Dayan, A. Bishop, B. O. Roep, M. Peakman, and T. I. Tree. 2005. Defective Suppressor Function in CD4+CD25+ T-Cells From Patients With Type 1 Diabetes. *Diabetes* 54:92-99.
24. Brusko, T. M., C. H. Wasserfall, M. J. Clare-Salzler, D. A. Schatz, and M. A. Atkinson. 2005. Functional defects and the influence of age on the frequency of CD4+ CD25+ T-cells in type 1 diabetes. *Diabetes* 54:1407-1414.
25. Bonelli, M., A. Savitskaya, C. W. Steiner, E. Rath, J. S. Smolen, and C. Scheinecker. 2009. Phenotypic and functional analysis of CD4+CD25−FoxP3+ T cells in patients with systemic lupus erythematosis. *J Immunol* 182:1689-1695.
26. Flores-Borja, F., E. C. Jury, C. Mauri, and M. R. Ehrenstein. 2008. Defects in CTLA-4 are associated with abnormal regulatory T cell function in rheumatoid arthritis. *Proc Natl Acad Sci USA* 105:19396-19401.
27. Berzins, S. P., E. S. Venanzi, C. Benoist, and D. Mathis. 2003. T-cell compartments of prediabetic NOD mice. *Diabetes* 52:327-334.
28. Tang, Q. and J. A. Bluestone. 2006. Regulatory T-cell physiology and application to treat autoimmunity. *Immunol Rev* 212:217-237.
29. Brusko, T., C. Wasserfall, K. McGrail, R. Schatz, H. L. Viener, D. Schatz, M. Haller, J. Rockell, P. Gottlieb, M. Clare-Salzler, and M. Atkinson. 2007. No Alterations in the Frequency of FOXP3+ Regulatory T-Cells in Type 1 Diabetes. *Diabetes* 56:604-612.
30. King, C., A. Ilic, K. Koelsch, and N. Sarvetnick. 2004. Homeostatic expansion of T cells during immune insufficiency generates autoimmunity. *Cell* 117:265-277.
31. Taneja, V. and C. S. David. 2010. Role of HLA class II genes in susceptibility/resistance to inflammatory arthritis: studies with humanized mice. *Immunol Rev* 233:62-78.
32. Lang, H. L., H. Jacobsen, S. Ikemizu, C. Andersson, K. Harlos, L. Madsen, P. Hjorth, L. Sondergaard, A. Svejgaard, K. Wucherpfennig, D. I. Stuart, J. I. Bell, E. Y. Jones, and L. Fugger. 2002. A functional and structural basis for TCR cross-reactivity in multiple sclerosis. *Nat Immunol* 3:940-943.
33. Black, K. E., J. A. Murray, and C. S. David. 2002. HLA-DQ determines the response to exogenous wheat proteins: a model of gluten sensitivity in transgenic knockout mice. *J Immunol* 169:5595-5600.

34. Serreze, D. V., M. Niens, J. Kulik, and T. P. DiLorenzo. 2010. Bridging mice to men: using HLA transgenic mice to enhance the future prediction and prevention of autoimmune type 1 diabetes in humans. *Methods Mol Biol* 602:119-134.
35. King, M., T. Pearson, A. A. Rossini, L. D. Shultz, and D. L. Greiner. 2008. Humanized mice for the study of type 1 diabetes and beta cell function. *Ann N Y. Acad Sci* 1150:46-53.
36. Gregersen, J. W., S. Holmes, and L. Fugger. 2004. Humanized animal models for autoimmune diseases. *Tissue Antigens* 63:383-394.
37. Wen, L., N. Y. Chen, J. Tang, R. Sherwin, and F. S. Wong. 2001. The regulatory role of DR4 in a spontaneous diabetes DQ8 transgenic model. *J Clin Invest* 107:871-880.
38. Brainard, D. M., E. Seung, N. Frahm, A. Cariappa, C. C. Bailey, W. K. Hart, H. S. Shin, S. F. Brooks, H. L. Knight, Q. Eichbaum, Y. G. Yang, M. Sykes, B. D. Walker, G. J. Freeman, S. Pillai, S. V. Westmoreland, C. Brander, A. D. Luster, and A. M. Tager. 2009. Induction of robust cellular and humoral virus-specific adaptive immune responses in human immunodeficiency virus-infected humanized BLT mice. *J. Virol.* 83:7305-7321.
39. Nikolic, B., J. P. Gardner, D. T. Scadden, J. S. Arm, D. H. Sachs, and M. Sykes. 1999. Normal development in porcine thymus grafts and specific tolerance of human T cells to porcine donor MHC. *J. Immunol.* 162:3402-3407.
40. Nizet, Y., A. A. Chentoufi, B. De La Parra, P. Lewalle, R. Rouas, A. Cornet, T. Besse, M. Mourad, J. Malaise, J.-P. Squifflet, H. Bazin, and D. Latinne. 2000. The experimental (in vitro) and clinical (in vivo) immunosuppressive effects of a rat IgG2b anti-human CD2 mAb, LO-CD2a/BTI-322. *Transplantation* 69:1420-1428.
41. Kraus, A. B., J. Shaffer, H. C. Toh, F. Preffer, D. Dombkowski, S. Saidman, C. Colby, R. George, S. MCafee, R. Sackstein, B. Dey, T. R. Spitzer, and M. Sykes. 2003. Early host CD8 T-cell recovery and sensitized anti-donor IL-2-producing and cytolytic T-cell responses associated with marrow graft rejection following nonmyeloablative bone marrow transplantation. *Exp. Hematol.* 31:609-621.
42. Wu, H. D., M. S. Maurer, R. A. Friedman, C. C. Marboe, E. M. Ruiz-Vazquez, R. Ramakrishnan, A. Schwartz, M. D. Tilson, A. S. Stewart, and R. Winchester. 2007. The lymphocytic infiltration in calcific aortic stenosis predominantly consists of clonally expanded T cells. *J. Immunol.* 178:5329-5339.

Example 14

The mouse genome contains endogenous retroviruses that can infect human cells. These include xenotropic murine leukemia virus (X-MLV) and polytropic murine leukemia viruses (P-MLV).

In one aspect, the invention provides for the development of a genetically modified mouse for use in the invention, in which these murine leukemia viruses are made incapable of infecting human cells. This can be achieved by methods known in the art, including but not limited to: introducing a transgene encoding small inhibitory RNAs that target critical envelope proteins required to infect human cells; introducing a transgene encoding a neutralizing antibody that targets critical envelope proteins required to infect human cells. In other non-limiting embodiments, the human CD34 cells used to generate the Mini Me mice can be transduced with a small inhibitory RNA (along with a marker gene allowing physical selection of transduced cells) to knock down the expression of receptors for X-MLV and P-MLV.

In other embodiments, these murine leukemia viruses are made incapable of infecting human cells, by using a mouse transgenic for a human Apolipoprotein B mRNA editing enzyme, for example but not limited to APOBEC3 gene family, such as, but not limited to, APOBEC3A, APOBEC3B, APOBEC3C, APOBEC3DE, APOBEC3F, APOBEC3G or APOBEC3H. See Conticello, 2008, The AID/APOBEC family of nnucleic acid mutators, *Genome Biol.*, 9:229.1-229.10, the content of which are hereby incorporated by reference in its entirety.

Without being bound by theory, the insertion of an APOBEC3 gene into the mouse genome can impede the ability of endogenous retroviruses, such as X-MLV and P-MLV, to infect human cells. The nucleic acid sequences and amino acid sequences of the APOBEC3 genes are well known in the art. Methods to develop a transgenic mouse are well known to one of skill in the art.

Example 15—Cancer Immunotherapy with Effector T Cells Generated in Humanized Mice Without being bound by theory, adoptive transfer of TCR-engineered cytotoxic T cells (CTLs) is a useful immunotherapy for cancers[1,1]. However, a limitations are difficulties in obtaining sufficient numbers of highly-effective CTLs and alteration of the antigen-specificity of the generated CTLs due to mispairing between endogenous and introduced TCR subunits.

In this example, humanized mice have the potential to produce a large quantity of cancer-specific CTLs expressing only the engineered tumor-specific TCR. Humanized mice, made by transplantation of human thymic tissue and CD34+ cells virally-transduced with HLA class I-restricted melanoma antigen (MART-1)-specific TCR gene, showed efficient MART-1-TCR+ human T cell development. MART-1-TCR+ cells were predominantly CD8+, but CD4+ cells were also detected. Only MART-1-TCR+CD8+ T cells showed specific responses following MART-1 peptide immunization. MART-1-TCR+CD8+ cells from these humanized mice mediated specific killing of melanoma cells, and fully retained their cytotoxicity after substantial in vitro expansion (up to tens of thousands of times). Adoptive transfer of in vitro expanded MART-1-TCR+CD8+ cells induced potent antitumor responses which were further enhanced by IL-15 treatment in melanoma-bearing recipients. Without being bound by theory, humanized mice generate human T cells for cancer immunotherapy.

Tumor associated antigens (TAA) are the antigens selectively expressed on tumor cells and provide potential targets for cancer immunotherapy. Infusion of in vitro expanded autologous tumor-infiltrating lymphocytes (TILs) following lymphodepletion was reported to achieve an objective response in over half of the patients with metastatic melanoma[6,7]. However, this therapy requires TILs with high-avidity T-cell receptors (TCRs) for tumor antigens, which are not available for most cancer patients. This issue has been resolved by genetic engineering of T cells with TAA-specific TCR genes[8-12]. Without being bound by theory, the misparing of endogenous TCR subunits with introduced TCR chains in the genetically-manipulated T cells, can alter TCR specificity leading to not only the loss of antitumor responses, but also to the formation of autoreactive T cells[3-5]. It has been shown first in mice[13,14], and more recently in humans (using humanized mice)[15] that T cells expressing only the transgenic TCR can be efficiently generated by introducing TCR genes into hematopoietic stem cells (HSCs). Without being bound by theory, the development of leukemias in patients following transplantation of virally-transduced HSCs[16,17] may not be without risk in using TCR gene-transduced HSCs in cancer immunotherapy.

It has previously been shown that cotransplantation of human fetal thymus tissue (FTHY; under kidney capsule) and CD34+ fetal liver cells (FLCs; i.v.) in immunodeficient mice leads to the development of human lymphohematopoietic cells including T, B and dendritic cells, and the formation of secondary lymphoid organs consisting of human lymphohematopoietic cells[18-20]. Here, use of a humanized mouse (hu-mouse) model to generate melanoma-specific human T cells for therapeutic use was investigated.

Figure 71:
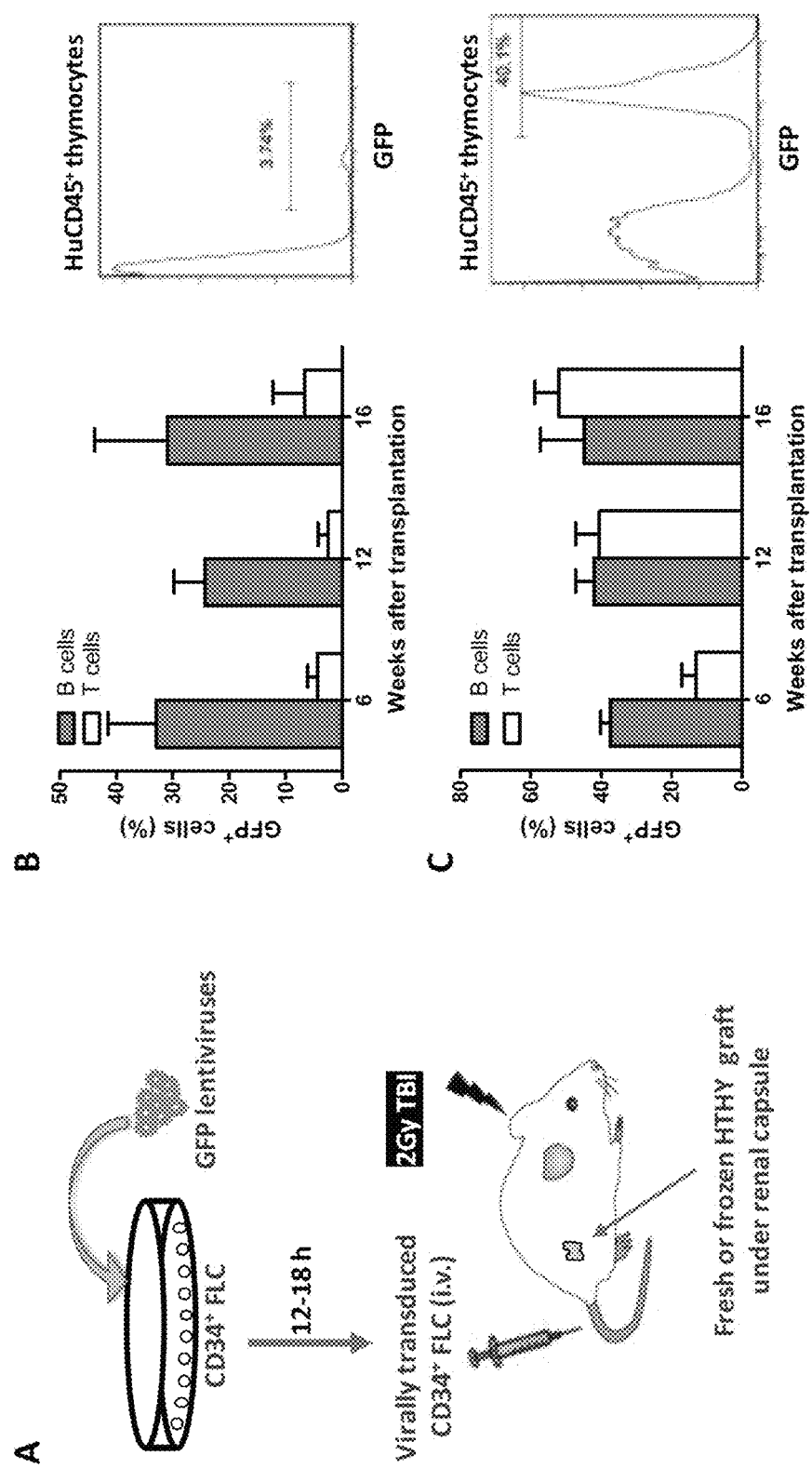

A lentiviral vector encoding HLA-A*0201-restricted TCR (DMFS clone)[12] specific for melanoma-associated antigen recognized by T cells (MART-1) was used to engineer CD34+ FLCs. The hu-mice were made by intravenous injection of TCR-engineered HLA-A*0201+ CD34+ FLCs into NOD.Cg-Prkdcscid Il2rgtm1Wjl/SzJ (NSG) mice grafted with cryopreserved-thawed autologous FTHY (FIG. 70). The purpose of using cryopreserved-thawed FTHY is to improve T cell development from virally-transduced CD34+ cells by eliminating preexisting T cell progenitors in the FTHY graft (FIG. 71).

Figure 73:
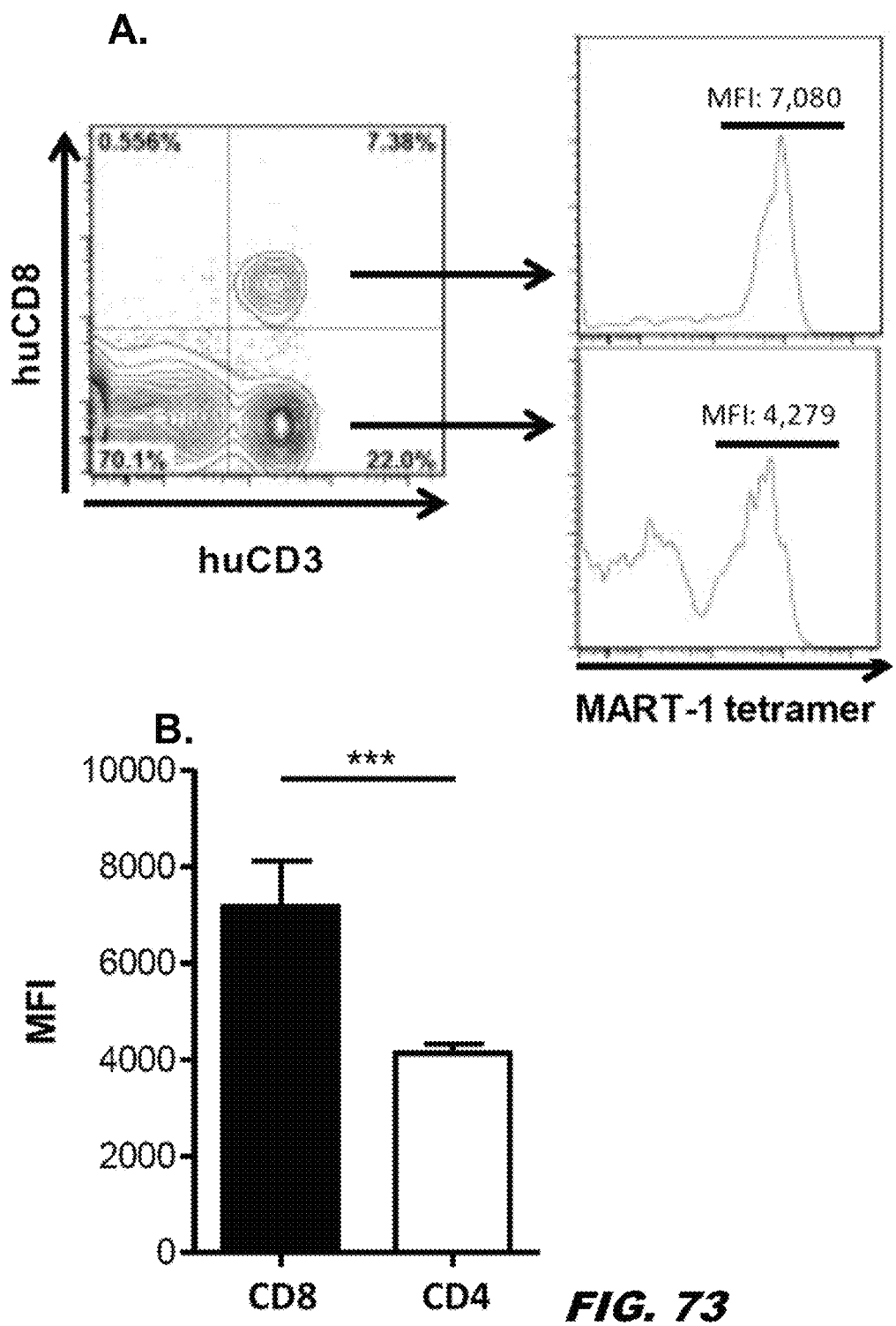

Hu-mice showed high levels of human T and B cell reconstitution (FIG. 72) and among human CD3+ T cells, a significant proportion was found to express MART-1-specific TCR, as identified by HLA-A2/MART-1 tetramer staining (FIG. 66a). The majority of tetramer+ T cells had a naïve phenotype as shown by expression of CD45RA and CCR7 (FIG. 66b). In concordance with the role of CD8 in recognition of MHC class I-restricted antigens, CD8 T cells consisted of a large number of tetramer+ cells, and the percentage of CD8+ T cells in CD3+tetramer+ cells was significantly higher than found in CD3+tetramer− T cells (FIG. 66c,d). Furthermore, most CD8 single positive (SP) and CD4+CD8+ double positive (DP) thymocytes expressed MART-1 TCR (FIG. 66e). Although the frequency was lower, peripheral human CD4 T cells and CD4SP thymocytes also contained a significant proportion of tetramer+ cells (with relatively lower levels of MART-1-TCR expression; FIG. 73) in almost all mice examined (FIG. 66c,d,e). Similar to our results, CD4+ TILs recognizing a MHC class I-restricted tumor antigen have previously been detected in a patient with metastatic melanoma[21].

Figure 67A:
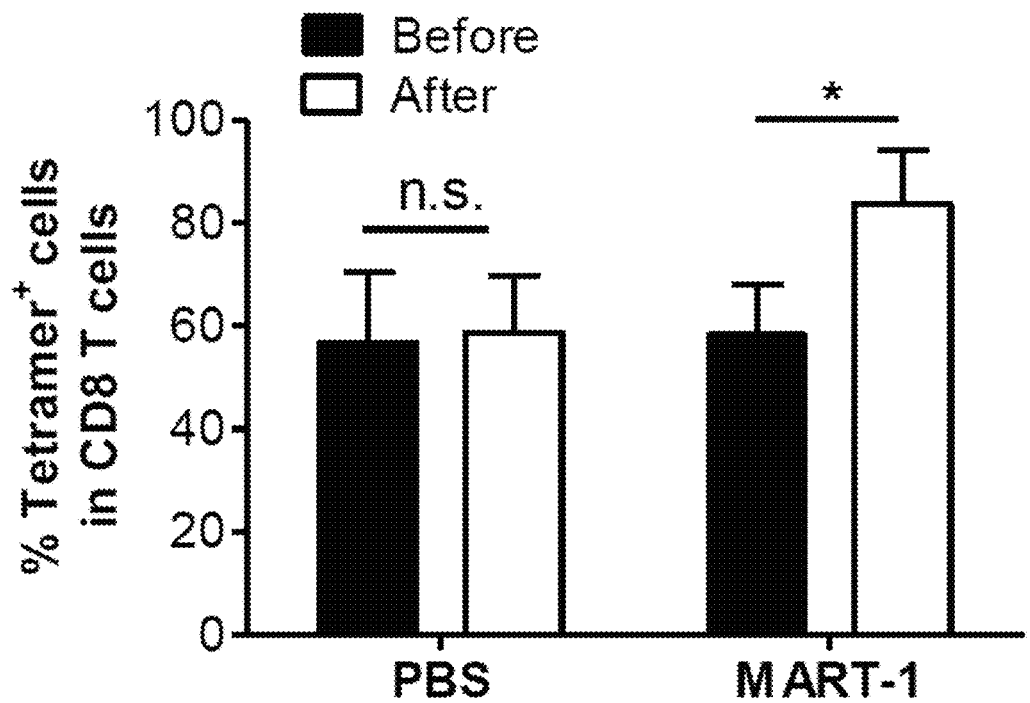
Figure 67B:
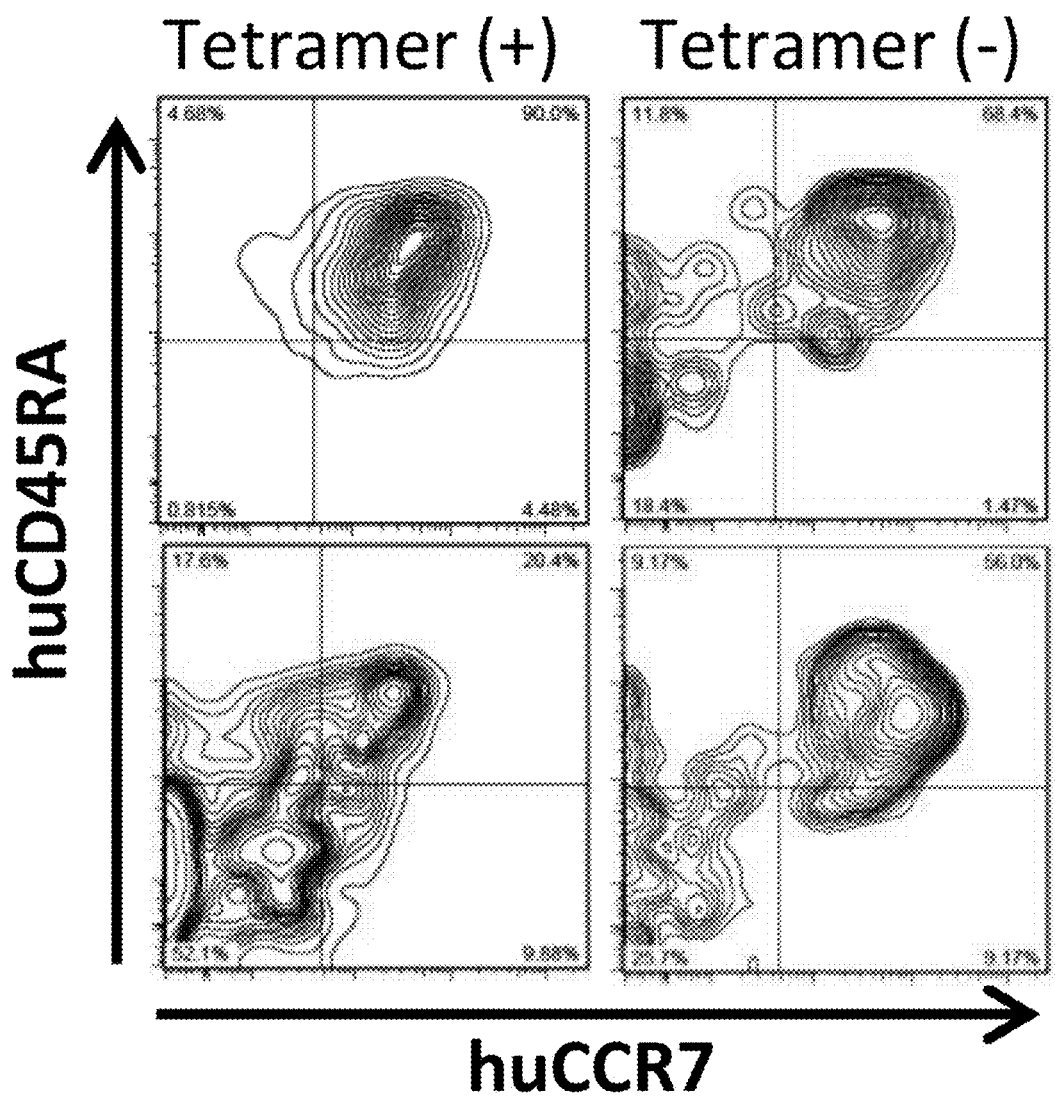
Figure 67C:
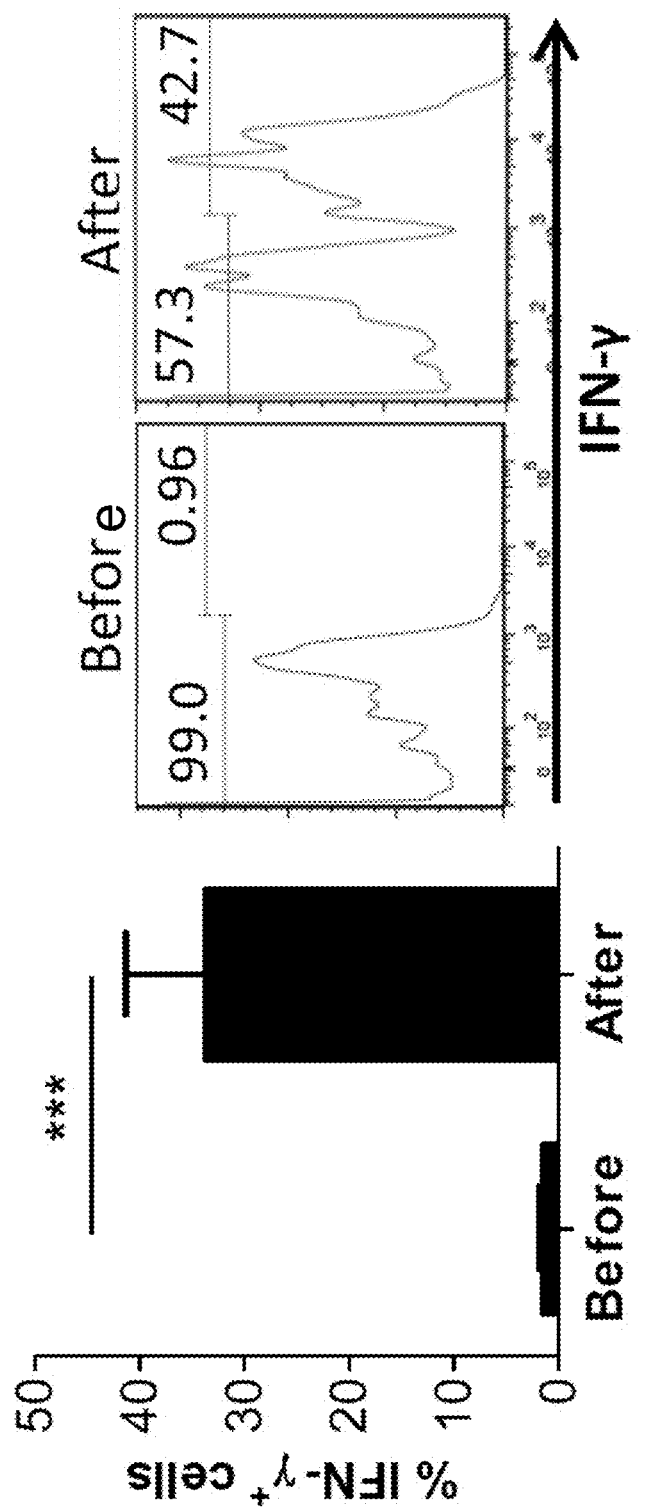
Figure 67D:
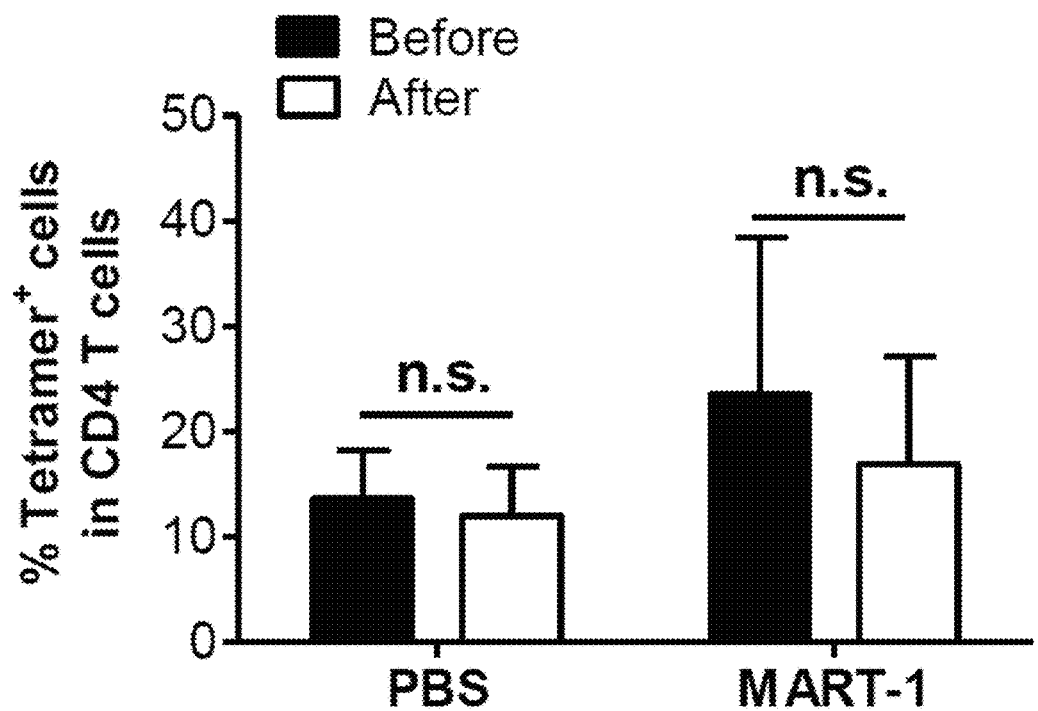
Figure 67E:
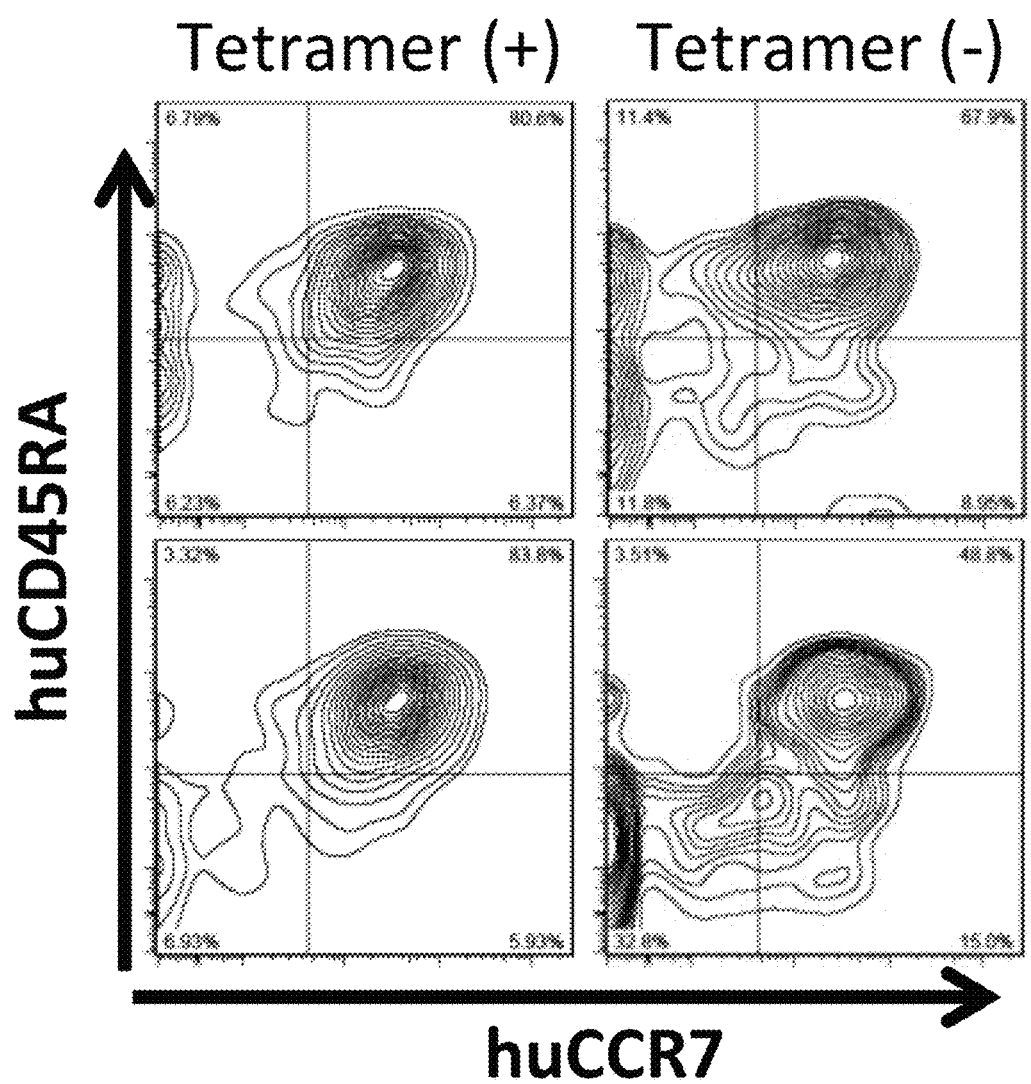
Figure 67F:
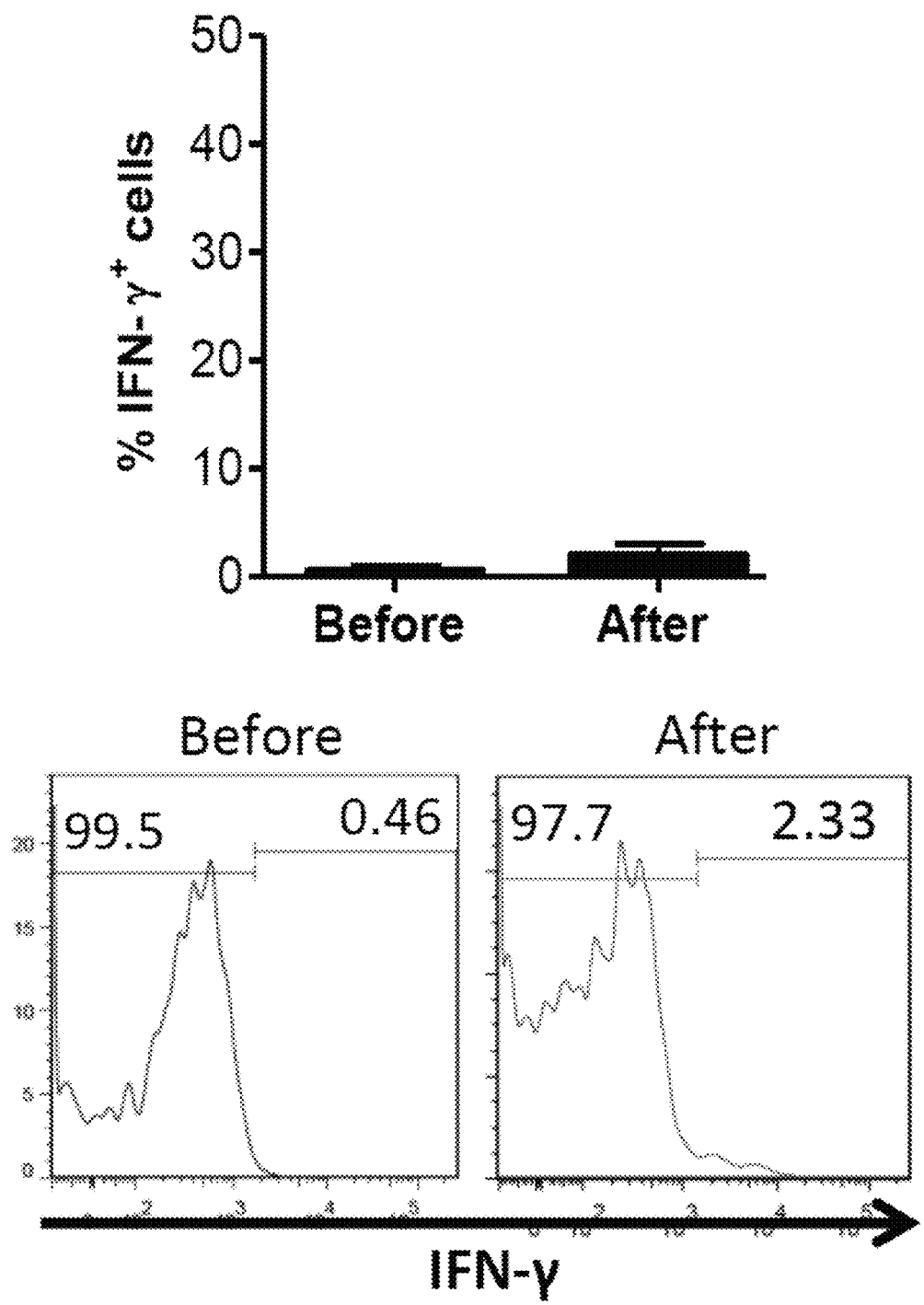

Next, it was questioned if the tetramer+ T cells generated in hu-mice were functional. The hu-mice were immunized with MART-1 peptides emulsified by complete Freud's adjuvant and were measured the immune response 3 weeks later. Tetramer+ CD8 T cells showed a MART-1-specific response following immunization, as shown by antigen-specific expansion (FIG. 67a), conversion from a naïve to effector/memory phenotype (i.e., losing CCR7 and CD45RA expression; FIG. 67b), and IFN-γ production (FIG. 67c). However, unlike CD8 T cells, neither tetramer+ nor tetramer− CD4 cells showed expansion (FIG. 67d), conversion to an effector/memory phenotype (FIG. 67e) or IFN-γ production (FIG. 67f) following MART-1 peptide immunization. These data indicate that tetramer+ CD8, but CD4, T cells could mount MART-1-specific responses following peptide immunization.

The killing of melanoma cells by tetramer+ T cells isolated from hu-mice was then measured. Tetramer+ human T cells purified from MART-1-immunized mice were stimulated for 5 days with anti-huCD3/CD28 microbeads, and their cytotoxicity against melanoma cells was assessed. As shown in FIG. 68a, tetramer+ T cells mediated significant killing of HLA-A2+MART-1+ (Mel 624), but not HLA-A2− MART-1+ (Mel 888) or HLA-A2+MART-1− (Mel A375) melanoma cells. These results demonstrate an efficient HLA-A2-restricted, MART-1-specific cytotoxic activity of tetramer+ T cells developed in the hu-mice.

The data presented above demonstrated the feasibility of generating functional tumor antigen-specific human T cells via genetic manipulation of CD34+ cells in hu-mice. However, an important requirement for using hu-mice developed tetramer+ T cells in the clinic is the ability to expand these T cells in vitro without losing antitumor activity. Tetramer+ human T cells were prepared from the hu-mice and expanded for 4-7 weeks in media containing anti-huCD3 (OTK3), rhIL-2 and feeder cells (FIG. 68b). CD8+ and CD4+ T cells were sorted from the expanded tetramer+ T cells and evaluated for antitumor activity. Tetramer+ CD8 T cells mediated efficient killing of HLA-A2+MART-1+ (Mel 624), but not HLA-A2−MART-1+ (Mel 888) melanoma cells (FIG. 68c, left panel). Furthermore, IFN-γ secretion was detected in tetramer+ CD8 T cells co-cultured with HLA-A2+MART-1+ (Mel 624) cells, but not in those co-cultured with HLA-A2− MART-1+ (Mel 888) cells (FIG. 68c, right panel). Although tetramer+ CD4 T cells were also capable of mediating specific cytotoxicity and producing IFN-γ when co-cultured with Mel 624 cells, the efficacy was significantly lower than that of tetramer+ CD8 T cells (FIG. 68d). This observation is consistent with a previous report that T cells transduced with high affinity MART-1-specific TCR gene can recognize antigen peptide/HLA-I and mediate antigen-specific cytotoxicity in a CD8-independent fashion[24]. These data, however, indicate that such CD8-independent activation of T cells expressing class I-restricted TCR can only occur in cultures with a high concentration of antigens added. Furthermore, since tetramer+ CD4 T cells showed significant proliferation after in vitro stimulation with MART-1 peptides (FIG. 74), the poor cytotoxicity by tetramer+ CD4 T cells could be due to their intrinsic properties, as CD4 T cells may have less efficient cytotoxic machineries[25].

In vitro-expanded tetramer+ CD8 T cells to mediate antitumor responses in melanoma-bearing mice was further evaluated. Tetramer+ CD8 T cells were sorted from hu-mouse splenocytes and expanded in vitro for approximately 30 days (FIG. 69a, left panel). At the end of expansion, the majority of expanded cells were tetramer+ CD8 T cells with a effector/memory (i.e., CCR7−CD45RA−) phenotype (FIG. 69a, middle panel), capable of mediating efficient killing of HLA-A2+MART-1+ (Mel 624) melanoma cells (FIG. 69a, right panel). To simulate the clinical trials, expanded tetramer+ CD8 T cells were adoptively transferred (i.v.) into NSG mice that were subcutaneously inoculated with melanoma cells. Tumor growth was significantly inhibited in mice receiving in vitro expanded tetramer+ CD8 T cells compared to controls (FIG. 69b, left panel). Flow cytometric analysis revealed that most TILs were tetramer+ CD8 T cells with a CD45RA−CCR7− effector/memory phenotype (FIG. 69b, right panel). Adoptive transfer of in vitro expanded tetramer+ CD8 T cells also significantly prolonged the survival of mice with metastatic melanoma (FIG. 69c). These data indicate that in vitro-expanded tetramer+ CD8 T cells can migrate to the tumor site and kill tumor cells.

IL-15 is an immune regulatory cytokine with broad activities that include inducing differentiation and proliferation of T, B and NK cells, enhancing the cytolytic activity of CD8 T cells and contributing to long term survival of memory T cells[26]. Studies in mice demonstrated that IL-15 improves the survival and antitumor immunity of adoptively transferred tumor reactive CD8 T cells[27,28]. However, the effect of IL-15 on the survival and antitumor activity of human tumor-specific CD8 T cells remains poorly understood, primarily due to the lack of an appropriate in vivo model system. To address this question, the survival and antitumor responses of in vitro-expanded tetramer+ CD8 T cells were compared in melanoma-bearing mice with or without human IL-15. IL-15 significantly improved both the survival (FIG. 69d) and antitumor activity (FIG. 69e) of tetramer+ T cells in mice with metastatic melanoma. Because treatment with IL-15 alone did not show detectable antitumor activity, this indicates that the enhancement of antitumor effects by IL-15 was mediated by the adoptively transferred tetramer+ T cells.

These findings indicate that hu-mice not only provide an excellent in vivo model system for translational and preclinical research, but also a means for producing therapeutic effector T cells. The recent development of "personalized immune" mice demonstrates the feasibility of making hu-mice using bedside aspirates of adult bone marrow[29]. Such "personalized immune" hu-mice make it possible to produce autologous human T cells for individualized immunotherapies in cancer patients. Since approximately $10^6$ cells of tetramer+ human T cells can be collected from one hu-mouse and the fact that these cells can be further expanded in vitro for tens of thousands of times (FIG. 69a), this indicates that the use of hu-mice to generate tumor-specific T cells for patient use is a practical option.

Methods

Animals and Human Tissues and Cells.

NOD.Cg-Prkdc$^{scid}$Il2rg$^{tm1Wjl}$/SzJ (NOD/SCID/γc$^{-/-}$ or NSG) mice were purchased from the Jackson Laboratory (Bar Harbor, Me.), housed in a specific pathogen-free microisolator environment and used in experiments at 6 to 8 weeks of age. Human fetal thymus and liver tissues of gestational age of 17 to 20 weeks were obtained from Advanced Bioscience Resource (Alameda, Calif.).

Humanized Mouse Preparation.

NSG mice were conditioned with sublethal (2 Gy) total body irradiation, and received human lentiviral vector transduced CD34+ fetal liver cells FLCs ($2\times10^5$/mouse, i.v.) with a fresh or cryopreservation treated human fetal thymic tissue fragment measuring about 1 mm$^3$ (under the recipient kidney capsule) from the same fetal donor, as previously described[P1,P2]. CD34+ FLCs were isolated by a magnetic-activated cell sorter (MACS) separation system using anti-CD34 microbeads (Miltenyi Biotech, Aubum, Calif.). Levels of human hematopoietic cells in humanized mice were determined by flow cytometric (FCM) analysis using various combinations of the following mAbs: anti-human CD45, CD19, CD3, CD4, CD8, CD45RA, CCR7; anti-mouse CD45 and Ter119; and isotype control mAbs (All antibodies were purchased from BD PharMingen, San Diego, Calif.). MART-1-TCR+ T cells were identified by HLA-A*0201/MART-1 (ELAGIGILTV) Tetramter (Beckman Coulter Immunotech). Mononuclear cells were prepared using density gradient centrifugation with Histopaque 1077 (Sigma-Aldrich, St. Louis, Mo.). Analysis was performed on a FACSCanto or LSR II (Becton Dickinson, Mountain View, Calif.). Dead cells were excluded from the analysis by gating out lower forward scatter and high propidium iodide-retaining cells.

Lentiviral Vector Production.

Pseudotyped lentiviral vectors were produced by transfection using Lipofectamine 2000 (Invitrogen, San Diego, Calif.) of 293FT cells in 10-cm plates. A 3-plasmid system consisting of pLVTHM (10 μg), psPAX2 (7.5 μg) and pMD2G (3 μg) was used for GFP-lentivirus production; a 4-plasmid system consisting of the transfer vector (MART-1 antigen specific TCR, DMFS clone; 10 μg) and 3 packaging plasmids (VSV-G 3.6 μg, pMDLg/pRRE 6.7 μg, and pRSV-Rev 6.7 μg) was used for MART-1 TCR-lentivirus production. The supernatant was collected 48 hour post-transfection and concentrated by ultracentrifugation at 50,000 g for 2 hours. Lentiviruses were stored at −80° C. until use.

Transduction of Human CD34+ FLCs by Lentiviral Vectors.

Human CD34+ FLCs were stimulated overnight in media containing 50 ng/mL rhSCF (R&D, Minneapolis, Minn.), 50 ng/mL Flt-3-1 (ebioscience, San Diego, Calif.), 25 ng/mL TPO (R&D, Minneapolis, Minn.), 10 ng/mL IL-3 (R&D, Minneapolis, Minn.), in a 24-well plate pre-coated with retronectin (Takara Bio Inc), followed by transduction with lentiviral vectors for 12 hours. Cells were washed twice and intravenously injected into sub-lethal irradiated mice as described above.

MART-1 Peptide Immunization.

MART-1 peptides (ELAGIGILTV, Biosynthesis Inc, Lewisville, Tex.) were emulsified with Freud's Complete Adjuvant (CFA) with 1:1 ratio and subcutaneously injected into humanized mice. Immunized mice were analyzed for MART-1-specific responses 3 weeks after immunization.

Proliferation Assay.

Spleen cells were cultured in 96-well plates ($1\times10^6$ cells per well) with or without MART-1 peptides (25 μg/mL). Three days later, MART-1 tetramer+ T cell proliferation was determined by Ki67 expression using flow cytometry.

CTL Assay.

Purified MART-1 tetramer+ human T cells were co-incubated with $^{51}$Cr-labeled melanoma cells at the indicated effector:target (E:T) ratios in 96-well plates at 37° C. for 4-6 hours. Lysis of tumor cells was measured by $^{51}$Cr release in the supernatant counted using a Perkin Elmer 1450 microbeta liquid scintillation & luminescence counter. Specific lysis (%) of target cells was calculated as: =[(experimental release (cpm)−spontaneous release (cpm)]/[(maximum release (cpm)−spontaneous release (cpm)]×100%.

In Vitro Expansion of MART-1 Antigen Specific T Cells from Humanized Mice.

MART-1 tetramer+ T cells were purified from lymphoid organs of humanized mice by cell sorting using an Influx cell sorter (BD Biosciences) and expanded in vitro using a previously described protocol with some modification[P3,P4]. Briefly, purified T cells were stimulated with pooled allogeneic PBMCs ($1.5\times10^7$/mL, 35 Gy irradiated) and Epstein-Barr virus-transformed lymphoblastoid cell lines (EBV-LCL, $4.3\times10^5$/mL, 60 Gy irradiated), 30 ng/mL anti-huCD3 (OKT3), and 100 U/mL recombinant human IL-2 (rhIL-2) in RMPI 1640 medium supplemented with 10% human AB serum. One third of the culture supernatant was replaced with fresh media containing 300 U/mL rhIL-2 every 2-3 days. The cells were restimulated with anti-human CD3 and freshly irradiated feeder cells (i.e., allogeneic PBMCs and EBV-LCL) every 2 weeks.

Assessment of Antitumor Effects of In Vitro-Expanded MART-1 TCR+ T Cells in Melanomabearing Mice.

Expanded CD8 MART-1 TCR+ T cells were adoptively transferred (i.v.) into NSG mice that were inoculated with Mel 624 cells (s.c. or i.v.) on the same day, and the antitumor effect was evaluated by measuring tumor mass or recipient survival time in mice receiving s.c. and i.v. injection of melanoma cells, respectively. Tumor mass was measured using fine calipers (Marathon, Richmond Hill, Canada) and calculated by the product of the two largest perpendicular diameters a×b (mm$^2$), as previously described[P5]. To assess the effect of IL-15 on antitumor responses, some recipient mice were given hydrodynamic injection (50 μg/2 mL/mouse via tail vein) of plasmid containing rhIL-15 gene one day prior to injection of melanoma cells, as previously described[P6].

Statistical Analysis.

The level of significant differences in group means was determined by the student's t test for parametric data sets. All statistical analysis was performed using Prism 4 (GraphPad Software, San Diego, Calif.). A P value of ≤0.05 was considered significant in all analyses herein.

REFERENCES

1. Leen, A. M., Rooney, C. M. & Foster, A. E. Improving T cell therapy for cancer. *Annu. Rev. Immunol.* 25, 243-265 (2007).
2. Rosenberg, S. A., Restifo, N. P., Yang, J. C., Morgan, R. A. & Dudley, M. E. Adoptive cell transfer: a clinical path to effective cancer immunotherapy. *Nat. Rev. Cancer* 8, 299-308 (2008).
3. Cohen, C. J., Zhao, Y., Zheng, Z., Rosenberg, S. A. & Morgan, R. A. Enhanced antitumor activity of murine-human hybrid T-cell receptor (TCR) in human lymphocytes is associated with improved pairing and TCR/CD3 stability. *Cancer research* 66, 8878-8886 (2006).
4. Kuball, J., et al. Facilitating matched pairing and expression of TCR chains introduced into human T cells. *Blood* 109, 2331-2338 (2007).
5. Bendle, G. M., et al. Lethal graft-versus-host disease in mouse models of T cell receptor gene therapy. *Nat Med* 16, 565-570, 561p following 570 (2010).
6. Dudley, M. E., et al. Adoptive cell transfer therapy following non-myeloablative but lymphodepleting chemotherapy for the treatment of patients with refractory metastatic melanoma. *J. Clin. Oncol.* 23, 2346-2357 (2005).
7. Dudley, M. E., et al. Cancer regression and autoimmunity in patients after clonal repopulation with antitumor lymphocytes. *Science* 298, 850-854 (2002).
8. Morgan, R. A., et al. High efficiency TCR gene transfer into primary human lymphocytes affords avid recognition of melanoma tumor antigen glycoprotein 100 and does not alter the recognition of autologous melanoma antigens. *J Immunol* 171, 3287-3295 (2003).
9. Zhao, Y., et al. Primary human lymphocytes transduced with NY-ESO-1 antigen-specific TCR genes recognize and kill diverse human tumor cell lines. *J Immunol* 174, 4415-4423 (2005).
10. Hughes, M. S., et al. Transfer of a TCR gene derived from a patient with a marked antitumor response conveys highly active T-cell effector functions. *Human gene therapy* 16, 457-472 (2005).
11. Morgan, R. A., et al. Cancer regression in patients after transfer of genetically engineered lymphocytes. *Science* 314, 126-129 (2006).
12. Johnson, L. A., et al. Gene therapy with human and mouse T-cell receptors mediates cancer regression and targets normal tissues expressing cognate antigen. *Blood* 114, 535-546 (2009).
13. Yang, L., Qin, X. F., Baltimore, D. & Van Parijs, L. Generation of functional antigen-specific T cells in defined genetic backgrounds by retrovirus-mediated expression of TCR cDNAs in hematopoietic precursor cells. *Proceedings of the National Academy of Sciences of the United States of America* 99, 6204-6209 (2002).
14. Yang, L. & Baltimore, D. Long-term in vivo provision of antigen-specific T cell immunity by programming hematopoietic stem cells. *Proceedings of the National Academy of Sciences of the United States of America* 102, 4518-4523 (2005).
15. Vatakis, D. N., et al. Antitumor activity from antigen-specific CD8 T cells generated in vivo from genetically engineered human hematopoietic stem cells. *Proceedings of the National Academy of Sciences* 108, E1408-E1416 (2011).
16. Hacein-Bey-Abina, S., et al. A serious adverse event after successful gene therapy for X-linked severe combined immunodeficiency. *The New England journal of medicine* 348, 255-256 (2003).
17. Hacein-Bey-Abina, S., et al. LMO2-Associated Clonal T Cell Proliferation in Two Patients after Gene Therapy for SCID-X1. *Science* 302, 415-419 (2003).
18. Lan, P., Tonomura, N., Shimizu, A., Wang, S. & Yang, Y. G. Reconstitution of a functional human immune system in immunodeficient mice through combined human fetal thymus/liver and CD34+ cell transplantation. *Blood* 108, 487-492 (2006).
19. Lan, P., et al. Induction of human T-cell tolerance to porcine xenoantigens through mixed hematopoietic chimerism. *Blood* 103, 3964-3969 (2004).
20. Tonomura, N., Habiro, K., Shimizu, A., Sykes, M. & Yang, Y. G. Antigen-specific human T-cell responses and T cell-dependent production of human antibodies in a humanized mouse model. *Blood* 111, 4293-4296 (2008).
21. Nishimura, M. I., et al. MHC Class I-restricted Recognition of a Melanoma Antigen by a Human CD4+ Tumor Infiltrating Lymphocyte. *Cancer Research* 59, 6230-6238 (1999).
22. Dixit, V. D. Thymic fatness and approaches to enhance thymopoietic fitness in aging. *Current Opinion in Immunology* 22, 521-528 (2010).
23. Li, Z., et al. Murine Leukemia Induced by Retroviral Gene Marking. *Science* 296, 497 (2002).
24. Johnson, L. A., et al. Gene transfer of tumor-reactive TCR confers both high avidity and tumor reactivity to nonreactive peripheral blood mononuclear cells and tumor-infiltrating lymphocytes. *J. Immunol.* 177, 6548-6559 (2006).
25. Marshall, N. B. & Swain, S. L. Cytotoxic CD4 T cells in antiviral immunity. *Journal of biomedicine & biotechnology* 2011, 954602 (2011).
26. Steel, J. C., Waldmann, T. A. & Morris, J. C. Interleukin-15 biology and its therapeutic implications in cancer. *Trends in Pharmacological Sciences* 33, 35-41 (2012).
27. Melchionda, F., et al. Adjuvant IL-7 or IL-15 overcomes immunodominance and improves survival of the CD8+ memory cell pool. *The Journal of Clinical Investigation* 115, 1177-1187 (2005).
28. Klebanoff, C. A., et al. IL-15 enhances the in vivo antitumor activity of tumor-reactive CD8+ T Cells. *Proceedings of the National Academy of Sciences of the United States of America* 101, 1969-1974 (2004).
29. Kalscheuer, H., et al. A model for personalized in vivo analysis of human immune responsiveness. *Science Translational Medicine* 4, 125ra130 (2012).
P1. Lan, P., Tonomura, N., Shimizu, A., Wang, S. & Yang, Y. G. Reconstitution of a functional human immune system in immunodeficient mice through combined human fetal thymus/liver and CD34+ cell transplantation. *Blood* 108, 487-492 (2006).

P2. Tonomura, N., Habiro, K., Shimizu, A., Sykes, M. & Yang, Y. G. Antigen-specific human T-cell responses and T cell-dependent production of human antibodies in a humanized mouse model. *Blood* 111, 4293-4296 (2008).

P3. Dudley, M. E., et al. Cancer regression and autoimmunity in patients after clonal repopulation with antitumor lymphocytes. *Science* 298, 850-854 (2002).

P4. Riddell, S. R. & Greenberg, P. D. The use of anti-CD3 and anti-CD28 monoclonal antibodies to clone and expand human antigen-specific T cells. *J. Immunol. Methods* 128, 189-201 (1990).

P5. Yang, L. & Baltimore, D. Long-term in vivo provision of antigen-specific T cell immunity by programming hematopoietic stem cells. *Proceedings of the National Academy of Sciences of the United States of America* 102, 4518-4523 (2005).

P6. Chen, Q., Khoury, M. & Chen, J. Expression of human cytokines dramatically improves reconstitution of specific human-blood lineage cells in humanized mice. *Proceedings of the National Academy of Sciences* 106, 21783-21788 (2009).

What is claimed is:

1. A non-human animal comprising:
    (a) human fetal thymus tissue transplanted under a kidney capsule of the animal, wherein the human fetal thymus tissue is substantially depleted of T-cells by cryopreservation and thawing before transplantation, and
    (b) human adult-bone-marrow-donor CD34+ cells administered by intravenous injection to the animal,
    wherein the human fetal thymus tissue and the CD34+ cells share HLA alleles, wherein the human fetal thymus tissue and the CD34+ cells are allogeneic, and wherein the non-human animal is immunodeficient prior to transplantation of the human fetal thymus tissue and the human adult-bone-marrow-donor CD34+ cells.

2. A non-human animal made by a method comprising the steps of:
    (a) transplanting human fetal thymus tissue into an immunodeficient animal, wherein the human fetal thymus tissue is substantially depleted of T cells by cryopreservation and thawing before transplantation, and
    (b) administering by intravenous injection human adult-bone-marrow-donor CD34+ cells to the animal, wherein the human fetal thymus tissue and the CD34+ cells share HLA alleles, and wherein the human fetal thymus tissue and the CD34+ cells are allogeneic.

3. The non-human animal of claim 1 or 2, wherein the animal is a mouse, a rat, or a pig.

4. The non-human animal of claim 1 or 2, wherein the animal is a NOD/SCID, NOG or NSG mouse.

5. The on-human animal of claim 1 or 2, wherein the animal exhibits a rejuvenated T-cell phenotype, which is characterized by the presence of naïve CD45RA+CD45RO−CD62L+CCR7+ cells.

6. The non-human animal of claim 1 or 2, wherein the animal exhibits peripheral multilineage cell reconstitution.

7. The non-human animal of claim 1 or 2, wherein the adult-bone-marrow-donor CD34+ cells are from a human donor suffering from Type I Diabetes.

8. The non-human animal of claim 1 or 2, wherein the animal is optionally treated with anti-CD2 mAb.

9. The non-human animal of claim 1 or 2, further comprising allograft-donor CD34+ cells or hematopoetic call transplant (HCT) recipient CD34+ cells, wherein the allograft-donor CD34+ cells and HCT recipient CD34+ cells share HLA alleles with the fetal thymus tissue and the adult-bone-marrow-donor CD34+ cells, so as to generate in the recipient animal T cells which are mutually tolerant of one another so as to generate T-cells in the animal, which T-cells are tolerant of both the adult-bone-marrow-donor and the allograft-donor or HCT recipient.

10. A method to make non-human animal that carries out thymopoiesis comprising:
    (a) transplanting human fetal thymus time into an immunodeficient animal, wherein the human fetal thymus tissue is substantially depleted of T cells by cryopreservation and thawing before transplantation, and
    (b) administering by intravenous injection human adult-marrow-donor CD34+ cells to the animal, wherein the human fetal thymus tissue and the CD34+ cells share HLA alleles, and wherein the human fetal thymus tissue and the CD34+ cells are allogeneic.

11. The method of claim 10, wherein the animal is a mouse, a rat, or a pig.

12. The method of claim 10, wherein the animal is a NOD/SCID, NOG or NSG mouse.

13. The method of claim 10, wherein the animal supports human thymopoiesis, exhibits rejuvenated T-cell phenotype, which is characterized by the presence of predominantly naive CD45RA+CD4SRO-CD62L+CCR7+ cells, exhibits peripheral multilineage cell reconstitution, or any combination thereof.

14. The method of claim 10, wherein the adult-bone-marrow-donor CD34+ cells are from a human donor suffering from Type I Diabetes.

15. The method of claim 10, wherein the animal is optionally treated with anti-CD2 mAb.

16. The method of claim 10, wherein the method farther comprises administering $1-5 \times 10^5$ allograft-donor CD34+ cells or $1-5 \times 10^5$ HCT recipient CD34+ cells, wherein the allograft-donor CD34+ cells and HCT recipient CD34+ cells share HLA alleles with the fetal thymus tissue and the adult-bone-marrow-donor CD34+ cells, so as to generate in the animal T-cells which are mutually tolerant of one another so as to generate T-cells in the animal, which T-cells are tolerant of both the adult-bone-marrow-donor as well as the allograft-donor or HCT recipient.

17. The method of claim 10, wherein the adult-bone-marrow-donor CD34+ cells have a genetic modification.

18. The method of claim 10, wherein the human adult-bone-marrow-donor CD34+ cells have a genetic modification, whereby the T-cells derived from the human adult-bone-mar w-donor CD34+ cells are resistant to viruses that persist in the adult donor.

19. The method of claim 17, wherein the genetic modification comprises a knockdown or a mutation of CCR5, or CXCR4, or a combination thereof, whereby the T-cells derived from the adult donor CD34+ cells are less susceptible or resistant to HIV.

20. A method to expand T-cells with specificity for an antigen of interest, comprising steps (a), and (b) of claim 10, and further comprising (c) administering to the animal an antigen of interest, whereby the T-cells recognize the antigen, wherein step (c) is carried out prior to step (a), or (b), concomitantly with step (a), or (b), or after step (a), and (b).

21. The non-human animal of claim 1 or 2, further comprising an antigen of interest, whereby T cells with specificity for the antigen of interest are expanded.

22. A method to differentiate T-cells, comprising steps (a), and (b) of claim 10, further comprising (c) exposing the animal to an antigen so as to differentiate regulatory T cell.

23. The method of claim 22, wherein exposing is conducted via administration of APCs, or cytokines, or a combination thereof to the non-human animal.

24. The method of claim 20, wherein the antigen is a tumor specific antigen or derived from a tumor, or a viral antigen, or an autoantigen.

25. The non-human animal of claim 1, wherein the animal is treated with sub-lethal total body irradiation prior to or concomitantly with transplantation of the human fetal thymus tissue.

26. The non-human animal of claim 2, wherein the method further comprising treating the animal with sub-lethal total body irradiation, prior to or concomitantly with step (a) or (b).

27. The method of claim 10, further comprising treating the animal with sub-lethal total body irradiation, prior to or concomitantly with step (a) or (b).

28. The method of claim 27, wherein the animal is treated with 2.5 Gy irradiation.

29. The non-human animal of claim 1 or 2, further comprising a gene encoding a human Apolipoprotein B mRNA editing enzyme.

30. The non-human animal of claim 29, wherein the gene encodes APOBEC3.

* * * * *